(12) United States Patent
Ashwell et al.

(10) Patent No.: US 6,451,814 B1
(45) Date of Patent: Sep. 17, 2002

(54) HETEROCYCLIC β-3 ADRENERGIC RECEPTOR AGONISTS

(75) Inventors: Mark Anthony Ashwell, Plainsboro; William Ronald Solvibile, East Windsor; Dominick Anthony Quagliato, Bridgewater; Albert John Molinari, Princeton, all of NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/903,841

(22) Filed: Jul. 12, 2001

Related U.S. Application Data
(60) Provisional application No. 60/218,628, filed on Jul. 17, 2000.

(51) Int. Cl.$^7$ .................. A61K 31/47; A61K 31/445; C07D 215/16; C07D 211/08; C07D 211/06
(52) U.S. Cl. ............ 514/313; 514/312; 514/317; 514/324; 546/156; 546/192; 546/195
(58) Field of Search ................ 546/156, 192, 546/195; 514/313, 312, 317, 324

(56) References Cited

U.S. PATENT DOCUMENTS
| | | |
|---|---|---|
| 5,153,210 A | 10/1992 | Ainsworth et al. |
| 5,561,142 A | 10/1996 | Fisher et al. |
| 5,578,620 A | 11/1996 | Fujita et al. |
| 5,614,523 A | 3/1997 | Audia et al. |
| 5,741,789 A | 4/1998 | Hibschman |
| 5,786,356 A | 7/1998 | Bell et al. |
| 5,789,402 A | 8/1998 | Audia et al. |
| 6,069,176 A | 5/2000 | Tsuchiya et al. |
| 6,346,532 B1 | 2/2002 | Maruyama et al. |

FOREIGN PATENT DOCUMENTS
| | | |
|---|---|---|
| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| WO | WO 99/65895 | 12/1999 |
| WO | WO 01/17989 A2 | 3/2001 |
| WO | WO 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard Leclerc et al., J. Med. Chem., 1980, 738–744, 23(7).
D. Mauleon et al., Il Farmaco, 1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med. Chem., 1994, 322–328, 37.
Sophie Vanwetswinkel et al., J. Anitbiotics, Sep. 1994, 1041–1051, 47(9).
S. Tamada et al., JP 01061468 A2 (English abstract), 1989.

*Primary Examiner*—D. Margaret Seaman
(74) *Attorney, Agent, or Firm*—Arnold S. Milowsky

(57) ABSTRACT

This invention provides compounds of Formula I having the structure

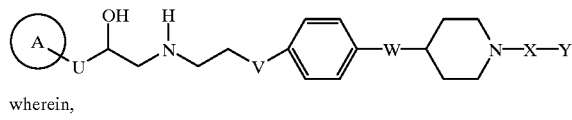

wherein,

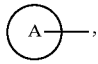

U, V, W, X, and Y are as defined hereinbefore, or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

8 Claims, No Drawings

HETEROCYCLIC β-3 ADRENERGIC RECEPTOR AGONISTS

This application claims the benefit of U.S. Provisional Application No. 60/218,628, filed Jul. 17, 2000.

BACKGROUND OF THE INVENTION

This invention relates to 4-substituted piperidine $\beta_3$-adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

The subdivision of β adrenergic receptors (β-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agnoists, see: 1. A. D. Strosberg, Annu. Rev. Pharmacol. Toxicol. 1997, 37, 421; 2. A. E. Weber, Ann. Rep. Med. Chem. 1998, 33, 193; 3. C. P. Kordik and A. B. Reitz, J. Med. Chem. 1999, 42, 181; 4. C. Weyer, J. F. Gautier and E. Danforth, Diabetes and Metabolism, 1999, 25, 11.

One essential requirement for the development of $\beta_3$-AR agonist is selectivity. Any substantial $\beta_1$- or $\beta_2$-agonism would likely cause increased heart rate or muscle tremor, respectively, both are unacceptable side effects in a drug. Early developments in the $\beta_3$-agonist field are described in European patent 427480, U.S. Pat. Nos. 4,396,627, 4,478, 849, 4,999,377, 5,153,210. Although the early developments purport to claim compounds with greater $\beta_3$-AR selectivity over the $\beta_1$- and $\beta_2$-AR, however, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436, 257, and 5,578,620. These compounds were evaluated in Chinese hamster ovary (CHO) cells test procedures which predicts the effects that can be expected in humans. These assays utilize cloned human β3 receptors, expressed in CHO cells (see refs. Granneman et al., *Mol Pharmacol.*, 1992, 42, 964; Emorine et al., *Science,* 1989, 245, 1118; Liggett *Mol. Pharmacol.,* 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T. Beta-adrenoceptor subtypes in the detrusor of guinea-pig urinary bladder. *Pharmacology* 1992; 44: 13–18). Recently, a number of laboratories have provided experimental evidence in a number of animal species including human (Yamazaki Y, Takeda H, Akahane M, Igawa Y, et al. Species differences in the distribution of the beta-adrenoceptor subtypes in bladder smooth muscle. *Br. J. Pharmacol.* 1998; 124: 593–599) that activation of the $\beta_3$ receptor subtype by norepinephrine is responsible for relaxation of the urinary bladder. Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

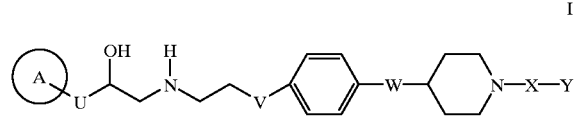

wherein,

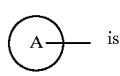 is (a) a 5–6 membered heterocyclic ring having 1–4 heteroatoms selected from O, N, and S, substituted with $(R^1)_m$;
(b) a phenyl ring substituted with $(R^1)_m$;
(c) a naphthyl ring substituted with $(R^1)_m$; or
(d) a phenyl fused heterocycle selected from the group consisting of

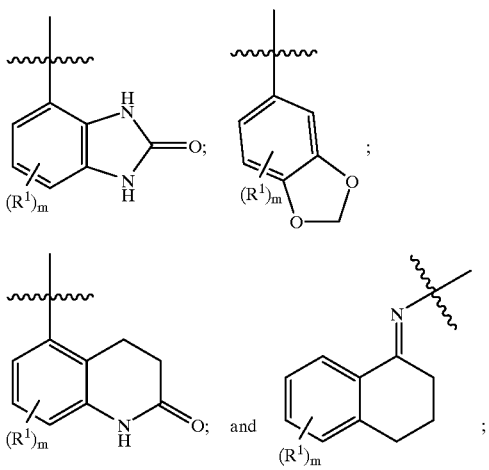

U is —OCH$_2$— or a bond;

V is O or a bond;

W is O, S(O)$_a$; NR$^2$, or NCOR$^2$;

X is SO$_2$, CO, —(CH$_2$)$_b$—, a bond, or Ar;

Y is —NR$^3$R$^4$, Het, Ar, alkyl of 1–8 carbon atoms, or —O(CH$_2$)$_d$R$^5$;

R$^1$ is alkyl of 1–8 carbon atoms, alkenyl of 2–7 carbon atoms, —OR$^6$, halogen, cyano, trifluoromethyl, —CO$_2$R$^6$, —CONR$^6$R$^7$, —NHCOR$^6$, or NHSO$_2$R$^8$;

R$^2$ is hydrogen, alkyl of 1–8 carbon atoms, or arylalkyl having 1–8 carbon atoms in the alkyl moiety;

R$^3$ and R$^4$ are each, independently, hydrogen, alkyl of 1–8 carbon atoms, cycloalkyl of 3–8 carbon atoms, arylalkyl having 1–8 carbon atoms in the alkyl group, —(CH$_2$)$_g$R$^9$, —(CH$_2$)$_h$COR$^9$, —(CH$_2$)$_j$CR$^{10}$R$^{11}$(CH$_2$)$_j$R$^9$, or —(CH$_2$)$_k$CONR$^{12}$R$^{13}$; or R$^3$ and R$^4$ may be taken together together with the nitrogen to which they are attached to form a 3–7 membered saturated heterocycle, which may optionally contain 1–2 additional heteroatoms selected from O and S, and said heterocycle may optionally be substituted with R$^{14}$;

R$^5$ is hydrogen; alkyl of 1–8 carbon atoms optionally substituted by 1–3 substituents selected from hydroxy, halogen, and aryl; cycloalkyl of 1–8 carbon atoms; Ar or Het;

R$^6$, R$^7$, and R$^8$ are each, independently, hydrogen, or alkyl of 1–8 carbon atoms, or aryl of 6–10 carbon atoms;

R$^9$ is hydrogen; alkyl optionally substituted with 1–3 substitutents selected from hydroxy, halogen, and aryl; cycloalkyl of 3–8 carbon atoms; Ar, or Het;

R$^{10}$ and R$^{11}$ are each, independently, hydrogen, alkyl, or aryl optionally substituted with alkyl of 1–8 carbon atoms or halogen; or R$^{10}$ and R$^{11}$ are taken together to form a spiro fused cycloalkyl ring of 3–8 carbon atoms;

R$^{12}$ and R$^{13}$ are each, independently, hydrogen, alkyl of 1–8 carbon atoms, aryl optionally substituted with alkyl of 1–8 carbon atoms or halogen; or R$^{12}$ and R$^{13}$ are taken together with the nitrogen to which they are attached to form a 3–7 membered saturated heterocycle, which may optionally contain 1–2 additional heteroatoms selected from O and S, and said heterocycle may optionally be substituted with R$^{14}$;

R$^{14}$ is CO$_2$R$^{15}$ or aryl optionally substituted with a 1–3 substituents selected from —OR$^{15}$ and cycloalkyloxy of 3–8 carbon atoms;

R$^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with R$^{16}$;

Het is (a) a 5–6 membered heterocyclic ring having 1–4 heteroatoms selected from O, S, and N which may be optionally mono- or di-substituted with R$^{16}$; or (b) a heterocyclic ring system optionally mono- or di-substituted by R$^{16}$ containing a 5–6 membered heterocyclic ring fused to one or two carbocyclic or heterocyclic rings such that the heterocyclic ring system contains 1–4 heteroatoms selected from O, S, and N;

R$^{16}$ is aryl, halogen, alkyl of 1–8 carbon atoms, —OR$^{17}$, cycloalkyl of 3–8 carbon atoms, trifluoromethyl, cyano, —CO$_2$R$^{17}$, —CONR$^{17}$R$^{18}$, —SO$_2$NR$^{17}$R$^{18}$, —NR$^{19}$CONR$^{17}$R$^{18}$, —NR$^{17}$R$^{18}$, —NR$^{17}$COR$^{18}$, —NO$_2$, —O(CH$_2$)$_p$CO$_2$R$^{17}$, —OCONR$^{17}$R$^{18}$, —O(CH$_2$)$_q$OR$^{17}$, or a 5–6 membered heterocyclic ring containing 1–4 heteroatoms selected from O, S, and N;

R$^{17}$, R$^{18}$, and R$^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when R$^{17}$ and R$^{18}$ are contained on a common nitrogen, R$^{17}$ and R$^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
j=0–6;
k=0–6;
m=0–2;
p=1–6;
q=1–6;

or a pharmaceutically acceptable salt thereof, which are selective agonists at human β$_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present on the molecule depending upon the nature of the various substituents on the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of know configuration. In the case of the asymmetric center represented by the asterisk in formula Ia, it has been found that the compound in which the hydroxy substituent is above the plane of the structure, is preferred over the compound in which the hydroxy substituent is below the plane of the structure.

Ia

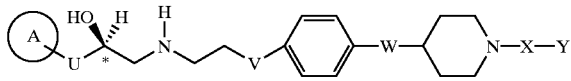

Alkyl and alkenyl include both straight chain as well as branched moieties. Halogen means bromine, chlorine, fluorine, and iodine. Aryl includes monocyclic or bicyclic aromatic carbocyclic groups such as phenyl and naphthyl. Benzyl is the preferred arylalkyl moiety.

As used herein, a heterocyclic ring is a ring confining 1–4 heteroatoms selected from N, O, and S, indicates a heterocycle which may be saturated, unstaurated, or partially unsaturated. Further definition may be derived from the substituents of the heterocycle. The monocyclic, bicyclic, or tricyclic heterocycles described above are unsubstituted, or mono- or di-substituted on any available carbon or nitrogen atoms. The heterocyclic ring may be attached within structural Formula I by any carbon atom or heteroatom. It is understood that the heterocyclic ring does not contain heteroatoms in arrangements which would make them inherently unstable. For example, the term heterocyclic ring does not include ring systems containing O—O bonds in the ring backbone. Preferred heterocycles include pyridyl, pyrimidinyl, pyrrolyl, piperidyl, pyrrolidinyl, indazolyl, morpholinyl, thienyl, furyl, imidazolyl, thiazolyl, thiadiazolyl, quinolinyl, isoquinolinyl, tetrahydroquinolinyl, tetrahydroisoquinolinyl, indolyl, isoindolyl, benzothiadiazolyl, benzodioxolyl, benzodioxanyl, benzoxazinyl, benzofuryl, dihydrobenzofuryl, benzothienyl, benzothiazolyl, benzoxazolyl, benzooxadiaxolyl, benzofurazanyl, furopyridine, and thienopyridine.

Preferred compounds of Formula I are those in which

is (a) a 5–6 membered heterocyclic ring having 1–4 heteroatoms selected from O, N, and S, substituted with $(R^1)_m$;
(b) a phenyl ring substituted with $(R^1)_m$;
(c) a phenyl fused heterocycle selected from the group consisting of

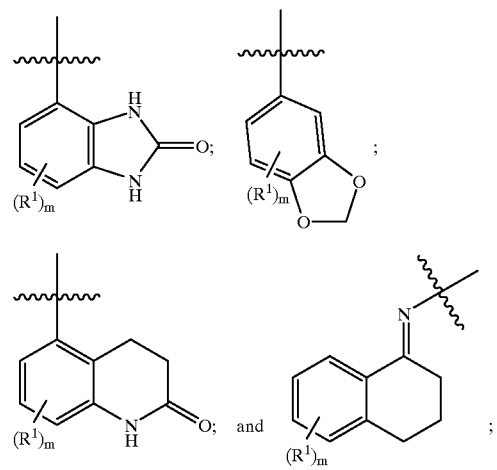

U is —OCH$_2$— or a bond;
V is O or a bond;
W is O, S(O)$_a$; or NR$^2$;
X is SO$_2$, CO, —(CH$_2$)$_b$—, a bond, or Ar;
Y is —NR$^3$R$^4$, Het, Ar, alkyl of 1–8 carbon atoms, or —O(CH$_2$)$_d$R$^5$;
R$^1$ is alkyl of 1–8 carbon atoms, alkenyl of 2–7 carbon atoms, aryl of 6–10 carbon atoms, —OR$^6$, cycloalkyl of 3–8 carbon atoms, halogen, cyano, trifluoromethyl, —CO$_2$R$^6$, —CONR$^6$R$^7$, —NHCOR$^6$, NHSO$_2$R$^6$, —NR$^6$CONR$^7$R$^8$, —NR$^6$R$^7$, alkenyl of 2–7 carbon atoms, S(O)$_a$R$^6$, NO$_2$, —O(CH$_2$)$_e$CO$_2$R$^6$, —OCONR$^6$R$^7$, —O(CH$_2$)$_f$OR$^6$, or a 5–6 membered heterocyclic ring containing 1 to 4 heteroatoms selected from O, S, and N;
R$^2$ is hydrogen, alkyl of 1–8 carbon atoms, or arylalkyl having 1–8 carbon atoms in the alkyl moiety;
R$^3$ and R$^4$ are each, independently, hydrogen, alkyl of 1–8 carbon atoms, cycloalkyl of 3–8 carbon atoms, arylalkyl having 1–8 carbon atoms in the alkyl group, —(CH$_2$)$_g$R$^9$, —(CH$_2$)$_h$COR$^9$, —(CH$_2$)$_j$CR$^{10}$R$^{11}$(CH$_2$)$_j$R$^9$, or —(CH$_2$)$_k$CONR$^{12}$R$^{13}$; or R$^3$ and R$^4$ may be taken together together with the nitrogen to which they are attached to form a 3–7 membered saturated heterocycle, which may optionally contain 1–2 additional heteroatoms selected from O and S, and said heterocycle may optionally be substituted with R$^{14}$;
R$^5$ is hydrogen; alkyl of 1–8 carbon atoms optionally substituted by 1–3 substituents selected from hydroxy, halogen, and aryl; cycloalkyl of 1–8 carbon atoms; Ar or Het;
R$^6$, R$^7$, and R$^8$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
R$^9$ is hydrogen; alkyl optionally substituted with 1–3 substitutents selected from hydroxy, halogen, and aryl; cycloalkyl of 3–8 carbon atoms; Ar, or Het;
R$^{10}$ and R$^{11}$ are each, independently, hydrogen, alkyl, or aryl optionally substituted with alkyl of 1–8 carbon atoms or halogen; or R$^{10}$ and R$^{11}$ are taken together to form a spiro fused cycloalkyl ring of 3–8 carbon atoms;
R$^{12}$ and R$^{13}$ are each, independently, hydrogen, alkyl of 1–8 carbon atoms, aryl optionally substituted with alkyl of 1–8 carbon atoms or halogen; or R$^{12}$ and R$^{13}$ are taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^{14}$ is $CO_2R^{15}$ or aryl optionally substituted with a 1–3 substituents selected from $—OR^{15}$ and cycloalkyloxy of 3–8 carbon atoms;

$R^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with $R^{16}$;

Het is (a) a 5–6 membered heterocyclic ring having 1–4 heteroatoms selected from O, S, and N which may be optionally mono- or di-substituted with $R^{16}$; or (b) a heterocyclic ring system optionally mono- or di-substituted by $R^{16}$ containing a 5–6 membered heterocyclic ring fused to one or two carbocyclic or heterocyclic rings such that the heterocyclic ring system contains 1–4 heteroatoms selected from O, S, and N;

$R^{16}$ is aryl, halogen, alkyl of 1–8 carbon atoms, $—OR^{17}$, cycloalkyl of 3–8 carbon atoms, trifluoromethyl, cyano, $—CO_2R^{17}$, $—CONR^{17}R^{18}$, $—SO_2NR^{17}R^{18}$, $—NR^{17}OR^{18}$, $—NR^{19}CONR^{17}R^{18}$, $—NR^{17}R^{18}$, $—NR^{17}COR^{18}$, $—S(O)_nR^{17}$, $—NO_2$, $—O(CH_2)_pCO_2R^{17}$, $—OCONR^{17}R^{18}$, $O(CH_2)_qOR^{17}$, or a 5–6 membered heterocyclic ring containing 1–4 heteroatoms selected from O, S, and N;

$R^{17}$, $R^{18}$, and $R^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when $R^{17}$ and $R^{18}$ are contained on a common nitrogen, $R^{17}$ and $R^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
e=1–6;
f=1–6;
g=0–6;
h=0–6;
j=0–6;
k=0–6;
m=0–2;
n=0–2;
p=1–6;
q=1–6;

or a pharmaceutically acceptable salt thereof.

Specifically preferred compounds of this invention are:

a) 4-(4-{2-[(2S)-2-Hydroxy-3-(4-hydroxy-phenoxy)-propylamino]-ethyl}-phenylamino)-piperidine-1-carboxylic acid 4-fluoro-benzylamide;

b) 4-(4-{2-[(2S)-2-Hydroxy-3-(4-hydroxy-phenoxy)-propylamino]-ethyl}-phenylamino)-piperidine-1-carboxylic acid cyclohexylamide;

c) 4-(4-{2-[(2S)-3-(4-Fluoro-phenoxy)-2-hydroxy-propylamino]-ethyl}-phenylamino)-piperidine-1-carboxylic acid octylamide;

d) 4-(4-{2-[(2S)-3-(2-Allyl-phenoxy)-2-hydroxy-propylamino]-ethyl}-phenylamino)-piperidine-1-carboxylic acid octylamide;

e) 4-(4-{2-[(2S)-3-(6-Amino-pyridin-3-yloxy)-2-hydroxy-propylamino]-ethyl}-phenylamino)-piperidine-1-carboxylic acid octylamide;

f) 4-(4-{2-[(2S)-2-Hydroxy-3-(4-hydroxy-phenoxy)-propylamino]-ethyl}-phenylamino)-piperidine-1-carboxylic acid [2-(3-methoxy-phenyl)-ethyl]-amide;

g) 4-(4-{2-[2-(3-Carbamoyl-4-hydroxy-phenyl)-2-hydroxy-ethylamino]-ethyl}-phenylamino)-piperidine-1-carboxylic acid octylamide;

h) 4-[Acetyl-(4-{2-[(2S)-2-hydroxy-3-(4-hydroxy-phenoxy)-propylamino]-ethyl}-phenyl)-amino]-piperidine-1-carboxylic acid octylamide;

i) 4-(4-{2-[(2S)-2-Hydroxy-3-(4-hydroxy-phenoxy)-propylamino]-ethyl}-phenylamino)-piperidine-1-carboxylic acid methylamide;

j) 4-(4-{2-[(2S)-2-Hydroxy-3-(4-hydroxy-phenoxy)-propylamino]-ethyl}-phenylamino)-piperidine-1-carboxylic acid ethylamide;

k) 4-(4-{2-[(2S)-2-Hydroxy-3-(4-hydroxy-phenoxy)-propylamino]-ethyl}-phenylamino)-piperidine-1-carboxylic acid isopropyl-amide;

l) 4-(4-{2-[(2S)-2-Hydroxy-3-(4-hydroxy-phenoxy)-propylamino]-ethyl}-phenylamino)-piperidine-1-carboxylic acid (3-cyclopentyl-propyl)-amide;

m) 4-(4-{2-[(2S)-2-Hydroxy-3-(4-hydroxy-phenoxy)-propylamino]-ethyl}-phenylamino)-piperidine-1-carboxylic acid (2,2,2-trifluoro-ethyl)-amide;

n) 4-(4-{2-[(2S)-2-Hydroxy-3-(4-hydroxy-phenoxy)-propylamino]-ethyl}-phenylamino)-piperidine-1-carboxylic acid diethylamide;

o) 4-(4-{2-[(2S)-2-Hydroxy-3-(4-hydroxy-phenoxy)-propylamino]-ethyl}-phenylamino)-piperidine-1-carboxylic acid [2-(4-fluoro-phenyl)-ethyl]-amide;

p) 4-(4-{2-[(2S)-3-(2-Chloro-4-hydroxy-phenoxy)-2-hydroxy-propylamino]-ethyl}-phenylamino)-piperidine-1-carboxylic acid octylamide;

q) [4-(3-Cyclopentyloxy-4-methoxy-phenyl)-piperidin-1-yl]-[4-(4-{2-[(2S)-2-hydroxy-3-(4-hydroxy-phenoxy)-propylamino]-ethyl}-phenylamino)-piperidin-1-yl]-methanone;

r) 4-(4-{2-[(2S)-2-Hydroxy-3-(4-hydroxy-phenoxy)-propylamino]-ethyl}-phenylamino)-piperidine-1-carboxylic acid amide;

s) 4-[4-(2-{(2S)-3-[4-(3-Ethyl-ureido)-phenoxy]-2-hydroxy-propylamino}-ethyl)-phenylamino]-piperidine-1-carboxylic acid [2-(4-fluoro-phenyl)-ethyl]-amide;

t) 4-(4-{2-[(2S)-2-Hydroxy-3-(4-hydroxy-phenoxy)-propylamino]-ethyl}-phenylamino)-piperidine-1-carboxylic acid 2,4-dichloro-benzylamide;

u) 4-(4-{2-[(2S)-2-Hydroxy-3-(4-hydroxy-phenoxy)-propylamino]-ethyl}-phenylamino)-piperidine-1-carboxylic acid 3,4-dichloro-benzylamide;

v) 4-(4-{2-[(2S)-2-Hydroxy-3-(4-methanesulfonylamino-phenoxy)-propylamino]-ethyl}-phenylamino)-piperidine-1-carboxylic acid octylamide;

w) 4-(4-{2-[(2S)-2-Hydroxy-3-(4-hydroxy-phenoxy)-propylamino]-ethyl}-phenylamino)-piperidine-1-carboxylic acid (3-thiophen-2-yl-propyl)-amide;

x) 4-(4-{2-[(2S)-2-Hydroxy-3-(4-hydroxy-phenoxy)-propylamino]-ethyl}-phenylamino)-piperidine-1-carboxylic acid 3,5-difluoro-benzylamide;

y) 4-(4-{2-[(2S)-2-Hydroxy-3-(4-hydroxy-phenoxy)-propylamino]-ethyl}-phenylamino)-piperidine-1-carboxylic acid 2,3-dimethoxy-benzylamide;

z) 4-(4-{2-[(2S)-2-Hydroxy-3-(4-hydroxy-phenoxy)-propylamino]-ethyl}-phenylamino)-piperidine-1-carboxylic acid 2-fluoro-benzylamide;

aa) 4-(4-{2-[(2S)-2-Hydroxy-3-(4-hydroxy-phenoxy)-propylamino]-ethyl}-phenylamino)-piperidine-1-carboxylic acid 3-fluoro-benzylamide;

bb) 4-(4-{2-[(2S)-2-Hydroxy-3-(4-hydroxy-phenoxy)-propylamino]-ethyl}-phenylamino)-piperidine-1-carboxylic acid (3-oxo-3-p-tolyl-propyl)-amide;

cc) 4-(4-{2-[(2S)-2-Hydroxy-3-(4-hydroxy-phenoxy)-propylamino]-ethyl}-phenylamino)-piperidine-1-carboxylic acid (3-p-tolyl-propyl)-amide;

dd) 4-(4-{2-[(2S)-2-Hydroxy-3-(4-hydroxy-phenoxy)-propylamino]-ethyl}-phenylamino)-piperidine-1-carboxylic acid [2-(4-ethyl-phenyl)-ethyl]-amide;

ee) 4-(4-{2-[(2S)-2-Hydroxy-3-(4-hydroxy-phenoxy)-propylamino]-ethyl}-phenylamino)-piperidine-1-carboxylic acid (2,2-diphenyl-ethyl)-amide;

ff) 4-(4-{2-[(2S)-2-Hydroxy-3-(4-hydroxy-phenoxy)-propylamino]-ethyl}-phenylamino)-piperidine-1-carboxylic acid 2,6-difluoro-benzylamide;

gg) 4-(4-{2-[(2S)-2-Hydroxy-3-(4-hydroxy-phenoxy)-propylamino]-ethyl}-phenylamino)-piperidine-1-carboxylic acid 2-trifluoromethyl-benzylamide;

hh) 4-(4-{2-[(2S)-2-Hydroxy-3-(4-hydroxy-phenoxy)-propylamino]-ethyl}-phenylamino)-piperidine-1-carboxylic acid 4-pyrazol-1-yl-2-trifluoromethyl-benzylamide;

ii) 4-(4-{2-[(2S)-2-Hydroxy-3-(4-hydroxy-phenoxy)-propylamino]-ethyl}-phenylamino)-piperidine-1-carboxylic acid (3-methyl-butyl)-amide;

jj) 4-(4-{2-[(2R)-2-(3-Chloro-phenyl)-2-hydroxy-ethylamino]-ethyl}-phenylamino)-piperidine-1-carboxylic acid octylamide;

kk) 4-(4-{2-[(2S)-2-Hydroxy-3-(4-hydroxy-phenoxy)-propylamino]-ethyl}-phenylamino)-piperidine-1-carboxylic acid 2,5-difluoro-benzylamide;

ll) 5-[(S)-3-[[2-[4-[[1-[[[(2,5-Difluorophenyl)methyl]amino]carbonyl]-4-piperidinyl]amino]phenyl]ethyl]amino]-2-hydroxypropoxy]-2-hydroxybenzoic acid;

mm) 4-(4-(2-[(2S)-2-Hydroxy-3-(4-hydroxy-phenoxy)-propylamino]-ethoxyl-phenylamino)-piperidine-1-carboxylic acid 4-fluoro-benzylamide;

nn) 4-(4-{2-[(2S)-2-Hydroxy-3-(4-hydroxy-phenoxy)-propylamino]-ethyl}-phenylsulfanyl)-piperidine-1-carboxylic acid phenylamide;

oo) 4-(4-{2-[(2S)-2-Hydroxy-3-(4-hydroxy-phenoxy)-propylamino]-ethyl}-phenylsulfanyl)-piperidine-1-carboxylic acid hexylamide;

pp) 4-(4-{2-[(2S)-2-Hydroxy-3-(4-hydroxy-phenoxy)-propylamino]-ethyl}-phenylsulfanyl)-piperidine-1-carboxylic acid 4-fluoro-benzylamide;

qq) 4-(4-{2-[(2S)-2-Hydroxy-3-(4-hydroxy-phenoxy)-propylamino]-ethyl}-phenylsulfanyl)-piperidine-1-carboxylic acid (1-phenyl-cyclopentylmethyl)-amide;

rr) 4-(4-{2-[(2S)-2-Hydroxy-3-(4-hydroxy-phenoxy)-propylamino]-ethyl}-benzenesulfonyl)-piperidine-1-carboxylic acid hexylamide;

ss) 4-(4-{2-[(2S)-2-Hydroxy-3-(4-hydroxy-phenoxy)-propylamino]-ethyl}-benzenesulfonyl)-piperidine-1-carboxylic acid 4-fluoro-benzylamide;

tt) 4-(4-{2-[(2S)-2-Hydroxy-3-(4-hydroxy-phenoxy)-propylamino]-ethyl}-benzenesulfonyl)-piperidine-1-carboxylic acid (1-phenyl-cyclopentylmethyl)-amide;

uu) 4-(4-{2-[(2S)-2-Hydroxy-3-(4-hydroxy-phenoxy)-propylamino]-ethyl}-benzenesulfonyl)-piperidine-1-carboxylic acid octylamide;

vv) 4-(4-{2-[(2S)-2-Hydroxy-3-(4-hydroxy-3-methyl-phenoxy)-propylamino]-ethyl}-benzenesulfonyl)-piperidine-1-carboxylic acid octylamide;

ww) 4-(4-{2-[(2S)-3-(Benzo[1,3]dioxol-5-yloxy)-2-hydroxy-propylamino]-ethyl}-benzenesulfonyl)-piperidine-1-carboxylic acid octylamide;

xx) 4-(4-{2-[(2S)-2-Hydroxy-3-(4-hydroxy-3-methanesulfonylamino-phenoxy)-propylamino]-ethyl}-phenylamino)-piperidine-1-carboxylic acid 2,5-difluorobenzylamide;

yy) 1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic acid ethyl ester;

zz) 1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic acid;

aaa) 4-(4-{2-[(2S)-2-Hydroxy-3-(4-hydroxy-phenoxy)-propylamino]-ethyl}-phenylamino)-piperidine-1-carboxylic acid octylamide;

bbb) 4-(4-{2-[(2S)-2-Hydroxy-3-(4-hydroxy-phenoxy)-propylamino]-ethyl}-phenoxy)-piperidine-1-carboxylic acid octylamide;

ccc) 4-(4-{2-[(2S)-2-Hydroxy-3-(4-hydroxy-phenoxy)-propylamino]-ethyl}-phenylamino)-piperidine-1-carboxylic acid (8-fluoro-octyl)-amide;

ddd) 4-(4-{2-[(2S)2-Hydroxy-3-(4-hydroxy-phenoxy)-propylamino]-ethyl}-phenoxy)-piperidine-1-carboxylic acid 4-fluoro-benzylamide;

eee) 4-(4-{2-[2-Hydroxy-3-(4-hydroxy-phenoxy)-propylamino]-ethyl}-phenylamino)-piperidine-1-carboxylic acid [4-(3,4-dimethoxy-phenyl)-butyl]-amide;

fff) (4-{[4-(4-{2-[(2S)-2-Hydroxy-3-(4-hydroxy-phenoxy)-propylamino]-ethyl}-phenylamino)-piperidine-1-carbonyl]-amino}-phenoxy)-acetic acid;

ggg) 4-(4-{2-[(2R)-2-Hydroxy-2-(4-hydroxy-3-methanesulfonylamino-phenyl)-ethylamino]-ethyl}-phenylamino)-piperidine-1-carboxylic acid octylamide;

hhh) 4-(4-{2-[(2S)-2-Hydroxy-3-(2-oxo-2,3-dihydro-1H-benzoimidazol-4-yloxy)-propylamino]-ethyl}-phenylamino)-piperidine-1-carboxylic acid octylamide;

iii) 1-[4-(4-{2-[(2S)-2-Hydroxy-3-(4-hydroxy-phenoxy)-propylamino]-ethyl}-phenylamino)-piperidine-1-carbonyl]-piperidine-4-carboxylic acid ethyl ester;

jjj) 1-[4-(4-{2-[(2S)-2-Hydroxy-3-(4-hydroxy-phenoxy)-propylamino]-ethyl}-phenylamino)-piperidine-1-carbonyl]-piperidine-4-carboxylic acid;

kkk) 4-(4-{2-[(2S)-3-(3-Acetylamino-phenoxy)-2-hydroxy-propylamino]-ethyl}-phenylamino)-piperidine-1-carboxylic acid octylamide;

lll) 4-(4-{2-[(2S)-2-Hydroxy-3-(5-hydroxy-3,4-dihydro-2H-naphthalen-1-ylideneaminooxy)-propylamino]-ethyl}-phenylamino)-piperidine-1-carboxylic acid octylamide;

mmm) 4-(4-{2-[(2S)-3-(3-Fluoro-4-hydroxy-phenoxy)-2-hydroxy-propylamino]-ethyl}-phenylamino)-piperidine-1-carboxylic acid octylamide;

nnn) 4-(4-{2-[(2S)-2-Hydroxy-3-(4-hydroxy-3-methanesulfonylamino-phenoxy)-propylamino]-ethyl}-phenylamino)-piperidine-1-carboxylic acid octylamide;

ooo) 4-(4-{2-[(2S)-2-Hydroxy-3-(4-hydroxy-phenoxy)-propylamino]-ethyl}-phenylamino)-piperidine-1-carboxylic acid 4-(3-hexyl-ureido)-benzylamide;

ppp) 4-(4-{2-[(2S)-2-Hydroxy-3-(4-hydroxy-phenoxy)-propylamino]-ethyl}-phenylamino)-piperidine-1-carboxylic acid (3-cyclohexyl-propyl)-amide;

qqq) 4-(4-{2-[(2S)-2-Hydroxy-3-(8-hydroxy-2-oxo-1,2,3,4-tetrahydro-quinolin-5-yloxy)-propylamino]-ethyl}-phenylamino)-piperidine-1-carboxylicacid octylamide;

rrr) 4-(4-{2-[(2S)-2-Hydroxy-3-(4-hydroxy-phenoxy)-propylamino]-ethyl}-phenylamino)-piperidine-1-carboxylic acid cyclopentylmethyl-amide;

sss) 4-(4-{2-[(2S)-2-Hydroxy-3-(4-hydroxy-phenoxy)-propylamino]-ethyl}-phenylamino)-piperidine-1-carboxylic acid {2-[2-methoxy-4-(3-phenoxy-propoxy)-phenyl]-ethyl}-amide;

ttt) 4-(4-{2-[(2S)-2-Hydroxy-3-(2-oxo-2,3-dihydro-1H-benzoimidazol-4-yloxy)-propylamino]-ethoxy}-phenylamino)-piperidine-1-carboxylic acid octylamide;

uuu) 4-(4-{2-[(2S)-2-Hydroxy-3-(4-hydroxy-phenoxy)-propylamino]-ethoxy}-phenylamino)-piperidine-1-carboxylic acid octylamide;

vvv) Dimethyl-carbamic acid 4-(2-{[4-(4-{2-[(2S)-2-hydroxy-3-(4-hydroxy-phenoxy)-propylamino]-ethyl}-phenylamino)-piperidine-1-carbonyl]-amino}-ethyl)-phenyl ester;

www) 4-(4-{2-[(2S)-2-Hydroxy-3-(3-methanesulfonylamino-phenoxy)-propylamino]-ethyl}-phenylamino)-piperidine-1-carboxylic acid 4-fluoro-benzylamide;

xxx) 4-(4-{2-[(2R)-2-Hydroxy-2-(4-hydroxy-3-methanesulfonylamino-phenyl)-ethylamino]-ethyl}-phenylamino)-piperidine-1-carboxylic acid 2,5-difluoro-benzylamide;

yyy) 1-[[4-[[4-[2-[[(2R)-2-Hydroxy-2-[4-hydroxy-3-[(methylsulfonyl)amino]phenyl]ethyl]amino]ethyl]phenyl]amino]-1-piperidinyl]carbonyl]-L-proline, methyl ester;

zzz) 1-[[4-[[4-[2-[[(2R)-2-Hydroxy-2-[4-hydroxy-3-[(methylsulfonyl)amino]phenyl]ethyl]amino]ethyl]phenyl]amino]-1-piperidinyl]carbonyl]-3-piperidine carboxylic acid, ethyl ester;

aaaa) 4-(4-{2-[(2S)-2-hydroxy-3-(4-hydroxy-phenoxy)-propylamino]ethyl}phenylamino)-piperidine-1-carboxylic acid 3-methoxy-benzylamide;

bbbb) 4-(4-{2-[(2S)-2-Hydroxy-3-(4-hydroxy-phenoxy)-propylamino]-ethyl}-phenylamino)-piperidine-1-carboxylic acid 2,4-difluoro-benzylamide;

cccc) 4-(4-{2-[(2S)-2-Hydroxy-3-(4-hydroxy-phenoxy)-propylamino]-ethyl}-phenylamino)-piperidine-1-carboxylic acid [2-(4-fluoro-phenylcarbamoyl)-ethyl]-amide;

dddd) 4-(4-{2-[(2S)-2-Hydroxy-3-(4-hydroxy-phenoxy)-propylamino]-ethyl}-phenylamino)-piperidine-1-carboxylic acid {2-[(4-chloro-phenyl)-methyl-carbamoyl]-ethyl}-amide;

eeee) 4-(4-{2-[2-Hydroxy-3-(4-hydroxy-phenoxy)-propylamino]-ethyl}-phenylamino)-piperidine-1-carboxylic acid 2-fluoro-4-hydroxy-benzylamide;

ffff) Dimethyl-carbamic acid 3-fluoro-4-({[4-(4-{2-[(2S)-2-hydroxy-3-(4-hydroxy-phenoxy)-propylamino]-ethyl}-phenylamino)-piperidine-1-carbonyl]-amino}-methyl)-phenyl ester;

gggg) 4-(4-{2-[(2S)-2-Hydroxy-3-(3-hydroxy-phenoxy)-propylamino]-ethyl}-phenylamino)-piperidine-1-carboxylic acid 4-fluoro-benzylamide;

hhhh) [3-Fluoro-4-[[[[4-[[4-[2-[[(S)-2-hydroxy-3-(4-hydroxyphenoxy)propyl]amino]ethyl]phenyl]amino]-1-piperidinyl]carbonyl]amino]methyl]phenoxy]acetic acid;

iiii) 4-(4-{2-[(2S)-2-Hydroxy-3-(3-hydroxy-phenoxy)-propylamino]-ethyl}-phenylamino)-piperidine-1-carboxylic acid 2-fluoro-4-hydroxy-benzylamide;

jjjj) 4-(4-{2-[(2S)-2-Hydroxy-3-(4-hydroxy-phenoxy)-propylamino]-ethyl}-phenylamino)-piperidine-1-carboxylic acid [2-(3-fluoro-phenyl)-ethyl]-amide;

kkkk) 4-(4-{2-[(2S)-2-Hydroxy-3-(4-hydroxy-phenoxy)-propylamino]-ethyl}-phenylamino)-piperidine-1-carboxylic acid (2-diethylcarbamoyl-ethyl)-amide;

llll) 4-(4-{2-[(2S)-2-Hydroxy-3-(4-hydroxy-phenoxy)-propylamino]-ethyl}-phenylamino)-piperidine-1-carboxylic acid (3-morpholin-4-yl-3-oxo-propyl)-amide;

mmmm) [4-(4-{2-[(2S)-2-Hydroxy-3-(4-hydroxy-phenoxy)-propylamino]-ethyl)-phenylamino)-piperidin-1-yl]-(1H-indol-2-yl)-methanone;

nnnn) 4-[4-(4-{2-[(2S)-2-Hydroxy-3-(4-hydroxy-phenoxy)-propylamino]-ethyl}-phenylamino)-piperidine-1-carbonyl]-piperidine-1-carboxylic acid octylamide;

oooo) 1-Hexyl-3-{4-[4-(4-{2-[(2S)-2-hydroxy-3-(4-hydroxy-phenoxy)-propylamino]-ethyl}-phenylamino)-piperidine-1-carbonyl]-phenyl}-urea;

pppp) [4-(4-{2-[2-Hydroxy-3-(4-hydroxy-phenoxy)-propylamino]-ethyl}-phenylamino)-piperidin-1-yl]-(5-methoxy-1H-indol-2-yl)-methanone;

qqqq) [4-(4-{2-[(2S)-2-Hydroxy-3-(4-hydroxy-phenoxy)-propylamino]-ethyl}-phenylamino)-piperidin-1-yl]-(7-nitro-1H-indol-2-yl)-methanone;

rrrr) (5-Bromo-1H-indol-2-yl)-[4-(4-{2-[(2S)-2-hydroxy-3-(4-hydroxy-phenoxy)-propylamino]-ethyl}-phenylamino)-piperidin-1-yl]-methanone;

ssss) [4-(4-2-[(2S)-2-Hydroxy-3-(4-hydroxy-phenoxy)-propylamino]-ethyl[-phenylamino)-piperidin-1-yl]-(3-methoxy-benzo[b]thiophen-2-yl)-methanone;

tttt) N-{3-[(2S)-2-Hydroxy-3-(2-{4-[1-(3-methoxy-benzo[b]thiophene-2-carbonyl)-piperidin-4-ylamino]-phenyl}-ethylamino)-propoxy]-phenyl}-acetamide;

uuuu) [4-(4-{2-[(2S)-2-Hydroxy-3-(4-hydroxy-phenoxy)-propylamino]-ethyl}-phenylamino)-piperidin-1-yl]-(1H-indol-3-yl)-methanone;

vvvv) [4-(4-{2-[(2S)-2-Hydroxy-3-(4-hydroxy-phenoxy)-propylamino]-ethyl}-phenylamino)-piperidin-1-yl]-(3-methyl-thiophen-2-yl)-methanone;

wwww) 4-[(2S)-2-Hydroxy-3-(2-{4-[1-(3-methyl-thiophene-2-carbonyl)-piperidin-4-ylamino]-phenyl}-ethylamino)-propoxy]-1,3-dihydro-benzoimidazol-2-one;

xxxx) [4-(4-{2-[(2S)-2-Hydroxy-3-(4-hydroxy-phenoxy)-propylamino]-ethyl}-phenylamino)-piperidin-1-yl]-(1H-indazol-3-yl)-methanone;

yyyy) 1-[4-(4-{2-[(2S)-2-Hydroxy-3-(4-hydroxy-phenoxy)-propylamino]-ethyl}-phenylamino)-piperidin-1-yl]-hexan-1-one;

zzzz) [(2S)-1-(4-Fluoro-benzenesulfonyl)-pyrrolidin-2-yl]-[4-(4-{2-[(2S)-2-hydroxy-3-(4-hydroxy-phenoxy)-propylamino]-ethyl}-phenylamino)-piperidin-1-yl]-methanone;

aaaaa) 4-[4-(4-{2-[(2R)-2-Hydroxy-2-(4-hydroxy-3-methanesulfonylamino-phenyl)-ethylamino]-ethyl}-phenylamino)-piperidine-1-carbonyl]-benzoic acid;

bbbbb) [4-(4-{2-[(2S)-2-Hydroxy-3-(4-hydroxy-phenoxy)-propylamino]-ethyl)-phenylsulfanyl)-piperidin-1-yl]-(3-methyl-thiophen-2-yl)-methanone;

ccccc) [4-(4-{2-[(2S)-2-Hydroxy-3-(4-hydroxy-phenoxy)-propylamino]-ethyl}-benzenesulfonyl)-piperidin-1-yl]-(2-methyl-thiophen-3-yl)-methanone;

ddddd) 1-Hexyl-3-{4-[4-(4-{2-[(2S)-2-hydroxy-3-(4-hydroxy-phenoxy)-propylamino]-ethylphenyl}amino)-piperidine-1-sulfonyl]-phenyl}-urea;

eeeee) 1-{4-[4-(4-{2-[(2S)-3-(4-Fluoro-phenoxy)-2-hydroxy-propylamino]-ethyl}-phenylamino)-piperidine-1-sulfonyl]-phenyl}-3-hexyl-urea;

fffff) 1-{4-[4-(4-{2-[3-(2-allyl-phenoxy)-2-hydroxy-propylamino]ethyl}-phenylamino)-piperidine-1-sulfonyl]-phenyl}-3-hexyl-urea;

ggggg) 4-[(2S)-2-Hydroxy-3-(2-{4-[1-(octane-1-sulfonyl)-piperidin-4-ylamino]-phenyl}-ethylamino)-propoxy]-phenol;

hhhhh) 4-[(2S)-2-Hydroxy-3-(2-{4-[1-(toluene-4-sulfonyl)-piperidin-4-ylamino]-phenyl}-ethylamino)-propoxy]-phenol;

iiiii) 4-[(2S)-2-Hydroxy-3-(2-{4-[1-(1-methyl-1H-imidazole-4-sulfonyl)-piperidin-4-ylamino]-phenyl}-ethylamino)-propoxy]-phenol;

jjjjj) N-{4-[4-(4-{2-[(2S)-2-Hydroxy-3-(4-hydroxy-phenoxy)-propylamino]-ethyl}-phenylamino)-piperidine-1-sulfonyl]-phenyl}-acetamide;

kkkkk) N-(5-{[4-(4-(2-[((2R)-2-hydroxy-2-{4-hydroxy-3-[(methylsulfonyl)amino]phenyl]ethyl)amino]ethyl}anilino)piperidin-1-yl]sulfonyl}-4-methyl-1,3-thiazol-2-ylacetamide;

llll) N-(2-Hydroxy-5-{(1R)-1-hydroxy-2-[2-(4-{-[4-(3-octyl-ureido)-benzenesulfonyl]-piperidin-4-ylamino}-phenyl)-ethylamino]-ethyl}-phenyl)-methanesulfonamide;

mmmmm) 4-[(2S)-2-Hydroxy-3-(2-{4-[1-(4-phenyl-thiazol-2-yl)-piperidin-4-ylamino]-phenyl}-ethylamino)-propoxy]-phenol;

nnnnn) (R)-N-{2-Hydroxy-5-[1-hydroxy-2-(2-{4-[1-(4-phenyl-thiazol-2-yl)-piperidin-4-ylamino]-phenyl}-ethylamino)-ethyl]-phenyl}-methanesulfonamide;

oooo) N-(2-Hydroxy-5-{(1R)-1-hydroxy-2-[2-(4-{1-[4-(piperidine-1-sulfonyl)-phenyl]-piperidin-4-ylamino}-phenyl)-ethylamino]-ethyl}-phenyl)-methanesulfonamide;

ppppp) 4-[4-(4-{2-[(2R)-2-Hydroxy-2-(4-hydroxy-3-methanesulfonylamino-phenyl)-ethylamino]-ethyl}-phenylamino)-piperidin-1-yl]-benzoic acid ethyl ester;

qqqqq) 4-(4-{2-[(2S)-2-Hydroxy-3-(4-hydroxy-phenoxy)-propylamino]-ethyl}-phenylamino)-piperidine-1-carboxylic acid 4-fluoro-benzyl ester;

rrrrr) 4-(4-{2-[(2S)-2-Hydroxy-3-(4-hydroxy-phenoxy)-propylamino]-ethyl}-phenylamino)-piperidine-1-carboxylic acid 2,5-difluoro-benzyl ester;

or a pharmaceutically acceptable salt thereof.

The compounds of this invention were be prepared according to the following schemes from commercially available starting materials or starting materials which can be prepared using literature procedures. These schemes show the preparation of representative compounds of this invention.

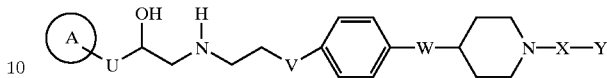

(I)

When U represents —OCH$_2$— compounds of the present invention can be prepared from epoxide intermediate such as those of Formula (II) and amine intermediates such as those of Formula (IV). The preparation of these intermediates is described in the following schemes.

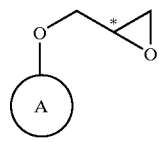

(II)

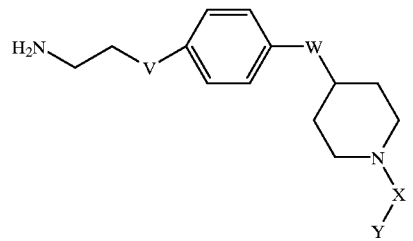

(III)

When U is a bond compounds of the present invention can be prepared from epoxide intermediates such as those of Formula (IV) and amine intermediates of Formula (III). Alternatively, an intermediate of Formula (V) may be reacted with amine intermediates of Formula (III). In a further method of preparation intermediates of Formula (VI) may be reacted with aldehydes having the Formula (VII). The preparation of these intermediates is described in the following schemes.

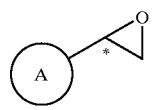

(IV)

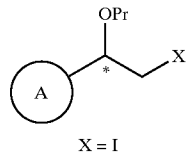

(V)

X = I

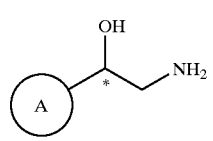

(VI)

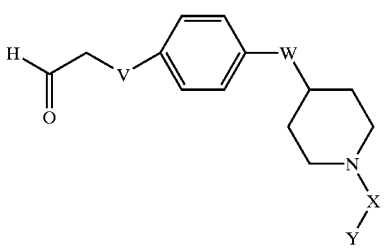

(VII)

Scheme 1

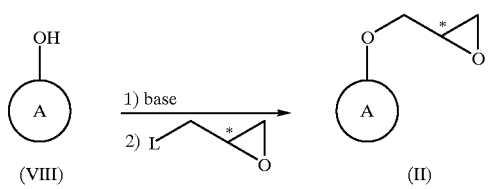

Compounds of Formula (II) can be conveniently prepared by a variety of methods familiar to those skilled in the art. One common route is illustrated in Scheme 1. Alcohol (VIII) is treated with base such as sodium hydride or potassium t-butoxide in a polar solvent such as anhydrous dimethylformamide. The resulting anion is alkylated with a suitable epoxide derivative, wherein, "L" is a leaving group such as a sulfonate ester or a halide, for 0.5 to 24 hours at a temperature of 20–100° C. to provide epoxide (II). The reacting epoxide derivative is conveniently the commercially available, enantiomerically pure (2S) or (2R)-glycidyl 3-nitrobenzene sulfonate, or (2R) or (2S)-glycidyl 4-toluenesulfonate, thus both (S) and (R) enantiomers of epoxide (III) are available. J. M. Klunder et al., *J. Org. Chem.*, 1989, 54, 1295.

Scheme 2

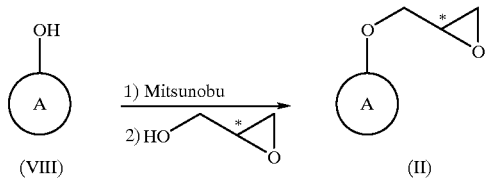

Alternatively, compounds of Formula (II) can be conveniently prepared from alcohol (VIII) under Mitsunobu conditions reaction (O. Mitsunobu, *Bull. Chem. Soc. Jpn.*, 1967, 60, 2380,) reacting the commercially available, enantiomerically pure (2S) or (2R)-glycidol, with triphenyl phosphine and a dialkyl azodicarboxylate in an anhydrous solvent such as tetrahydrofuran at 20–35° C. for 12–36 hours, suitable alkyl groups are ethyl, isopropyl etc., Scheme 2.

Many of the alcohols are commercially available or readily prepared by methods described in the literature and known to those skilled in the art. $R_1$ substitutions on the alcohol (VIII) may need to be protected during the reaction with the epoxide derivatives and subsequent procedures. A description of such protecting groups may be found iN Protective Groups in Organic Synthesis, $2^{nd}$ Ed., T. W. Greene and P. G. M. Wut, John Wiley and Sons, New York, 1991.

A useful method for protecting the preferred alcohol wherein $(R_1)_m$ is 4-hydroxyphenyl is as its tert-butyldiphenylsilyl (TBDPS) derivative shown in Scheme 3. Commercially available 4-(benzyloxy)phenol is treated with a silylating agent such as tert-butyldiphenylsilyl chloride in the presence of an organic base such as imidazole in an inert anhydrous solvent such as dichloromethane. The resulting compound (IX) is then treated under transfer hydrogenation conditions using Pd/C and cyclohexene in ethanol at reflux for 12–24 hours to prepare the alcohol (X).

Scheme 3

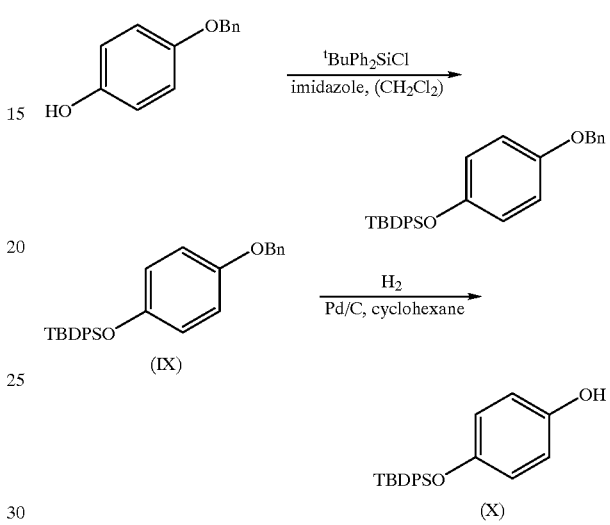

Epoxides of Formula (IV) are known in the literature or may be conveniently prepared by a variety of methods familiar to those skilled in the art. One common route is shown in Scheme 4.

Scheme 4

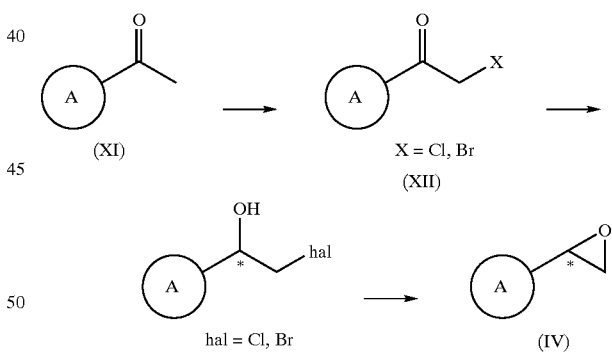

Methyl ketone (XI) may be converted to the corresponding haloketone using a variety of reagents known to those skilled in the art and summarised in Larock, Comprehensive Organic Transformations, VCH, New York, 1989, 369–372. For the synthesis wherein X=Br, bromine or dibromobarbituric acid may be used. The reduction of the haloketone is conveniently performed with a reducing agent such as sodium borohydride. The resulting alcohol when treated with a base such as sodium hydroxide or potassium carbonate in a suitable solvent such as 2-butanone or acetone yields the epoxide of Formula (IV).

The enantiomercially enriched (R) or (S)-epoxide (IV) are readily available by asymmetric reduction of haloketones (XII) using chiral reducing agents in place of sodium borohydride. Such chiral reducing agents include (−) or (+)-DIP-Cl, (R) or (S)-Alpine borane or (R) or (S)-tetrahydro-1-methyl-3,3-diphenyl-1H,3H-pyrrolo[1,2-c][1,3,2]oxazaborole-borane ((R) or (S)-OAB.BH$_3$). Alternatively the haloketones (XII) may be treated with borane in the presence of a chiral auxiliary agent such as described by E. J. Corey et al., *J. Org. Chem.*, 1991, 56, 442, Compound (V) can be conveniently prepared by substantially following the literature procedure reported by E. J. Corey and J. O. Link, *J. Org. Chem.*, 1991, 56, 422, and patent WO 9737646 wherein haloketones such as (XII) are transformed into compounds (V) by sequential halogenation, asymmetric reduction followed by transformation to the iodide and finally protection of the alcohol as a silyl ether.

Scheme 5

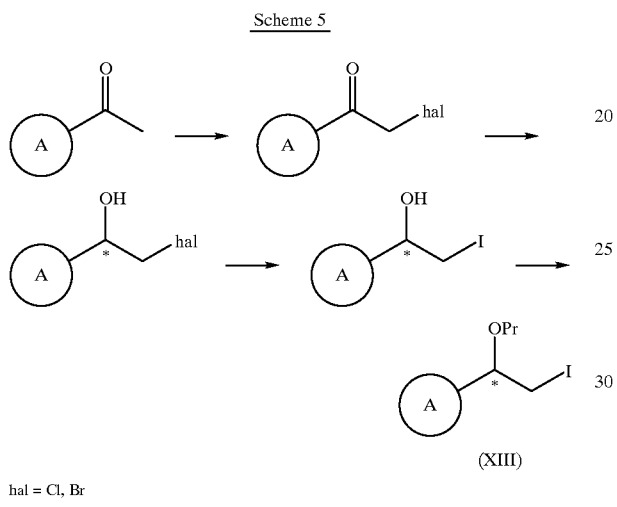

(XIII)

hal = Cl, Br

Compound (XIV) can be, conveniently prepared by utilizing the alcohol (XV) (following asymmetric reduction) and displacement of the halogen with a metal azide such as sodium or lithium azide in an a aprotic solvent such as dimethylformamide in the presence of sodium iodide at 20–40° C. for 5–10 days. Reduction of the azide group to generate amines of the Formula (XIV) is conveniently performed by catalytic reduction on a Parr apparatus with a suitable catalyst such as palladium on carbon. If $(R_1)_m$ contains a protecting group removed by hydrogen such as benzyl then this group will also be removed under the reaction conditions.

Scheme 6

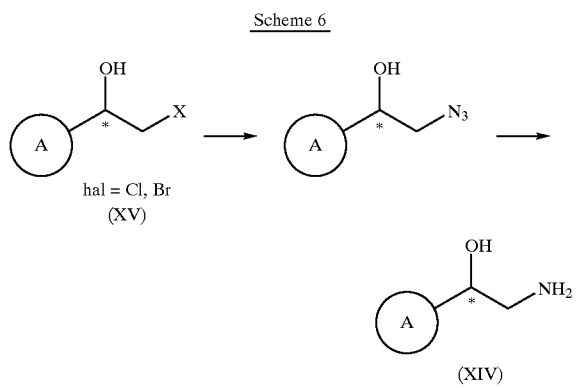

hal = Cl, Br
(XV)

(XIV)

Many of the methyl ketones are commercially available or readily prepared by methods described in the literature and known to those skilled in the art. $R_1$ substitutions on the methyl ketones may need to be protected during the reaction with the epoxide derivatives and subsequent procedures. A description of such protecting groups may be found in Protective Groups in Organic Synthesis, 2$^{nd}$ Ed., T. W. Greene and P. G. M. Wut, John Wiley and Sons, New York, 1991.

Compounds of Formula (III) can be conveniently prepared by a variety of methods familiar to those skilled in the art.

A convenient route for their preparation when W is nitrogen is illustrated in Scheme 7. Compound (XVI) is selectively protected as a suitable carbamate derivative. Di-tert-butyl dicarbonate reacts preferrentially in an inert solvent such dichloromethane at ambient temperature to provide the tert-butyl carbamate protected primary amine (XVII)

Compounds of Formula (XVIII) may be conveniently formed under reductive amination conditions. Such conditions and reagents are well known in the art. They are typically performed by mixing the amine and carbonyl compound in a solvent and adding a reducing agent. Solvents typically include lower alcohols, dichloromethane, DMF and the like. A wide variety of reducing agents can be utilized, most commonly utilized are sodium borohydride, sodium cyanoborohydride or sodium triacetoxyborohydride. The temperature of the reaction is typically room temperature to the reflux of the solvent.

Scheme 7

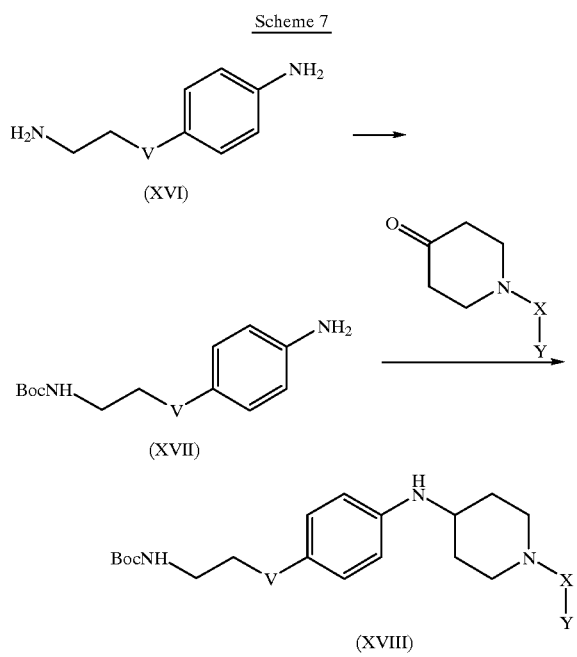

(XVI)

(XVII)

(XVIII)

This reaction is most conveniently performed substantially as described by J. W. Coe et al *Tet. Letts.*, 1996, 37, 6045,. Wherein compounds of Formula (XVII) are pre-stirred at ambient temperature with the ketone in an inert solvent such as dichloromethane or dichloroethane in the presence of a drying agent such as anhydrous sodium sulfate and an acid such as acetic acid. Typically the reductant employed is sodium triacetoxyborohydride which is added in excess after 45–50 minutes.

When X-Y together represent a benzyl protecting group then the commercially available 1-benzyl-4-piperidinone provides a most convenient route to compounds of the general Formula (XIX) shown in Scheme 8.

The protecting benzyl group of compounds of Formula (XIX) can be removed under a number of condition described in Protective Groups in Organic Synthesis, 2<sup>nd</sup> Ed., T. W. Greene and P. G. M. Wut, John Wiley and Sons, New York, 1991. One such method is palladium catalysed transfer hydrogenation with cyclohexene in boiling ethanol essentially as described by S. Ram, *Synthesis,* 1988, 91,.

This strategy, in addition to that in Scheme 7, thus provides an alternative method to provide compounds of Formula (III) since they can be conveniently prepared from compounds of Formula (XX) by a variety of methods familiar to those skilled in the art and described below. Where W of Formula (III) represents an alkylated or acylated nitrogen atom of reaction of the nitrogen with for example, in the case of acylation, acetic anhydride in pyridine prior to the removal of the benzyl group and reaction of the liberated secondary amine.

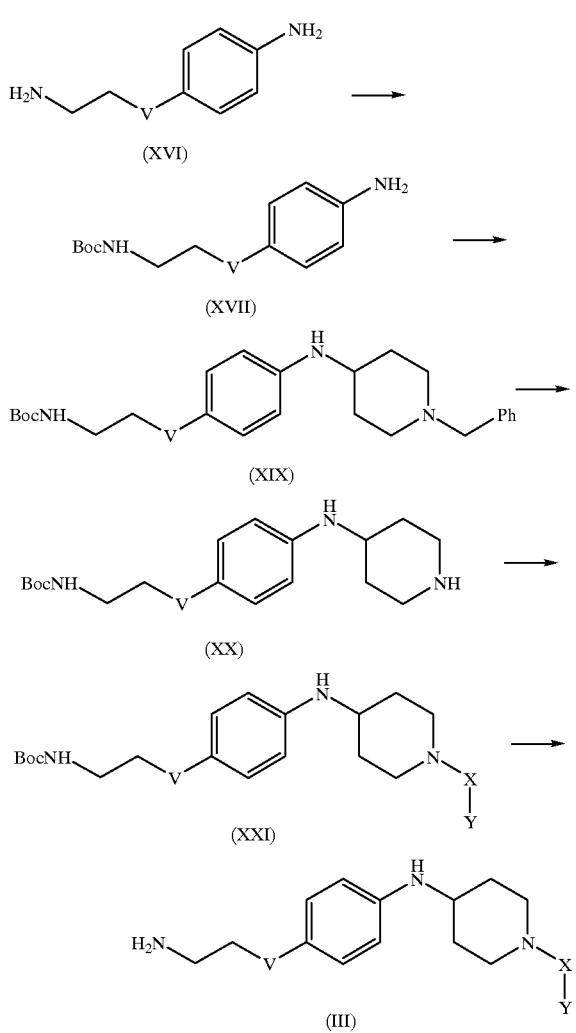

Scheme 8

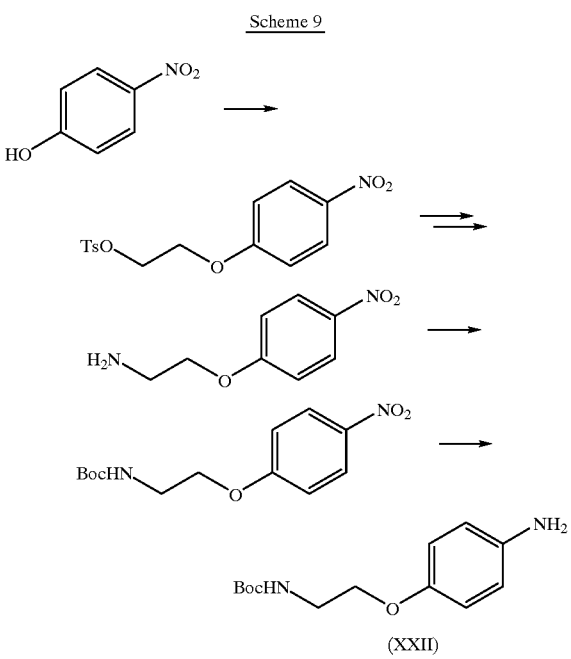

Scheme 9

When V is a bond commercially available 4-(2-aminoethyl)aniline can be conveniently used in the sequence described above.

When V is —OCH$_2$— then methods described in the literature can be conveniently employed to prepare as shown in Scheme 9.

The sodium salt of 4-nitrophenol is alkylated with 1-p-tosylchloroethane, conveniently in refluxing 2-butanone with a base such as potassium carbonate to give the corresponding tosyl derivative as described by N. Ackerley et al., *J. Med. Chem.,* 1995, 38(10), 1608–28. The tosyl group is converted to the amine by treatment with a metal azide such as sodium or lithium azide in an a protic solvent such as dimethylformamide followed by reduction with, for example, triphenylphosine in aqueous tetrahydrofuran as described by H. Staudinger, *Helv. Chim. Acta,* 1919, 2, 635,. Protection of the resulting amine, conveniently as the t-butyl carbamate with di-tert-butyl dicarbonate is followed by reduction of the nitro group by, for example, palladium catalyzed hydrogenation to provide the amine (XXII). Aniline (XXII) is thus able to undergo essentially similar transformations as amine (XVII) to provide compounds of Formula (III).

Aldehydes of Formula (VII) may be prepared by a variety of procedures known in the art. The following is an example for the preparation of aldehydes of general Formula (VII).

Scheme 10

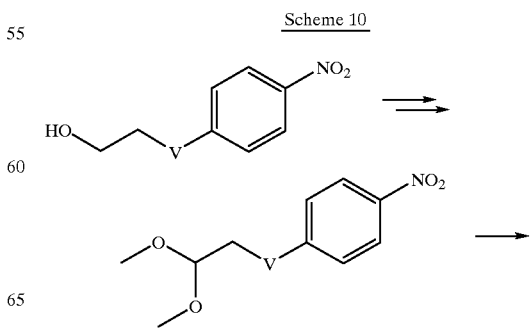

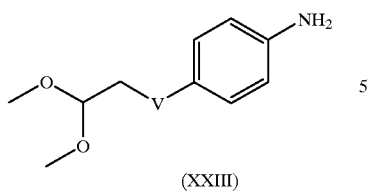

(XXIII)

When V is a bond commercially available 4-nitrobenzeneethanol provides a suitable convenient starting material. Mild neutral oxidation using reagents such as Dess-Martin periodinane (P. B. Martin, *J. Am. Chem. Soc.,* 1978, 100, 300) in an inert solvent such as dichloromethane is advantageous. The resulting aldehyde can be protected as an acetal or ketal in situ. A number of such groups are described in Protective Groups in Organic Synthesis, $2^{nd}$ Ed., T. W. Greene and P. G. M. Wut, John Wiley and Sons, New York, 1991. A convenient procedure is to protect the aldehyde as the di-methyl acetal by reaction of the aldehyde with anhydrous trimethylorthoformate and an organic acid such as p-toluenesulfonic acid. Reduction of the nitro group can be carried out in a variety of ways, conveniently reduction with palladium on carbon in refluxing ethanol with an excess of ammonium formate provides the desired aniline. Aniline (XXIII) is thus able to undergo essentially similar transformations as amine (XVII) to provide compounds of Formula (III).

When W is oxygen or sulfur compounds of Formula (III) can be conveniently prepared by a variety of methods familiar to those skilled in the art. One such route (W=O and V=bond) is illustrated in Scheme 11.

Commercially available tyramine can be selectively protected as a suitable carbamate derivative with, for example, di-tert-butyl dicarbonate or carbobenzyloxy chloride. 4-Piperidinol can be preferentially reacted at the nitrogen or protected at the oxygen with a suitable protecting group such as tert-butyldiphenyl silyl. Once groups X-Y have been added (as described below) then removal of the protecting group with for example tetrabutylammonium fluoride can be performed if needed or the alcohol reacted directly. Methods to convert the alcohol group of the N-substituted 4-piperidinol to a suitable leaving group shown in (XXIV) are known to those skilled in the art. One particularly mild and convenient procedure is shown in Scheme 12. Treatment with carbon tetrabromide and tripheny phosphine in an inert solvent such as dichloromethane as described by J. Hooz et. al., *Can. J. Chem.,* 1968, 46, 96 provides bromide (XXVI).

Scheme 11

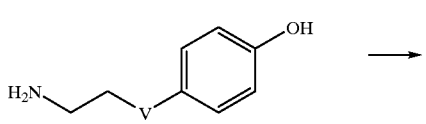

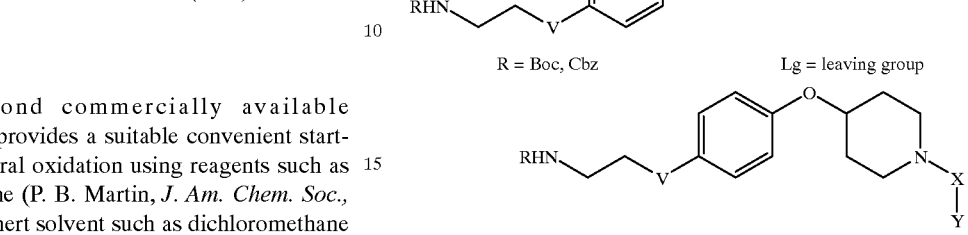

R = Boc, Cbz      Lg = leaving group

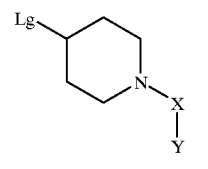

(XXV)

Scheme 12

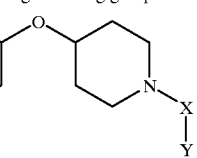

(XXVI)      (XXVII)

An alternative procedure is the Mitsunobu reaction (O. Mitsunobu, *Bull. Chem. Soc. Jpn.,* 1967, 60, 2380). Treatment of (XXVI) with triphenyl phosphine and a dialkyl azodicarboxylate in an anhydrous solvent such as tetrahydrofuran at 20–35° C. for 12–36 hours, suitable alkyl groups are ethyl, isopropyl etc. occurs readily and provides a preferred mild method for the in situ reaction (XXVI) to provide compounds Formula (XXV).

When W is sulfur compounds of Formula (III) can be conveniently prepared by a variety of methods familiar to those skilled in the art. One such route is illustrated in Scheme 13.

Scheme 13

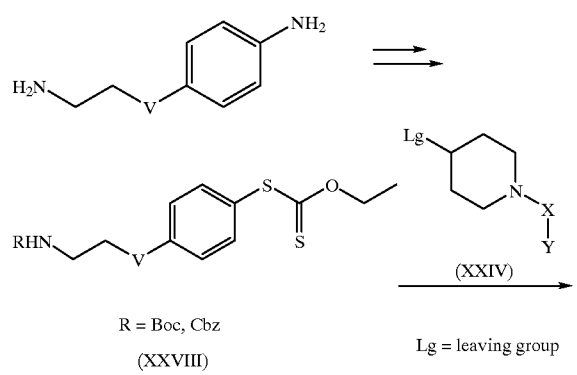

R = Boc, Cbz (XXVIII)      Lg = leaving group

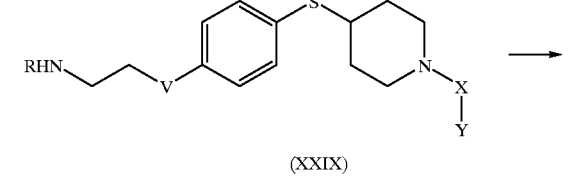

(XXIX)

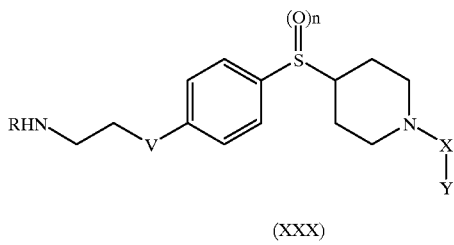

(XXX)

The aniline group of (XVII) wherein R=BOC is diazotized with sodium nitrite in cold hydrochloric acid and then coupled to potassium ethylxanthate (K. K. Jensen and V. H. Mikkelsen, *Arch. Pharm. Chemi.*, 1941, 48, 665). The xanthate (XXVIII) is then treated under standard reducing conditions with a alkali metal hydride such as sodium borohydride or lithium aluminum hydride (D. A. Jaeger and J. Wang, *J. Org. Chem.*, 1993, 58, 6745) and reacted with (XXIV) to provide (XXIX). The preparation of suitable intermediates (XXIV) has been described above. Oxidation of sulfur in (XXIX) provides access to compounds of the Formula (XXX) where a=1 or 2. Standard oxidation conditions for this transformation may be found in M. Hudlicky, Oxidation in Organic Chemistry, American Chemical Society, Washington, D.C., 1990. Most conveniently 3-chloroperoxybenzoic acid in an inert solvent such as dichloromethane when reacted with an equimolar amount of (XXIX) provides (XXX) wherein a=2 and with (XXIX) in a halfmolar amount provides (XXX) wherein a=1.

Scheme 14

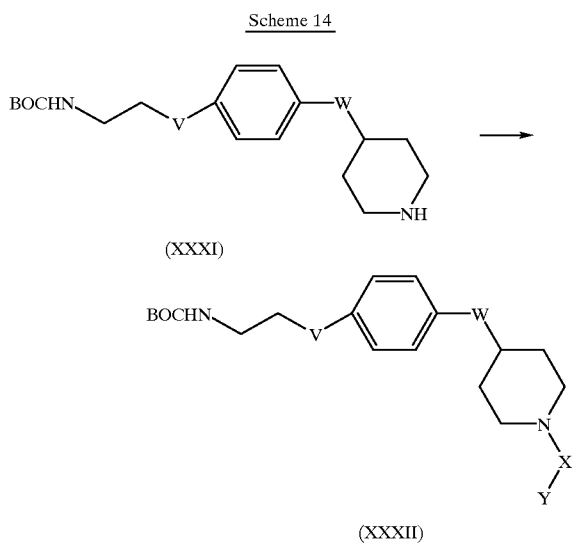

When X-Y in Formula (XXXII) (Scheme 14) represents a urea group compounds of this nature may be prepared under a variety of conditions. Many isocyanates are commercially available and can be conveniently reacted directly with (XXXI) in an inert solvent such as tetrahydrofuran to yield the desired ureas. Alternatively, amines can be reacted in the presence of triphosgene and a hindered organic base such as di-isopropylethylamine as described by P. Mayer and R. M. Randad, *J. Org. Chem.*, 1994, 59, 1937. Furthermore, acids can be reacted in a one-pot procedure with diphenylphosphoryl azide and compound (XXIV) to yield the desired ureas as described by K. Ninomiya et al *Tetrahedron*, 1974, 30, 2151.

When X-Y in Formula (XXXII) (Scheme 14) represents a sulfonamide group compounds of this general Formula can be prepared directly with sulfonyl halides, many of which are commercially available. Typical reaction conditions include treating compound (XXXI) with the sulfonyl halide in an anhydrous solvent such as dichloromethane or chloroform for 0.5 to 24 hours at temperatures of −20 to 50° C. to provide sulfonamides of Formula (XXXII). Sulfonyl halides can also be prepared by a number of methods familiar to those skilled in the art. One such method for aromatic and heteroaromatic compounds is the treatment of the aromatic or heteroaromatic compound directly with Vilsmier's reagent or chlorosulfonyl chloride.

When X-Y in Formula (XXXII) (Scheme 14) represents an amide bond compounds of this general Formula can be conveniently prepared by reaction of the corresponding acid suitably activated. Many such activating groups may be employed. Such methodology is described in M. Bodansky and A. Bodansky, The Practice of Peptide Synthesis, Springer-Verlag, 1984, 87–150. Many acids are commercially available and can be readily prepared by those skilled in the art. Two most convenient reagents are the water-soluble carbodiimide 1-[3-(dimethylamino)propyl]-3-ethylcarbodiimide hydrochloride typically in an inert solvent such as dichloromethane and the BOP-reagent: benzotriazol-1-yloxy-tris(dimethylamino)phosphonium hexafluorophophate typically in an aprotic solvent such as N,N-dimethylformamide with an tertiary organic base such as triethylamine.

When X-Y in Formula (XXXII) (Scheme 14) represents a carbamate group compounds of this general Formula can be conveniently prepared by a variety of conditions. A typical representative is illustrated by the reaction of a corresponding alcohol suitably activated. One convenient procedure is described by N. Choy Organic Preparations and Procedures International, 1996, 28, 173,. A cooled combined solution of an alcohol and 4-nitrochloroformate in a suitable anhydrous solvent such as tetrahydrofuran together with a hindered organic base such as triethylamine or an inorganic base such as potassium carbonate is prepared and subsequently treated with the amine (XXXI) to provide compounds wherein (XXXII) is a carbamate group. Many of the alcohols are commercially available or readily prepared by methods described in the literature and known to those skilled in the art.

Alternatively, suitably protected amines (XXI) can be prepared conveniently by following Scheme 15. Wherein the secondary amine is first reacted before reductive amination occurs. Ordinarily suitable protection step of the ketone group will need to be utilized. Commercially available 1,4-dioxa-8-azaspiro[4.5]decane provides a convenient intermediate.

Scheme 15

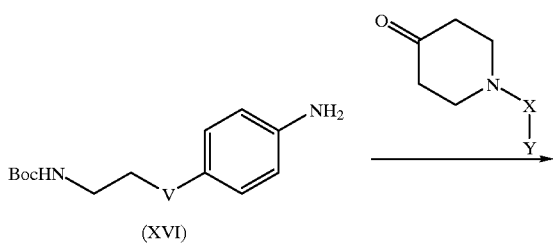

(XVI)

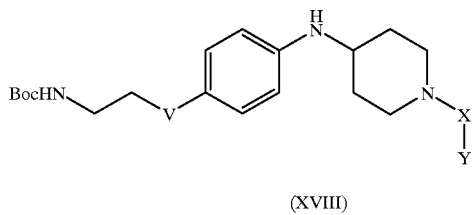

(XVIII)

Commercially available 1,4-dioxa-8-azaspiro[4.5]decane can be reacted to elaborate X-Y prior to removal of the cyclic ketal for which a variety of methods are available as described in Protective Groups in Organic Synthesis, $2^{nd}$ Ed., T. W. Greene and P. G. M. Wut, John Wiley and Sons, New York, 1991. One convenient procedure is the use of formic acid for 0–2 hours at 45–65° C. Reductive amination of the ketone with the aniline (XVI) or (XXII) as described above furnishes compounds of Formula (XVIII). Alternatively reductive amination with (XXIII) may be utilized. However, this methodology is particularly useful when the presence of the aniline nitrogen in compound of Formula (XX) could lead to unwanted side reactions. Representative examples are shown below.

When X in Formula (XXXII) represents a direct bond this methodology is a favored method of preparation. A variety of conditions can be utilized to provide such compounds. One such procedure which is provided as an example (Scheme 16) involves reaction of 1,4-dioxa-8-azaspiro[4.5] decane (XXXIII) with an aromatic or heteroaromatic halide in the presence of an acid scavenger such as potassium carbonate in an anhydrous aprotic solvent such as N,N-dimethylformamide. The reaction is typically performed at temperatures 90–120° C. for 12 to 48 hours.

Scheme 16

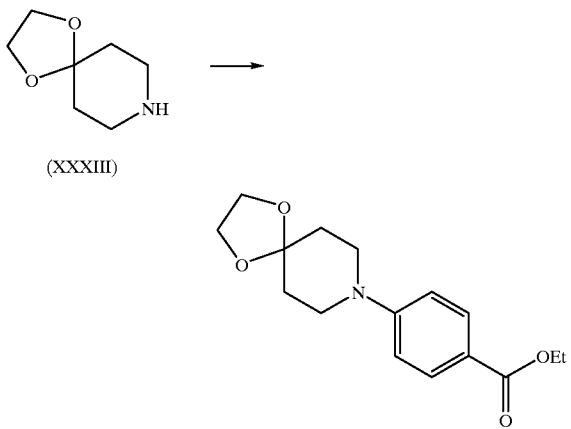

Further transformations may be carried out, such as hydrolysis of ester groups typically with an aqueous base such as aqueous lithium hydroxide in tetrahydrofuran or sodium hydroxide in aqueous methanol, the protecting ketal can be directly removed and reductive amination performed to furnish compounds of Formula (XXXII).

In another method aromatic groups may be introduced by construction of the aromatic group rather than halide displacement. This method is most suitable to heteroaromatic groups and one such example is given in Scheme 17.

Scheme 17

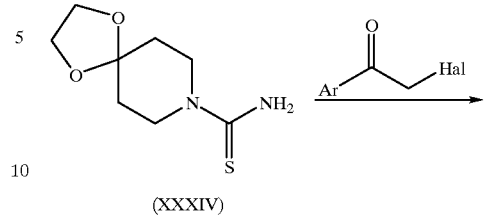

(XXXIV)

Thiourea (XXXV) was prepared using substantially the method described by M. A. Poss *Tet. Letts.*, 1992, 33, 5933,. Ring formation can be brought about with a a-halo ketone in an anhydrous aprotic solvent such as N.N-dimethylformamide at 50–90° C. for 0.5–24 hours. Further transformations may be carried out or the ketal can be directly removed and reductive amination performed with (XVI) to furnish compounds of Formula (XVIII).

Final deprotection of the elaborated protected amines can be conducted using a number of acidic conditions.

When the protecting group is the tert-butyl carbamate one such convenient acid is formic acid. On dissolving the protected tert-butylcarbamate-amines in formic acid with warming removal of the protecting group is smoothly performed.

Reaction with Epoxides

The correspondingly obtained formate salts may be either be utilized with the epoxides of Formula (II) or (IV) to furnish the amino alcohols by reaction in an alcoholic solvent with heat in the presence of a hindered organic base such triethylamine or N,N-diisopropylamine or may be treated with aqueous base to yield the amines free of salt. The desired amino alcohols can thus be obtained by reaction with epoxides (II) or (IV). In those cases where the amine or amine salt is reacted with iodide (XIII) then the procedure described by E. J. Corey and J. O. Link,*J. Org. Chem.*, 1991, 56, 422, , namely heated in an anhydrous solvent such as tetrahydrofuran, furnished the desired amino alcohols.

When the protecting group is the dimethyl acetal then a number of methods are described in Protective Groups in Organic Synthesis, $2^{nd}$ Ed., T. W. Greene and P. G. M. Wut, John Wiley and Sons, New York, 1991, for the removal of the dimethyl acetal to furnish compounds of Formula (VII). However, one such method was preferred. Thus essentially as described by G. A. Olah et. al., *J. Org. Chem.*, 1983, 48, 3667, protected acetals were treated with trichloromethylsilane and sodium iodide in acetonitrile to furnish compounds of Formula (VII).

Aldehydes of Formula (VII) can be conveniently reacted with amines of Formula (III) under reductive amination conditions. Such conditions and reagents are well known in the art. They are typically performed by mixing the amine and carbonyl compound in a solvent and adding a reducing agent. Solvents typically include lower alcohols, dichloromethane, DMF and the like. A wide variety of reducing agents can be utilized, most commonly utilized are sodium borohydride, sodium cyanoborohydride or sodium triacetoxyborohydride. The temperature of the reaction is typically room temperature to the reflux of the solvent.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was confirmed with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., , *Eur. J. Biochem.*, 196:357–361(1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and anti-sense primer 5'CTGGCGCCCAACGGCCAGTGGC-CAGTC3'; a NarI-AccI fragment, 5'TTGGCGCTGATGGC-CACTGGCCGTTTG3' as sense and 5'GCGCGTAGACGAAGAGCATCACGAG3' as anti-sense primer; an AccIi-StyI fragment, sense primer 5'CTCGT-GATGCTCTTCGTCTCACGCGC3' and anti-sense primer 5'GTGAAGGTGCCCATGATGAGACCCAAGG3' and a StyI-TAG fragment, with sense primer 5'CCCTGTGCAC-CTTGGGTCTCATCATGG3' and anti-sense primer 5'CCTCTGCCCCGGTTACCTACCC3'. The corresponding primer sequences are described in Mantzoros, C. S., et al., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$—AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were tested over a concentration range of $10^{-9}$ M to $10^{-5}$M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as percent of the maximal isoproterenol response at $10^{-5}$ M. Activity curves were plotted using the SAS statistical and graphics software. $EC_{50}$ values were generated for each compound and the maximal response (IA) developed for each compound iscompared to the maximal response of isoproternol at $10^{-5}$ M from the following formula:

$$IA = \frac{\% \text{ activity compound}}{\% \text{ activity isoproterenol}}$$

Table I shows the $\beta$3-adronergic receptor $EC_{50}$ and IA values for the representative compounds of this invention that were evaluated in this standard pharmacological test procedure. These results show that compounds of the present invention have activity at the $\beta$3-adrenergic receptor. The compounds of this inventon had weaker or no activity at $\beta$1 and/or $\beta$2-adrenergic receptor.

TABLE I

| Compound No. | $EC_{50}(\beta3, \mu M)$ | IA($\beta$3) |
|---|---|---|
| Example 1 | 0.032 | 0.95 |
| | 0.036 | 0.71 |
| | 0.05 | 0.91 |
| Example 2 | 0.08 | 1.12 |
| Example 5 | 0.29 | 0.68 |
| Example 6 | 0.106 | 1.21 |
| Example 8 | 0.064 | 0.82 |
| Example 9 | 0.047 | 0.85 |
| Example 10 | 0.043 | 0.85 |
| Example 11 | 0.09 | 1.05 |
| Example 12 | 0.05 | 0.9 |
| Example 13 | 0.066 | 0.82 |
| Example 14 | 0.036 | 0.96 |
| Example 15 | 0.034 | 0.91 |
| Example 16 | 0.542 | 1 |
| Example 17 | 0.015 | 0.63 |
| Example 18 | 0.03 | 1 |
| Example 20 | 0.25 | 0.91 |
| Example 21 | 0.03 | 1 |
| Example 23 | 0.01 | 0.88 |
| Example 24 | 0.04 | 0.84 |
| Example 25 | 0.064 | 0.87 |
| Example 26 | 0.037 | 0.91 |
| Example 27 | 0.06 | 0.86 |
| Example 28 | 0.01 | 0.76 |
| Example 29 | 0.043 | 1 |
| Example 30 | 0.034 | 1 |
| | 0.049 | 0.87 |
| | 0.022 | 0.84 |
| | 0.098 | 0.65 |
| Example 31 | 0.136 | 0.69 |
| | 0.068 | 0.4 |
| Example 32 | 0.032 | 1.04 |
| | 0.032 | 0.77 |
| Example 33 | 0.055 | 0.78 |
| Example 34 | 0.062 | 0.83 |
| Example 35 | 0.133 | 0.96 |
| Example 36 | 1.02 | 0.77 |
| Example 37 | 0.023 | 0.92 |
| Example 39 | 0.036 | 0.9 |
| Example 40 | 0.101 | 0.9 |
| Example 41 | 0.62 | 0.84 |
| Example 42 | 0.095 | 0.72 |
| Example 43 | 0.39 | 0.81 |
| Example 44 | 0.036 | 0.99 |
| Example 45 | 0.064 | 1.07 |
| Example 46 | 0.162 | 0.82 |
| Example 47 | 0.031 | 1 |
| Example 48 | 0.05 | 0.7 |
| Example 50 | 0.001 | 1 |
| Example 51 | 0.001 | 0.82 |
| Example 52 | 0.069 | 0.82 |
| Example 53 | 0.069 | 1.17 |
| | 0.008 | 1.5 |

TABLE I-continued

| Compound No. | EC$_{50}$(β3, μM) | IA(β3) |
| --- | --- | --- |
| Example 54 | 1.01 | 0.7 |
|  | 0.398 | 0.78 |
|  | 0.4 | 0.51 |
| Example 55 | 0.171 | 1.07 |
| Example 56 | 0.052 | 0.84 |
| Example 57 | 0.093 | 0.94 |
| Example 58 | 0.32 | 1.61 |
| Example 59 | 0.003 | 1 |
| Example 60 | 0.012 | 0.45 |
| Example 61 | 0.089 | 1.34 |
| Example 62 | 0.134 | 1.05 |
| Example 65 | 0.3 | 0.57 |
| Example 66 | 0.2 | 0.99 |
| Example 67 | 0.029 | 0.92 |
| Example 68 | 0.039 | 1.1 |
| Example 69 | 0.066 | 0.67 |
| Example 70 | 0.106 | 1 |
| Example 71 | 0.14 | 0.94 |
| Example 73 | 0.07 | 0.8 |
| Example 74 | 0.045 | 0.88 |
| Example 76 | 0.005 | 1 |
| Example 77 | 0.028 | 0.99 |
| Example 78 | 0.015 | 1 |
| Example 79 | 0.041 | 0.8 |
| Example 80 | 0.03 | 0.84 |
| Example 81 | 0.021 | 1 |
| Example 82 | 0.053 | 0.94 |
| Example 83 | 0.027 | 0.88 |
| Example 84 | 0.096 | 0.75 |
| Example 85 | 0.003 | 0.82 |
| Example 86 | 0.127 | 1.1 |
| Example 87 | 0.004 | 0.84 |
| Example 88 | 0.021 | 0.81 |
| Example 89 | 0.093 | 0.83 |
| Example 90 | 0.077 | 0.73 |
| Example 91 | 0.051 | 1 |
| Example 92 | 0.01 | 0.92 |
| Example 94 | 0.01 | 0.59 |
|  | 0.054 | 0.78 |
| Example 95 | 0.066 | 0.9 |
| Example 96 | 0.306 | 0.83 |
| Example 97 | 0.034 | 0.79 |
| Example 99 | 0.009 | 1.08 |
| Example 100 | 0.016 | 0.98 |
| Example 101 | 0.01 | 0.63 |
| Example 102 | 0.009 | 0.95 |
| Example 103 | 0.074 | 0.9 |
| Example 104 | 0.085 | 0.97 |
| Example 105 | 0.037 | 1 |
| Example 106 | 0.127 | 0.79 |
| Example 107 | 0.04 | 0.92 |
| Example 108 | 0.007 | 1.08 |
| Example 111 | 0.125 | 0.78 |
| Example 112 | 0.086 | 0.89 |
| Example 113 | 0.13 | 1 |
| Example 114 | 0.033 | 1.1 |
| Example 115 | 0.013 | 0.97 |
| Example 116 | 0.001 | 1.1 |
| Example 117 | 0.208 | 1.1 |
| Example 118 | 0.022 | 0.96 |
| Example 119 | 0.008 | 1.03 |
| Example 120 | 0.025 | 1.1 |
| Example 121 | 0.09 | 0.69 |
| Example 122 | 0.1 | 0.81 |

Based on the results obtained in these standard pharmacological test procedures, representative compounds of this invention have been shown to be selective β$_3$ adrenergic receptor agonists and are therefore useful in treating metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following general procedures were used in preparing representative compounds of this invention, and are referred to as applicable.

PROCEDURE A

A mixture of 1 molar equivalent of a hydroxyaryl compound, 1 molar equivalent of (S)-(+)-glycidyl 3-nitrobenzenesulfonate and 1.2 molar equivalent of potassium carbonate in approx. 0.25 molar 2-butanone was heated at reflux for 18 hours. The reaction mixture was cooled and partitioned between ethyl acetate and water. The organic phase was washed with brine and dried over anhydrous magnesium sulfate. The solvent was removed in vacuo and the residue purified by flash chromatography on silica gel Merck-60.

PROCEDURE B

An approx. 0.3 molar solution of a hydroxyaryl compound, R-(+)-glycidol and triphenylphosphine in anhydrous tetrahydrofuran was treated drop-wise with 1.1 molar equivalent of diethyl azodicarboxylate. After stirring the reaction mixture at ambient temperature overnight, the solvent was removed in vacuo and the residue purified by flash chromatography on silica gel Merck-60 eluting with the specified solvent.

PROCEDURE C

Triphosgene (0.37 molar equivalent) was dissolved in anhydrous dichloromethane. To this solution, was added drop-wise, a mixture of the amine (1 molar equivalent) and N,N-diisopropylethylamine (1.1 molar equivalents) in dichloromethane over 1 hour at ambient temperature. After the addition, a second mixture containing an amine (1 molar equivalent) and anhydrous N,N-diisopropylethylamine (1.1 equivalent) in anhydrous dichloromethane was added in one portion. In those cases where solubility needed to be increased then anhydrous tetrahydrofuran was substituted for anhydrous dichloromethane either in part or in total. The reaction was stirred at ambient temperature for 1 hour. The solvent was removed in vacuo and the residue dissolved in a suitable organic solvent and washed with aqueous sodium bicarbonate solution, brine and water. The organic layer was dried over anhydrous sodium (or magnesium) sulfate and evaporated to dryness in vacuo. The residue was purified by flash chromatography on silica gel Merck-60 eluting with the specified solvent.

PROCEDURE D

An acid (1 molar equivalent) and anhydrous N,N-diisopropylethylamine (1.1 molar equivalents) were combined anhydrous toluene (approx. 0.1 M solution). Diphenylphosphoryl azide (1.2 molar equivalents) was added and the reaction stirred at ambient temperature for 0.5 hour. The reaction was heated to 85° C. for 1 hour prior to the addition of the amine (1 molar equivalent). The heat was removed, and the reaction allowed to cool, dichloromethane was added and the organic phases washed with 1 N sodium hydroxide, 1 N hydrochloric acid, 1 N sodium hydroxide, water, brine, and dried with anhydrous sodium (or magnesium) sulfate. The solvent was removed in vacuo and the residue purified by flash chromatography on silica gel Merck-60 eluting with the specified solvent.

PROCEDURE E

A mixture of 1 molar equivalent each of the amine and substituted isocyanate was stirred at ambient temperature in dichloromethane or tetrahydrofuran for lhour. The reaction mixture was diluted with dichloromethane and washed with 1N hydrochloric acid, water, and brine. The organic layer was dried over anhydrous sodium (or magnesium) sulfate, filtered, and the solvent removed in vacuo. The product was purified by flash chromatography on silica gel Merck-60 eluting with the specified solvent.

PROCEDURE F

The tert-butylcarbamate protected amine was dissolved in formic acid (excess) and stirred at room temperature (heating to 60° C. for 5–10 minutes may also be employed). The formic acid was evaporated under reduced pressure co-evaporating in vacuo with a mixture of chloroform/ethanol achieve a 1:1 formate salt.

PROCEDURE G

The amine (either as the formate salt or as a free base) was dissolved in ethanol with anhydrous N,N-diisopropylethylamine (if the amine salt were employed theN 1.1–1.5 molar equivalents). The reaction mixture was heated at 60° C. overnight. The solvent was removed in vacuo and the residue purified by flash chromatography on silica gel Merck-60 eluting with the specified solvent.

PROCEDURE H

The diphenyl-tert-butylsilyl protected phenol was dissolved in anhydrous tetrahydofuran at ambient temperature and tert-butylammonium fluoride (generally 1 molar equivalent of a 1M tetrahydrofuran solution was sufficient) was added. The reaction was stirred at ambient temperature for 10–60 minutes. The solvent was removed in vacuo and the residue purified by flash chromatography on silica gel Merck-60 eluting with the specified solvent.

PROCEDURE K

A solution of the secondary amine was prepared by dissolving the amine (1 molar equivalents) in acetic acid. Succinic anhydride (1 molar equivalent) was added. The suspension was stirred overnight at ambient temperature. The acetic acid was removed in vacuo and the resulting oil was taken up in ethyl acetate and washed with 0.1N hydrochloric acid and water. The organic layer was dried over anhydrous sodium sulfate, filtered, and evaporated in vacuo to give the title acid. An analytical sample was obtained by crystallization from ethyl acetate.

PROCEDURE L

To a solution of a molar equivalent of the alcohol and 2.1 molar equivalents of carbon tetrabromide in a mixture of dichloromethane and tetrahydrofuran (3 to 1 ratio) at 5° C. was added 2.1 molar equivalents of triphenylphosphine, portion-wise. After addition, the ice/water bath was removed and the reaction was stirred overnight at ambient temperature. Diethyl ether was added and the reaction mixture filtered. The filtrate was concentrated in vacuo and the residue was purified by flash chromatography on silica gel Merck-60 eluting with the specified solvent.

PROCEDURE M

To a solution of a molar equivalent of S-(4-{2-[(tert-butoxycarbonyl)amino]-ethyl}phenyl) O-ethyl carbonodithioate in degassed dry ethanol was added 2.5 molar equivalents of sodium borohydride. This was warmed to 45° C. for 1 hour. The reaction was cooled to room temperature and 1 molar equivalent of the bromide added, the reaction mixture was warmed to 50° C. and stirred for 3 hours. The cooled treated with dilute hydrochloric acid and the pH adjusted to 7.5. The mixture was concentrated in vacuo, taken up into dichloromethane, dried, filtered, and evaporated in vacuo. The residue was purified by flash chromatography on silica gel Merck-60 (elutant: 1:2 ethyl acetate-hexane).

PROCEDURE N

The tert-butylcarbamate protected amine was dissolved in dichloromethane/trifluoroacetic acid/methanol (100/25/1 v/v ratio) and stirred for 4 hours at ambient temperature. The volatile components were evaporated in vacua and the residue taken up into dichloromethane and washed with aqueous sodium bicarbonate. The organic phase was dried, filtered and evaporated in vacuo to provide the deprotected amine.

PROCEDURE O

To a solution of a molar equivalent of the sulfide (tert-butyl carbamate protected amine) in dichloromethane at 0° C. was added 2.2 molar equivalents of 3-chloroperoxybenzoic acid in dichloromethane. After 1 hour, the ice/water bath was removed and the reaction was stirred 1 hour more. Additional dichloromethane was added and the reaction mixture was washed with dilute aqueous sodium dithionite followed by aqueous sodium bicarbonate. The organic phase was dried, filtered and evaporated in vacua. The residue was purified by filtration through silica gel Merck-60 eluting with dichloromethane-diethyl ether (1/1)

The following describes the preparation of intermediates useful in the preparation of the compounds of this invention.

EXAMPLE A

Methyl 2-hydroxy-5-[(2S)(oxiranyl) methoxynbenzoate

A stirred suspension of methyl 2,5-dihydroxy benzoate (16.81 g, 100 mmol), (2S)oxiranylmethyl 3-nitrobenzenesulfonate (25.9 g, 100 mmol), and potassium carbonate (13.82 g, 100 mmol) in 2-propanone (300 mL) was refluxed under nitrogen for 12 hours. The reaction mixture was filtered, and the filtrate evaporated in vacuo to a residue. The residue was dissolved in ethyl acetate and washed sequentially with 1 N hydrochloric acid and water. The organic phase was dried over anhydrous sodium sulfate, filtered, and the filtrate evaporated in vacuo to a crude product. The crude product was purified by flash column chromatography on silica gel Merck-60 (eluant: 3:1 hexane-ethyl acetate) to yield the title compound (6.5 g, 29 mmol).

$^1$H NMR (DMSO-$d_6$, 300 MHz) δ 10.13 (s,1H), 7.27 (d, J=3.2 Hz,1H), 7.21 (dd, J=8.9, 3.2 Hz,1H), 6.94 (d, J=8.9 Hz, 1H), 4.31 (dd, J=11.3, 2.4 Hz, 1H), 3.90 (s, 3H), 3.78 (dd, J=11.3, 6.5 Hz, 1H), 3.31 (dddd, J=6.5, 4.2, 2.7, 2.4 Hz, 1H), 2.84 (dd, J=5.1, 4.2 Hz, 1H), 2.72 (dd, J=5.1, 2.7 Hz, 1H).

(2S)-2-[(4-Benzyloxyphenoxy)methyl]oxirane

4-Benzyloxyphenol (15.00 g, 74.91 mmol) in anhydrous N,N-dimethylformamide (50 mL) was added to a solution of sodium hydride (60% dispersion in oil) (2.88 g, 74.9 mmol) in N,N-dimethylformamide (50 mL). The solution was stirred for 30 minutes and (S)-(+)-glycidyl 4-methylbenzenesulfonate (17.12, 75.0 mmol) was added. The mixture was heated to 80° C. for 2 hours. The solvent was removed and the residue partitioned between diethyl ether and water. The organic phase was washed with brine and dried over anhydrous magnesium sulfate. The solution was filtered and the solvent evaporated to dryness in vacuo. To yield the title compound as a white solid (13.6 g, 53.3 mmol).

MS (EI, m/z): 256 [M]$^+$

EXAMPLE B tert-Butyl-(4-oxiranylmethoxy-phenoxy)-diphenyl-silane

Step A. (4-Benzyloxy-phenoxy)-tert-butyl-diphenyl-silane

To a solution of imidazole (12.97 g, 190 mmol) and 4-benzyloxy phenol (34.7 g, 173 mmol) in anhydrous dichloromethane (500 mL) was added drop-wise a solution of tert-butyldiphenylchlorosilane (50.0 g, 181 mmol) in dichloromethane (100 mL). The solution was stirred overnight at ambient temperature. The mixture was poured into water (500 mL) and the organic layer washed with saturated sodium hydrogen carbonate, water, brine and dried over anhydrous magnesium sulfate. The solution was filtered and the solvent evaporated to dryness. The solid was crystallized from diethyl ether to provide the title compound (68.9 g, 142 mmol).

Mp: 97–98° C.
MS (EI, m/z): 438 [M]$^+$
Anal. calcd. for $C_{29}H_{30}O_2Si$: C 79.41 H 6.89 found: C 79.34 H 6.95

Step B. (4-tert-Butyl-diphenyl-silyloxy)-phenol (4-Benzyloxy-phenoxy)-tert-butyl-diphenyl-silane (32.5 g, 67 mmol) was dissolved in ethanol. 10% Palladium on carbon (3.0 g) was added followed by cyclohexene (100 mL). The mixture was heated at reflux for 16 hours. The reaction was cooled to room temperature and filtered through Celite. The solvent was removed in vacuo to yield the title compound (22.0 g, 63 mmol).

MS (EI, m/z): 348 [M]$^+$

Step C. tert-Butyl-(4-oxiranylmethoxy-phenoxy)-diphenyl-silane (4-tert-Butyl-diphenyl-silyloxy)-phenol (7.0 g, 20.0 mmol) was reacted according to Procedure B (eluant: 2:1 hexane-diethyl ether) to give the title compound (4.5 g, 11.1 mmol).

Mp: 97–99° C.
MS (EI, m/z): 404 [M]$^+$
Anal. calcd. for $C_{25}H_{28}O_3Si$: C 74.22 H 6.98 N 0 found: C 74.24 H 6.93 N 0

EXAMPLE C 2-(Benzyloxy)-5-(2-oxiranyl)benzamide

Step A. 2-(Benzyloxy)-5-(2-bromoacetyl)benzamide

5-Acetyl-2-(phenylmethoxy)benzamide (10.0 g, 37.1 mmol) was dissolved in chloroform and brought to reflux. Bromine (1.98 g, 12.4 mmol) was added. The solution was allowed to cool to room temperature. After 10 minutes the bromine color had disappeared and a second portion of bromine was added. A third portion of bromine was added after the color had again discharged and the solution refluxed for a further 10 minutes. The flask was allowed to cool and placed in the freezer overnight. The solvent was removed in vacuo and the residue crystallized from ethanol to provide the title compound (11.3 g, 32.4 mmol).

Step B. 2-(Benzyloxy)-5-(2-bromo-1-hydroxyethyl)benzamide 2-(Benzyloxy)-5-(2-bromoacetyl)benzamide (11.3 g, 32.30 mmol) was dissolved in anhydrous tetrahydrofuran (250 mL) and cooled in an ice bath. The solution was diluted with ethanol (250 mL). Sodium borohydride (1.2 g, 32.3 mmol) was added in three portions. Following addition the solvent was removed in vacuo and the residue partitioned between water and ethyl acetate. The organic layer was washed with water, brine, and dried over anhydrous magnesium sulfate. The solution was filtered and the solvent evaporated to dryness in vacuo to yield crude title compound (1 0.88 g, 31.06 mmol).

Step C. 2-(Benzyloxy)-5-(2-oxiranyl)benzamide 2-(Benzyloxy)-5-(2-bromo-1-hydroxyethyl)benzamide (10.88 g, 31.0 mmol) was reacted according to Procedure A. The residue was purified by flash chromatography on silica gel Merck-60 to yield the title compound (6.22 g, 23.04 mmol).

EXAMPLE D

N-Ethyl-N-{4-[(2S)oxiranylmethoxy]phenyl}urea

Step A. N-[4-(Benzyloxy)phenyl]-N'-ethylurea 4-(Phenylmethoxy)-benzenamine (5.1 g, 25.5 mmol) was dissolved in anhydrous tetrahydrofuran and ethyl isocyanate (2.00 g, 28.1 mmol) added. The solution was heated to reflux. After 24 hours ethyl isocyanate (2.00 g, 28.1 mmol) was again added to the reaction mixture and refluxing continued for a further 24 hours. The reaction mixture was taken to dryness in vacuo and the residue purified by flash chromatography on silica gel Merck-60 (eluant: 3:1 hexane-ethyl acetate) to yield the title compound (6.3 g, 23.30 mmol).

$^1$H NMR (DMSO-$d_6$, 300 MHz): d 1.08 (t, 3H), 3.14 (q, 2H), 5.10 (s, 2H), 5.93 (t, 1H), 6.92 (d, 2H), 7.24 (d, 2H), 7.4 (m, 5H), 8.20 (s, 1H)

Step B. N-Ethyl-N-(4-hydroxyphenyl)urea

N-[4-(Benzyloxy)phenyl]-N'-ethylurea (6.3 g, 23.30 mmol) was dissolved in ethanol (150 mL). 10% Palladium on carbon (0.6 g) was added and the mixture shaken overnight under 50 psi hydrogen on a Parr apparatus. The solution was filtered through a Celite pad, the residue washed with ethanol and the solvent removed in vacuo to yield the title compound (3.84 g, 21.2 mmol).

$^1$H NMR (DMSO-$d_6$, 300 MHz): d 1.06 (t, 3H), 3.14 (q, 2H), 5.93 (t, 1H), 6.68 (d, 2H), 7.19 (d, 2H), 8.06 (s, 1H), 8.99 (s, 1H)

Step C. N-Ethyl-N'-{4-[(2S)oxiranylmethoxy]phenyl}urea

N-Ethyl-N'-(4-hydroxyphenyl)urea (0.5 g, 2.77 mmol) was reacted according to Procedure A. The residue was purified by flash chromatography on silica gel Merck-60 (eluant: 2:1 hexane-ethyl acetate) to yield the title compound (0.34 g, 1.4 mmol).

EXAMPLE E

N-{4-[(2S)-Oxiranylmethoxy]phenyl}methanesulfonamide

Step A. N-[4-(Benzyloxy)phenyl]methanesulfonamide 4-(Phenyl-methoxy)-benzenamine (5.0 g, 25.0 mmol) was dissolved in anhydrous dichloromethane (100 mL).

Methane sulfonyl chloride (3.16 g, 27.1 mmol) and anhydrous N,N-diisopropylethylamine (4.8 mL) were added and the solution stirred overnight at ambient temperature. The solvent was removed in vacuo and the residue purified by flash chromatography on silica gel Merck-60 (eluant: 3:1 hexane-ethyl acetate) to yield the title compound (6.3 g, 22.7 mmol).

$^1$H NMR (DMSO-$d_6$, 300 MHz): d 2.89 (s, 3H), 5.11 (s, 2H), 7.05 (d, 2H), 7.19 (d, 2H), 7.4 (m, 5H), 9.41 (s,1H)

Step B. N-(4-Hydroxyphenyl)methanesulfonamide

N-[4-(Benzyloxy)phenyl]methanesulfonamide (3.0 g, 10.8 mmol) was dissolved in ethanol (150 mL). 10% Palladium on carbon (0.3 g) was added and the mixture shaken overnight under 50 psi hydrogen on a Parr apparatus. The solution was filtered through a Celite pad and the solvent removed to yield the title compound (1.32 g, 7.4 mmol).

$^1$H NMR (DMSO-$d_6$, 300 MHz): d 2.84 (s, 3H), 6.76 (d, 2H), 7.05 (d, 2H), 9.20 (s, 1H), 9.41 (s, 1H)

Step C. N-{4-[(2S)-Oxiranylmethoxy]phenyl}methanesulfonamide

N-(4-Hydroxyphenyl)methanesulfonamide (0.30 g, 1.62 mmol) was reacted according to Procedure B. The residue was purified by flash chromatography on silica gel Merck-60 (eluant: 2:1 hexane-ethyl acetate) to give the title compound as a solid (0.22 g, 0.90 mmol).

$^1$H NMR (DMSO-$d_6$, 300 MHz): d 2.44 (m, 1H), 2.71 (m, 1H), 3.00 (s, 3H), 3.08 (m, 1H), 3.62 (m,1H), 3.78 (m,1H), 6.79 (d, 2H), 7.21 (d, 2H), 9.71 (s, 1H)

EXAMPLE F tert-Butyl 2-{[tert-butyl(diphenyl)silyl]oxy}-5-[(2S)-oxiranylmethoxy]phenyl(methylsulfonyl)carbamate Step A. (4-tert-Butyl-diphenyl-silyloxy)-3-nitro-acetophenone To a solution of imidazole (9.0 g, 132 mmol) and 4-hydroxy-3-nitro-acetophenone (22.83 g, 126 mmol) in dichloromethane (500 mL) was added drop-wise a solution of tert-butyldiphenylchlorosilane (36.37 g, 132 mmol) in anhydrous dichloromethane (100 mL). The solution was stirred overnight at ambient temperature. The mixture was poured into water (500 mL) and the organic layer separated and washed with saturated sodium hydrogen carbonate, water, brine and dried over anhydrous magnesium sulfate. The solution was filtered and the solvent evaporated to dryness in vacuo to give the title compound as a solid (51.63 g, 123 mmol).

$^1$H NMR (DMSO-$d_6$, 300 MHz): d 1.10 (s, 9H), 2.48 (s, 3H), 6.64 (d, 1H), 7.55 (m, 6H), 7.76 (m, 4H), 7.93 (dd, 1H), 8.46 (d, 1H)

Step B. Acetic Acid 3-nitro-4-(tert-butyl-diphenyl-silanyloxy)-phenyl Ester (4-tert-Butyl-diphenyl-silyloxy)-3-nitro-acetophenone (51.63 g, 123 mmol) was dissolved in chloroform (300 mL). 3-Chloroperoxybenzoic acid (31.85 g, 184 mmol) was added and the solution heated to reflux for 48 hours. The solution was diluted with dichloromethane, washed with saturated sodium hydrogen sulfate, saturated sodium hydrogen carbonate, brine and dried over anhydrous magnesium sulfate. The solution was filtered and the solvent evaporated to dryness in vacuo to yield crude title compound (45.29 g, 104 mmol).

$^1$H NMR (DMSO-$d_6$, 300 MHz): d 1.10 (s, 9H), 2.25 (s, 3H), 6.58 (d, 1H), 7.19 (dd, 1H), 7.41 (m, 1H), 7.52 (m, 6H), 7.73 (m, 4H)

Step C. Acetic Acid 3-amino-4-(tert-butyl-diphenyl-silanyloxy)-phenyl Ester

Acetic acid 3-nitro-4-(tert-butyl-diphenyl-silanyloxy)-phenyl ester (5.0 g, 11.86 mmol) was dissolved in anhydrous tetrahydrofuran (100 mL). Excess Raney Ni was added and the mixture placed under an atmospheric of hydrogen overnight. The mixture was filtered through a Celite pad and the solvent removed to give the title compound as a solid (3.5 g, 8.6 mmol).

$^1$H NMR (DMSO-$d_6$, 300 MHz): d 1.08 (s, 9H), 2.20 (s, 3H), 4.97 (s, 2H), 5.92 (dd, 1H), 6.51 (d, 1H), 7.44 (m, 6H), 7.73 (m, 4H)

Step D. 4-{[tert-Butyl(diphenyl)silyl]oxy}-3-[(methylsulfonyl)amino]phenyl Acetate Acetic acid 3-amino-4-(tert-butyl-diphenyl-silanyloxy)-phenyl ester (3.5 g, 8.6 mmol) was dissolved in anhydrous dichloromethane (150 mL) and anhydrous N,N-diisoproplyamine (1.5 mL) added. The solution was cooled to −78° C. and methane sulfonyl chloride (1.08 g, 9.05 mmol) added. The solution was stirred for 30 minutes and allowed to come to room temperature. The solution was stirred overnight. The reaction mixture was washed with water. The organic solvent was dried over anhydrous magnesium sulfate. The solution was filtered and the solvent evaporated to dryness in vacuo to yield the title compound as a solid (2.8 g, 5.7 mmol).

$^1$H NMR (DMSO-$d_6$, 300 MHz): d 1.08 (s, 9H), 2.22 (s, 3H), 3.13 (s, 3H), 6.31 (d, 1H), 6.62 (dd, 1H), 7.18 (d, 1H), 7.44 (m, 6H), 7.76 (m, 4H), 8.92 (s, 2H),

Step E. 3-[(tert-Butoxycarbonyl)(methylsulfonyl)amino]-4-{[tert-butyl(diphenyl)-silyl]oxy}phenyl acetate 4-{[tert-Butyl(diphenyl)silyl]oxy}-3-[(methylsulfonyl)amino]phenyl acetate (2.8 g, 5.7 mmol) was dissolved in anhydrous dichloromethane (100 mL) and 4-(dimethylamino)pyridine (0.069 g, 5.7 mmol) added. Di-tert-butyl dicarbonate (1.39 g, 6.37 mmol) in anhydrous dichloromethane was added drop-wise over 1 hour. The solution was stirred overnight at ambient temperature. The solvent was washed with water, 1 N hydrochloric acid, and dried over anhydrous magnesium sulfate. The solution was filtered and the solvent evaporated to dryness in vacuo to give the title compound (3.20 g, 5.48 mmol).

Step F. tert-Butyl 2-{[tert-butyl(diphenyl)silyl]oxy}-5-hydroxyphenyl (methylsulfonyl)carbamate 3-[(tert-Butoxycarbonyl)(methylsulfonyl)amino]-4-{[tert-butyl(diphenyl)-silyl]oxy}phenyl acetate was dissolved in methanol (25 mL), 1 N sodium hydroxide (5.5 mL) was added and the solution stirred for 30 minutes at ambient temperature. 1N hydrochloric acid (5.5 mL) was added, the solvent removed in vacuo and the residue partitioned between dichloromethane and water. The aqueous phase was washed with dichloromethane. The combined organic extracts were dried over anhydrous magnesium sulfate. The solution was filtered and the solvent evaporated to dryness in vacuo to give the title compound (2.34 g, 4.31 mmol).

$^1$H NMR (DMSO-$d_6$, 300 MHz): d 0.94 (s, 9H), 1.41 (s, 9H), 3.49 (s, 3H), 6.06 (d, 1H), 6.37 (dd, 1H), 6.75 (d, 1H), 7.40 (m, 6H), 7.71 (m, 4H), 9.10 (s, 2H),

Step G. tert-Butyl 2-{[tert-butyl(diphenyl)silyl]oxy}-5-[(2S)-oxiranylmethoxy]phenyl(methylsulfonyl)carbamate tert-Butyl 2-{[tert-butyl(diphenyl)silyl]oxy}-5-hydroxyphenyl(methyl-sulfonyl)carbamate (2.34 g, 4.31 mmol) was reacted according to Procedure B. The residue was purified by passage through a silica gel pad (eluant: 2:1 hexane-diethyl ether). The solvent was removed in vacuo to yield the title compound as a solid (1.8 g, 3.0 mmol).

EXAMPLE G (2S)-2-[(4-Fluorophenoxy)methyl]oxirane

4-Fluoro-phenol (2.9 g, 26.0 mmol) was reacted according to Procedure A. The residue was purified by flash chromatography on silica gel Merck-60 (eluant: 2:1 hexane-diethyl ether) to yield the title compound (2.92 g, 17.34 mmol).

MS (EI, m/z): 168 [M]$^+$

EXAMPLE H (2S)-2-[(2-Allylphenoxy)methyl]oxirane

2-Allyphenol (2.03 g, 15.13 mmol) was reacted according to Procedure A. The title compound was used without further purification.

EXAMPLE I

N-{3-[(2S)Oxiranylmethoxy]phenyl}acetamide

N-(3-Hydroxyphenyl)acetamide (3.03 g, 20.0 mmol) was reacted according to Procedure A. The residue was purified by flash chromatography on silica gel Merck-60 (eluant: 50:1 chloroform-methanol to yield the title compound (2.92 g, 14 mmol).

EXAMPLE J tert-Butyl methylsulfonyl{3-[(2S)oxiranylmethoxy]phenyl}carbamate

Step A. N-[3-(Benzyloxy)phenyl]methanesulfonamide 3-(Benzyloxy)aniline (9.9 g, 49.7 mmol) was dissolved in anhydrous dichloromethane (200 mL) and cooled to 0° C. Methane sulfonyl chloride (5.41 g, 47.2 mmol) and triethylamine (9 mL) were added. The reaction was stirred for 2 hours at ambient temperature. The mixture was diluted with dichloromethane, washed with 1N hydrochloric acid and brine. The solvent was dried over anhydrous magnesium sulfate, the solution filtered and the solvent evaporated to dryness in vacuo. The residue was crystallized from a mixture of diethyl ether and hexane to yield the title compound (8.3 g, 30.0 mmol).

$^1$H NMR (DMSO-d$_6$, 300 MHz): d 2.89 (s, 3H), 5.11 (s, 2H), 7.05 (d, 2H), 7.19 (d, 2H), 7.4 (m, 5H), 9.41 (s, 1H)

Step B. tert-Butyl 3-(benzyloxy)phenyl(methylsulfonyl)carbamate

N-[3-(Benzyloxy)phenyl]methanesulfonamide (1.74 g, 9.3 mmol) was dissolved in anhydrous dichloromethane (25 mL) and di-tert-butyl dicarbonate (2.23 g, 10.2 mmol) and 4-(dimethylamino)pyridine were added and the reaction stirred overnight at ambient temperature. The solution was washed with 1 N hydrochloric acid, brine and dried over anhydrous magnesium sulfate. The solution was filtered and the solvent evaporated to dryness in vacuo to yield the title compound (2.6 g, 6.88 mmol).

Step C. tert-Butyl-3-hydroxyphenyl (methylsulfonyl)carbamate tert-Butyl 3-(benzyloxy)phenyl(methylsulfonyl)carbamate (2.6 g, 6.88 mmol) was dissolved in ethanol (25 mL), 10% palladium on carbon (0.75 g) and cyclohexene (1.5 mL) were added. The solution was heated to reflux for 3 hours. The solution was cooled and filtered through Celite. The solvent was removed in vacuo to yield crude title compound (1.93 g, 6.7 mmol).

Step D. tert-Butyl methylsulfonyl{3-[(2S)oxiranylmethoxy]phenyl}carbamate tert-Butyl-3-hydroxyphenyl (methylsulfonyl)carbamate (1.93 g, 6.7 mmol) was reacted according to Procedure A. The title compound was obtained as a yellow oil. (1.24 g, 3.5 mmol) and used without further purification.

EXAMPLE K tert-Butyl{2-fluoro-4-[(2S)oxiranylmethoxy]phenoxy}diphenylsilane

Step A. 2-Fluorophenyl Acetate

2-Fluorophenol (99.4 g, 886.7 mmol) was stirred in thionyl chloride (71.2 mL) and acetic acid (51 mL) added. After the initial reaction had subsided the mixture was heated to reflux for 4 hours. The solution was then heated at 150° C. overnight. The resulting dark solution was distilled under reduced pressure at an oil bath temperature of 190° C. to give the title compound as a pale yellow oil (120.9 g, 784.4 mmol).

MS (EI, m/z): 154 [M]$^+$

Step B. 1-(3-Fluoro-4-hydroxyphenyl)-1-ethanone

2-Fluorophenyl acetate (91.0 g, 590.4 mmol) was added to a solution of anhydrous aluminum chloride (98.3 g, 737.2 mmol) in carbon disulfide (150 mL). The reaction was heated to reflux for 48 hours. The excess solvent was removed by heating at 80° C. for 3 hours followed by 2 hours heating at 140° C. The dark reaction was sonicated under ice/hydrochloric acid. The solid was removed by filtration, dissolved in diethyl ether and filtered. Removal of the solvent gave a solid which was recrystallized twice from toluene to give the title compound (51.0 g, 330.9 mmol).

Step C. 1-(4-{[tert-Butyl(diphenyl)silyl]oxy}-3-fluorophenyl)-1-ethanone

To a solution of imidazole (7.29 g, 107.0 mmol) and 1-(3-fluoro-4-hydroxyphenyl)-1-ethanone (15.0 g, 97.3 mmol) in anhydrous dichloromethane (500 mL) was added drop-wise a solution of tert-butyldiphenylchlorosilane (28.09 g, 102.0 mmol) in anhydrous dichloromethane (100 mL). The solution was stirred overnight at room temperature. The mixture was poured into water (500 mL) and the organic layer separated and washed with saturated sodium hydrogen carbonate, water, brine and dried over anhydrous magnesium sulfate. The solution was filtered and the solvent evaporated to dryness in vacuo to give the title compound which was used without further purification (37.9 g, 96.55 mmol).

MS ((+)APCI, m/z): 393 [M+H]$^+$

Step D. 4-{[tert-Butyl(diphenyl)silyl]oxy}-3-fluorophenyl Acetate 1-(4-{[tert-Butyl(diphenyl)silyl]oxy}-3-fluorophenyl)-1-ethanone (8.27 g, 21.07 mmol) was dissolved in chloroform (300 mL). 3-Chloroperoxybenzoic acid (4.0 g, 23.18 mmol) was added and the solution heated to reflux for 72 hours. The solution was diluted with dichloromethane, washed with saturated sodium hydrogen sulfate, saturated sodium hydrogen carbonate, brine and dried over anhydrous magnesium sulfate. The solution was filtered and the solvent evaporated to dryness in vacuo to yield the title compound which was used without further purification (5.28 g, 12.92 mmol).

MS ((+)APCI, m/z): 426 [M+NH$_4$]$^+$

Step E. 4-{[tert-Butyl(diphenyl)silyl]oxy}-3-fluorophenol

4-{[tert-Butyl(diphenyl)silyl]oxy}-3-fluorophenyl acetate (5.28 g, 12.92 mmol) was dissolved in methanol (100 mL). 1 N Sodium hydroxide (15.5 mL) was added. The solution was stirred for 30 minutes at ambient temperature. 1N Hydrochloric acid (16 mL) was added. The solvent was removed in vacuo and the solid partitioned between dichloromethane and water. The aqueous phase was washed with dichloromethane. The organic layers were combined and the solvent dried over anhydrous magnesium sulfate. The solution was filtered and the solvent evaporated to dryness in vacuo to yield crude title compound (4.5 g, 12.28 mmol).

MS ((−)ESI, m/z): 365 [M−H]$^-$

Step F. tert-Butyl{2-fluoro-4-[(2S)oxiranylmethoxy]phenoxy}diphenylsilane

4-{[tert-Butyl(diphenyl)silyl]oxy}-3-fluorophenol (4.5 g, 12.28 mmol) was reacted according to Procedure B. The residue was purified by passage through a silica gel pad (eluant: 2:1 hexane-diethyl ether) to yield the title compound (2.64 g, 6.25 mmol).

EXAMPLE L

5-{[tert-Butyl(dimethyl)silyl]oxy}-3,4-dihydro-1(2H)-naphthalenone O-(2S)oxiranylmethyl]oxime Step A. 5-{[tert-Butyl(dimethyl)silyl]oxy}-3,4-dihydro-1(2H)-naphthalenone To a solution of imidazole (3.77 g, 55.0 mmol) and 5-hydroxy-3,4-dihydro-1(2H)-naphthalenone (7.8 g, 48.1 mmol) in anhydrous N,N-dimethylformamide (50 mL) was added t-butyldimethylchlorosilane (7.97 g, 5.5 mmol). The solution was stirred overnight at ambient temperature. The solvent was removed and the residue partitioned between dichloromethane and water. The organic layer washed with saturated sodium hydrogen carbonate, water, brine and dried over anhydrous magnesium sulfate. The solution was filtered and the solvent evaporated to dryness in vacuo. The solid was crystallized from hexane-diethyl ether to yield the title compound (6.38 g, 23.08 mmol).

MS (EI, m/z): 276 [M]$^+$

Step B. 5-{[tert-Butyl(dimethyl)silyl]oxy}-3,4-dihydro-1(2H)-naphthalenone oxime 5-{[tert-Butyl(dimethyl)silyl]oxy}-3,4-dihydro-1(2H)-naphthalenone (3.0 g, 10.9 mmol) was dissolved in ethanol (50 mL). To this solution was added a solution of hydroxylamine hydrochloride (0.754 g, 10.9 mmol) and sodium acetate (0.836, 10.9 mmol) in water. The reaction was heated at 85° C. for 1 hour. The solution was cooled. The solid was removed by filtration and dried to furnish the title compound (2.75 g, 9.44 mmol).

MS (EI, m/z): 292 [M]$^+$

Step C. 5-{[tert-Butyl(dimethyl)silyl]oxy}-3,4-dihydro-1(2H)-naphthalenone O-(2S)oxiranylmethvyloxime A mixture of 5-{[tert-butyl(dimethyl)silyl]oxy}-3,4-dihydro-1 (2H)-naph-thalenone oxime (0.483 g, 1.66 mmol) was reacted according to Procedure A. The residue was purified by flash chromatography on silica gel Merck-60 (eluant: 2:1 hexane-diethyl ether) to yield the title compound as a solid (0.21, g, 0.60 mmol).

MS ((+)ESI, m/z): 348 [M+H]$^+$

EXAMPLE M

4-[(2S)Oxiranylmethoxy]-1,3-dihydro-2H-benzimidazol-2-one

Step A. 2-Nitro-6-[(2S)oxiranylmethoxy]aniline

2-Amino-3-nitrophenol (12.0 g, 77.8 mmol) was reacted according to Procedure A. The residue was purified by flash chromatography on silica gel Merck-60 (eluant: 2:1 hexane-diethyl ether) to yield the title compound (4.30 g, 20.46 mmol).

Step B. 4-[(2S)Oxiranylmethoxy]-1,3-dihydro-2H-benzimidazol-2-one

2-Nitro-6-[(2S)oxiranylmethoxy]aniline (0.20 g, 0.96 mmol) was dissolved in anhydrous tetrahydrofuran (10 mL). Excess Raney Ni was added and the mixture hydrogenated under an atmosphere of hydrogen overnight. The mixture was filtered through a Celite pad. To the anhydrous tetrahydrofuran solution was added with cooling anhydrous N,N-diisopropylethylamine (0.365 mL) followed by phosgene in toluene (0.525 mL). The solvent was partially removed and the title compound collected by filtration (0.10 g, 0.49 mmol).

MS ((+)ESI, m/z): 207 [M+H]$^+$

EXAMPLE O 8-(Benzyloxy)-5-[(2S)oxiranylmethoxy]-3,4-dihydro-2(1H)-quinolinone Step A. 5,8-Dihydroxy-3,4-dihydro-2(1H)-quinolinone 5,8-Dimethoxy-3,4-dihydro-2(1)-quinolinone (prepared as described in Chem. Pharm. Bull., 1981, 129, 2161) (1.5 g, 7.24 mmol) was heated at 120° C. in 40% hyrobromic acid (15 mL) for 4 hours. The reaction mixture was cooled in ice and the solid filtered and washed with water. The aqueous phase was extracted with ethyl acetate. The solvent was removed and the residue combined with the filtrate to give crude title compound (1.04 g, 5.80 mmol).

MS ((+)ESI, m/z): 180 [M+H]$^+$, 359 [2M+H]$^+$

Step B. 8-(Benzyloxy)-5-hydroxy-3,4-dihydro-2(1H)-quinolinone 5,8-Dihydroxy-3,4-dihydro-2(1H)-quinolinone (2.0 g, 11.16 mmol) and potassium carbonate (1.8 g, 13.02 mmol) were stirred at reflux in acetone (35 mL). Benzyl bromide (1.33 mL, 11.2 mmol) was added and refluxing continued for 4 hours. The solvents were removed and the reaction mixture partitioned between chloroform and water. The organic phase was washed with brine and dried over anhydrous magnesium sulfate. The solution was filtered and the solvent evaporated to dryness in vacuo. The residue was purified by flash chromatography on silica gel Merck-60 (eluant: 1:1 hexane-ethyl acetate) to yield the title compound (0.80 g, 2.97 mmol).

MS ((+)ESI, m/z): 270 [M+H]$^+$

Step C. 8-(Benzyloxy)-5-[(2S)oxiranylmethoxy]-3,4-dihydro-2(1H)-quinolinone 8-(Benzyloxy)-5-hydroxy-3,4-dihydro-2(1-quinolinone (0.20 g, 0.743 mmol) was reacted according to Procedure A. The residue was purified by flash chromatography on silica gel Merck-60 (eluant: 50:1 chloroform-methanol) to yield the title compound (0.210 g, 0.61 mmol).

MS ((+)APCI, m/z): 326 [M+H]$^+$

EXAMPLE P tert-Butyl{3-[(2S)oxiranylmethoxy]phenoxy}diphenylsilane

Step A. 3-{[tert-butyl(diphenyl)silyl]oxy}phenol

Resorcinol (15 g, 136 mmol) was dissolved in anhydrous dichloromethane (377 mL). tert-butylchlorodiphenyl silane (37.44 g,136 mmol) and imidazole (10.20 g, 149.6 mmol) were added. The reaction was stirred overnight at ambient temperature. The solvent was removed in vacuo and the residue purified by flash chromatography on silica gel Merck-60 (eluant: 4:1 hexane-diethyl ether) to yield the title compound (5.5 g, 16.0 mmol).

¹H NMR (DMSO-d₆, 300 MHz): d 1.00 (s, 9H), 6.20 (m, 2H), 6.30 (d, 1H), 6.90 (t, 1H), 7.50 (m, 6H), 7.70 (m, 4H), 9.30 (broad s,1H).

Step B. tert-Butyl[3-[(2S)oxiranylmethoxy]phenoxy}diphenylsilane

3-{[tert-Butyl(diphenyl)silyl]oxy}phenol (5.5 g, 16 mmol) was reacted according to Procedure B. The residue was purified by flash chromatography on silica gel Merck-60 (eluant: 3:1 hexane-diethyl ether) to yield the title compound (3.4 g, 8.4 mmol).

¹H NMR (DMSO-d₆, 300 MHz): d 1.00 (s, 9H), 2.60 (m,1H), 2.80 (m,1H), 3.50 (m,1H), 3.70 (m, 1H), 4.20 (m, 1H), 6.40 (m, 2H), 6.50 (m, 1H), 7.10 (m, 1H), 7.50 (m, 6H), 7.70 (m, 4H).

EXAMPLE Q

2-[(E)-2-(4-Nitrophenyl)diazenyl]-5-[(2S)oxiranylmethoxy]pyridine

Step A. 6-[(E)-2-(4-Nitrophenyl)diazenyl]-3-pyridinol

To a slurry of 4-nitroaniline (27.63 g, 200 mmol) and sodium nitrite (13.81 g, 200 mmol) in ice-water (400 mL) was added concentrated hydrochloric acid (79 mL) so as to maintain the internal temperature between 0° C. and minus 1° C. The resulting near-solution was used directly. To a cooled solution (between 0° C. and minus 2° C. internal temperature) of 3-hydroxypyridine (19.0 g, 200 mmol) and potassium hydroxide (11.2 g, 200 mmol) in water (300 mL) was added at the same time and with cooling, a solution of potassium hydroxide (58.0 g, 103 mmol) in water (500 mL) and the first prepared near-solution above. Following the addition of the reactants the dark reaction was stirred at 0° C. for 1 hour. Acetic acid (50 mL) was added and the resulting dark solid removed and air-dried. The solid was taken up in ethanol and treated with charcoal. Following removal of the solid the solution was cooled and the resulting solid removed. Further crystallization from ethanol afforded (10.1 g, 41 mmol). A further batch of material was obtained following pooling of the supernatants, partial solvent removal and a further crystallization (10.6 g, 43 mmol).

MS ((+)ESI, m/z): 245 [M+H]⁺

Step B. 2-[(E)-2-(4-Nitrophenyl)diazenyl]-5-[(2S)oxiranylmethoxy]pyridine

6-[(E)-2-(4-Nitrophenyl)diazenyl]-3-pyridinol (0.50 g, 2.05 mmol was reacted according to Procedure A. The residue was purified by flash chromatography on silica gel Merck-60 (eluant: 1:1 ethyl acetate-hexane) to yield the title compound (0.20 g, 0.66 mmol).

¹H NMR (DMSO-d₆, 300 MHz): d 2.80 (m, 1H), 2.92 (m, 1H), 3.5 (m, 1H), 4.15 (m, 1H), 4.62 (m, 1H), 7.75 (dd, 1H), 7.90 (m, 1H), 8.16 (d, 2H), 8.5 (m, 3H)

EXAMPLE R

Step A. 4-{[tert-butyl(diphenyl)silyl]oxy}-2-chlorobenzaldehyde

To a solution of imidazole (4.28 g, 62.89 mmol) and 2-chloro-4-hydroxybenzaldehyde (8.95 g, 57.16 mmol) in CH₂Cl₂ (500 ml) was added drop-wise a solution of tert-butyldiphenylchlorosilane (17.27 g, 62.86 mmol) in anhydrous dichloromethane, (200 ml). The solution was stirred overnight at ambient temperature. The mixture was poured into water (500 ml) and the organic layer washed with saturated sodium hydrocarbonate solution, water, brine and dried over anhydrous magnesium sulfate. The solvent was filtered and removed in vacuo to furnish the title compound (24.2 g, 61.2 mmol).

¹H NMR (DMSO-d₆, 300 MHz): d 1.11 (s, 9H), 6.88 (dd, 1H), 6.94 (d, 1H), 7.40 (m, 1H), 7.51 (m, 6H), 7.75 (m, 4H), 10.13 (s, 1H)

Step B. 4-{[tert-butyl(diphenyl)silyl]oxy}-2-chlorophenyl formate

4-{[tert-Butyl(diphenyl)silyl]oxy}-2-chlorobenzaldehyde (11.00 g, 28 mmol) was dissolved in chloroform (150 ml). 3-Chloroperoxybenzoic acid (7.21 g, 41.8 mmol) was added and the solution heated to reflux for 72 hours. The solution was diluted with dichloromethane, washed with saturated sodium hydrogen sulfate solution, saturated sodium hydrogen carbonate solution, brine and dried over anhydrous magnesium sulfate. The solvent was filtered and removed in vacuo to furnish the title compound (9.42g, 22.9 mmol).

¹H NMR (DMSO-d₆, 300 MHz): d 1.11 (s, 9H), 6.69 (dd, 1H), 6.94 (d, 1H), 7.16 (d, 1H), 7.42 (m, 6H), 7.68 (m, 4H), 8.13 (s, 1H)

Step C. 4-{[tert-Butyl(diphenyl)silyl]oxy}-2-chlorophenol

4-{[tert-Butyl(diphenyl)silyl]oxy}-2-chlorophenyl formate (9.42 g, 22.4 mmol) was dissolved in methanol (50 mL). 10% Potassium hydroxide (15 mL) was added. The solution was stirred for 30 minutes at ambient temperature. The solvent was removed in vacuo and the solid partitioned between ethyl acetate and water. The aqueous phase was acidified with hydrochloric acid and extracted three times with ethyl acetate. The organic layers were combined and the solvent dried over anhydrous magnesium sulfate. The solution was filtered and the solvent evaporated to dryness in vacuo to yield crude title compound (8.04 g, 21 mmol).

¹H NMR (DMSO-d₆, 300 MHz): d 1.11 (s, 9H), 6.58 (dd, 1H), 6.67 (d, 1H), 6.78 (d, 1H), 7.46 (m, 6H), 7.70 (m, 4H), 9.64 (s, 1H)

Part D. tert-Butyl(diphenyl)silyl 3-chloro-4-[(2S)oxiranylmethoxy]phenyl ether

4-{[tert-Butyl(diphenyl)silyl]oxy}-2-chlorophenol (8.04 g, 21 mmol) was reacted according to Procedure B. The residue was purified by passage through a silica gel plug eluting with (eluant: 2:1 hexane-diethyl ether) to furnish the title compound (4.8 g, 10.9 mmol).

¹H NMR (DMSO-d₆, 300 MHz): d 1.11 (s, 9H), 2.69 (m, 1H), 2.81 (m, 1H), 3.33 (m, 1H), 3.82 (m, 1H), 4.28 (dd, 1H), 6.62 (dd, 1H), 6.81 (d, 1H), 6.94 (d, 1H), 7.46 (m, 6H), 7.70 (m, 4H)

EXAMPLE S

Triisopropyl{2-methyl-4-[(2S)oxiranylmethoxy]phenoxy}silane

The title compound (5.83 g, 17.32 mmol)was prepared according to Procedure B using the following amounts: 4-(triisopropylsilyloxy)-3-methylphenol (prepared according to B. A. Wood et. al., *Xenobiotica*, 1975, 5, 183) (7.73 g, 27.56 mmol), R-(+)-glycidol (4.02 mL, 60.63 mmol), triphenylphosphine (15.90 g, 60.63 mmol), diethyl azodicarboxylate (9.76 mL, 62.01 mmol).

¹H NMR (CDCl₃, 300 MHz,) d 6.67 (m, 2H), 6.58 (dd, J=8.2 and 3.1 Hz, 1H), 4.12 (AXm, 1H), 3.90 (AXm, 1H), 3.32 (m, 1H), 2.88 (AXt, J=5.0 Hz, 1H), 2.74 (AXm, 1H), 2.21 (s, 3H), 1.27 (m, 3H) and 1.10 (m, 18H).

EXAMPLE T

5-[(2S)Oxiranylmethoxy]-1,3-benzodioxole

The title compound (2.01 g, 10.35 mmol) was prepared according to Procedure A using the following amounts: sesamol (2.49 g, 18.02 mmol), potassium carbonate (2.74 g, 19.83 mmol) and (2S)-(+)-glycidyl-3-nitrobenzenesulfonate (4.67 g, 18.02 mmol).

¹H NMR (CDCl₃, 300 MHz,) d 6.69 (d, J=8.4 Hz, 1H), 6.52 (d, J=2.5 Hz, 1H), 6.33 (dd, J=8.4 and 2.5 Hz, 1H), 5.91

(s, 2H), 4.14 (ABdd, J=11.0 and 3.3 Hz, 1H), 3.86 (ABdd, J=11.0 and 5.7 Hz, 1H), 3.33 (m, 1H), 2.88 (m, 1H) and 2.74 (m, 1H).

The following describe the preparation of representative examples of this invention.

EXAMPLE 1

4-(4-{2-[(2S)-2-Hydroxy-3-(4-hydroxy-phenoxy)-propylamino]-ethyl}-phenylamino)-piperidine-1-carboxylic Acid 4-fluoro-benzylamide Step A. [2-(4-Amino-phenyl)-ethyl]-carbamic acid tert-butyl ester 4-(2-Aminoethyl)aniline (20.0 g, 146 mmol) was dissolved in anhydrous dichloromethane (500 mL). Di-tert-butyl dicarbonate in anhydrous dichloromethane was added drop-wise over 1 hour. The solution was stirred overnight. The solvent was evaporated to dryness in vacuo to yield a solid. Recrystallization from diethyl ether/hexane gave the title compound (33.0 g, 135 mmol).

m.p 78–79° C.

MS (EI, m/z): [M]$^+$236

$^1$H NMR (DMSO-d$_6$, 300 MHz): d 1.35 (s, 9H), 2.48 (m, 2H), 2.99 (m, 2H), 4.81 (s, 2H), 6.45 (d, 2H), 6.79 (t, 1H), 6.81 (d, 2H)

Step B. tert-Butyl 4-[(1-benzyl-4-piperidinyl)amino] phenethylcarbamate

[2-(4-Amino-phenyl)-ethyl]-carbamic acid tert-butyl ester (16.64 g, 70 mmol) and benzyl piperidone (20.00 g, 104 mmol) were dissolved in dichloroethane (300 mL). Anhydrous sodium sulfate (100 g, 700 mmol) was added followed by acetic acid (20 mL). Stirring was continued for 45 minutes. Sodium triacetoxyborohydride (44.8 g, 211 mmol) was added and stirring continued overnight. The mixture was filtered, diluted with dichloromethane (600 mL), and washed with 40% sodium hydroxide, water and brine. The organic layer was dried over anhydrous magnesium sulfate and the solution filtered. The solvent was evaporated to dryness in vacuo to yield an oil which was stirred in hexane. The resulting title compound was obtained as a white solid. (26.0 g, 63.5 mmol).

MS ((+)ESI, m/z): 410 [M+H]$^+$

Step C. 2-[4-(Piperidin-4-ylamino)-phenyl]-ethyl}-carbamic Acid tert-butyl Ester tert-Butyl 4-[(1-benzyl-4-piperidinyl)amino] phenethylcarbamate (26.0 g, 63.5 mmol) was dissolved in ethanol (500 mL), 10% palladium on carbon (5.5 g) was added followed by cyclohexene (100 mL). The solution was heated to reflux for 1.5 hours. The mixture was cooled to ambient temperature, filtered through a Celite pad, and the solvent removed in vacuo to yield the title compound (19.67 g, 61.59 mmol).

m.p 109–111° C.

MS ((+)APCI, m/z): 320 [M+H]$^+$ $^1$H NMR (DMSO-d$_6$, 300 MHz): d 1.18 (qd, 2H), 1.35 (s, 9H), 1.80 (d, 2H), 2.49 (m, 4H), 2.90 (dt, 2H), 3.01 (q, 2H), 3.18 (m, 1H), 5.17 (d, 1H), 6.46 (d, 2h), 6.76 (t, 1H), 6.85 (d, 2H)

Step D. tert-Butyl 4-[(1-{[(4-fluorobenzyl)amino] carbonyl}-4-piperidinyl)amino]phenethylcarbamate The title compound (0.95 g, 2.00 mmol) was prepared from 4-fluoro benzyl amine (0.5 g, 4 mmol) and {2-[4-(piperidin-4-ylamino)-phenyl]-ethyl}-carbamic acid tert-butyl ester (1.276 g, 4 mmol) according to Procedure C.

MS ((+)APCI, m/z): 471 [M+H]$^+$

Step E. 4-[4-(2-Aminoethyl)anilino]-N-(4-fluorobenzyl)-1-piperidinecarboxamide formate tert-Butyl 4-[(1-{[(4-fluorobenzyl)amino]carbonyl}-4-piperidinyl)amino]phenethyl carbamate (0.870 g, 1.85 mmol) was reacted according to the Procedure F to obtain the title compound which was used without further purification.

$^1$H NMR (DMSO-d$_6$, 300 MHz): d 1.83 (d, 2H), 2.66 (t, 2H), 2.82 (m, 4H), 3.42 (m,1H), 3.92 (d, 2H), 4.22 (d, 2H), 5.38 (m, 1H), 6.58 (d, 1H), 6.90(d, 2H) 7.18 (m , 6H), 7.35 (m, 4H), 8.41 (s, 1H)

Step F. 4-[4-(2-{[(2S)-3-(4-{[tert-Butyl(diphenyl)silyl] oxy}phenoxy)-2-hydroxypropyl]amino}ethyl)anilino]-N-(4-fluorobenzyl)-1-piperidinecarboxamide 4-[4-(2-Aminoethyl)anilino]-N-(4-fluorobenzyl)-1-piperidinecarboxamide formate (0.77 g, 1.85 mmol) was reacted with tert-butyl-(4-oxiranylmethoxy-phenoxy)-diphenyl-silane (0.671 g, 1.66 mmol) according to Procedure G to give the title compound (0.53 g, 0.67 mmol).

Step G. 4-(4-{2-[(2S)-2-hydroxy-3-(4-hydroxy-phenoxy)-propylamino]-ethyl}-phenylamino)-piperidine-1-carboxylic Acid 4-fluoro-benzylamide 4-[4-(2-{[(2S)-3-(4-{[tert-Butyl(diphenyl)silyl] oxy}phenoxy)-2-hydroxy-propyl]amino}ethyl)anilino]-N-(4-fluorobenzyl)-1-piperidinecarboxamide (0.320, 0.41 mmol) was reacted following Procedure H (eluant: 5:1 chloroform-methanol) to give the title compound (0.141 g, 0.26 mmol).

m.p 89–91° C.

MS ((+)ESI, m/z): 537 [M+H]$^+$

Anal. calcd. for $C_{30}H_{37}FN_4O_4 \cdot HCl+0.1$ $H_2O$: C 62.68 H 6.70 N 9.75 found: C 62.45 H 6.53 N 9.54

EXAMPLE 2

4-{2-[(2S)-2-Hydroxy-3-(4-hydroxy-phenoxy)-propylamino]-ethyl}-phenylamino)-piperidine-1-carboxylic Acid Cyclohexylamide Step A. tert-Butyl 4-({1-[(cyclohexylamino)carbonyl]-4-piperidinyl}amino)phenethyl carbamate {2-[4-(Piperidin-4-ylamino)-phenyl]-ethyl}-carbamic acid tert-butyl ester (1.05 g, 3.28 mmol) was reacted with cylohexylisocyanate (0.41 g, 3.28 mmol) according to Procedure E. The title compound was obtained (eluant: 50:1 chloroform-methanol) as a solid (0.595 g, 1.33 mmol).

$^1$H NMR (DMSO-d$_6$, 300 MHz): d 1.15 (m, 8H), 1.31(s, 9H), 1.70 (m, 8H), 2.78(t, 2H), 3.02(m, 2H), 3.89(d, 2H), 5.10(s, 2H), 5.24 (d, 1H), 6.1 (d, 1H), 6.50 (d, 2H), 6.80(t, 1H), 6.90(d, 2H).

Step B. 4-[4-(2-Aminoethyl)anilino]-N-cyclohexyl-1-piperidinecarboxamide formate tert-Butyl 4-[(1-{[(cyclohexylmethyl)amino]carbonyl}-4-piperidinyl)-amino]-phenethylcarbamate (0.595, 1.33 mmol) was reacted according to procedure F to obtain the title compound (0.461 g, 1.1 mmol) which was used without further purification.

Step C. 4-[4-(2-{[(2S)-3-(4-{[tert-Butyl(diphenyl)silyl] oxy}phenoxy)-2-hydroxypropyl]amino}ethyl)anilino]-N-(cyclohexyl)-1-piperidinecarboxamide 4-[4-(2-Aminoethyl)anilino]-N-(cyclohexylmethyl)-1-piperidinecarboxamide formate (0.461 g, 1.1 mmol) was reacted with tert-butyl-(4-oxiranylmethoxy-phenoxy)-diphenyl-silane (0.358 g, 0.88 mmol) according to Procedure G to give the title compound (eluant: 20:1 chloroform-methanol) (0.19 g, 0.25 mmol).

$^1$H NMR (DMSO-d$_6$, 400 MHz): d 1.12 (s, 9H), 1.2 (m, 9H), 1.79 (m, 9H), 2.78(m, 4H), 3.85 (m, 4H), 5.30(s, 1H), 6.14 (d, 1H), 6.55 (d, 2H), 6.70 (q, 4H), 6.92 (d, 2H), 7.45(m, 6H), 7.75(m, 4H).

Step D. 4-{2-[(2S)-2-Hydroxy-3-(4-hydroxy-phenoxy)-propylamino]-ethyl}-phenylamino)-piperidine-1-carboxylic acid cyclohexylamide 4-[4-(2-{[(2S)-3-(4-{[tert-Butyl(diphenyl)silyl]oxy}phenoxy)-2-hydroxy-propyl]amino}ethyl)anilino]-N-(cyclohexylmethyl)-1-piperidinecarboxamide (0.19 g, 0.25 mmol) was reacted according to Procedure H to furnish (eluant: 5:1 chloroform-methanol) the title compound (0.02 g, 0.03 mmol)

m.p. 77–86° C.

MS ((+)ESI, m/z): 511 [M+H]$^+$

Anal. calcd. for $C_{29}H_{42}N_4O_4 \cdot HCl$: C 64.04 H 8.16 N 10.06 found: C 64.05 H 7.93 N 9.95

EXAMPLE 3

4-(4-{2-[(2S)-3-(4-Fluoro-phenoxy)-2-hydroxy-propylamino]-ethyl}-phenylamino)-piperidine-1-carboxylic Acid Octylamide Step A. (2-{4-[1-(Octylcarbamoyl)-piperidin-4-ylamino]-phenyl}-ethyl)-carbamic acid tert-butyl ester {2-[4-(Piperidin-4-ylamino)-phenyl]-ethyl}-carbamic acid tert-butyl ester (6.0 g, 18.7 mmol) was reacted with octyl isocyanate (2.91 g, 18.7 mmol) according to Procedure E. The title compound was obtained (eluant: 50:1 chloroform-methanol) (6.1 g, 12.8 mmol) as a solid.

MS ((+)ESI, m/z): 475 [M+H]$^+$

Step B. 4-[4-(2-Aminoethyl)anilino]-N-octyl-1-piperidinecarboxamide formate (2-{4-[1-(Octylcarbamoyl)-piperidin-4-ylamino]-phenyl}-ethyl)-carbamic acid tert-butyl ester (0.45 g, 0.95 mmol) was reacted according to Procedure F to obtain the title compound (0.400 g, 0.95 mmol) which was used without further purification.

Step C. 4-(4-{2-[(2S)-3-(4-Fluoro-phenoxy)-2-hydroxy-propylamino]-ethyl}-phenylamino)-piperidine-1-carboxylic acid octylamide 4-[4-(2-Aminoethyl)anilino]-N-octyl-1-piperidinecarboxamide formate (0.400 g, 0.95 mmol) was reacted with (2S)-2-[(4-fluorophenoxy)methyl]oxirane (0.119 g, 0.713 mmol) according to Procedure G to give the title compound (eluant: 20:1 chloroform-methanol) (0.085 g, 0.15 mmol).

MP: 58–64° C.

MS ((+)ESI, m/z): 543 [M+H]$^+$

Anal. calcd. for $C_{31}H_{47}FN_4O_3 + 0.5 H_2O$: C 67.48 H 8.77 N 10.15 found: C 67.43 H 8.59 N 10.02

EXAMPLE 4

4-(4-{2-[(2S)-3-(2-Allyl-phenoxy)-2-hydroxy-propylamino]-ethyl}-phenylamino)-piperidine-1-carboxylic Acid Octylamide 4-[4-(2-Aminoethyl)anilino]-N-octyl-1-piperidinecarboxamide formate (0.40 g, 0.95 mmol) was reacted with (2S)-2-[(2-allylphenoxy)methyl]oxirane (0.125 g, 0.713 mmol) according to Procedure G to give the title compound (eluant: 20:1 chloroform-methanol) (0.060 g, 0.1 mmol).

MP: 73–80° C.

MS ((+)ESI, m/z): 565 [M+H]$^+$

Anal. calcd. for $C_{34}H_{52}N_4O_3 \cdot 2HCl$: C 64.04 H 8.53 N 8.79 found: C 64.6 H 8.68 N 8.63

EXAMPLE 5

4-(4-{2-[(2S)-3-(6-Amino-pyridin-3-yloxy)-2-hydroxy-propylamino]-ethyl}-phenylamino)-piperidine-1-carboxylic Acid Octylamide Step A. 4-[4-(2-{[(2S)-2-Hydroxy-3-({2-[(E)-2-(4-nitrophenyl)diazenyl]-4-pyridinyl}oxy)propyl]amino}ethyl)anilino]-N-octyl-1-piperidinecarboxamide 4-[4-(2-Aminoethyl)anilino]-N-octyl-1-piperidinecarboxamide formate (0.35 g, 0.825 mmol) was reacted with 2-[(E)-2-(4-nitrophenyl)diazenyl]-4-[(2S)oxiranylmethoxy]pyridine (0.200 g, 0.66 mmol) according to Procedure G to give the title compound (eluant: 20:1 chloroform-methanol) (0.1 g, 0.15 mmol).

Step B. 4-(4-{2-[(2S)-3-(6-Amino-pyridin-3-yloxy)-2-hydroxy-propylamino]-ethyl}-phenylamino)-piperidine-1-carboxylic Acid Octylamide 4-[4-(2-{[(2S)-2-Hydroxy-3-({2-[(E)-2-(4-nitrophenyl)diazenyl]-4-pyridinyl}oxy)propyl]amino}ethyl)anilino]-N-octyl-1-piperidinecarboxamide (0.1 g, 0.15 mmol) was dissolved in ethanol (10 mL) and 10% palladium on carbon (0.015 g) added. The solution was shaken in a Parr apparatus at 50 psi hydrogen atmosphere for 1.5 hours, filtered through a Celite pad and the solvent removed in vacuo. The residue was purified by flash chromatography on silica gel Merck-60 (eluant: 10:1 chloroform-methanol) to furnish the title compound (0.02 g, 0.037 mmol).

m.p 134–138° C.

MS ((+)ESI, m/z): 541 [M+H]$^+$

Anal. calcd. for $C_{30}H_{48}N_6O_3 \cdot HCl + 0.25 H_2O$: C 61.94 H 8.58 N 14.45 found: C 62.27 H 8.73 N 13.98

EXAMPLE 6

4-(4-{2-[(2S)-2-Hydroxy-3-(4-hydroxy-phenoxy)-propylamino]-ethyl}-phenylamino)-piperidine-1-carboxylic Acid [2-(3-methoxy-phenyl)-ethyl]-amide Step A. tert-Butyl 4-[(1-{[(3-methoxyphenethyl)amino]carbonyl}-4-piperidinyl)amino]phenethylcarbamate The title compound (0.446 g, 0.899 mmol) was prepared from 3-methoxy phenethylamine (0.302 g, 2.0 mmol) and {2-[4-(piperidin-4-ylamino)-phenyl]-ethyl}-carbamic acid tert-butyl ester (0.638 g, 2 mmol) according to Procedure C (eluant: 50:1 chloroform-methanol).

Step B. 4-[4-(2-Aminoethyl)anilino]-N-(3-methoxyphenethyl)-1-piperidinecarbox-amide formate tert-Butyl 4-[(1-{[(3-methoxyphenethyl)amino]carbonyl}-4-piperidinyl)-amino]phenethyl carbamate (0.446 g, 0.899 mmol) was reacted according to the Procedure F to obtain the title compound (0.398 g, 0.899 mmol) which was used without further purification.

Step C. 4-[4-(2-{[(2 S)-3-(4-{[tert-Butyl(diphenyl)silyl]oxy}phenoxy)-2-hydroxypropyl]amino}ethyl)anilino]-N-(3-methoxyphenethyl)-1-piperidinecarboxamide 4-[4-(2-Aminoethyl)anilino]-N-(3-methoxyphenethyl)-1-piperidine-carboxamide formate (0.398 g, 0.899 mmol) was reacted with tert-butyl-(4-oxiranylmethoxy-phenoxy)-diphenyl-silane (0.290 g, 0.71 mmol) according to Procedure G to yield (eluant: 20:1 chloroform-methanol) the title compound (0.110 g, 0.14 mmol)

$^1$H NMR (DMSO-$d_6$, 300 MHz): d 1.05 (s, 9H), 1.25 (m, 2H), 1.83 (d, 2H), 2.51 (m, 1H), 2.75 (m, 6H), 3.23 (m, 2H), 3.68 (s, 3H), 3.88 (m, 4H), 5.1 (m, 1H), 5.4 (d, 1H), 6.55 (d, 2H), 6.60 (t, 1H), 6.75 (m, 4H), 6.79 ( d, 2H),6.96 (d, 2H), 7.2 (t, 1H), 7.48 (m, 6H), 7.75 (m, 4H).

Step D. 4-(4-{2-[(2S)-2-Hydroxy-3-(4-hydron-phenon)-propylamino]-ethyl}-phenylamino)-piperidine-1-carboxylic Acid [2-(3-methoxy-phenyl)-ethyl]-amide 4-[4-(2-{[(2S)-3-(4-{[tert-Butyl(diphenyl)silyl]oxy}phenoxy)-2-hydroxy-propyl]amino}ethyl)anilino]-N-(3-methoxyphenethyl)-1-piperidinecarboxamide (0.110 g, 0.14 mmol) was reacted according to Procedure H to yield (eluant: 5:1 chloroform-methanol) the title compound (0.025 g, 0.044 mmol).

MP: 103–108° C.

MS ((+)ESI, m/z): 563 [M+H]+

Anal. calcd. for $C_{32}H_{42}N_4O_5 \cdot HCl + 0.15\ H_2O$: C 63.86 H 7.25 N 9.31 found: C 63.75 H 7.44 N 9.55

EXAMPLE 7

4-(4-{2-[2-(3-Carbamoyl-4-hydroxy-phenyl)-2-hydroxy-ethylamino]-ethyl}-phenylamino)-piperidine-1-carboxylic Acid Octylamide Step A. 4-{4-[2-({2-[3-(Aminocarbonyl)-4-(benzyloxy)phenyl]-2-hydroxyethyl}-amino)ethyl]anilino}-N-octyl-1-piperidinecarboxamide 4-[4-(2-Aminoethyl)anilino]-N-octyl-1-piperidinecarboxamide formate (0.50 g, 1.18 mmol) was reacted with 2-(benzyloxy)-5-(2-oxiranyl)benzamide (0.255 g, 0.95 mmol) according to Procedure G to give the title compound (eluant: 20:1 chloroform-methanol) (0.143 g, 0.22 mmol).

Step B. 4-(4-{2-[2-(3-Carbamoyl-4-hydroxy-phenyl)-2-hydroxy-ethylamino]-ethyl}-phenylamino)-piperidine-1-carboxylic acid octylamide 4-{4-[2-({2-[3-(Aminocarbonyl)-4-(benzyloxy)phenyl]-2-hydroxyethyl}-amino)ethyl]anilino}-N-octyl-1-piperidinecarboxamide was dissolved in ethanol (20 mL) and 10% palladium on carbon added (0.1 g). The mixture was shaken overnight on a Parr apparatus under 50 psi hydrogen, filtered through a Celite pad and the solvent removed in vacuo. The residue was purified by flash chromatography on silica gel Merck-60 (eluant: 5:1 chloroform-methanol) to yield the title compound (0.030 g, 0.05 mmol)

m.p. 101–104° C.

MS ((+)ESI, m/z): 554 [M+H]+

Anal. calcd. for $C_{31}H_{47}N_5O_4 \cdot HCl + 0.75\ H_2O$: C 61.67 H 8.26 N 11.60 found: C 61.53 H 8.49 N 10.61

EXAMPLE 8

4-[Acetyl-(4-{2-[(2S)-2-hydroxy-3-(4-hydroxy-phenoxy)-propylamino]-ethyl}-phenyl)-amino]-piperidine-1-carboxylic Acid Octylamide Step A. tert-Butyl 4-[acetyl(1-benzyl-4-piperidinyl)amino]phenethylcarbamate tert-Butyl 4-[(1-benzyl-4-piperidinyl)amino]phenethylcarbamate (4.1 g, 10.0 mmol) was dissolved in anhydrous pyridine (20 mL) and acetic anhydride (1.02 g, 10.0 mmol) added. The solution was stirred overnight at ambient temperature. The solvent was removed in vacuo and the residue partitioned between ethyl acetate and water. The organic layer was washed with 0.1 N hydrochloric acid, brine and dried over anhydrous magnesium sulfate. The solution was filtered and the solvent evaporated to dryness to yield the title compound as a solid (3.5 g, 7.75 mmol).

MS ((+)ESI, m/z): 452 [M+H]+

Step B. tert-Butyl 4-[acetyl(4-piperidinyl)amino]phenethylcarbamate tert-Butyl 4-[acetyl(1-benzyl-4-piperidinyl)amino]phenethylcarbamate (3.5 g, 7.75 mmol) was dissolved in ethanol (120 mL), 10% palladium on carbon (1.5 g) was added followed by cyclohexene (15 mL). The solution was heated to reflux for 1.5 hours. The mixture was cooled to ambient temperature, filtered through a Celite pad, and the solvent removed in vacuo to yield the title compound (2.49 g, 6.9 mmol).

Step C. tert-Butyl 4-(acetyl{1-[(octylamino)carbonyl]-4-piperidinyl amino)phenethylcarbamate tert-Butyl 4-[acetyl(4-piperidinyl)amino]phenethylcarbamate (1.0 g, 2.76 mmol) was reacted with octyl isocyanate (0.42 g, 2.76 mmol) according to Procedure E to yield the title compound (eluant: 50:1 chloroform-methanol) (0.30 g, 0.59 mmol).

MS ((+)ESI, m/z): 517 [M+H]+

Step D. 4-[acetyl-4-(2-aminoethyl)anilino]-N-octyl-1-piperidinecarboxamide formate tert-Butyl 4-(acetyl{1-[(octylamino)carbonyl]-4-piperidinyl}amino)phenethyl carbamate (0.30 g, 0.59 mmol) was reacted according to Procedure F to obtain the title compound (0.25 g, 0.59 mmol) which was used without further purification.

Step E. 4-{4-[2-(([{2S}-3-[4-(benzyloxy)phenoxy]-2-hydroxypropyl}-amino)ethyl]anilino}-N-octyl-1-piperidinecarboxamide 4-[Acetyl-4-(2-aminoethyl)anilino]-N-octyl-1-piperidinecarboxamide formate (0.25 g, 0.59 mmol) was reacted with (2S)-2-{[4-(benzyloxy)phenoxy]methyl}oxirane (0.137 g, 0.53 mmol) according to Procedure G to give the title compound (eluant: 20:1 chloroform-methanol) (0.1 g, 0.15 mmol).

Step F. 4-[Acetyl-(4-{2-[(2S)-2-hydroxy-3-(4-hydroxy-phenoxy)-propylamino]-ethyl}-phenyl)-amino]-piperidine-1-carboxylic acid octylamide 4-{4-[2-({(2S)-3-[4-(Benzyloxy)phenoxy]-2-hydroxypropyl}amino)-ethyl]anilino}-N-octyl-1-piperidinecarboxamide (0.1 g, 0.15 mmol) was dissolved in ethanol (20 mL) and 10% palladium on carbon (0.1 g) added. The mixture was shaken on a Parr apparatus overnight under 50 psi hydrogen. The mixture was cooled to ambient temperature, filtered through a Celite pad, and the solvent removed in vacuo to yield the title compound (eluant: 5:1 chloroform-methanol) (0.033 g, 0.05 mmol)

m.p 71–74° C.

MS ((+)ESI, m/z): 583 [M+H]+

Anal. calcd. for $C_{33}H_{50}N_4O_5 \cdot HCl + 0.04\ CHCl_3$: C 63.59 H 8.24 N 8.98 found: C 63.25 H 8.57 N 8.9

EXAMPLE 9

4-(4-{2-[(2S)-2-Hydroxy-3-(4-hydroxy-phenoxy)-propylamino]-ethyl}-phenylamino)-piperidine-1-carboxylic Acid Methylamide Step A. tert-Butyl 4-({1-[(methylamino)carbonyl]-4-piperidinyl}amino)-phenethylcarbamate {2-[4-(Piperidin-4-ylamino)-phenyl]-ethyl}-carbamic acid tert-butyl ester (1.05 g, 3.22 mmol) and methyl isocyanate (0.182 g, 3.22 mmol) were reacted according to Procedure E. The title compound was obtained (eluant: 50:1 chloroform-methanol) (0.367 g, 1.0 mmol)

MS ((+)ESI, m/z): 377 [M+H]+

Step B. 4-[4-(2-Aminoethyl)anilino]-N-methyl-1-piperidinecarboxamide formate tert-Butyl 4-({1-[(methylamino)carbonyl]-4-piperidinyl}amino)phenethyl-carbamate (0.367 g, 1.0 mmol) was reacted according to the Procedure F to obtain the title compound (0.322 g, 1.0 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-methyl-1-piperidinecarboxamide 4-[4-(2-Aminoethyl)anilino]-N-methyl-1-piperidinecarboxamide formate (0.322 g, 1.0 mmol) was reacted with tert-butyl-(4-oxiranylmethoxy-phenoxy)-diphenyl-silane (0.364 g, 0.90 mmol) according to Procedure G to give the title compound (eluant: 20:1 chloroform-methanol) (0.1 g, 0.15 mmol).

Step D. 4-(4-{2-[(2S)-2-Hydroxy-3-(4-hydroxy-phenoxy)-propylamino]-ethyl}-phenylamino)-piperidine-1-carboxylic Acid Methylamide 4-[4-(2-{[(2S)-3-(4-{[tert-Butyl(diphenyl)silyl]oxy}phenoxy)-2-hydroxy-propyl]amino}ethyl)anilino]-N-methyl-1-piperidinecarboxamide (0.1 g, 0.15 mmol) was reacted with according to Procedure H to give the title compound (eluant: 5:1 chloroform-methanol) (0.02 g, 0.045 mmol).

m.p 72–77° C.

MS ((+)ESI, m/z): 443 [M+H]$^+$

Anal. calcd. for $C_{24}H_{34}N_4O_4$·HCl+0.14 $C_2H_6O$+0.28 $CHCl_3$+0.5 $H_2O$: C 55.88 H 7.04 N 10.61 found: C 56.12 H 6.7 N 10.21

EXAMPLE 10

4-(4-{2-[(2S)-2-Hydroxy-3-(4-hydroxy-phenoxy)-propylamino]-ethyl}-phenylamino)-piperidine-1-carboxylic Acid Ethylamide Step A. tert-Butyl 4-({1-[(ethylamino)carbonyl]-4-piperidinyl}amino)-phenethylcarbamate {2-[4-(Piperidin-4-ylamino)-phenyl]-ethyl}-carbamic acid tert-butyl ester (1.05 g, 3.22 mmol) and ethyl isocyanate (0.228 g, 3.22 mmol) were reacted according to Procedure E. The title compound was obtained (eluant: 50:1 chloroform-methanol) (0.39 g, 1.0 mmol)

Step B. 4-[4-(2-Aminoethyl)anilino]-N-ethyl-1-piperidinecarboxamide tert-Butyl 4-({1-[(ethylamino)carbonyl]-4-piperidinyl}amino)phenethyl-carbamate (0.39 g, 1.0 mmol) was reacted according to Procedure F to obtain the title compound (0.336 g, 1.0 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-ethyl-1-piperidinecarboxamide 4-[4-(2-Aminoethyl)anilino]-N-ethyl-1-piperidinecarboxamide formate (0.336 g, 1.0 mmol) was reacted with tert-butyl-(4-oxiranylmethoxy-phenoxy)-diphenyl-silane (0.364 g, 0.90 mmol) according to Procedure G to give the title compound (eluant: 20:1 chloroform-methanol) (0.17 g, 0.24 mmol).

Step D. 4-(4-{2-[(2S)-2-Hydroxy-3-(4-hydroxy-phenoxy)-propylamino]-ethyl}-phenylamino)-piperidine-1-carboxylic Acid Ethylamide 4-[4-(2-{[(2S)-3-(4-{[tert-Butyl(diphenyl)silyl]oxy}phenoxy)-2-hydroxy-propyl]amino}ethyl)anilino]-N-ethyl-1-piperidinecarboxamide (0.17 g, 0.24 mmol) was reacted according to Procedure H to give the title compound (eluant: 5:1 chloroform-methanol) (0.031 g, 0.067 mmol).

m.p 81–85° C.

MS ((+)ESI, m/z): 457 [M+H]$^+$

Anal. calcd. for $C_{25}H_{36}N_4O_4$·HCl+0.75 $H_2O$+0.28 $CHCl_3$: C 56.23 H 7.24 N 10.38 found: C 56.29 H 7.01 N 10.29

EXAMPLE 11

4-(4-{2-[(2S-2-Hydroxy-3-(4-hydroxy-phenoxy)-propylamino]-ethyl}-phenylamino)-piperidine-1-carboxylic Acid Isopropyl-amide Step A. tert-Butyl 4-({1-[(isopropylamino)carbonyl]-4-piperidinyl}amino)-phenethylcarbamate {2-[4-(Piperidin-4-ylamino)-phenyl]-ethyl}-carbamic acid tert-butyl ester ester (1.05 g, 3.22 mmol) and isopropyl isocyanate (0.274 g, 3.22 mmol) were reacted according to Procedure E. The title compound was obtained (eluant: 50:1 chloroform-methanol) (0.4 g, 1 mmol).

Step B. 4-[4-(2-Aminoethyl)anilino]-N-isopropyl-1-piperidinecarboxamide formate tert-Butyl 4-({1-[(isopropylamino)carbonyl]-4-piperidinyl}amino)phenethyl-carbamate (0.4 g, 1.0 mmol) was reacted according to Procedure F to obtain the title compound (0.35 g, 1.0 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-isopropyl-1-piperidinecarboxamide 4-[4-(2-Aminoethyl)anilino]-N-isopropyl-1-piperidinecarboxamide formate (0.35 g, 1.0 mmol) was reacted with tert-butyl-(4-oxiranylmethoxy-phenoxy)-diphenyl-silane (0.364 g, 0.90 mmol) according to Procedure G to give the title compound (eluant: 20:1 chloroform-methanol) (0.152 g, 0.214 mmol).

Step D. 4-(4-{2-[(2S)-2-Hydroxy-3-(4-hydroxy-phenoxy)-propylamino]-ethyl}-phenylamino)-piperidine-1-carboxylic acid isopropyl-amide 4-[4-(2-{[(2S)-3-(4-{[tert-Butyl(diphenyl)silyl]oxy}phenoxy)-2-hydroxy-propyl]amino}ethyl)anilino]-N-isopropyl-1-piperidinecarboxamide (0.152 g, 0.214 mmol) was reacted according to Procedure H to give the title compound (eluant: 5:1 chloroform-methanol) (0.05 g, 0.1 mmol).

m.p 89–96° C.

MS ((+)ESI, m/z): 471 [M+H]$^+$

Anal. calcd. for $C_{26}H_{38}N_4O_4$·HCl+0.75 $H_2O$: C 55.88 H 7.04 N 10.61 found: C 56.12 H 6.7 N 10.21

EXAMPLE 12

1-4-(4-{2-[(2S)-2-Hydroxy-3-(4-hydroxy-phenoxy)-propylamino]-ethyl}-phenylamino)-piperidine-1-carboxylic Acid (3-cyclopentyl-propyl)-amide Step A. tert-Butyl 4-[(1-{[(3-cyclopentylpropyl)amino]carbonyl}-4-piperidinyl)amino]phenethylcarbamate The title compound (1.12 g, 2.38 mmol) was prepared from 3-cyclopentyl propylamine (1.02 g, 8.0 mmol) and {2-[4-(piperidin-4-ylamino)-phenyl]-ethyl}-carbamic acid tert-butyl ester ester (2.54 g, 8.0 mmol) according to Procedure C.

Step B. 4-[4-(2-Aminoethyl)anilino]-N-(3-cyclopentylpropyl)-1-piperidine-carboxamide formate tert-Butyl 4-[(1-{[(3-cyclopentylpropyl)amino]carbonyl}-4-piperidinyl)amino]-phenethylcarbamate (1.12 g, 2.38 mmol) was reacted according to Procedure F to obtain the title compound (1.0 g, 2.38 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(3-cyclopentylpropyl)-1-piperidinecarboxamide formate 4-[4-(2-Aminoethyl)anilino]-N-(3-cyclopentylpropyl)-1-piperidine-carboxamide formate (1.0 g, 2.38 mmol) was reacted with tert-butyl-(4-oxiranylmethoxy-phenoxy)-diphenyl-silane silane (0.869 g, 2.15 mmol) according to Procedure G to give the title compound (eluant: 20:1 chloroform-methanol) (0.52 g, 0.66 mmol).

Step D. 1-4-(4-{2-[(2S)-2-Hydroxy-3-(4-hydroxy-phenoxy)-propylamino]-ethyl}-phenylamino)-piperidine-1-carboxylic acid (3-cyclopentyl-propyl)-amide 4-[4-(2-{[(2S)-3-(4-{[tert-Butyl(diphenyl)silyl]oxy}phenoxy)-2-hydroxypropyl]amino}ethyl)anilino]-N-isopropyl-1-piperidinecarboxamide (0.52 g, 0.66 mmol) was reacted according to Procedure H to give the title compound (eluant: 5:1 chloroform-methanol) (0.20 g, 0.37 mmol).

m.p 71–74° C.

MS ((+)ESI, m/z): 539 [M+H]$^+$

Anal. calcd. for $C_{31}H_{46}N_4O_4$·HCl: C 64.73 H 7.24 N 9.74 found: C 65.15 H 7.9 N 9.57

EXAMPLE 13

4-(4-{2-[(2S)-2-Hydroxy-3-(4-hydroxy-phenoxy)-propylamino]-ethyl}-phenylamino)-piperidine-1-carboxylic Acid (2,2,2-trifluoro-ethyl)-amide Step A. tert-Butyl 4-[(1-{[(2,2,2-trifluoroethyl)amino]carbonyl}-4-piperidinyl)amino]phenethylcarbamate The title compound (0.68 g, 1.53 mmol) was prepared from 2,2,2-trifluoro ethyl amine (0.792 g, 8.0 mmol) and {2-[4-(piperidin-4-ylamino)-phenyl]-ethyl}-carbamic acid tert-butyl ester ester (2.54 g, 8.0 mmol) according to Procedure C.

Step B. 4-[4-(2-Aminoethyl)anilino]-N-(2,2,2-trifluoroethyl)-1-piperidinecarboxamide formate tert-Butyl 4-[(1-{[(2,2,2-trifluoroethyl)amino]carbonyl}-4-piperidinyl)amino]phenethylcarbamate (0.68 g, 1.53 mmol) was reacted according to Procedure F to obtain the title compound (0.60 g, 1.53 mmol which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(2,2,2-trifluoroethyl)-1-piperidinecarboxamide 4-[4-(2-Aminoethyl)anilino]-N-(2,2,2-trifluoroethyl)-1-piperidinecarboxamide formate (0.60 g, 1.53 mmol) was reacted with tert-butyl-(4-oxiranylmethoxy-phenoxy)-diphenyl-silane (0.550 g, 1.38 mmol) according to Procedure G to give the title compound (eluant: 20:1 chloroform-methanol) (0.188 g, 0.25 mmol).

Step D. 4-(4-{2-[(2S)-2-Hydroxy-3-(4-hydroxy-phenoxy)-propylamino]-ethyl}-phenylamino)-piperidine-1-carboxylic acid (2,2,2-trifluoro-ethyl)-amide 4-[4-(2-{[(2S)-3-(4-{[tert-Butyl(diphenyl)silyl]oxy}phenoxy)-2-hydroxypropyl]amino}-ethyl)anilino]-N-(2,2,2-trifluoroethyl)-1-piperidinecarboxamide (0.188 g, 0.25 mmol) was reacted according to Procedure H to give the title compound (eluant: 5:1 chloroform-methanol) (0.02 g, 0.039 mmol).

m.p 89–94° C.

MS ((+)ESI, m/z): 511 [M+H]$^+$

Anal. calcd. for $C_{25}H_{33}F_3N_4O_4$+1.6 $H_2O$: C 64.73 H 7.24 N 9.74 found: C 65.15 H 7.9 N 9.57

EXAMPLE 14

4-(4-{2-[(2S)-2-Hydroxy-3-(4-hydroxy-phenoxy)-propylamino]-ethyl}-phenylamino)-piperidine-1-carboxylic Acid Diethylamide Step A. tert-Butyl 4-({1-[(diethylamino)carbonyl]-4-piperidinyl}amino) phenethylcarbamate The title compound (0.423 g, 1.01 mmol) was prepared from diethyl amine (0.585 g, 8.0 mmol) and {2-[4-(piperidin-4-ylamino)-phenyl]-ethyl}-carbamic acid tert-butyl ester ester (2.54 g, 8.0 mmol) according to Procedure C.

Step B. 4-[4-(2-Aminoethyl)anilino]-N N-diethyl-1-piperidinecarboxamide tert-Butyl 4-({1-[(diethylamino)carbonyl]-4-piperidinyl}amino)phenethyl-carbamate (0.423 g, 1.01 mmol) was reacted according to Procedure F to obtain the title compound (0.37 g, 1.01 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N,N-diethyl-1-piperidinecarboxamide 4-[4-(2-Aminoethyl)anilino]-N,N-diethyl-1-piperidinecarboxamide formate (0.37 g, 1.01 mmol) was reacted with tert-butyl-(4-oxiranylmethoxy-phenoxy)-diphenyl-silane silane (0.367 g, 0.909 mmol) according to Procedure G to give the title compound (eluant: 20:1 chloroform-methanol) (0.159 g, 0.22 mmol).

Step D. 4-(4-{2-[(2S)-2-Hydroxy-3-(4-hydroxy-phenoxy)-propylamino]-ethyl}-phenylamino)-piperidine-1-carboxylic acid diethylamide 4-[4-(2-{[(2S)-3-(4-{[tert-Butyl(diphenyl)silyl]oxy}phenoxy)-2-hydroxypropyl]amino}ethyl)anilino]-N,N-diethyl-1-piperidinecarboxamide (0.159 g, 0.22 mmol) was reacted according to Procedure H to give the title compound (eluant: 5:1 chloroform-methanol containing 1% ammonium hydroxide) (0.045 g, 0.09 mmol).

m.p 61–65° C.

MS ((+)ESI, m/z): 485 [M+H]$^+$

Anal. calcd. for $C_{27}H_{40}N_4O_4$+0.75 $H_2O$: C 65.10 H 8.40 N 11.25 found: C 65.09 H 8.12 N 11.17

EXAMPLE 15

4-(4-{2-[(2S)-2-Hydroxy-3-(4-hydroxy-phenoxy)-propylamino]-ethyl}-phenylamino)-piperidine-1-carboxylic Acid [2-(4-fluoro-phenyl)- ethyl]-amide Step A. tert-Butyl 4-[(1-{[(4-fluorophenethyl)amino]carbonyl}-4-piperidinyl)amino]phenethylcarbamate The title compound (0.98 g, 2.03 mmol) was prepared from 4-fluoro phenethyl amine hydrochloride (1.405 g, 8.0 mmol) and {2-[4-(piperidin-4-ylamino)-phenyl]-ethyl}-carbamic acid tert-butyl ester ester (2.54 g, 8.0 mmol) according to Procedure C.

Step B. 4-[4-(2-Aminoethyl)anilino]-N-(4-fluorophenethyl)-1-piperidinecarboxamide formate tert-Butyl 4-[(1-{[(4-fluorophenethyl)amino]carbonyl}-4-piperidinyl)amino]-phenethylcarbamate (0.98 g, 2.03 mmol) was reacted according to Procedure F to obtain the title compound (0.875, 2.03 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(4-fluorophenethyl)-1-piperidinecarboxamide 4-[4-(2-Aminoethyl)anilino]-N-(4-fluorophenethyl)-1-piperidinecarboxamide formate (0.875 g, 2.03 mmol) was reacted with tert-butyl-(4-oxiranylmethoxy-phenoxy)-diphenyl-silane silane (0.740 g, 1.86 mmol) according to Procedure G to give the title compound (eluant: 20:1 chloroform-methanol) (0.275 g, 0.35 mmol).

Step D. 4-(4-{2-[(2S)-2-Hydroxy-3-(4-hydroxy-phenoxy)-propylamino]-ethyl}-phenylamino)-piperidine-1-carboxylic acid [2-(4-fluoro-phenyl)- ethyl]-amide 4-[4-(2-{[(2S)-3-(4-{[tert-Butyl(diphenyl)silyl]oxy}phenoxy)-2-hydroxy-propyl]amino}ethyl)anilino]-N,N-diethyl-1-piperidinecarboxamide (0.275 g, 0.35 mmol) was reacted according to Procedure H to give the title compound (eluant: 5:1 chloroform-methanol containing 1% ammonium hydroxide) (0.095 g, 0.172 mmol).

m.p 73–77° C.

MS ((+)ESI, m/z): 551 [M+H]$^+$

Anal. calcd. for $C_{31}H_{39}FN_4O_4$+1.0 $H_2O$+0.1 $CHCl_3$: C 64.33 H 7.13 N 9.65 found: C 64.28 H 6.86 N 9.36

EXAMPLE 16

4-[4-(2-{[(2S)-3-(2-Chloro-4-hydroxyphenoxy)-2-hydroxypropyl]amino}ethyl)anilino]-N-octyl-1-piperidinecarboxamide Step A. 4-[4-(2-{[(2S)-3-(4-{[tert-butyl(diphenyl)silyl]oxy}-2-chlorophenoxy)-2-hydroxypropyl]amino}ethyl)anilino]-N-octyl-1-piperidinecarboxamide 4-[4-(2-Aminoethyl)anilino]-N-octyl-1-piperidinecarboxamide formate (0.57 g, 1.35 mmol) was reacted with tert-butyl(diphenyl)silyl 3-chloro-4-[(2S) oxiranyl-methoxy]phenyl ether (0.59 g, 1.35 mmol) according to Procedure G (eluant: 20:1 chloroform-methanol) to give the title compound (0.185 g, 0.23 mmol).

Step B. 4-[4-(2-{[(2S)-3-(2-Chloro-4-hydroxyphenoxy)-2 hydroxy-propyl]amino}ethyl)anilino]-N-octyl-1-piperidinecarboxamide 4-[4-(2-{[(2S)-3-(4-{[tert-Butyl(diphenyl)silyl]oxy}-2-chlorophenoxy)-2-hydroxypropyl]amino}ethyl)anilino]-N-octyl-1-piperidinecarboxamide(0.185 g, 0.23 mmol) was reacted according to Procedure H (eluant: 10:1 going to 5:1 chloroform-methanol containing 2% triethylamine) to give the title compound (0.053 g, 0.09 mmol).

m.p 61–65° C.
MS ((+)ESI, m/z): 575 [M+H]$^+$
Anal. calcd. for $C_{31}H_{47}ClN_4O_4$+0.6 $H_2O$: C 63.54 H 8.29 N 9.56 found: C 63.56 H 8.04 N 9.47

EXAMPLE 17

[4-(3-Cyclopentyloxy-4-methoxy-phenyl)-piperidin-1-yl]-[4-(4-{2-[(2S)-2-hydroxy-3-(4-hydroxy-phenoxy)-propylamino]-ethyl}-phenylamino)-piperidin-1-yl]-methanone Step A. tert-Butyl 4-{[1-({4-[3-(cyclopentyloxy)-4-methoxyphenyl]-1-piperidinyl}carbonyl)-4-piperidinyl]amino}phenethylcarbamate The title compound (0.546 g, 0.88 mmol) was prepared from 4-[3-(cyclopentyloxy)-4-methoxyphenyl]piperidine (1.10 g, 4.0 mmol) (U.S. Pat. No. 5,459,151) and {2-[4-(piperidin-4-ylamino)-phenyl]-ethyl}-carbamic acid tert-butyl ester (1.276 g, 4.0 mmol) according to Procedure C (eluant: 50:1 chloroform-methanol).

Step B. {4-[4-(2-Aminoethyl)anilino]-1-piperidinyl}[4-[3-(cyclopentyloxy)-4-methoxyphenyl]-1-piperidinyl}methanone formate tert-Butyl 4-{[1-({4-[3-(cyclopentyloxy)-4-methoxyphenyl]-1-piperidinyl}-carbonyl)-4-piperidinyl]amino}phenethylcarbamate (0.546 g, 0.88 mmol) was reacted according to the Procedure F to obtain the title compound (0.50 g, 0.88 mmol) which was used without further purification.

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}{4-3-(cyclopentyloxy)-4-methoxyphenyl]-1-piperidinyl}methanone {4-[4-(2-Aminoethyl)anilino]-1-piperidinyl}{4-[3-(cyclopentyloxy)-4-methoxyphenyl]-1-piperidinyl}methanone formate (0.50 g, 0.88 mmol) was reacted with tert-butyl-(4-oxiranylmethoxy-phenoxy)-diphenyl-silane (0.350 g, 0.88 mmol) according to Procedure G to yield (eluant: 20:1 chloroform-methanol) the title compound (0.168 g, 0.181 mmol)

Step D. [4-(3-Cyclopentyloxy-4-methoxy-phenyl)-piperidin-1-yl]-[4-(4-{2-[(2S)-2-hydroxy-3-(4-hydroxy-phenoxy)-propylamino]-ethyl}-phenylamino)- piperidin-1-yl]-methanone {4-[4-(2-{[(2S)-3-(4-{[tert-Butyl(diphenyl)silyl]oxy}phenoxy)-2-hydroxy-propyl]amino}ethyl)anilino]-1-piperidinyl}{4-[3-(cyclopentyloxy)-4-methoxyphenyl]-1-piperidinyl}methanone (0.168 g, 0.181 mmol) was reacted according to Procedure H to yield (eluant: 5:1 chloroform-methanol) the title compound (0.085 g, 0.123 mmol).

MP: 92–95° C.
MS ((+)ESI, m/z): 687 [M+H]$^+$
Anal. calcd. for $C_{40}H_{54}N_4O_6$+1.33 $H_2O$: C 67.59 H 8.03 N 7.88 found: C 67.52 H 7.89 N 7.55

EXAMPLE 18

4-(4-{2-[(2S)-2-Hydroxy-3-(4-hydroxy-phenoxy)-propylamino]-ethyl}-phenylamino)-piperidine-1-carboxylic Acid Amide Step A. tert-Butyl 4-[(1-{[(1,1,3-trimethylbutyl)amino]carbonyl}-4-piperidinyl)amino]phenethylcarbamate The title compound (1.3 g, 2.37 mmol) was prepared from 1,1-3,3-tetramethyl butyl isocyanate (0.971 g, 6.26 mmol) and {2-[4-(piperidin-4-ylamino)-phenyl]-ethyl}-carbamic acid tert-butyl ester ester (2.0 g, 6.26 mmol) according to Procedure E.

$^1$H NMR (DMSO-d$_6$, 300 MHz): d 1.00 (S, 9H), 1.2 (M, 4H), 1.32 (S, 6H), 1.4 (S, 9H), 1.75 (s, 2H), 1.84 (d, 2H), 2.80 (t, 2H), 3.08 (m, 2H), 3.90 (d, 2H), 5.35 (d, 1H), 5.60 (s, 1H), 6.50 (d, 2H), 6.80(t, 1H), 6.90(d, 2H).

Step B. 4-[4-(2-Aminoethyl)anilino]-1-piperidinecarboxamide formate tert-Butyl 4-[(1-{[(1,1,3-trimethylbutyl)amino]carbonyl}-4-piperidinyl)amino]-phenethylcarbamate (1.3 g, 2.37 mmol) was reacted according to Procedure F to obtain the title compound which was used without further purification.

Step C. 4-[4-(2-{[(2S)-3-(4-{[tert-Butyl(diphenyl)silyl]oxy}phenoxy)-2-hydroxypropl]amino}ethyl)anilino]-1-piperidinecarboxamide 4-[4-(2-Aminoethyl)anilino]-1-piperidinecarboxamide formate (0.76 g, 2.37 mmol) was reacted with tert-butyl-(4-oxiranylmethoxy-phenoxy)-diphenyl-silane (0.817 g, 2.02 mmol) according to Procedure G to give the title compound (eluant: 20:1 chloroform-methanol) (0.175 g, 0.26 mmol).

Step D. 4-(4-{2-[(2S)-2-Hydroxy-3-(4-hydroxy-phenoxy)-propylamino]-ethyl}-phenylamino)-piperidine-1-carboxylic acid amide 4-[4-(2-{[(2S)-3-(4-{[tert-Butyl(diphenyl)silyl]oxy}phenoxy)-2-hydroxy-propyl]amino}ethyl)anilino]-1-piperidinecarboxamide (0.175 g, 0.26 mmol) was reacted according to Procedure H to give the title compound (eluant: 5:1 chloroform-methanol containing 1% ammonium hydroxide) (0.02 g, 0.046 mmol).

m.p 84–89° C.
MS ((+)ESI, m/z): 429 [M+H]$^+$
Anal. calcd. for $C_{23}H_{32}N_4O_4$+1.0 $H_2O$: C 61.86 H 7.67 N 12.55 found: C 61.61 H 7.59 N 12.15

EXAMPLE 19

[4-(2-{(2S)-3-[4-(3-Ethyl-ureido)-phenoxy]-2-hydroxy-propylamino}-ethyl)-phenylamino]-piperidine-1-carboxylic Acid [2-(4-fluoro-phenyl)-ethyl]-amide 4-[4-(2-Aminoethyl)anilino]-N-(4-fluorophenethyl)-1-piperidinecarboxamide formate (0.30 g, 0.698 mmol) was reacted with N-ethyl-N'-{4-[(2S)oxiranylmethoxy]phenyl}urea (0.15 g, 0.635 mmol) according to Procedure G to give the title compound (eluant: 20:1 chloroform-methanol) (0.06 g, 0.096 mmol).

m.p 88–93° C.
MS ((+)APCI, m/z): 621 [M+H]$^+$
Anal. calcd. for $C_{34}H_{45}FN_6O_4$+1.5 $H_2O$: C 63.04 H 7.47 N 12.97 found: C 63.05 H 7.13 N 12.63

EXAMPLE 20

4-(4-{2-[(2S)-2-Hydroxy-3-(4-hydroxy-phenoxy)-propylamino]-ethyl}-phenylamino)-piperidine-1-carboxylic Acid 2,4-dichloro-benzylamide Step A. tert-Butyl 4-[(1-{[(2,4-dichlorobenzyl)amino]carbonyl}-4-piperidinyl)amino]phenethylcarbamate The title compound (0.33 g, 0.64 mmol) was prepared from 2,4-dichloro benzyl amine (0.704 g, 4.0 mmol and {2-[4-(piperidin-4-ylamino)-phenyl]-ethyl}-carbamic acid tert-butyl ester ester (1.276 g, 4.0 mmol) according to Procedure C.

¹H NMR (DMSO-d₆, 300 MHz): d 1.22 (m, 2H), 1.39 (s, 9H), 1.89 (d, 2H), 2.90 (t, 2H), 3.10 (m, 2H), 3.94 (m, 2H), 4.26 (d, 2H), 5.36 (d, 1H), 6.58 (m, 3h), 6.84 (t, 1H), 6.91 (d, 2H), 7.18 (t, 1H), 7.29 (d, 1H), 7.45 (dd, 1H), 7.65 (s, 1H)

Step B. 4-[4-(2-Aminoethyl)anilino]-N-(2,4-dichlorobenzyl)-1-piperidinecarboxamide formate tert-Butyl 4-[(1-{[(2,4-dichlorobenzyl)amino]carbonyl}-4-piperidinyl)amino]-phenethylcarbamate (0.33 g, 0.64 mmol) was reacted according to Procedure F to obtain the title compound (0.30 g, 0.64 mmol) which was used without further purification.

Step C. 4-[4-(2-{[(2S)-3-(4-{[tert-butyl(diphenyl)silyl]oxy}phenoxy)-2-hydroxypropyl]amino}ethyl)anilino]-N-(2,4-dichlorobenzyl)-1-piperidinecarboxamide 4-[4-(2-Aminoethyl)anilino]-N-(2,4-dichlorobenzyl)-1-piperidinecarboxamide formate (0.30 g, 0.64 mmol) was reacted with tert-butyl-(4-oxiranylmethoxy-phenoxy)-diphenyl-silane (0.233 g, 0.577 mmol) according to Procedure G to give the title compound (eluant: 20:1 chloroform-methanol) (0.145 g, 0.175 mmol).

Step D. 4-(4-{2-[(2S)-2-Hydroxy-3-(4-hydrox-phenoxy)-propylamino]-ethyl}-phenylamino)-piperidine-1-carboxylic acid 2,4-dichloro-benzylamide 4-[4-(2-{[(2S)-3-(4-{[tert-butyl(diphenyl)silyl]oxy}phenoxy)-2-hydroxy-propyl]amino}ethyl)anilino]-N-(2,4-dichlorobenzyl)-1-piperidinecarboxamide (0.145 g, 0.175 mmol) was reacted according to Procedure H to give the title compound (eluant: 5:1 chloroform-methanol ammonium (0.018 g, 0.03 mmol).

m.p 93–99° C.

MS ((+)ESI, m/z): 587 [M+H]⁺

Anal. calcd. for $C_{30}H_{36}Cl_2N_4O_4+1.25\ H_2O+0.26\ CH_4O$: C 58.77 H 6.44 N 9.06 found: C 58.65 H 6.32 N 8.92

EXAMPLE 21

4-(4-{2-[(2S)-2-Hydroxy-3-(4-hydroxy-phenoxy)-propylamino]-ethyl}-phenylamino)-piperidine-1-carboxylic Acid 3,4-dichloro-benzylamide Step A. tert-Butyl 4-[(1-{[(3,4-dichlorobenzyl)amino]carbonyl}-4-piperidinyl)amino]phenethylcarbamate The title compound (0.33 g, 0.64 mmol) was prepared from 3,4-dichioro benzyl amine (0.704 g, 4.0 mmol) and {2-[4-(piperidin-4-ylamino)-phenyl]-ethyl}-carbamic acid tert-butyl ester ester (1.276 g, 4.0 mmol) according to Procedure C.

¹H NMR (DMSO-d₆, 300 MHz): d 1.18 (m, 2H), 1.39 (s, 9H), 1.84 (d, 2H), 2.90 (m, 2H), 3.05 (m, 2H), 3.90 (m, 2H), 4.22 (d, 2H), 5.36 (d, 1H), 6.51 (m, 3h), 6.84 (t, 1H), 6.91 (d, 2H), 7.18 (t, 1H), 7.29 (dd, 1H), 7.55 (s, 1H), 7.65 (d, 1H)

Step B. 4-[4-(2-Aminoethyl)anilino]-N-(3,4-dichlorobenzyl)-1-piperidinecarboxamide formate tert-Butyl 4-[(1-{[(3,4-dichlorobenzyl)amino]carbonyl}-4-piperidinyl)amino]phenethylcarbamate (0.33 g, 0.64 mmol) was reacted according to Procedure F to obtain the title compound (0.30 g, 0.64 mmol) which was used without further purification.

Step C. 4-[4-(2-{[(2S)-3-(4-{Ftert-Butyl(diphenyl)silyl]oxy}phenoxy)-2-hydroxypropyl]amino}ethyl)anilino]-N-(2,3-dichlorobenzyl)-1-piperidinecarboxamide 4-[4-(2-Aminoethyl)anilino]-N-(3,4-dichlorobenzyl)-1-piperidinecarboxamide formate (0.30 g, 0.64 mmol) was reacted with tert-butyl-(4-oxiranylmethoxy-phenoxy)-diphenyl-silane (0.233 g, 0.577 mmol) according to Procedure G to give the title compound (eluant: 20:1 chloroform-methanol) (0.14 g, 0.17 mmol).

Step D. 4-(4-{2-[(2S)-2-Hydroxy-3-(4-hydroxy-phenoxy)-propylamino]-ethyl}-phenylamino)-piperidine-1-carboxylic acid 2,4-dichloro-benzylamide 4-[4-(2-{[(2S)-3-(4-{[tert-Butyl(diphenyl)silyl]oxy}phenoxy)-2-hydroxy-propyl]amino}ethyl)anilino]-N-(2,4-dichlorobenzyl)-1-piperidinecarboxamide (0.14 g, 0.17 mmol) was reacted according to Procedure H to give the title compound (eluant: 5:1 chloroform-methanol ammonium (0.026 g, 0.044 mmol).

m.p 94–97° C.

MS ((+)ESI, m/z): 587 [M+H]⁺

Anal. calcd. for $C_{30}H_{36}Cl_2N_4O_4+1.75\ H_2O$: C 58.20 H 6.43 N 9.05 found: C 58.07 H 6.32 N 8.81

EXAMPLE 22

4-(4-{2-[(2S)-2-Hydroxy-3-(4-methanesulfonylamino-phenoxy)-propylamino]-ethyl}-phenylamino)-piperidine-1-carboxylic Acid Octylamide 4-[4-(2-Aminoethyl)anilino]-N-octyl-1-piperidinecarboxamide (0.245 g, 0.58 mmol) was reacted with N-(4-[(2S)oxiranylmethoxy]phenyl)methanesulfonamide (0.13 g, 0.53 mmol) according to Procedure G (eluant: 20:1 chloroform-methanol) to give the title compound (0.04 g, 0.064mmol).

m.p 89–95° C.

MS ((+)ESI, m/z): 618 [M+H]⁺

Anal. calcd. for $C_{32}H_{51}N_5O_5S +1.0\ H_2O$: C 60.45 H 8.40 N 11.01 found: C 60.51 H 8.41 N 10.9

EXAMPLE 23

4-(4-{2-[(2S)-2-Hydroxy-3-(4-hydroxy-phenoxy)-propylamino]-ethyl}-phenylamino)-piperidine-1-carboxylic Acid (3-thiophen-2-yl-propyl)-amide Step A. tert-Butyl 4-{[1-({[3-(2-thienyl)propyl]amino}carbonyl)-4-piperidinyl]amino}phenethylcarbamate The title compound (0.353 g, 0.67 mmol) was prepared form 4-(2-thienyl) butyric acid (0.319 g, 1.87 mmol) and {2-[4-(piperidin-4-ylamino)-phenyl]-ethyl}-carbamic acid tert-butyl ester (0.60 g, 1.87 mmol) according to Procedure D.

MS ((+)ESI, m/z): 487 [M+H]⁺

Step B. 4-[4-(2-Aminoethyl)anilino]-N-[3-(2-thienyl)propyl]-1-piperidinecarboxamide formate tert-Butyl 4-{[1-({[3-(2-thienyl)propyl]amino}carbonyl)-4-piperidinyl]-amino}phenethylcarbamate (0.353 g, 0.67 mmol) was reacted according to Procedure F to provide the title compound (0.33 g, 0.67 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-[3-(2-thienyl)propyl]-1-piperidinecarboxamide 4-[4-(2-Aminoethyl)anilino]-N-[3-(2-thienyl)propyl]-1-piperidinecarboxamide formate (0.33 g, 0.67 mmol) was reacted with tert-butyl-(4-oxiranylmethoxy-phenoxy)-diphenyl-silane (0.275 g, 0.686 mmol) according to Procedure G (eluant: 20:1 chloroform-methanol) to give the title compound (0.182 g, 0.230 mmol).

Step D. 4-(4-{2-[(2S)-2-Hydroxy-3-(4-hydroxy-phenoxy)-propylamino]-ethyl}-phenylamino)-piperidine-1-carboxylic acid (3-thiophen-2-yl-propyl)-amide 4-[4-(2-{[(2S)-3-(4-{[tert-Butyl(diphenyl)silyl]oxy}phenoxy)-2-hydroxy-propyl]amino}ethyl)anilino]-N-[3-(2-thienyl)propyl]-1-piperidinecarboxamide (0.182 g, 0.230 mmol) was reacted according to Procedure H (eluant: 5:1 chloroform-methanol containing 1% ammonium hydroxide) to give the title compound (0.05 g, 0.095 mmol)

m.p 73–77° C.

MS ((+)ESI, m/z): 553 [M+H]+

Anal. calcd. for $C_{30}H_{40}N_4O_4S+0.5\ H_2O+0.3\ CHCl_3$: C 60.90 H 6.97 N 9.38 found: C 60.86 H 6.77 N 9.23

EXAMPLE 24

4-(4-{2-[(2S)-2-Hydroxy-3-(4-hydroxy-phenoxy)-propylamino]-ethyl}-phenylamino)-piperidine-1-carboxylic Acid 3,5-difluoro-benzylamide Step A. tert-Butyl 4-[(1-{[(3,5-difluorobenzyl)amino]carbonyl}-4-piperidinyl)amino]phenethylcarbamate The title compound (0.371 g, 0.76 mmol) was prepared from 3,5-difluoro acetic acid (0.322 g, 1.87 mmol) and {2-[4-(piperidin-4-ylamino)-phenyl]-ethyl}-carbamic acid tert-butyl ester (0.60 g, 1.87 mmol) according to Procedure D.

MS ((+)ESI, m/z): 489 [M+H]+

Step B. 4-[4-(2-Aminoethyl)anilino]-N-(3,5-difluorobenzyl)-1-piperidinecarboxamide formate tert-Butyl 4-[(1-{[(3,5-difluorobenzyl)amino]carbonyl}-4-piperidinyl)amino]phenethylcarbamate (0.371 g, 0.76 mmol) was reacted according to Procedure F to provide the title compound (0.33 g, 0.76 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(3,5-difluorobenzyl)-1-piperidinecarboxamide 4-[4-(2-Aminoethyl)anilino]-N-(3,5-difluorobenzyl)-1-piperidinecarboxamide formamide (0.33 g, 0.76 mmol) was reacted with tert-butyl-(4-oxiranylmethoxy-phenoxy)-diphenyl-silane (0.276 g, 0.68 mmol) according to Procedure G (eluant: 20:1 chloroform-methanol) to give the title compound (0.165 g, 0.20 mmol).

Step D. 4-(4-{2-[(2S)-2-Hydroxy-3-(4-hydroxy-phenoxy)-propylamino]-ethyl}-phenylamino)-piperidine-1-carboxylic acid 3,5-difluoro-benzylamide 4-[4-(2-{[(2S)-3-(4-{[tert-Butyl(diphenyl)silyl]oxy}phenoxy)-2-hydroxy-propyl]amino}ethyl)anilino]-N-(3,5-difluorobenzyl)-1-piperidinecarboxamide (0.165 g, 0.20 mmol) was reacted according to Procedure H (eluant: 5:1 chloroform-methanol containing 1% ammonium hydroxide) to give the title compound (0.05 g, 0.095 mmol) m.p 89–95° C.

MS ((+)ESI, m/z): 555 [M+H]+

Anal. calcd. for $C_{30}H_{36}F_2N_4O_4+1.25\ H_2O+0.10\ CHCl_3$: C 61.37 H 6.60 N 9.51 found: C 61.36 H 6.39 N 9.3

EXAMPLE 25

4-(4-{2-[(2S)-2-Hydroxy-3-(4-hydroxy-phenoxy)-propylamino]-ethyl}-phenylamino)-piperidine-1-carboxylic Acid 2,3-dimethoxy-benzylamide Step A. tert-Butyl 4-[(1-{[(2,3-dimethoxybenzyl)amino]carbonyl}-4-piperidinyl)amino]phenethylcarbamate The title compound (0.32 g, 0.64 mmol) was prepared from 2,3-dimethoxy benzyl amine (0.668 g, 4.0 mmol) and {2-[4-(piperidin-4-ylamino)-phenyl]-ethyl}-carbamic acid tert-butyl ester (1.276 g, 4.0 mmol) according to Procedure C.

Step B. 4-[4-(2-Aminoethyl)anilino]-N-(2,3-dimethoxybenzyl)-1-piperidinecarboxamide formate tert-Butyl 4-[(1-{[(2,3-dimethoxybenzyl)amino]-carbonyl}-4-piperidinyl)-amino]phenethylcarbamate (0.32 g, 0.64 mmol) was reacted according to Procedure F to provide the title compound (0.30 g, 0.64 mmol) which was used without further purification.

Step C 4-[4-(2-{[(2S)-3-(4-{[tert-Butyl(diphenyl)silyl]oxy}phenoxy)-2-hydroxypropyl]amino}ethyl)anilino]-N-(2,3-dimethoxybenzyl)-1-piperidinecarboxamide 4-[4-(2-Aminoethyl)anilino]-N-(2,3-dimethoxybenzyl)-1-piperidine-carboxamide formate (0.30 g, 0.64 mmol) was reacted with tert-butyl-(4-oxiranylmethoxy-phenoxy)-diphenyl-silane (0.238 g, 0.588 mmol) according to Procedure G (eluant: 20:1 chloroform-methanol) to give the title compound (0.163 g, 0.20 mmol).

Step D. 4-(4-{2-[(2S)-2-Hydroxy-3-(4-hydroxy-phenoxy)-propylamino]-ethyl}-phenylamino)-piperidine-1-carboxylic acid 4-fluoro-benzylamide 4-[4-(2-{[(2S)-3-(4-{[tert-Butyl(diphenyl)silyl]oxy}phenoxy)-2-hydroxy-propyl]amino}ethyl)anilino]-N-(2,3-dimethoxybenzyl)-1-piperidinecarboxamide ((0.163 g, 0.20 mmol) was reacted according to Procedure H (eluant: 5:1 chloroform-methanol containing 1% ammonium hydroxide) to give the title compound (0.035 g, 0.06 mmol) m.p 87–91° C.

MS ((+)ESI, m/z): 579 [M+H]+

Anal. calcd. for $C_{32}H_{42}N_4O_6+1.75\ H_2O$: C 62.98 H 7.52 N 9.18 found: C 62.87 H 7.45 N 8.92

EXAMPLE 26

4-(4-{2-[(2S)-2-Hydroxy-3-(4-hydroxy-phenoxy)-propylamino]-ethyl}-phenylamino)-piperidine-1-carboxylic Acid 2-fluoro-benzylamide Step A. tert-Butyl 4-[(1-{[(2-fluorobenzyl)amino]carbonyl}-4-piperidinyl)amino]phenethylcarbamate The title compound (0.56 g, 1.2 mmol) was prepared from 2-fluoro benzyl amine (0.50 g, 4.0 mmol) and {2-[4-(piperidin-4-ylamino)-phenyl]-ethyl}-carbamic acid tert-butyl ester (1.276 g, 4.0 mmol) according to Procedure C.

Step B. 4-[4-(2-Aminoethyl)anilino]-N-(2-fluorobenzyl)-1-piperidinecarboxamide formate tert-Butyl 4-[(1-{[(2-fluorobenzyl)amino]carbonyl}-4-piperidinyl)amino]phenethylcarbamate formate (0.56 g, 1.2 mmol) was reacted according to Procedure F to provide the title compound (0.50 g, 1.2 mmol) which was used without further purification.

Step C. 4-[4-(2-{[(2S)-3-(4-{[tert-Butyl (diphenyl)silyl]oxy}phenoxy)-2-hydroxypropyl]amino}ethyl)anilino]-N-(2-fluorobenzyl)-1-piperidinecarboxamide 4-[4-(2-Aminoethyl)anilino]-N-(2-fluorobenzyl)-1-piperidinecarboxamide (0.50 g, 1.2 mmol) was reacted with tert-butyl-(4-oxiranylmethoxy-phenoxy)-diphenyl-silane (0.436 g, 1.08 mmol) according to Procedure G (eluant: 20:1 chloroform-methanol) to give the title compound (0.21 g, 0.27 mmol).

Step D. 4-(4-{2-[(2S)-2-Hydroxy-3-(4-hydroxy-phenoxy)-propylamino]-ethyl}-phenylamino)-piperidine-1-carboxylic acid 2-fluoro-benzylamide 4-[4-(2-{[(2S)-3-(4-{[tert-Butyl(diphenyl)silyl]oxy}phenoxy)-2-hydroxy-propyl]amino}ethyl)anilino]-N-(2-fluorobenzyl)-1-piperidinecarboxamide (0.21 g, 0.27 mmol) was reacted according to Procedure H (eluant: 5:1 chloroform-methanol containing 1% ammonium hydroxide) to give the title compound (0.085 g, 0.15 mmol) m.p 79–84° C.

MS ((+)APCI, m/z): 537[M+H]+

Anal. calcd. for $C_{30}H_{37}FN_4O_4+1.25\ H_2O+0.1\ C_2H_6O$: C 63.83 H 7.20 N 9.86 found: C 63.77 H 6.88 N 9.63

EXAMPLE 27

4-(4-{2-[(2S)-2-Hydroxy-3-(4-hydroxy-phenoxy)-propylamino]-ethyl}-phenylamino)-piperidine-1-carboxylic Acid 3-fluoro-benzylamide Step A. tert-Butyl 4-[(1-{[(3-fluorobenzyl)amino]carbonyl}-4-piperidinyl)amino]phenethylcarbamate The title compound (0.56 g, 1.2 mmol) was prepared from 3-fluoro benzyl amine (0.50 g, 4.0 mmol) and {2-[4-(piperidin-4-ylamino)-phenyl]-ethyl}-carbamic acid tert-butyl ester (1.276 g, 4 mmol) according to Procedure C.
Step B. 4-[4-(2-Aminoethyl)anilino]-N-(3-fluorobenzyl)-1-piperidinecarboxamide formate tert-Butyl 4-[(1-{[(3-fluorobenzyl)amino]carbonyl}-4-piperidinyl)amino]phenethylcarbamate (0.56 g, 1.2 mmol) was reacted according to Procedure F to provide the title compound (0.50 g, 1.2 mmol) which was used without further purification.
Step C. 4-[4-(2-{[(2S)-3-(4-{[tert-Butyl(diphenyl)silyl]oxy}phenoxy)-2-hydroxypropyl]amino}ethyl)anilino]-N-(3-fluorobenzyl)-1-piperidinecarboxamide 4-[4-(2-Aminoethyl)anilino]-N-(3-fluorobenzyl)-1-piperidinecarboxamide formate (0.50 g, 1.20 mmol) was reacted with tert-butyl-(4-oxiranylmethoxy-phenoxy)-diphenyl-silane (0.436 g, 1.08 mmol) according to Procedure G (eluant: 20:1 chloroform-methanol) to give the title compound (0.174 g, 0.225 mmol).
Step D. 4-(4-{2-[(2S)-2-Hydroxy-3-(4-hydroxy-phenoxy)-propylamino]-ethyl}-phenylamino)-piperidine-1-carboxylic acid 3-fluoro-benzylamide 4-[4-(2-{[(2S)-3-(4-{[tert-Butyl(diphenyl)silyl]oxy}phenoxy)-2-hydroxy-propyl]amino}ethyl)anilino]-N-(3-fluorobenzyl)-1-piperidinecarboxamide (0.174 g, 0.225 mmol) was reacted according to Procedure H (eluant: 5:1 chloroform-methanol containing 1% ammonium hydroxide) to give the title compound (0.085 g, 0.15 mmol).
m.p 68–73° C.
MS ((+)ESI, m/z): 537 [M+H]$^+$
Anal. calcd. for $C_{30}H_{37}FN_4O_4$+1.5 $H_2O$+0.3 $CHCl_3$: C 60.71 H 6.78 N 9.35 found: C 60.33 H 6.41 N 8.95

EXAMPLE 28

4-(4-{2-[(2S)-2-Hydroxy-3-(4-hydroxy-phenoxy)-propylamino]-ethyl}-phenylamino)-piperidine-1-carboxylic Acid (3-oxo-3-p-tolyl-propyl-amide Step A. tert-Butyl 4-{[1-({[3-(4-methylphenyl)-3-oxopropyl]amino}carbonyl)-4-piperidinyl]amino}phenethylcarbamate The title compound (0.508 g, 1.0 mmol) was prepared from 3-(4-methylbenzoyl)propionic acid (0.721 g, 3.76 mmol) and {2-[4-(piperidin-4-ylamino)-phenyl]-ethyl}-carbamic acid tert-butyl ester (1.2 g, 3.67 mmol) according to Procedure D.
Step B. 4-[4-(2-Aminoethyl)anilino]-N-[3-(4-methylphenyl)-3-oxopropyl]-1-piperidinecarboxamide formate tert-Butyl 4-{[1-({[3-(4-methylphenyl)-3-oxopropyl]amino}carbonyl)-4-piperidinyl]amino}phenethylcarbamate foramte (0.508 g, 1.0 mmol) was reacted according to Procedure F to provide the title compound (0.45 g, 1.0 mmol) which was used without further purification.
Step C. 4-[4-(2-{[(2S)-3-(4-{[tert-Butyl(diphenyl)silyl]oxy}phenoxy)-2-hydroxypropyl]amino}ethyl)anilino]-N-[3-(4-methylphenyl)-3-oxopropyl]-1-piperidinecarboxamide 4-[4-(2-Aminoethyl)anilino]-N-[3-(4-methylphenyl)-3-oxopropyl]-1-piperidinecarboxamide (0.45 g, 1.0 mmol) was reacted with tert-butyl-(4-oxiranylmethoxy-phenoxy)-diphenyl-silane (0.40 g, 1.0 mmol) according to Procedure G (eluant: 20:1 chloroform-methanol) to give the title compound (0.16 g, 0.196 mmol).
Step D. 4-(4-{2-[(2S)-2-Hydroxy-3-(4-hydroxy-phenoxy)-propylamino]-ethyl}-phenylamino)-piperidine-1-carboxylic acid (3-oxo-3-p-tolyl-propyl-amide 4-[4-(2-{[(2S)-3-(4-{[tert-Butyl(diphenyl)silyl]oxy}phenoxy)-2-hydroxy-propyl]amino}ethyl)anilino]-N-[3-(4-methylphenyl)-3-oxopropyl]-1-piperidinecarboxamide (0.160g, 0.196 mmol) was reacted according to Procedure H (eluant: 5:1 chloroform-methanol containing 1% ammonium hydroxide) to give the title compound (0.038 g, 0.066 mmol).
m.p 85–89° C.
MS ((−)APCI, m/z): 573 [M−H]$^-$
Anal. calcd. for $C_{33}H_{42}N_4O_5$+1.22 $H_2O$+0.01 $CHCl_3$: C 66.09 H 7.80 N 9.34 found: C 65.72 H 7.4 N 9.06

EXAMPLE 29

4-(4-{2-[(2S)-2-Hydroxy-3-(4-hydroxy-phenoxy)-propylamino]-ethyl}-phenylamino)-piperidine-1-carboxylic Acid (3-p-tolyl-propyl)-amide Step A. tert-Butyl 4-{[1-({[3-(4-methylphenyl)propyl]amino}carbonyl)-4-piperidinyl]amino}phenethylcarbamate The title compound (0.494 g, 1.0 mmol) was prepared from 4-(p-tolyl)buytric acid (0.67 g, 3.76 mmol) and {2-[4-(piperidin-4-ylamino)-phenyl]-ethyl}-carbamic acid tert-butyl ester (1.2 g, 3.76 mmol) according to Procedure D.
$^1$H NMR (DMSO-d$_6$, 300 MHz): d 1.18 (m, 2H), 1.39 (s, 9H), 1.70 (m, 2H), 1.84 (d, 2H), 2.28 (s, 3H), 2.90 (m, 2H), 3.11 (m, 2H), 3.90 (m, 2H), 5.29 (d, 1H), 6.51 (m, 3h), 6.80 (t, 1H), 6.85 (d, 2H), 7.15 (s, 3H).
Step B. 4-[4-(2-Aminoethyl)anilino]-N-[3-(4-methylphenyl)propyl]-1-piperidinecarboxamide formate tert-Butyl 4-{[1-({[3-(4-methylphenyl)propyl]amino}carbonyl)-4-piperidinyl]amino}phenethylcarbamate (0.494g, 1.0 mmol) was reacted according to Procedure F to provide the title compound (0.44 g, 1.0 mmol) which was used without further purification.
Step C. 4-[4-(2-{[(2S)-3-(4-{[tert-Butyl(diphenyl)silyl]oxy}phenoxy)-2-hydroxypropyl]amino}ethyl)anilino]-N-[3-(4-methylphenyl)propyl]-1-piperidinecarboxamide 4-[4-(2-Aminoethyl)anilino]-N-[3-(4-methylphenyl)propyl]-1-piperidine-carboxamide foramte (0.44 g, 1.0 mmol) was reacted with tert-butyl-(4-oxiranylmethoxy-phenoxy)-diphenyl-silane (0.40 g, 1.0 mmol) according to Procedure G (eluant: 20:1 chloroform-methanol) to give the title compound (0.185 g, 0.23 mmol).
Step D. 4-(4-{2-[(2S)-2-Hydroxy-3-(4-hydroxy-phenoxy)-propylamino]-ethyl}-phenylamino)-piperidine-1-carboxylic acid (3-oxo-3-p-tolyl-propyl-amide 4-[4-(2-{[(2S)-3-(4-{[tert-Butyl(diphenyl)silyl]oxy}phenoxy)-2-hydroxy-propyl]amino}ethyl)anilino]-N-[3-(4-methylphenyl)propyl]-1-piperidine-carboxamide (0.185 g, 0.23 mmol) was reacted according to Procedure H (eluant: 5:1 chloroform-methanol containing 1% ammonium hydroxide) to give the title compound (0.058 g, 0.1 mmol)
m.p 69–72° C.
MS ((+)ESI, m/z): 561 [M+H]$^+$
Anal. calcd. for $C_{33}H_{44}N_4O_4$+1.50 $H_2O$+0.28 $CHCl_3$: C 64.35 H 7.67 N 9.02 found: C 64.45 H 7.35 N 8.76

EXAMPLE 30

4-(4-{2-[(2S)-2-Hydroxy-3-(4-hydroxy-phenoxy)-propylamino]-ethyl}-phenylamino)-piperidine-1-carboxylic Acid [2-(4-ethyl-phenyl)-ethyl]-amide Step A. tert-Butyl 4-[(1-{[(4-ethylphenethyl)amino]carbonyl}-4-piperidinyl)amino]phenethylcarbamate The title compound (0.642 g, 1.3 mmol) was prepared from 3-(4-ethyl-phenyl) propionic acid (0.67 g, 3.76 mmol) and {2-[4-(piperidin-4-ylamino)-phenyl]-ethyl}-carbamic acid tert-butyl ester (1.20 g, 3.76 mmol) according to Procedure D.

Step B. 4-[4-(2-Aminoethyl)anilino]-N-(4-ethylphenethyl)-1-piperidinecarboxamide formate tert-Butyl 4-[(1-{[(4-ethylphenethyl)amino]carbonyl}-4-piperidinyl)amino]-phenethyl carbamate (0.642 g, 1.3 mmol) was reacted according to Procedure F to provide the title compound (0.60 g, 1.3 mmol) which was used without further purification.

MS ((+)APCI, m/z): 394 [M+H]$^+$

Step C. 4-[4-(2-{[(2S)-3-(4-{[tert-Butyl(diphenyl)silyl]oxy}phenoxy)-2-hydroxypropyl]amino}ethyl)anilino]-N-(4-ethylphenethyl)-1-piperidinecarboxamide 4-[4-(2-Aminoethyl)anilino]-N-(4-ethylphenethyl)-1-piperidinecarboxamide formate (0.60 g, 1.3 mmol) was reacted with tert-butyl-(4-oxiranylmethoxy-phenoxy)-diphenyl-silane (0.55 g, 1.3 mmol) according to Procedure G (eluant: 20:1 chloroform-methanol) to give the title compound (0.295 g, 0.369 mmol).

Step D. 4-(4-{2-[(2S)-2-Hydroxy-3-(4-hydroxy-phenoxy)-propylamino]-ethyl}-phenylamino)-piperidine-1-carboxylic acid [2-(4-ethyl-phenyl)-ethyl]-amide 4-[4-(2-{[(2S)-3-(4-{[tert-Butyl(diphenyl)silyl]oxy}phenoxy)-2-hydroxy-propyl]amino}ethyl)anilino]-N-(4-ethylphenethyl)-1-piperidinecarboxamide (0.295 g, 0.369 mmol) -was reacted according to Procedure H (eluant: 5:1 chloroform-methanol containing 1% ammonium hydroxide) to give the title compound (0.078 g, 0.13 mmol).

m.p 79–81° C.

MS ((+)ESI, m/z): 561 [M+H]$^+$

Anal. calcd. for $C_{33}H_{44}N_4O_4$+0.5 $H_2O$: C 69.57 H 7.96 N 9.83 found: C 69.57 H 7.94 N 9.78

EXAMPLE 31

4-(4-{2-[(2S)-2-Hydroxy-3-(4-hydroxy-phenoxy)-propylamino]-ethyl}-phenylamino)-piperidine-1-carboxylic Acid (2,2-diphenyl-ethyl)-amide Step A. tert-Butyl 4-[(1-{[(2,2-diphenylethyl)amino]carbonyl}-4-piperidinyl)amino]phenethylcarbamate The title compound (0.662 g, 1.2 mmol) was prepared from 3,3 diphenyl-propionic acid (0.85 g, 3.76 mmol) and {2-[4-(piperidin-4-ylamino)-phenyl]-ethyl}-carbamic acid tert-butyl ester (1.20 g, 3.76 mmol) according to Procedure D.

Step B. 4-[4-(2-Aminoethyl)anilino]-N-(2,2-diphenylethyl)-1-piperidinecarboxamide formate tert-Butyl 4-[(1-{[(2,2-diphenylethyl)amino]carbonyl}-4-piperidinyl)-amino]-phenethyl carbamate (0.662 g, 1.2 mmol) was reacted according to Procedure F to provide the title compound (0.60 g, 1.2 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(2,2-diphenylethyl)-1-piperidinecarboxamide 4-[4-(2-Aminoethyl)anilino]-N-(2,2-diphenylethyl)-1-piperidinecarboxamide formate (0.60 g, 1.2 mmol) was reacted with tert-butyl-(4-oxiranylmethoxy-phenoxy)-diphenyl-silane (0.496 g, 1.2 mmol) according to Procedure G (eluant: 20:1 chloroform-methanol) to give the title compound (0.20 g, 0.236 mmol).

Step D. 4-(4-{2-[(2S)-2-Hydroxy-3-(4-hydroxy-phenoxy)-propylamino]-ethyl}-phenylamino)-piperidine-1-carboxylic acid (2,2-diphenyl-ethyl)-amide 4-[4-(2-{[(2S)-3-(4-{[tert-Butyl(diphenyl)silyl]oxy}phenoxy)-2-hydroxypropyl]amino}ethyl)anilino]-N-(2,2-diphenylethyl)-1-piperidinecarboxamide (0.20 g, 0.236 mmol) was reacted according to Procedure H (eluant: 5:1 chloroform-methanol containing 1% ammonium hydroxide) to give the title compound (0.095 g, 0.15 mmol)

m.p 91–94° C.

MS ((+)ESI, m/z): 609 [M+H]$^+$

Anal. calcd. for $C_{37}H_{44}N_4O_4$+1.0 $H_2O$: C 70.9 H 7.4 N 8.94 found: C 70.88 H 7.22 N 8.94

EXAMPLE 32

4-(4-{2-[(2S)-2-Hydroxy-3-(4-hydroxy-phenoxy)-propylamino]-ethyl}-phenylamino)-piperidine-1-carboxylic Acid 2,6-difluoro-benzylamide Step A. tert-Butyl 4-[(1-{[(2,6-difluorobenzyl)amino]carbonyl}-4-piperidinyl)amino]phenethylcarbamate The title compound (0.56 g, 1.15 mmol) was prepared from 2,6-difluoro benzyl amine (0.572 g, 4.0 mmol) and {2-[4-(piperidin-4-ylamino)-phenyl]-ethyl}-carbamic acid tert-butyl ester (1.276 g, 4.0 mmol) according to Procedure C.

$^1$H NMR (DMSO-d$_6$, 300 MHz): d 1.18 (m, 2H), 1.40 (s, 9H), 1.86 (d, 2H), 2.90 (t, 2H), 3.08 (q, 2H), 3.88 (d, 2H), 4.31 (d, 2H), 5.27 (d, 1H), 6.46 (d, 2h), 6.85 (m, 4H), 7.09 (t, 2H), 7.39 (m, 1H)

Step B. 4-[4-(2-Aminoethyl)anilino]-N-(2,6-difluorobenzyl)-1-piperidinecarboxamide formate tert-Butyl 4-[(1-{[(2,6-difluorobenzyl)amino]carbonyl}-4-piperidinyl)amino]phenethyl carbamate (0.56 g, 1.15 mmol) was reacted according to Procedure F to provide the title compound (0.50 g, 1.15 mmol) which was used without further purification.

MS ((+)APCI, m/z): 389 [M+H]$^+$

Step C. 4-[4-(2-{[(2S)-3-(4-{[tert-Butyl(diphenyl)silyl]oxy}phenoxy)-2-hydroxypropyl]amino}ethyl)anilino]-N-(2,6-difluorobenzyl)-1-piperidinecarboxamide 4-[4-(2-Aminoethyl)anilino]-N-(2,6-difluorobenzyl)-1-piperidinecarboxamide formate (0.50 g, 1.15 mmol) was reacted with tert-butyl-(4-oxiranylmethoxy-phenoxy)-diphenyl-silane (0.465 g, 1.15 mmol) according to Procedure G (eluant: 20:1 chloroform-methanol) to give the title compound (0.192 g, 0.24 mmol).

Step D. 4-(4-{2-[(2S)-2-Hydroxy-3-(4-hydroxy-phenoxy)-propylamino]-ethyl}-phenylamino)-pipieridine-1-carboxylic acid 2,6-difluoro-benzylamide 4-[4-(2-{[(2S)-3-(4-{[tert-Butyl(diphenyl)silyl]oxy}phenoxy)-2-hydroxypropyl]amino}ethyl)anilino]-N-(2,6-difluorobenzyl)-1-piperidinecarboxamide (0.192 g, 0.24 mmol) was reacted according to Procedure H (eluant: 5:1 chloroform-methanol containing 1% ammonium hydroxide) to give the title compound (0.085 g, 0.15 mmol).

m.p 80–84° C.

MS ((+)ESI, m/z): 555 [M+H]$^+$

Anal. calcd. for $C_{30}H_{36}F_2N_4O_4$+0.75 $H_2O$+0.25 $CHCl_3$: C 60.76 H 6.36 N 9.37 found: C 60.66 H 6.19 N 9.11

EXAMPLE 33

4-(4-{2-[(2S)-2-Hydroxy-3-(4-hydroxy-phenoxy)-propylamino]-ethyl}-phenylamino)-piperidine-1-carboxylic Acid 2-trifluoromethyl-benzylamide Step A. tert-Butyl 4-{[1-({[2-(trifluoromethyl)benzyl]amino}carbonyl)-4-piperidinyl]amino}phenethylcarbamate The title compound (0.56 g, 1.07 mmol) was prepared from 2-trifluoromethyl-benzyl amine (0.70 g, 4.0 mmol) and {2-[4-(piperidin-4-ylamino)-phenyl]-ethyl}-carbamic acid tert-butyl ester (1.276 g, 4.0 mmol) according to Procedure C.

Step B. 4-[4-(2-Aminoethyl)anilino]-N-[2-(trifluoromethyl)benzyl]-1-piperidinecarboxamide formate tert-Butyl 4-{[1-({[2-(trifluoromethyl)benzyl]amino}carbonyl)-4-piperidinyl]amino}phenethylcarbamate (0.56 g, 1.07 mmol) was reacted according to Procedure F to provide the title compound (0.50 g, 1.07 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-[2-(trifluoromethyl)benzyl]-1-piperidinecarboxamide formate 4-[4-(2-Aminoethyl)anilino]-N-[2-(trifluoromethyl)benzyl]-1-piperidinecarboxamide formate (0.50 g, 1.07 mmol) was reacted with tert-butyl-(4-oxiranylmethoxy-phenoxy)-diphenyl-silane (0.433 g, 1.07 mmol) according to Procedure G (eluant: 20:1 chloroform-methanol) to give the title compound (0.211 g, 0.24 mmol).

Step D. 4-(4-{2-[(2S)-2-Hydroxy-3-(4-hydroxy-phenoxy)-propylamino]-ethyl}-phenylamino)-piperidine-1-carboxylic acid 2-trifluoromethyl-benzylamide 4-[4-(2-{[(2S)-3-(4-{[tert-Butyl(diphenyl)silyl]oxy}phenoxy)-2-hydroxypropyl]amino}ethyl)anilino]-N-[2-(trifluoromethyl)benzyl]-1-piperidinecarboxamide (0.211 g, 0.24 mmol) was reacted according to Procedure H (eluant: 5:1 chloroform-methanol containing 1% ammonium hydroxide) to give the title compound (0.085 g, 0.14 mmol).
m.p 83–86° C.
MS ((+)ESI, m/z): 587 [M+H]+
Anal. calcd. for $C_{31}H_{37}F_3N_4O_4$+1.0 $H_2O$+0.1 $C_2H_6O$: C 61.51 H 6.55 N 9.20 found: C 61.21 H 6.27 N 9.34

EXAMPLE 34

4-(4-{2-[(2S)-2-Hydroxy-3-(4-hydroxy-phenoxy)-propylamino]-ethyl}-phenylamino)-piperidine-1-carboxylic Acid 4-pyrazol-1-yl-2-trifluoromethyl-benzylamide Step A. 4-(1H-Pyrazol-1-yl)-2-(trifluoromethyl)benzonitrile To a suspension of sodium hydride (1.13 g (60% in oil), 27 mmol) in anhydrous N,N-dimethylformamide (75 mL) was added drop-wise pyrazole (1.75 g, 25.6 mmol) in anhydrous N,N-dimethylformamide (25 mL). After 30 minutes 4-fluoro-2-(trifluoromethyl)-benzonitrile (4.85 g, 25.6 mmol) was added and the solution stirred overnight at 100° C. The solvent was removed in vacuo and the residue partitioned between water and dichloromethane. The organic layer was washed with 1 N sodium hydroxide, water, brine, and dried over anhydrous magnesium sulfate. The organic layer was filtered and the solvent evaporated in vacuo to give the title compound (0.75 g, 3.16 mmol).
MS ((+)ESI, m/z): 237 [M+H]+
$^1$H NMR (DMSO-$d_6$, 300 MHz): d 6.75 (m, 1H), 7.99 (s, 1H), 8.40 (m, 3H), 8.92 (s, 1H)

Step B. 4-(1H-Pyrazol-1-yl)-2-(trifluoromethyl)benzylamine

To a solution of 4-(1H-pyrazol-1-yl)-2-(trifluoromethyl)benzonitrile (0.75 g, 3.16 mmol) in anhydrous diethyl ether (10 mL) was added drop-wise lithium aluminum hydride in anhydrous tetrahydrofuran (3.47 mL, 1M in tetrahydrofuran, 3.47 mmol). The mixture was heated to reflux for 2 hours and allowed to stand overnight at ambient temperature. Water (1.44 mL), 15% sodium hydroxide (1.44 mL) and water (7.24 mL) were added. Ethyl acetate was added and the mixture filtered, the filter cake washed with ethyl acetate. The organic layers were pooled and washed with brine and dried over anhydrous magnesium sulfate. The solvent was removed in vacuo. The residue was purified by flash chromatography on silica gel Merck-60 (eluant: 20:1 chloroform-methanol) to give the title compound (0.46 g, 2.0 mmol).
MS ((+)ESI, m/z): 242 [M+H]+

Step C. tert-Butyl 4-{[1-({[4-(1H-pyrazol-1-yl)-2-(trifluoromethyl)benzyl]amino}carbonyl)-4-piperidinyl]amino}phenethylcarbamate The title compound (0.586 g, 1.0 mmol) was prepared from 4-pyrazole-2-trifluoromethyl-benzyl amine (0.46 g, 2.0 mmol) and {2-[4-(piperidin-4-ylamino)-phenyl]-ethyl}-carbamic acid tert-butyl ester (0.611 g, 2.0 mmol) according to Procedure C.
MS ((+)ESI, m/z): 587 [M+H]+

Step D. 4-[4-(2-Aminoethyl)anilino]-N-[4-(1H-pyrazol-1-yl)-2-(trifluoromethyl)benzyl]-1-piperidinecarboxamide formate tert-Butyl 4-{[1-({[4-(1H-pyrazol-1-yl)-2-(trifluoromethyl)benzyl]amino} carbonyl)-4-piperidinyl]amino}phenethylcarbamate (0.586 g, 1.0 mmol) was reacted according to Procedure F to provide the title compound (0.532 g, 1.0 mmol) which was used without further purification.

Step E. 4-[4-(2-{[(2S)-3-(4-{[tert-Butyl(diphenyl)silyl]oxy}phenoxy)-2-hydroxypropyl]amino}ethyl)anilino]-N-[4-(1H-pyrazol-1-yl)-2-(trifluoromethyl)benzyl]-1-piperidinecarboxamide 4-[4-(2-Aminoethyl)anilino]-N-[4-(1H-pyrazol-1-yl)-2-(trifluoromethyl)benzyl]-1-piperidinecarboxamide formate (0.532 g, 1.0 mmol) was reacted with tert-butyl-(4-oxiranylmethoxy-phenoxy)-diphenyl-silane (0.404 g, 1.0 mmol) according to Procedure G (eluant: 20:1 chloroform-methanol) to give the title compound (0.18 g, 0.20 mmol)

Step F. 4-(4-{2-[(2S)-2-Hydroxy-3-(4-hydroxy-rhenoxy)-propylamino]-ethyl}-phenylamino)-piperidine-1-carboxylic acid 4-pyrazol-1-yl-2-trifluoromethyl-benzylamide 4-[4-(2-{[(2S)-3-(4-{[tert-Butyl(diphenyl)silyl]oxy}phenoxy)-2-hydroxypropyl]amino}ethyl)anilino]-N-[4-(1H-pyrazol-1-yl)-2-(trifluoromethyl)benzyl]-1-piperidinecarboxamide (0.18 g, 0.20 mmol) was reacted according to Procedure H (eluant: 5:1 chloroform-methanol containing 1% ammonium hydroxide) to give the title compound (0.09 g, 0.13 mmol)
m.p 96–100° C.
MS ((+)APCI, m/z): 653 [M+H]+
Anal. calcd. for $C_{34}H_{39}F_3N_6O_4$+0.75 $H_2O$: C 61.30 H 6.13 N 12.61 found: C 61.31 H 6.08 N 11.9

EXAMPLE 35

4-(4-{2-[(2S)-2-Hydroxy-3-(4-hydroxy-phenoxy)-propylamino]-ethyl}-phenylamino)-piperidine-1-carboxylic Acid (3-methyl-butyl)-amide Step A. tert-Butyl 4-({1-[(isopentylamino)carbonyl]-4-piperidinyl}amino)phenethyl carbamate The title compound (0.454 g, 1.05 mmol) was prepared from 4-methylvaleric acid (0.436 g, 3.76 mmol) and {2-[4-(piperidin-4-ylamino)-phenyl]-ethyl}-carbamic acid tert-butyl ester (1.20 g, 3.76 mmol) according to Procedure D.
$^1$H NMR (DMSO-$d_6$, 300 MHz): d 0.81 (d, 6H), 1.15 (m, 6H), 1.26 (q, 2 H) 1.41 (s, 9H), 1.60 (m 1H), 1.82 (d, 2H), 2.78(t, 2H), 3.02(m, 3H), 3.92 (d, 2H), 5.24 (d, 1H), 6.41 (d, 1H), 6.54 (d, 2H), 6.80(t, 1H), 6.90(d, 2H).

Step B. 4-[4-(2-Aminoethyl)anilino]-N-isopentyl-1-piperidinecarboxamide formate tert-Butyl 4-({1-[(isopentylamino)carbonyl]-4-piperidinyl}amino)phenethyl carbamate (0.454 g, 1.05 mmol) was reacted according to Procedure F to provide the title compound (0.40 g, 1.05 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-isopentyl-1-piperidinecarboxamide 4-[4-(2-Aminoethyl)anilino]-N-isopentyl-1-piperidinecarboxamide formate (0.40 g, 1.05 mmol) was reacted with tert-butyl-(4-oxiranylmethoxy-phenoxy)- diphenyl-silane (0.427 g, 1.05 mmol) according to Procedure G (eluant: 20:1 chloroform-methanol) to give the title compound (0.194 g, 0.26 mmol).

Step D. 4-(4-{2-[(2S)-2-hydroxy-3-(4-hydroxy-phenoxy)-propylamino]-ethyl}-phenylamino)-piperidine-1-carboxylic acid (2,2-diphenyl-ethyl)-amide 4-[4-(2-{[(2S)-3-(4-{[tert-Butyl(diphenyl)silyl]oxy}phenoxy)-2-hydroxypropyl]amino}ethyl)anilino]-N-(2,2-diphenylethyl)-1-piperidinecarboxamide (0.194 g, 0.26 mmol) was reacted according to Procedure H (eluant: 5:1 chloroform-methanol containing 1% ammonium hydroxide) to give the title compound (0.05 g, 0.10 mmol).

m.p 72–77° C.

MS ((+)APCI, m/z): 499 [M+H]$^+$

Anal. calcd. for $C_{28}H_{42}N_4O_4$+1.0 $H_2O$: C 65.09 H 8.58 N 10.84 found: C 65.09 H 8.45 N 10.53

EXAMPLE 36

4-(4-{2-[(2R)-2-(3-Chloro-phenyl)-2-hydroxy-ethylamino]-ethyl}-phenylamino)-piperidine-1-carboxylic Acid Octylamide 4-[4-(2-Aminoethyl)anilino]-N-octyl-1-piperidinecarboxamide (0.50 g, 1.18 mmol) was reacted with (2R)-2-(3-chlorophenyl)oxirane (0.183 g, 1.18 mmol) according to Procedure G (eluant: 20:1 chloroform-methanol) to give the title compound (0.063 g, 0.19 mmol).

m.p 168-171° C.

MS ((+)APCI, m/z): 529 [M+H]$^+$

Anal. calcd. for $C_{30}H_{45}ClN_4O_2$·HCl+1.00 $H_2O$+0.05 $CH_2Cl_2$: C 61.39 H 8.25 N 9.53 found: C 61.01 H 7.83 N 9.3

EXAMPLE 37

4-(4-{2-[(2S)-2-Hydroxy-3-(4-hydroxy-phenoxy)-propylamino]-ethyl}-phenylamino)-piperidine-1-carboxylic Acid 2,5-difluoro-benzylamide Step A. tert-Butyl 4-[(1-{[(2,5-difluorobenzyl)amino]carbonyl}-4-piperidinyl)amino]phenethylcarbamate The title compound (0.561 g, 1.15 mmol) was prepared from 2,5-difluoro-benzyl amine (0.572 g, 4.0 mmol) and {2-[4-(piperidin-4-ylamino)-phenyl]-ethyl}-carbamic acid tert-butyl ester (1.276 g, 4.0 mmol) according to Procedure C.

$^1$H NMR (DMSO-d$_6$, 300 MHz) δ 7.20 (ddd, J=9.0, 9.0, 4.4 Hz, 1H), 7.02–7.15 (m, 2H), 6.88 (d, J=8.6 Hz, 2H), 6.80 (broad t, J=5.5 Hz, 1H), 6.52 (d, J=8.6 Hz, 2H), 5.50 (d, J=7.4 Hz, 1H), 4.25 (d, J=5.5 Hz, 2H), 3.90 (broad d, J=13.4 Hz, 2H), 3.36 (m, 1H), 3.04 (broad q, J=7.0 Hz, 2H), 2.90 (broad t, J=13.4 Hz, 2H), 2.50 (t, J=7.4 Hz, 2H), 1.84 (broad d, J=12.3 Hz, 2H), 1.38 (s, 9H), 1.22 (dddd, J=12.9, 12.9, 12.9, 3.7 Hz, 2H).

Step B. 4-[4-(2-Aminoethyl)anilino]-N-(2,5-difluorobenzyl)-1-piperidinecarboxamide foramte tert-Butyl 4-[(1-{[(2,5-difluorobenzyl)amino]carbonyl}-4-piperidinyl)amino]phenethyl carbamate (0.561 g, 1.15 mmol) was reacted according to Procedure F to provide the title compound (0.50 g, 1.15 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(2,5-difluorobenzyl)-1-piperidinecarboxamide 4-[4-(2-Aminoethyl)anilino]-N-(2,5-difluorobenzyl)-1-piperidinecarboxamide formate (0.50 g, 1.15 mmol) was reacted with tert-butyl-(4-oxiranylmethoxy-phenoxy)-diphenyl-silane (0.465 g, 1.15 mmol) according to Procedure G (eluant: 20:1 chloroform-methanol) to give the title compound (0.238 g, 0.29 mmol).

Step D. 4-(4-{2-[(2S)-2-hydroxy-3-(4-hydroxy-phenoxy)-propylamino]-ethyl}-phenylamino)-piperidine-1-carboxylic acid 2,5-difluoro-benzylamide 4-[4-(2-{[(2S)-3-(4-{[tert-Butyl(diphenyl)silyl]oxy}phenoxy)-2-hydroxypropyl]amino}ethyl)anilino]-N-(2,5-difluorobenzyl)-1-piperidinecarboxamide (0.238 g, 0.29 mmol) was reacted according to Procedure H (eluant: 5:1 chloroform-methanol containing 1% ammonium hydroxide) to give the title compound (0.075 g, 0.13 mmol).

m.p 69–72° C.

MS ((+)ESI, m/z): 555 [M+H]$^+$

Anal. calcd. for $C_{30}H_{36}F_2N_4O_4$+1.9 $H_2O$+0.22 $CH_4O$: C 60.91 H 6.88 N 9.40 found: C 60.84 H 6.39 N 9.23

EXAMPLE 38

5-{[(2S)-3-({4-[(1-{[(2,5-Difluorobenzyl)]amino]carbonyl}-4-piperidinyl)amino]phenethyl}amino)-2-hydroxypropyl]oxy}-2-hydroxybenzoic Acid Step A. Methyl 5-{[(2S)-3-({4-[(1-{[(2,5-difluorobenzyl)]amino]carbonyl}-4-piperidinyl)amino]phenethyl}amino)-2-hydroxypropyl]oxy}-2-hydroxybenzoate 4-[4-(2-Aminoethyl)anilino]-N-(2,5-difluorobenzyl)-1-piperidinecarboxamide (1.2 g, 3.1 mmol) was reacted methyl 2-hydroxy-5-[(2S)(oxiranyl)methoxy]benzoate (0.694 g, 3.1 mmol) according to Procedure G (eluant: 20:1 going to 9:1 dichloromethane-methanol) to give the title compound (0.95 g, 1.5 mmol) as a mixture of methyl and ethyl esters, in a ratio 3:1 respectively, as determined by high pressure liquid chromatography.

MS ((+)APCI), m/z 613 [M+H]$^+$ $^1$H NMR (DMSO-d$_6$, 400 MHz) δ 7.03–7.24 (m, 6H), 6.88–6.93 (m, 3H), 6.50 (d, J=8.6 Hz, 2H), 5.26 (d, J=8.3 Hz, 1H), 4.24 (d, J=5.5 Hz, 2H), 3.80–3.92 (m, 5H), 3.31 (m, 1H), 2.89 (broad t, J=13.4 Hz, 2H), 2.49–2.72 (m, 6H), 1.84 (broad d, J=13.0 Hz, 2H), 1.20 (dddd, J=13.4, 13.4, 13.4, 3.7 Hz, 2H).

Step B. 5-{[(2S)-3-({4-[(1-{[(2,5-Difluorobenzyl)]amino]carbonyl}-4-piperidinyl)-amino]phenethyl}amino)-2-hydroxypropyl]oxy}-2-hydroxybenzoic Acid A solution of methyl 5-{[(2S)-3-({4-[(1-{[(2,5-difluorobenzyl)]amino]carbonyl}-4-piperidinyl)amino]phenethyl}amino)-2-hydroxypropyl]oxy}-2-hydroxybenzoate (0.306 g, 0.5 mmol) in methanol (5 mL) was treated with 1N sodium hydroxide (1 mL, 1.0 mmol) and stirred at room temperature for 2 hours. The reaction mixture was neutralized with 1N hydrochloric acid (1 mL, 1.0 mmol) and the solvent evaporated in vacuo to a residue. The residue was dissolved in ethyl acetate, filtered, and the filtrate evaporated in vacuo to afford a second residue. The second residue was triturated with hexane-diethyl ether to yield the title compound (0.27 g, 0.45 mmol).

m.p. 138–141° C.

MS ((-)APCI), m/z 597 [M-H]$^{-1}$

IR (KBr), v 1610, 1520, 1490, 1230, 1190, 810 cm$^{-1}$ $^1$H NMR (DMSO-d$_6$, 400 MHz) δ ($D_2O$ Exchanged) 7.28 (d, J=3.3 Hz, 1H), 7.16 (ddd, J=9.0, 9.0, 4.4 Hz, 1H), 6.99–7.08 (m, 2H), 6.94 (d, J=8.6 Hz, 2H), 6.93 (d, J=8.6 Hz, 2H), 6.82 (dd, J=8.8, 3.3 Hz, 1H), 6.61 (d, J=8.8 Hz, 1H), 6.54 (d, J=8.6 Hz, 2H). 4.22 (s, 2H), 4.08 (m, 1H), 3.84 (m, 4H), 3.35 (m, 1H), 2.98–3.31 (m, 4H), 2.88 (broad t, J=11.4 Hz, 2H), 2.75 (m, 2H), 1.83 (broad d, J=12.5 Hz, 2H), 1.18 (dddd, J=13.8, 13.8, 13.8, 3.7 Hz, 2H).

EXAMPLE 39

4-(4-{2-[(2S)-2-Hydroxy-3-(4-hydroxy-phenoxy)-propylamino]-ethoxy}-phenylamino)-piperidine-1-carboxylic Acid 4-fluoro-benzylamide Step A. tert-Butyl 2-{4-[(1-{[(4-fluorobenzyl)amino]carbonyl}-4-piperidinyl)amino]phenoxulethylcarbamate The title compound (0.68 g, 1.4 mmol) was prepared from 4-fluoro-benzyl amine (0.25 g, 2.0 mmol) and tert-butyl 2-[4-(4-piperidinylamino)phenoxy]ethyl carbamate (0.67 g, 2.0 mmol) according to Procedure C.

Step B. 4-[4-(2-Aminoethoxy)anilino]-N-(4-fluorobenzyl)-1-piperidinecarboxamide tert-Butyl 2-{4-[(1-{[(4-fluorobenzyl)amino]carbonyl}-4-piperidinyl)amino]phenoxy}ethylcarbamate (0.68 g, 1.4 mmol) was reacted according to Procedure F to provide the title compound (0.63 g, 1.4 mmol) which was used without further purification.

Step C. 4-[4-(2-{[(2S)-3-(4-{[tert-Butyl(diphenyl)silyl]oxy}phenoxy)-2-hydroxypropyl]-amino}ethoxy)anilino]-N-(4-fluorobenzyl)-1-piperidinecarboxamide 4-[4-(2-Aminoethoxy)anilino]-N-(4-fluorobenzyl)-1-piperidinecarboxamide (0.63 g, 1.4 mmol) was reacted with tert-butyl-(4-oxiranylmethoxy-phenoxy)-diphenyl-silane (0.53 g, 1.3 mmol) according to Procedure G (eluant: 20:1 chloroform-methanol) to give the title compound (0.125 g, 0.15 mmol).

Step D. 4-(4-{2-[(2S)-2-Hydroxy-3-(4-hydroa-phenoxy)-propylamino]-ethoxy}-phenylamino)-piperidine-1-carboxylic Acid 4-fluoro-benzylamide 4-[4-(2-{[(2S)-3-(4-{[tert-Butyl(diphenyl)silyl]oxy}phenoxy)-2-hydroxypropyl]amino}ethoxy)anilino]-N-(4-fluorobenzyl)-1-piperidinecarboxamide (0.125 g, 0.15 mmol) was reacted according to Procedure H (eluant: 5:1 chloroform-methanol containing 1% ammonium hydroxide) to give the title compound (0.075 g, 0.13 mmol).

m.p 73–77° C.

MS ((+)ESI, m/z): 553 [M+H]$^+$

Anal. calcd. for $C_{30}H_{37}FN_4O_5$+1.0 $H_2O$: C 63.14 H 6.89 N 9.82 found: C 63.18 H 6.59 N 9.96

EXAMPLE 40

4-(4-{2-[(2S)-2-Hydroxy-3-(4-hydroxy-phenoxy)-propylamino]-ethyl}-phenylsulfanyl)-piperidine-1-carboxylic Acid Phenylamide Step A. N-(tert-butoxycarbonyl)-4-nitrophenethyl-2-amine To a cold suspension of 4-nitrophenethylamine hydrochloride (20.0 g, 98.7 mmol) in chloroform (200 mL) was added triethylamine (9.99 g, 98.7 mmol). This solution was treated with di-tert-butyl dicarbonate (23.70 g, 108.6 mmol) portion-wise. After 15 minutes the ice/water bath was removed and the reaction was stirred at room temperature overnight. The reaction mixture was successively washed with the following: water, 0.5M hydrochloric acid, dilute aqueous sodium bicarbonate and brine. The organic phase was dried over anhydrous sodium sulfate, filtered and evaporated in vacuo. The residue was purified by flash chromatography on silica gel Merck-60 (eluant: 2:1 ethyl acetate hexane) to furnish the title compound (24.2 g, 82.21 mmol).

$^1$H NMR (CDCl$_3$, 300 MHz) d 8.05 (d, J=8.2 Hz, 2H), 7.42 (d, J=8.2 Hz, 2H), 3.06 (q, J=7.1 Hz, 2H), 2.58 (t, J=7.1 Hz, 2H) and 1.29 (s, 9H).

Step B. 4-Aniline-(2-[N-(tert-butoxycarbonyl)]-ethylamine)

To a solution of N-(tert-butoxycarbonyl)-4-nitrophenethyl-2-amine (24.2 g, 82.21 mmol) in a mixture of ethanol (150 mL) and tetrahydrofuran (50 mL) was added 5% palladium on carbon (4.0 g). This solution was placed on a Parr apparatus under 40 psi of hydrogen gas and shaken for 5 hours. The reaction mixture was filtered and evaporated in vacuo to leave a colorless oil. This oil was taken up into hot hexane/ethyl acetate and allowed to crystallized overnight. The solid was collected via vacuum filtration and placed under high vacuum for eight hours to furnish the title compound (19.31 g, 73.04 mmol).

$^1$H NMR (DMSO-d$_6$, 300 MHz) d 6.81 (d, J=8.1 Hz, 2H), 6.46 (d, J=8.1 Hz, 2H), 4.82 (s, 2H(exch.)), 3.01 (q, J=7.2 Hz, 2H), 2.48 (t, J=7.2 Hz, 2H) and 1.36 (s, 9H).

Step C. S-(4-{2-[(tert-Butoxycarbonyl)amino]ethyl}phenyl) O-ethyl carbonodithioate 4-Aniline-(2-[N-(tert-butoxycarbonyl)]-ethylamine) (6.91 g, 29.24 mmol) was stirred into cold dilute hydrochloric acid (made from 50 mL of water and 6 mL of concentrated hydrochloric acid) and treated with a solution of sodium nitrite (3.00 g, 43.48 mmol) in water (14 mL) portionwise over 20 minutes. After addition was complete vigorous stirring was continued for 5 minutes. To this cold solution was added nickel(II)chloride hexahydrate (5–10 mg). During the sodium nitrite additions, a solution of potassium ethyl xanthate (10.26 g, 64.0 mmol) in dilute aqueous sodium bicarbonate (made from 65 mL of water and 6.5 g of sodium bicarbonate) was prepared and warmed to 75° C.

The cold diazonium solution above was added portionwise (2.5 mL every 30 seconds) to the well stirred warm xanthate solution. A yellow oil formed upon the evolution of gas bubbles. The mixture was stirred and heated for an additional 10 minutes after additions were complete. The solution was then cooled to 5° C., and the aqueous solvent decanted from the yellow oil. The oily residue was taken up into dichloromethane, dried over anhydrous sodium sulfate, filtered and evaporated in vacuo. The residue was purified by flash chromatography on silica gel Merck-60 (eluant: 2:1 diethyl ether-hexane) to furnish the title compound as an oil which solidified on standing (3.75 g, 10.98 mmol).

$^1$H NMR (CDCl$_3$, 300 MHz) d 7.44 (d, J=8.2 Hz, 2H), 7.26 (d, J=8.2 Hz, 2H), 4.62 (q, J=7.2 Hz, 2H), 3.40 (m, 2H), 2.85 (t, J=7.0 Hz, 2H), 1.44 (s, 9H) and 1.34 (t, J=7.0 Hz, 3H).

Step D. 4-Hydroxy-N-phenyl-1-piperidinecarboxamide

4-Hydroxypiperidine (2.50 g, 24.70 mmol) was reacted with phenylisocyanate (2.80 g, 23.48 mmol) according to Procedure E. The title compound was obtained as a solid (4.70 g, 21.33 mmol).

$^1$H NMR (DMSO-d$_6$, 300 MHz) d 8.44 (br s, 1H), 7.43 (d, J=7.6 Hz, 2H), 7.20 (t, J=7.3 Hz, 2H), 6.90 (t, J=7.3 Hz, 1H), 4.70 (d, J=4.2 Hz, 1H), 3.81 (m, 2H), 3.63 (m, 1H), 3.02 (m, 2H), 1.75(m, 2H) and 1.30 (m, 2H).

MS ((+)ESI, m/z): 221 [M+H]$^+$

Step E. 4-Bromo-N-phenyl-1-piperidinecarboxamide

To a solution of 4-hydroxy-N-phenyl-1-piperidinecarboxamide (2.57 g, 11.67 mmol) and carbon tetrabromide (8.13 g, 24.50 mmol) in a mixture of dichloromethane (30 mL) and tetrahydrofuran (10 mL) at 5° C. was added triphenylphosphine (6.43 g, 24.50 mmol) portionwise. After addition, the ice/water bath was removed and the reaction was stirred overnight. Diethyl ether (20 mL) was added and the reaction mixture was filtered. The filtrate was concentrated in vacuo and the residue purified by flash chromatography on silica gel Merck-60 (eluant: 1:1 ethyl acetate-hexane) to furnish the title (2.50 g, 8.82 mmol).

$^1$H NMR (DMSO-d$_6$, 300 MHz) d 7.30 (m, 4H), 7.03 (t, 1H), 6.65 (br s, 1H), 4.40 (m, 1H), 3.64 (m, 2H), 3.40 (m, 2H), 2.12 (m, 2H) and 2.00 (m, 2H).

MS ((+)ESI, m/z): 283,285 [M+H]$^+$

Step F. tert-butyl 4-{[1-(anilinocarbonyl)-4-piperidinyl]sulfanyl}phenethylcarbamate To a room temperature degassed solution of the S-(4-{2-[(tert-butoxycarbonyl) amino]ethyl}phenyl) O-ethyl carbonodithioate (1.04 g, 3.36 mmol) in dry ethanol (20 mL) was added freshly powdered sodium borohydride (0.32 g, 8.40 mmol). 30 Minutes after addition the solution was warmed to 45° C. for 1 hour. The reaction mixture was re-cooled to room temperature and 4-bromo-N-phenyl-1-piperidinecarboxamide (0.95 g, 3.36 mmol) added. The reaction was warmed to 50° C. for 3 hours. The reaction was quenched with dilute hydrochloric acid and the pH adjusted to 7.5 with aqueous sodium bicarbonate. The ethanol was removed by evaporation in vacuo and the residue was extracted with dichloromethane. The residue was purified by flash chromatography on silica gel Merck-60 (eluant: 2:1 ethyl acetate-hexane) to furnish the title compound (0.90 g, 1.98 mmol).

$^1$H NMR (CDCl$_3$, 300 MHz) d 7.40 (d, J=8.1 Hz, 2H), 7.30 (m, 4H), 7.17 (d, J=8.1 Hz, 2H), 7.05 (t, 1H), 6.42 (br s, 1H), 4.58 (br, 1H), 3.98 (t, J=3.2 Hz, 1H), 3.93 (t, J=3.2 Hz, 1H), 3.38 (m, 2H), 3.24 (m, 1H), 3.08 (m, 2H), 2.77 (t, J=6.8 Hz, 2H), 2.00 (m, 2H), 1.65 (m, 2H) and 1.43 (s, 9H).

Step G. 4-{[4-(2-Aminoethyl)phenyl]sulfanyl}-N-phenyl-1-piperidinecarboxamide

To a solution of tert-butyl 4-{[1-(anilinocarbonyl)-4-piperidinyl]sulfanyl}phenethylcarbamate (0.609 g, 1.34 mmol) in dichloromethane (8 mL) and methanol (2 drops) was added trifluoroacetic acid (2 mL). This mixture was stirred for 4 hours at ambient temperature. The volatile components were removed in vacuo and the residue taken up into dichloromethane (25 mL) and washed with dilute aqueous sodium bicarbonate. The organic phase was dried over anhydrous sodium sulfate, filtered and evaporated in vacuo to furnish the title compound (0.46 g, 1.29 mmol)

MS ((+)ESI, m/z): 356 [M+H]$^+$

Step H. 4-{[4-(2-{[(2S)-3-(4-{[tert-butyl(diphenyl)silyl]oxy}phenoxy)-2-hydroxypropyl]amino}ethyl)phenyl]sulfanyl}-N-phenyl-1-piperidinecarboxamide 4-{[4-(2-Aminoethyl)phenyl]sulfanyl}-N-phenyl-1-piperidinecarboxamide (0.45 g, 1.27 mmol) was reacted with tert-butyl{4-[(2S)oxiranylmethoxy]phenoxy}diphenylsilane (0.512 g, 1.27 mmol) according to Procedure G (eluant: 12:3:1 dichloromethane-chloroform-methanol) to give the title compound (0.25 g, 0.33 mmol).

Step I. 4-(4-{2-[2-Hydroxy-3-(4-hydroxy-phenoxy)-propylamino]-ethyl}-phenylsulfanyl)-piperidine-1-carboxylic acid phenylamide 4-{[4-(2-{[(2S)-3-(4-([tert-Butyl(diphenyl)silyl]oxy}phenoxy)-2-hydroxy-propyl]amino}ethyl)phenyl]sulfanyl}-N-phenyl-1-piperidinecarboxamide (0.25 g, 0.33 mmol) was reacted according to Procedure H (eluant: 12:3:1 dichloromethane-chloroform-methanol) to give the title compound (0.12 g, 0.23 mmol).

m.p. 121° C.

MS ((+)ESI, m/z): 522 [M+H]$^+$ $^1$H NMR (DMSO-d$_6$, 400 MHz) d 8.90 (s, 1H), 8.49 (s, 1H), 7.42 (d, J=7.8 Hz, 2H), 7.34 (d, J=7.8 Hz, 2H), 7.22 (m, 4H), 6.91 (t, J=7.3 Hz, 1H), 6.73 (d, J=9.0 Hz, 2H), 6.66 (d, J=9.0 Hz, 2H), 5.00 (br s, 1H), 4.00 (m, 1H), 3.97 (m, 1H), 3.80 (m, 3H), 3.39 (m, 1H), 2.98 (m, 2H), 2.80 (m, 2H), 2.72 (m, 3H), 2.61 (m, 1H), 1.91 (m, 2H) and 1.40 (m, 2H).

Anal. calcd. for C$_{29}$H$_{35}$N$_3$O4S+1.5H$_2$O: C: 63.48 H: 6.98 N: 7.66. Found: C:63.62 H: 6.52 N: 7.50.

EXAMPLE 41

N-hexyl-4-{[4-(2-{[(2S)-2-hydroxy-3-(4-hydroxyphenoxy)propyl]amino}ethyl)phenyl]sulfanyl}-1-piperidinecarboxamide Step A. N-hexyl-4-hydroxy-1-piperidinecarboxamide 4-Hydroxypiperidine (2.75 g, 27.23 mmol) was reacted with hexylisocyanate (3.46 g, 27.23 mmol) according to Procedure E. The title compound was used without further purification.

Step B. 4-Bromo-N-hexyl-1-piperidinecarboxamide

N-hexyl-4-hydroxy-1-piperidinecarboxamide (6.22 g 27.23 mmol) was reacted according to Procedure L to afford the title compound (6.90 g, 23.69 mmol).

MS ((+)ESI, m/z): 292 [M+H]$^+$

Step C. tert-Butyl 4-({1-[(hexylamino)carbonyl]-4-piperidinyl}sulfanyl) phenethylcarbamate 4-Bromo-N-hexyl-1-piperidinecarboxamide (2.43 g, 8.34 mmol) and S-(4-{2-[(tert-butoxycarbonyl)amino]ethyl}phenyl) O-ethyl carbonodithioate (2.58 g, 8.34 mmol) were reacted according to Procedure M to afford the title compound (2.54 g, 5.48 mmol).

$^1$H NMR (CDCl$_3$, 300 MHz) d 7.38 (d, J=8.5 Hz, 2H), 7.16 (d, J=0.5 Hz, 2H), 4.56 (br, 1H), 4.40 (br t, 1H), 3.85 (br t, 1H), 3.80 (br t, 1H), 3.36 (m, 2H), 3.21 (m, 4H), 2.94 (m, 2H), 2.78 (t, J=6.5 Hz, 2H), 1.95 (m, 2H), 1.60–1.40 (m, 2H), 1.41 (s, 9H), 1.28 (m, 7H) and 0.86 (m, 3H).

Step D. 4-{[4-(2-Aminoethyl)phenyl]sulfanyl}-N-hexyl-1-piperidinecarboxamide tert-Butyl 4-({1-[(hexylamino)carbonyl]-4-piperidinyl}sulfanyl)phenethylcarbamate (0.75 g, 1.617 mmol) was reacted according to Procedure N to afford the title compound (0.588 g, 1.617 mmol).

MS ((+)ESI, m/z): 364 [M+H]$^+$

Step E. 4-{[4-(2-{[(2S)-3-(4-{[tert-butyl(diphenyl)silyl]oxy}phenoxy)-2-hydroxypropyl]amino}ethyl)phenyl]sulfanyl}-N-hexyl-1-piperidinecarboxamide 4-{[4-(2-Aminoethyl)phenyl]sulfanyl}-N-hexyl-1-piperidinecarboxamide (0.588 g, 1.617 mmol) was reacted with tert-butyl-(4-oxiranylmethoxy-phenoxy)-diphenylsilane (0.589 g, 1.455 mmol) according to Procedure G to give the title compound (eluant: 20/1 chloroform-methanol) (0.395 g, 0.514 mmol).

MS ((+)ESI, m/z): 769 [M+H]$^+$

Step F. N-hexyl-4-{[4-(2-{[(2S)-2-hydroxy-3-(4-hydroxyphenoxy)propyl]amino}ethyl)phenyl]sulfanyl}-1-piperidinecarboxamide 4-{[4-(2-{[(2 S)-3-(4-{[tert-Butyl(diphenyl)silyl]oxy}phenoxy)-2-hydroxy-propyl]amino}ethyl)phenyl]sulfanyl}-N-hexyl-1-piperidinecarboxamide (0.395 g, 0.514 mmol) was reacted according to Procedure H to give the title compound (eluant: 20:3 chloroform-methanol) (0.155 g, 0.28 mmol).

$^1$H NMR (DMSO-d$_6$, 400 MHz) d 8.88 (s, 1H), 7.29 (d, J=7.9 Hz, 2H), 7.17 (d, J=7.9 Hz, 2H), 6.71 (d, J=8.8 Hz, 2H), 6.64 (d, J=8.8 Hz, 2H), 6.40 (t, J=5.5 Hz, 1H), 4.98 (br s, 1H), 3.83–3.71 (series of m, 6H), 3.29 (m, 1H), 2.95 (q, J=6.8 Hz, 2H), 2.83–2.68 (series of m, 7H), 2.60 (m, 1H), 1.79 (m, 2H), 1.40–1.15 (series of m, 10H) and 0.84 (t, J=6.8 Hz, 3H).

m.p. 181–195° C.

MS ((+)ESI, m/z): 530 [M+H]$^+$

Anal. calcd. for C$_{29}$H$_{43}$N$_3$O$_4$S+H$_2$O: C 63.59 H 8.28 N 7.67 found: C 63.89 H 8.51 N 7.61

EXAMPLE 42

4-(4-{2-[(2S)-2-Hydroxy-3-(4-hydroxy-phenoxy)-propylamino]-ethyl}-phenylsulfanyl)-piperidine-1-carboxylic Acid-4-fluorobenzylamide Step A. 4-Hydroxy-N-(4-fluorobenzyl)-1-piperidinecarboxamide The title compound (4.33 g, 17.16 mmol) was prepared from 4-fluorobenzylamine (3.97 g, 19.11 mmol) and 4-hydroxypiperidine (1.93 g, 19.11 mmol) according to Procedure C (eluant: 20:1 chloroform-methanol).

MS ((+)ESI, m/z): 253 [M+H]$^+$

Step B. 4-Bromo-N-(4-fluorobenzyl)-1-piperidinecarboxamide

4-Hydroxy-N-(4-fluorobenzyl)-1-piperidinecarboxamide (4.33 g 17.16 mmol) was reacted according to Procedure L to afford the title compound (3.25 g, 10.31 mmol).

MS ((+)ESI, m/z): 316,318 [M+H]$^+$

Step C. tert-Butyl 4-{[1-(4-fluorobenzylaminocarbonyl)-4-piperidinyl]-sulfanyl}phenethylcarbamate 4-Bromo-N-(4-fluorobenzyl)-1-piperidinecarboxamide (3.25 g, 10.31 mmol) and S-(4-{2-[(tert-butoxycarbonyl)amino]ethyl}phenyl) O-ethyl carbonodithioate (3.52 g, 10.31 mmol) were reacted according to Procedure M to afford the title compound (3.86 g, 7.92 mmol).

Step D. 4-{[4-(2-Aminoethyl)phenyl]sulfanyl}-N-(4-fluorobenzylamino)-1-piperidinecarboxamide tert-Butyl 4-{[1-(4-fluorobenzylaminocarbonyl)-4-piperidinyl]sulfanyl} phenethylcarbamate (1.50 g, 3.076 mmol) was reacted according to Procedure N to afford the title compound (1.01 g, 2.606 mmol).

MS ((+)ESI, m/z): 388 [M+H]$^+$

Step E. 4-{[4-(2-{[(2S)-3-(4-{[tert-Butyl(diphenyl)silyl]oxy}phenoxy)-2-hydroxypropyl]amino}ethyl)phenyl]sulfanyl}-N-(4-fluorobenzyl)-1-piperidinecarboxamide 4-{[4-(2-Aminoethyl)phenyl]sulfanyl}-N-(4-fluorobenzylamino)-1-piperidinecarboxamide (1.01 g, 2.606 mmol) was reacted with tert-butyl-(4-oxiranylmethoxy-phenoxy)-diphenylsilane (0.98 g, 2.416 mmol) according to Procedure G to give the title compound (eluant: 20:1 chloroform/methanol) (0.236 g, 0.298 mmol).

MS ((+)ESI, m/z): 793 [M+H]$^+$

Step F. 4-(4-{2-[(2S)-2-Hydroxy-3-(4-hydroxy-phenoxy)-propylamino]-ethyl}-phenylsulfanyl)-piperidine-1-carboxylic acid-4-fluorobenzylamide 4-{[4-(2-{[(2S)-3-(4-{[tert-Butyl(diphenyl)silyl]oxy}phenoxy)-2-hydroxy-propyl]amino}ethyl)phenyl]sulfanyl}-N-(4-fluorobenzyl)-1-piperidinecarboxamide (0.236 g, 0.236 mmol) was reacted according to Procedure H to give the title compound (eluant: 20:3 chloroform-methanol) (0.070 g, 0.126 mmol).

m.p 181–183° C.

MS ((+)ESI, m/z): 554 [M+H]$^+$ $^1$H NMR (DMSO-d$_6$, 400 MHz) d 8.92 (s, 1H), 7.35–7.04 (series of m, 9H), 6.72 (d of AB, J=9.0 Hz, 2H), 6.64 (d of AB, J=9.0 Hz, 2H), 5.07 (br, 1H), 4.17 (d, J=5.7 Hz, 2H), 3.90–3.70 (series of m, 5H), 2.90–2.60 (series of m, 8H), 1.78 (m, 2H) and 1.31 (m, 3H).

Anal. calcd. for C$_{30}$H$_{36}$FN$_3$O$_4$S+0.5 H$_2$O: C 63.03 H 6.70 N 7.35 found: C 62.96 H 6.71 N 6.92.

EXAMPLE 43

4-(4-{2-[(2S)-2-Hydroxy-3-(4-hydroxy-phenoxy)-propylamino]-ethyl}-phenylsulfanyl)-piperidine-1-carboxylic Acid (1-phenyl-cyclopentylmethyl)-amide Step A. 4-hydroxy-N-[(1-phenylcyclopentyl)methyl]-1-piperidinecarboxamide The title compound (6.00 g, 19.83 mmol) was prepared from 4-hydroxypiperidine (2.01 g, 19.84 mmol) and 4-hydroxypiperidine (2.01 g, 19.84 mmol) according to Procedure C (eluant: 20:1 chloroform-methanol).

MS ((+)ESI, m/z): 303 [M+H]$^+$

Step B. 4-bromo-N-[(1-phenylcyclopentyl)methyl]-1-piperidinecarboxamide

4-Hydroxy-N-[(1-phenylcyclopentyl)methyl]-1-piperidinecarboxamide (3.89 g, 12.86 mmol) was reacted according to Procedure L to afford the title compound (4.70 g, 12.86 mmol).

MS ((+)ESI, m/z): 366 [M+H]$^+$

Step C. tert-butyl 4-{[1-({[(1-phenylcyclopentyl)methyl]amino}carbonyl)-4-piperidinyl]sulfanyl}phenethylcarbamate 4-Bromo-N-[(1-phenylcyclopentyl)methyl]-1-piperidinecarboxamide (2.67 g, 7.32 mmol) and S-(4-{2-[(tert-butoxycarbonyl)amino]ethyl}phenyl) methyl carbonodithioate (2.50 g, 7.32 mmol) were reacted according to Procedure M to afford the title compound (1.97 g, 3.66 mmol).

Step D. 4-{[4-(2-aminoethyl)phenyl]sulfanyl}-N-[(1-phenylcyclopentyl)methyl]-1-piperidinecarboxamide tert-Butyl 4-{[1-({[(1-phenylcyclopentyl)methyl]amino}carbonyl)-4-piperidinyl]-sulfanyl}phenethylcarbamate (0.97 g, 1.804 mmol) was reacted according to Procedure N to afford the title compound (0.785 g, 1.793 mmol).

MS ((+)ESI, m/z): 438 [M+H]$^+$

Step E. 4-{[4-(2-{[(2S)-3-(4-{[tert-butyl(diphenyl)silyl]oxy}phenoxy)-2-droxypropyl]amino}ethyl)phenyl]sulfanyl}-N-[(1-phenylcyclopentyl)methyl]-1-piperidinecarboxamide 4-{[4-(2-Aminoethyl)phenyl]sulfanyl}-N-[(1-phenylcyclopentyl)methyl]-1-piperidinecarboxamide (0.785 g, 1.793 mmol) was reacted with tert-butyl-(4-oxiranylmethoxy-phenoxy)-diphenylsilane (0.62 g, 1.533 mmol) according to Procedure G to give the title compound (eluant: 20:1 chloroform-methanol) (0.830 g, 0.986 mmol).

Step F. 4-(4-{2-[(2S)-2-Hydroxy-3-(4-hydroxy-phenoxy)-propylamino]-ethyl}-phenylsulfanyl)-piperidine-1-carboxylic acid (1-phenyl-cyclopentylmethyl)-amide 4-(4-{2-[(2S)-2-Hydroxy-3-(4-{[tert-Butyl(diphenyl)silyl]oxy}phenoxy)-propylamino]-ethyl}-phenylsulfanyl)-piperidine-1-carboxylic acid (1-phenyl-cyclopentylmethyl)-amide (0.830 g, 0.986 mmol) was reacted according to Procedure H to give the title compound (eluant: 20:3 chloroform-methanol) (0.328 g, 0.543 mmol).

m.p. 132° C.

MS ((−)APCI, m/z): 602 [M−H]$^-$ $^1$H NMR (DMSO-d$_6$, 400 MHz) d 8.86 (s, 1H), 7.32-7.10 (m, 9H), 6.71 (d, J=9.0 Hz, 2H), 6.64 (d, J=9.0 Hz, 2H), 5.97 (t, J=5.9 Hz, 1H), 4.90 (br, 1H), 3.85–3.65 (m, 5H), 3.24, (m, 1H), 3.16 (d, J=6.2 Hz, 2H), 2.80–2.62 (m, 7H), 2.59 (m, 1H), 1.90 (m, 2H), 1.70 (m, 6H), 1.53 (m, 2H) and 1.22 (m, 2H).

Anal. calcd. for C$_{35}$H$_{45}$N$_3$O$_4$S+0.5 H$_2$O: C 68.59 H 7.57 N 6.86 found C 68.84 H 7.78 N 6.60

EXAMPLE 44

4-(4-{2-[(2S)-2-Hydroxy-3-(4-hydroxy-phenoxy)-propylamino]-ethyl}-benzenesulfonyl)-piperidine-1-carboxylic Acid Hexylamide Step A. tert-Butyl 4-({1-[(hexylamino)carbonyl]-4-piperidinyl}sulfonyl) phenethylcarbamate tert-Butyl 4-({1-[(hexylamino)carbonyl]-4-piperidinyl}sulfanyl)phenethylcarbamate (0.860 g, 1.85 mmol) was reacted according to Procedure 0 to afford the title compound (0.800 g, 1.610 mmol).

$^1$H NMR (CDCl$_3$, 300 MHz) d 7.79 (d, J=8.3 Hz, 2H), 7.40 (d, J=8.3 Hz, 2H), 4.62 (br s, 1H), 4.44 (br s, 1H), 4.04 (m, 2H), 3.40 (m, 2H), 3.28–3.11 (series of m, 3H), 3.04 (m, 1H), 2.91 (t, J=7.0 Hz, 2H), 2.73 (m, 2H), 2.00 (m, 2H), 1.65 (m, 1H), 1.47 (m, 1H), 1.43 (s, 9H), 1.29 (m, 7H) and 0.87 (m, 3H).

Step B. (4-{[4-(2-aminoethyl)phenyl]sulfonyl}-1-piperidinyl)(3-methyl-2-thienyl)methanone tert-Butyl 4-{[1-(n-hexylaminocarbonyl)-4-piperidinyl]sulfonyl}phenethylcarbamate (0.800 g, 1.610 mmol) was reacted according to Procedure N to afford the title compound (0.538 g, 1.36 mmol).

MS ((+)ESI, m/z): 396 [M+H]$^+$

Step C. 4-{[4-(2-{[(2S)-3-(4-{[tert-butyl(diphenyl)silyl]oxy}phenoxy)-2-hydroxypropyl]amino}ethyl)phenyl]sulfonyl}-N-hexyl-1-piperidinecarboxamide 4-{[4-(2-aminoethyl)phenyl]sulfonyl}-N-hexyl-1-piperidinecarboxamide (0.53 g, 1.34 mmol) was reacted with tert-butyl-(4-oxiranylmethoxy-phenoxy)-diphenylsilane (0.461 g, 1.14 mmol) according to Procedure G to give the title compound (eluant: 20:1 chloroform-methanol) (0.260 g, 0.325 mmol).

MS ((+)ESI, m/z): 801 [M+H]$^+$

Step D. 4-(4-{2-[(2S)-2-Hydroxy-3-(4-hydroxy-phenoxy)-propylamino]-ethyl}-benzenesulfonyl)-piperidine-1-carboxylic acid hexylamide 4-{[4-(2-{[(2S)-3-(4-{[tert-Buty[(diphenyl)silyl]oxy}phenoxy)-2-hydroxy-propyl]amino}ethyl)phenyl]sulfonyl}-N-hexyl-1-piperidinecarboxamide (0.260 g, 0.325 mmol) was reacted according to Procedure H to give the title compound (eluant: 20:3 chloroform-methanol) (0.105 g, 0.187 mmol).

MS ((+)ESI, m/z): 562 [M+H]$^+$ $^1$H NMR (DMSO-d$_6$, 400 MHz) d 8.89 (s, 1H), 7.72 (d, J=8.3 Hz, 2H), 7.52 (d, J=8.3 Hz, 2H), 6.73 (d<J=9.0 Hz, 2H), 6.66 (d, J=9.0 Hz, 2H), 6.46 (t, J=5.3 Hz, 1H), 4.95 (br s, 1H), 4.00 (m, 2H), 3.87–3.72 (series of m, 3H), 3.40 (m, 1H), 2.96 (q, J=6.8 Hz, 2H), 2.84 (br s, 4H), 2,70 (m, 1H), 2.62 (m, 3H), 1.74 (m, 2H), 1.39–1.21 (series of m, 1 OH) and 0.86 (t, J=6.8 Hz, 3H).

Anal. calcd. for C$_{29}$H$_{43}$N$_3$O$_6$S+0.4 H$_2$O: C 61.22 H 7.76 N 7.39 found: C 61.29 H 7.77 N 7.23.

EXAMPLE 45

4-(4-{2-[(2S)-2-Hydroxy-3-(4-hydroxy-phenoxy)-propylamino]-ethyl}-benzenesulfonyl)-piperidine-1-carboxylic Acid 4-fluoro-benzylamide Step A. tert-Butyl 4-{[1-(4-fluorobenzylaminocarbonyl)-4-piperidinyl]sulfonyl}phenethylcarbamate tert-Butyl 4-{[1-(4-fluorobenzylaminocarbonyl)-4-piperidinyl]sulfanyl}phenethylcarbamate (1.906 g, 3.91 mmol) was reacted according to Procedure O to afford the title compound (1.81 g, 3.48 mmol).

Step B. 4-{[4-(2-Aminoethyl)phenyl]sulfonyl}-N-(4-fluorobenzylamino)-1-piperidinecarboxamide tert-Butyl 4-{[1-(4-fluorobenzylaminocarbonyl)-4-piperidinyl]sulfonyl}phenethylcarbamate (1.775 g, 3.42 mmol) was reacted according to Procedure N to afford the title compound (1.04, 2.48 mmol).

MS ((+)ESI, m/z): 420 [M+H]$^+$

Step C. 4-{[4-(2-{[(2S)-3-(4-{[tert-Butyl(diphenyl)silyl]oxy}phenoxy)-2-hydroxypropyl]amino}ethyl)phenyl]sulfonyl]-N-(4-fluorobenzyl)-1-piperidinecarboxamide 4-{[4-(2-Aminoethyl)phenyl]sulfonyl}-N-(4-fluorobenzylamino)-1-piperidinecarboxamide (1.00 g, 2.384 mmol) was reacted with tert-butyl-(4-oxiranylmethoxy-phenoxy)-diphenylsilane (0.676 g, 1.67 mmol) according to Procedure G to give the title compound (eluant: 20:1 chloroform/methanol) (0.425 g, 0.516 mmol).

MS ((+)ESI, m/z): 825 [M+H]$^+$

Step D. 4-(4-{2-[(2S)-2-Hydroxy-3-(4-hydroxy-phenoxy)-propylamino]-ethyl}-benzenesulfonyl)-piperidine-1-carboxylic acid 4-fluoro-benzylamide 4-{[4-(2-{[(2S)-3-(4-{[tert-Butyl(diphenyl)silyl]oxy}phenoxy)-2-hydroxypropyl]amino}ethyl)phenyl]sulfonyl}-N-(4-fluorobenzyl)-1-piperidinecarboxamide (0.410 g, 0.50 mmol) was reacted according to Procedure H to give the title compound (0.241 g, 0.410 mmol).

MS ((+)APCI, m/z): 586 [M+H]$^+$ $^1$H NMR (DMSO-d$_6$, 400 MHz) d 8.90 (s, 1H), 7.73 (d, J=8.4 Hz, 2H), 7.53 (d, J=8.4 Hz, 2H), 7.23 (m, 2H), 7.10 (m, 1H), 6.73 (d, J=5.9 Hz, 2H), 6.66 (d, J=9.0 Hz, 2H), 4.97 (br, 1H), 4.18 (d, J=5.9 Hz, 2H), 4.10 (m, 2H), 3.88–3.70 (m, 3H), 3.43 (m, 1H), 3.30 (m, 1H), 2.85 (s, 4H), 2.65 (m, 4H), 1.76 (m, 2H) and 1.35 (m, 2H).

Anal. calcd. for C$_{30}$H$_{36}$FN$_3$O$_6$S+0.5 H$_2$O+0.25 C$_4$H$_8$0: C 60.59 H 6.27 N 7.07 found C 60.59 H 6.34 N 6.51.

EXAMPLE 46

4-(4-{2-[(2S)-2-Hydroxy-3-(4-hydroxy-phenoxy)-propylamino]-ethyl}-benzenesulfonyl)-piperidine-1-carboxylic Acid (1-phenyl-cyclopentylmethyl)-amide Step A. tert-Butyl 4-{[1-({[(1-phenylcyclopentyl)methyl]amino}carbonyl)-4-piperidinyl]sulfonyl}phenethylcarbamate tert-Butyl 4-([1-({[(1-phenylcyclopentyl)methyl]amino}carbonyl)-4-piperidinyl]-sulfanyl}phenethylcarbamate (0.825 g, 1.534 mmol) was reacted according to Procedure O to afford the title compound (0.805 g, 1.413 mmol).

Step B. 4-{[4-(2-aminoethyl)phenyl]sulfonyl}-N-[(1-phenylcyclopentyl)methyl]-1-piperidinecarboxamide tert-Butyl 4-{[1-({[(1-phenylcyclopentyl)methyl]amino}carbonyl)-4-piperidinyl]-sulfonyl}phenethylcarbamate(0.770 g, 1.35 mmol) was reacted according to Procedure N to afford the title compound (0.575 g, 1.22 mmol).

MS ((+)ESI, m/z): 470 [M+H]$^+$

Step C. 4-{[4-(2-{[(2S)-3-(4-{[tert-butyl(diphenyl)silyl]oxy}phenoxy)-2-hydroxypropyl]amino}ethyl)phenyl]sulfonyl}-N-[(1-phenylcyclopentyl)methyl]-1-piperidinecarboxamide 4-{[4-(2-Aminoethyl)phenyl]sulfonyl}-N-[(1-phenylcyclopentyl)methyl]-1-piperidinecarboxamide (0.570 g, 1.20 mmol) was reacted with tert-butyl-(4-oxiranylmethoxy-phenoxy)-diphenylsilane (0.417 g, 1.03 mmol) according to Procedure G to give the title compound (eluant: 20:1 chloroform-methanol) (0.298 g, 0.341 mmol).

Step D. 4-(4-{2-[(2S)-2-Hydroxy-3-(4-hydroxy-phenoxy)-propylamino]-ethyl}-benzenesulfonyl)-piperidine-1-carboxylic acid (1-phenyl-cyclopentylmethyl)-amide 4-(4-{2-[(2S)-2-Hydroxy-3-(4-{[tert-Butyl(diphenyl)silyl]oxyphenoxy)-propylamino]-ethyl}-phenylsulfonyl)-piperidine-1-carboxylic acid (1-phenyl-cyclopentylmethyl)-amide (0.290 g, 0.330 mmol) was reacted according to Procedure H to give the title compound (eluant: 20:3 chloroform-methanol) (0.096 g, 0.150 mmol).

MS ((+)ESI, m/z): 636 [M+H]$^+$ $^1$H NMR (DMSO-d$_6$, 400 MHz) d 8.91 (s, 1H), 7.74 (d, J=8.1 Hz, 2H), 7.54 (d, J=8.1 Hz, 2H), 7.24 (m, 2H), 7.17 (m, 3H), 6.73 (d, J=9.0 Hz, 2H), 6.65 (d, J=9.0 Hz, 2H), 6.08 (t, J=5.9 Hz, 1H), 5.30 (br, 1H), 3.94 (br, 1H), 3.88 (m, 2H), 3.79 (d, J=5.3 Hz, 2H), 3.39 (m, 1H), 3.13 (d, J=5.9 Hz, 2H), 3.05–2.85 (series of m, 5H), 2.78 (m, 1H), 2.57 (t, J=12.4 Hz, 2H), 1.82 (m, 2H), 1.67 (m, 7H), 1.52 (m, 2H) and 1.27 (m, 2H).

EXAMPLE 47

4-(4-{2-[(2S)-2-Hydroxy-3-(4-hydroxy-phenoxy)-propylamino]-ethyl}-benzenesulfonyl)-piperidine-1-carboxylic Acid Octylamide Step A. 4-Hydroxy-N-octyl-1-piperidinecarboxamide 4-Hydroxypiperidine (2.48 g, 24.00 mmol) was reacted with octyl isocyanate (3.72 g, 24.0 mmol) according to Procedure E to yield the title compound (6.15 g, 24.00 mmol) which was used without further purification.

MS ((+)ESI, m/z): 257 [M+H]$^+$

Step B. 4-Bromo-N-octyl-1-piperidinecarboxamide

4-Hydroxy-N-octyl-1-piperidinecarboxamide (6.15 g 24.00 mmol) was reacted according to Procedure L to afford the title compound (7.65 g, 23.96 mmol).

Step C. tert-Butyl 4-({1-[(octylamino)carbonyl]-4-piperidinyl}sulfanyl) phenethylcarbamate 4-Bromo-N-octyl-1-piperidinecarboxamide (2.99 g, 9.371 mmol) and S-(4-{2-[(tert-butoxycarbonyl)amino] ethyl}phenyl) O-ethyl carbonodithioate (3.20 g, 9.371 mmol) were reacted according to Procedure M to afford the title compound (3.57 g, 7.26 mmol).

Step D. tert-Buyl 4-({1-[(octylamino)carbonyl]-4-piperidinvylsulfonyl) phenethylcarbamate tert-Butyl 4-({1-[(octylamino)carbonyl]-4-piperidinyl}sulfanyl) phenethylcarbamate (3.57 g, 7.26 mmol) was reacted according to Procedure 0 to afford the title compound (3.20 g, 6.11 mmol).

Step E. 4-{[4-(2-Aminoethyl)phenyl]sulfonyl}-N-octyl-1-piperidinecarboxamide tert-Butyl 4-{[1-(n-octylaminocarbonyl)-4-piperidinyl] sulfonyl}phenethylcarbamate (3.20 g, 6.11 mmol) was reacted according to Procedure N to afford the title compound (2.58 g, 6.09 mmol).

MS ((+)ESI, m/z): 424 [M+H]$^+$

Step F. 4-{[4-(2-{[(2S)-3-(4-{[tert-Butyl(diphenyl)silyl] oxy}phenoxy)-2-hydroxypropyl]amino}ethyl)phenyl] sulfonyl}-N-octyl-1-piperidinecarboxamide 4-{[4-(2-Aminoethyl)phenyl]sulfonyl}-N-octyl-1-piperidinecarboxamide (1.53 g, 3.612 mmol) was reacted with tert-butyl-(4-oxiranylmethoxy-phenoxy)-diphenylsilane (1.39 g, 3.431 mmol) according to Procedure G to give the title compound (eluant: 20: chloroform-ethanol) (0.500 g, 0.604 mmol).

MS ((+)ESI, m/z): 829 [M+H]$^+$

Step H. 4-(4-{2-[(2S)-2-Hydroxy-3-(4-hydroxy-phenoxy)-propylamino]-ethyl}-benzenesulfonyl)-piperidine-1-carboxylic acid octylamide 4-{[4-(2-{[(2S)-3-(4-{[tert-Butyl(diphenyl)silyl] oxy}phenoxy)-2-hydroxypropyl]amino}ethyl)phenyl] sulfonyl}-N-octyl-1-piperidinecarboxamide (0.500 g, 0.604 mmol) was reacted according to Procedure H to give the title compound (eluant: 20:3 chloroform-methanol) (0.280 g, 0.475 mmol).

m.p. 52–56° C.

MS ((+)ESI, m/z): 590 [M+H]$^+$ $^1$H NMR (DMSO-d$_6$, 400 MHz) d 8.83 (s, 1H), 7.68 (d, J=8.4 Hz, 2H), 7.48 (d, J=8.4 Hz, 2H), 6.69 (d from AB, J=9.0 Hz, 2H), 6.62 (d from AB, J=9.0 Hz, 2H), 6.40 (t, J=5.3 Hz, 1H), 4.86 (br, 1H), 3.96 (br m, 2H), 3.78–3.67 (m, 3H), 3.33 (m, 1H), 2.92 (q, J=6.8 Hz, 2H), 2.79 (s, 4H), 2.68–2.52 (series of m, 4H), 1.70 (br m, 2H), 1.35–1.18 (series of m, 14H) and 0.82 (t, J=7.0 Hz, 3H).

Anal. calcd. for C$_{31}$H$_{47}$N$_3$O$_6$S+0.5 H$_2$O: C 62.18 H 8.08 N 7.02 found: C 62.36 H 8.15 N 6.91

EXAMPLE 48

4-(4-{2-[(2S)-2-Hydroxy-3-(4-hydroxy-3-methyl-phenoxy)-propylamino]- ethyl}-benzenesulfonyl)-piperidine-1-carboxylic Acid Octylamide Step A. 4-{[4-{2-[((2S)-2-hydroxy-3-[3-methyl-4-[(triisopropylsilyl)oxy]phenoxy}propyl)amino] ethyl}phenyl)sulfonyl]-N-octyl-1-piperidinecarboxamide 4-{[4-(2-Aminoethyl)phenyl]sulfonyl}-N-octyl-1-piperidinecarboxamide (1.38 g, 3.258 mmol) was reacted with triisopropyl{2-methyl-4-[(2S)oxiranylmethoxy] phenoxy}silane (1.04 g, 3.095 mmol) according to Procedure G to give the title compound (eluant: 20:1 chloroform:methanol) (0.395 g, 0.520 mmol).

MS ((+)ESI, m/z): 761 [M+H]$^+$

Step B. 4-(4-{2-[(2S)-2-Hydroxy-3-(4-hydroxy-3-methyl-phenoxy)-propylamino]-ethyl}-benzenesulfonyl)-piperidine-1-carboxylic acid octylamide 4-{[4-(2-{[(2S)-3-(4-{[tert-Butyl(diphenyl)silyl]oxy}3-methyl-phenoxy)-2-hydroxypropyl]amino}ethyl)phenyl] sulfonyl}-N-octyl-1-piperidinecarboxamide (0.395 g, 0.520 mmol) was reacted according to Procedure H to give the title compound (eluant: 20/3(v/v) chloroform/methanol) (0.225 g, 0.373 mmol).

M.p. 58–71° C.

$^1$H NMR (DMSO-d$_6$, 400 MHz) d 8.72 (s, 1H), 7.71 (d, J=8.4 Hz, 2H), 7.50 (d, J=8.4 Hz, 2H), 6.64 (m, 2H, 1 exch), 6.53 (m, 1H), 6.43 (t, J=5.3 Hz, 1H), 4.91 (br s, 1H), 3.98 (br m, 2H), 3.81–3.70 (series of m, 3H), 3.38 (m, 1H), 2.94 (q, J=5.9 Hz, 2H), 2.83 (s, 4H), 2.72–2.56 (series of m, 4H), 2.07 (s, 3H), 1.73 (br m, 2H), 1.38–1.18 (series of m, 14H) and 0.85 (t, J=6.8 Hz, 3H).

MS ((+)APCI, m/z): 604 [M+H]$^+$

Anal. calcd. for C$_{32}$H$_{49}$N$_3$O$_6$S+0.6 H$_2$O: C 62.79 H 8.22 N 6.86 found: C 62.69 H 8.26 N 6.63

EXAMPLE 49

4-(4-{2-[(2S)-3-(Benzo[1,3]dioxol-5-yloxy)-2-hydroxy-propylamino]-ethyl}-benzenesulfonyl)-piperidine-1-carboxylic Acid Octylamide 4-{[4-(2-Aminoethyl)phenyl]sulfonyl}-N-octyl-1-piperidinecarboxamide (0.920 g, 2.172 mmol) was reacted with 5-[(2S)oxiranylmethoxy]-1,3-benzodioxole(0.211 g, 1.086 mmol) according to Procedure G to give the title compound (eluant: 20:1 chloroform-methanol) (0.209 g, 0.338 mmol).

M.p. 84–86° C.

MS ((+)APCI, m/z): 618 [M+H]$^+$ $^1$H NMR (DMSO-d$_6$, 400 MHz) d 7.70 (d, J=8.1 Hz, 2H), 7.50 (d, J=8.1 Hz, 2H), 6.77 (d, J=8.4 Hz, 1H), 6.59 (d, J=2.4 Hz, 1H), 6.44 (t, J=5.3 Hz, 1H), 6.32 (dd, J=8.1 and 2.4 Hz, 1H), 5.94 (s, 2H), 4.95 (br s, 1H), 3.98 (br m, 2H), 3.84–3.75 (series of m, 3H), 3.39 (m, 1H), 2.94 (q, J=6.2 Hz, 2H), 2.82 (s, 4H), 2.70–2.55 (series of m, 4H), 1.72 (br m, 2H), 1.38–1.18 (series of m, 14H) and 0.84 (t, J=6.6 Hz, 3H).

Anal. calcd. for C$_{32}$H$_{47}$N$_3$O$_7$S+H$_2$O: C 60.45 H 7.77 N 6.61 found: C 60.66 H 7.48 N 6.63

EXAMPLE 50

4-(4-{2-[(2S)-2-Hydroxy-3-(4-hydroxy-3-methanesulfonylamino-phenoxy)-propylamino]-ethyl}-phenylamino)-piperidine-1-carboxylic Acid 2,5-difluoro-benzylamide Step A. tert-Butyl 2-{[tert-butyl(diphenyl)silyl]oxy}-5-{[(2S)-3-({4-[(1-{[(2,5-difluorobenzyl)amino]carbonyl}-4-piperidinyl)amino]phenethyl}amino)-2-hydroxypropyl] oxy}phenyl(methylsulfonyl)carbamate 4-[4-(2-Aminoethyl)anilino]-N-(2,5-difluorobenzyl)-1-piperidinecarboxamide formate (0.306 g, 0.69 mmol) was reacted with tert-butyl 2-{[tert-butyl(diphenyl)silyl]oxy}-5-[(2S)oxiranylmethoxy]phenyl (methylsulfonyl)carbamate (0.40 g, 0.69 mmol) according to Procedure G (eluant: 20:1 chloroform-methanol) to give the title compound (0.112 g, 0.113 mmol)

Step B. 4-(4-{2-[(2S)-2-Hydroxy-3-(4-hydroxy-3-methanesulfonylamino-phenoxy)-propylamino]-ethyl}-phenylamino)-piperidine-1-carboxylic acid 2,5-difluoro-benzylamide tert-Butyl 2-{[tert-butyl(diphenyl)silyl]oxy}-5-{[(2S)-3-({4-[(1-{[(2,5-difluorobenzyl)-amino]carbonyl}-4-piperidinyl)amino]phenethyl}amino)-2-hydroxypropyl]oxy}phenyl (methylsulfonyl)carbamate (0.112 g, 0.113 mmol) was dissolved in methanol (5 mL) and hydrochloric acid (0.141 mL, 4M in dioxane, 0.567 mmol) added. The mixture was stirred for 2 hours at ambient temperature, the solvent removed in vacuo and the residue purified by flash chromatography on silica gel Merck-60 (eluant: 5:1 Chloroform-methanol containing 1% ammonium hydroxide) to give the title compound (0.037 g, 0.05 mmol).
m.p 103–108° C.
MS ((−)ESI, m/z): 646 [M−H]−
Anal. calcd. for $C_{31}H_{39}F_2N_5O_6S+1.2\ H_2O+0.1\ C_4H_{10}O$: C 55.73 H 6.31 N 10.35 found: C 55.4 H 6.27 N 10.14

EXAMPLE 51

1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic Acid Ethyl Ester Step A. 1-(2,2-Dimethoxyethyl)-4-nitro-benzene 2-(4-Nitrophenyl)-1-ethanol (10.0 g, 59 mmol) was added to a near solution of 1,1,1-triacetoxy-1,1-dihydro-1,2-benziodoxyl-3(1H)-one 1-oxide (29.0 g, 68 mmol) in anhydrous dichloromethane (200 mL). After 15 minutes the mixture was poured into a methanol solution (50 mL) containing trimethyl orthoformate (50 mL) and 4-methylbenzenesulfonic acid (0.10 g, 0.58 mmol). After ten minutes at ambient temperature the solvent was removed in vacuo and the residue purified by suction filtration through silica gel Merck-60 eluting with 4:1 hexane-diethyl ether. The solvent was removed in vacuo to provide the title compound as an oil (11.2 g, 53 mmol).
MS ((+)APCI, m/z): 229 [M+NH4]+

Step B. 4-(2,2-Dimethoxyethyl)aniline 1-(2,2-Dimethoxyethyl)-4-nitro-benzene (22 g, 104.16 mmol) was dissolved in ethanol (500 mL), 10% palladium on carbon (4 g) was added followed by ammonium formate (32.84 g, 520.8 mmol). The solution was heated to reflux for 0.5 hours The mixture was cooled to ambient temperature, filtered through a Celite pad, and the solvent removed in vacuo to provide the title compound as an oil (7.07 g, 3.90 mmol).
MS (EI, m/z): 181 [M]+

Step C. 1-Benzyl-N-[4-(2,2-dimethoxyethyl)phenyl]-4-piperidinamine 4-(2,2-Dimethoxyethyl)aniline (7.07 g, 39.0 mmol) and benzyl piperidone (11.07 g, 58.5 mmol) were dissolved in dichloroethane. Anhydrous sodium sulfate (50.0 g) was added followed by acetic acid (11 mL). Stirring was continued for 45 minutes. Sodium triacetoxyborohydride (24.2 g, 114.2 mmol) was added and stirring continued overnight. The mixture was filtered, diluted with dichloromethane, and washed with 40% sodium hydroxide, water and brine. The organic layer was dried over anhydrous magnesium sulfate and the solution filtered. The solvent was evaporated to dryness in vacuo. The residue was purified by flash chromatography on silica gel Merck-60 (eluant: 3:1 hexane-ethyl acetate) to furnish the title compound (10.0 g, 28 mmol).
MS ((+)ESI, m/z): 355 [M+H]+

Step D. N-[4-(2,2-Dimethoxyethyl)phenyl]-N-(4-piperidinyl)amine 1-Benzyl-N-[4-(2,2-dimethoxyethyl)phenyl]-4-piperidinamine (10.0 g, 28 mmol) was dissolved in ethanol (200 mL) 10% palladium on carbon (2.0 g) added followed by cyclohexene (20 mL). The solution was heated to reflux for 1.5 hours. The mixture was cooled to ambient temperature, filtered through a Celite pad, and the solvent removed in vacuo to furnish the title compound (6.2 g, 23.5 mmol).
MS ((+)APCI, m/z): 265 [M+H]+

Step E. 4-[1-(1,4-Dioxa-8-azaspiro[4.5]dec-8-ylcarbonyl)]-piperidinecarboxylic acid ethyl ester Triphosgene (0.44 g, 1.48 mmol) was dissolved in anhydrous dichloromethane (50 mL), ethyl isonipecotate (0.628 g, 4.0 mmol) and N,N-diisopropylethylamine (0.768 mL) in anhydrous dichloromethane (40 mL) were added drop-wise. Following the addition 1,4-dioxa-8-azaspiro[4.5]decane (0.572 g, 4.0 mmol) and N,N-diisopropylethylamine (0.768 mL) were added. The reaction was stirred for 15 minutes and the solvent removed in vacuo. The residue was purified by flash chromatography on silica gel Merck-60 (eluant: 50:1 chloroform-methanol) to furnish the title compound (1.09 g, 3.36 mmol).

Step F. Ethyl 1-[(4-oxo-1-piperidinyl)carbonyl]-4-piperidinecarboxylate

4-[1-(1,4-Dioxa-8-azaspiro[4.5]dec-8-ylcarbonyl)]-piperidinecarboxylic acid ethyl ester (1.09 g, 3.36 mmol) was dissolved in formic acid (10 mL) and heated at 60° C. for 0.5 hours. The solvent was removed in vacuo and the residue dissolved in dichloromethane, washed with water, 1 N sodium hydroxide, brine, dried over anhydrous magnesium sulfate. The solution was filtered and the solvent removed in vacuo to generate the title compound (0.95 g, 3.36 mmol).

Step G. 4-[1-({4-[4-(2,2-dimethoxyethyl)anilino]-1-piperidinyl}carbonyl)]-piperidinecarboxylic Acid Ethyl Ester 4-(2,2-Dimethoxyethyl)aniline (0.61 g, 3.36 mmol) and ethyl 1-[(4-oxo-1-piperidinyl)carbonyl]-4-piperidinecarboxylate (0.95 g, 3.36 mmol) were dissolved in dichloroethane (50 mL). Anhydrous sodium sulfate (4.75 g) was added followed by acetic acid (0.2 mL). Stirring was continued for 45 minutes. Sodium triacetoxyborohydride (0.747 g, 3.54 mmol) was added and stirring continued overnight. The mixture was filtered, diluted with dichloromethane, and washed with 2 N sodium hydroxide, water and brine. The organic layer was dried over anhydrous magnesium sulfate and the solution filtered The solvent was evaporated to dryness in vacuo. The residue was purified by flash chromatography on silica gel Merck-60 (eluant: 3:1 hexane-ethyl acetate) to furnish the title compound (0.74 g, 1.65 mmol).

Step H. 1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic Acid Ethyl Ester 4-[1-({4-[4-(2,2-Dimethoxyethyl)anilino]-1-piperidinyl}carbonyl)]-piperidinecarboxylic acid ethyl ester (0.74 g, 1.65 mmol) was added to a pre-prepared mixture of sodium iodide (0.618 g, 4.125 mmol) and trichloro(methyl)silane (0.495 g, 3.30 mmol) in anhydrous acetonitrile (10 mL). The reaction was stirred at ambient temperature for 3 minutes. Dichloromethane was added and the reaction washed with 10% sodium thiosulfate solution, water and brine. The organic layer was dried with anhydrous magnesium sulfate, filtered and the solvent partially removed under vacuo. The aldehyde solution was used directly and treated with methanol (30 mL), tetrahydrofuran (5 mL), acetic acid (0.2 mL), N-{5-[(1R)-2-amino-1-hydroxyethyl]-2- hydroxyphenyl}methanesulfonamide (0.406 g, 1.65 mmol) followed by sodium cyanoborohydride (0.103 g, 1.65 mmol). The reaction was stirred at ambient temperature overnight. The reaction was taken to dryness in vacuo, adsorbed onto silica and purified by flash chromatography on silica gel Merck-60 (eluant: 5:1 chloroform-methanol to which 1% ammonium hydroxide had been) to provide the title compound (0.175 g, 0.276 mmol).

m.p 93–97° C.

MS ((+)APCI, m/z): 632 [M+H]$^+$

Anal. calcd. for $C_{31}H_{45}N_5O_7S+2.0\ H_2O$: C 55.75 H 7.40 N 10.49 found: C 55.66 H 7.26 N 10.35

EXAMPLE 52

1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic Acid To a solution of 1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic acid ethyl ester (0.135 g, 0.213 mmol) was dissolved in methanol (5 mL) and sodium hydroxide (0.5 mL, 1N, 0.5 mmol) was added. The mixture was stirred at ambient temperature for thirty minutes and 1N hydrochloric acid (0.55 mL, 0.55 mmol) was added. The solvent was removed and the mixture partitioned between dichloromethane and water. The organic layer was dried over magnesium sulfate and the solvent removed in vacuo to yield the title compound (0.031 g, 0.05 mmol).

m.p Decomposes above 120° C.

MS ((−)ESI, m/z): 602 [M−H]$^-$

Anal. calcd. for $C_{29}H_{41}N_5O_7S.HCl+1.20\ H_2O+05\ C_4H_{10}O$: C 52.70 H 6.80 N 10.52 found: C 52.44 H 6.96 N 10.45

EXAMPLE 53

4-(4-{2-[(2S)-2-Hydroxy-3-(4-hydroxy-phenoxy)-propylamino]-ethyl}-phenylamino)-piperidine-1-carboxylic Acid 4-fluoro-benzylamide Step A. 4-[4-(2-{[(2S)-3-(4-{[tert-Butyl(diphenyl)silyl]oxy}phenoxy)-2-hydroxypropyl]amino}ethyl)anilino]-N-octyl-1-piperidinecarboxamide 4-[4-(2-Aminoethyl)anilino]-N-octyl-1-piperidinecarboxamide (0.40 g, 0.98 mmol) was reacted with tert-butyl-(4-oxiranylmethoxy-phenoxy)-diphenyl-silane (0.40 g, 0.99 mmol) according to the method described in Procedure G to give the title compound (eluant: 20:1 chloroform-methanol) (0.23 g, 0.30 mmol).

Step B. 4-(4-{2-[(2S)-2-Hydroxy-3-(4-hydroxy-phenoxy)-propylamino]-ethyl}-phenylamino)-piperidine-1-carboxylic acid 4-fluoro-benzylamide 4-[4-(2-{[(2S)-3-(4-{[tert-Butyl(diphenyl)silyl]oxy}phenoxy)-2-hydroxypropyl]amino}ethyl)anilino]-N-octyl-1-piperidinecarboxamide (0.23 g, 0.30 mmol) was reacted according to Procedure H (eluant: 10:1 chloroform-methanol containing 2% triethylamine) to give the title compound (0.12 g, 0.22 mmol).

m.p 66–69° C.

MS ((−)ESI m/z): 539 (M−H)$^-$

Anal. calcd. for $C_{31}H_{48}N_4O_4.HCl$: C 64.51 H 8.56 N 9.71 found: C 64.21 H 8.8 N 10.04

EXAMPLE 54

4-[4-(2-{[(2S)-2-Hydroxy-3-(4-hydroxyphenoxy)propyl]amino}ethyl)phenoxy]-N-octyl-1-piperidinecarboxamide Step A. tert-Butyl 4-hydroxyphenethylcarbamate A solution of tryamine (13.72 g, 100 mmol) in dichloromethane (250 mL) was treated with solid di-tert-butyl dicarbonate (21.82 g, 100 mmol) at 25° C. and stirred for three hours. The mixture was extracted sequentially with 1N hydrochloric acid and water. The organic phase was dried over anhydrous sodium sulfate and filtered through a short silica gel pad. The filtrate was evaporated in vacuo to yield tert-butyl 4-hydroxyphenethylcarbamate (22.7 g, 96 mmol) as a homogeneous, colorless oil, which solidified on standing. The product was used without further purification.

Step B. 4-Hydroxy-N-octyl-1-piperidinecarboxamide

The title compound (3.07 g, 12 mmol) was prepared from 4-hydroxypiperidine (1.21 g, 12 mmol) and octyl isocyanate (1.86 g, 12 mmol) according to Procedure C.

$^1$H NMR (DMSO-d$_6$, 300 MHz) δ 6.24 (t, J=5.5 Hz, 1H), 4.63 (d, J=4.7 Hz, 1H), 3.66 (dt, J=13.4, 4.0 Hz, 2H), 3.57 (tq, J=8.9, 4.0 Hz, 1H), 2.97 (q, J=6.5 Hz, 2H), 2.83 (ddd, J=13.4, 10.1, 2.8 Hz, 2H), 1.64 (dq, J=13.4, 4.0 Hz, 2H), 1.37 (p, J=7.3 Hz, 2H), 1.24 (s, 10H), 1.18 (dddd, J=13.4, 10.5, 10.5, 4.0 Hz, 2H), 0.88 (t, J=7.3 Hz, 3H).

Step C. tert-Butyl 4-({1-[(octylamino)carbonyl]-4piperidinyl}oxy)phenethylcarbamate A solution of 4-hydroxy-N-octyl-1-piperidinecarboxamide (3.0 g, 11.7 mmol), and triphenylphosphine (3.28 g, 12.5 mmol) in anhydrous tetrahydrofuran was treated drop-wise at 0° C. with a solution of diisopropyl 1,2-diazenedicarboxylate (2.66 g, 12.5 mmol) in anhydrous tetrahydrofuran. A solution of tert-butyl 4-hydroxyphenethylcarbamate (2.85 g, 12 mmol) in anhydrous tetrahydrofuran was added drop-wise over a period of three hours while maintaining the reaction temperature at 0° C. during the addition. The stirred reaction mixture was allowed to warm to room temperature overnight. The solvent was evaporated in vacuo and the residue stirred with hexane-diethyl ether (~1:1). The precipitate (4.5 g) was filtered and discarded. The filtrate was evaporated in vacuo to an amber-colored, oily crude product (6.95 g). The crude product was purified by flash chromatography on silica gel Merck-60 (eluant: 3:1 going to 1:1 hexane-methanol) to give the title compound (2.5 g, 5.26 mmol).

m.p. 79–81° C.

MS ((+)APCI), m/z 476 [M+H]$^+$

IR (KBr), v 3350, 1685, 1620, 1525, 1510, 1230, 1175 cm$_{-1}$ $^1$H NMR (DMSO-d$_6$, 400 MHz) δ 7.06 (d, J=8.6 Hz, 2H), 6.86 (d, J=8.8 Hz, 2H), 6.81 (t, J=5.5 Hz, 1H), 6.43 (t, J=5.5 Hz, 1H), 4.45 (tt, J=8.1, 4.2 Hz, 1H), 3.64 (ddd, J=14.1, 5.5, 4.2, 2H), 3.02–3.10 (m, 4H), 2.98 (q, J=6.8 Hz, 2H), 2.59 (t, J=7.9 Hz, 2H), 1.82–1.86 (m, 2H), 1.41–1.47 (m, 2H), 1.38 (m, 2H), 1.35 (s, 9H), 1.24 (s, 1 OH), 0.85 (t, J=7.0 Hz, 3H)

Analysis calc'd for $C_{27}H_{45}N_3O_4$: C 68.18, H 9.54, N 8.83: found: C 68.01, H 9.58, N 8.88

Step D. 4-[4-(2-Aminoethyl)phenoxy] N-octyl-1-piperidinecarboxamide tert-butyl 4-({1-[(octylamino)carbonyl]-4-piperidinyl}oxy)phenethylcarbamate (2.5 g, 5.26 mmol) was reacted according to Procedure F. The formate salt was partitioned between ethyl acetate and solution of saturated aqueous sodium bicarbonate, the organic layer was washed with water, dried over anhydrous sodium sulfate and taken to dryness in vacuo to provide the title compound (2.24 g, 4.72 mmol) as a clear oil, which solidified on standing.

Step E. 4-{4-[2-({(2S)-3-[4-(Benzyloxy)phenoxy]-2-hydroxypropyl}amino)ethyl]phenoxy}-N-octyl-1-piperidinecarboxamide 4-[4-(2-Aminoethyl)phenoxy] N-octyl-1-piperidinecarboxamide (0.825 g, 2.2 mmol) was reacted with (2S)-2-{[4-(benzyloxy)phenoxy]methyl}oxirane (0.564 g, 2.2 mmol) according to Procedure G (eluant: 33:1 going to 9:1 dichloromethane-methanol) to give the title compound following crystallization from hexane (0.533 g, 0.84 mmol).

Step F. 4-[4-(2-{[(2S)-2-Hydroxy-3-(4-hydroxyphenoxy)propyl]amino}ethyl)phenoxy]-N-octyl-1-piperidinecarboxamide A suspension of 4-{4-[2-({(2S)-3-[4-(benzyloxy)phenoxy]-2-hydroxypropyl}amino)ethyl]phenoxy}-N-octyl-1-piperidinecarboxamide (0.2 g, 0.32 mmol), and 10% palladium on carbon (0.3 g) in ethanol (5 mL) was stirred under atmospheric hydrogen for 11 hours. The catalyst was filtered and the filtrate evaporated in vacuo to a residue (0.1 g). The residue was treated with a solution of anhydrous hydrogen chloride in methanol followed by ethyl acetate and diethyl ether. The precipitate was filtered and after drying in vacuo overnight yielded the title compound (0.1 g, 0.17 mmol).

m.p. 153–155° C.

MS ((+)APCI), m/z 542 [M+H]$^+$

IR(KBr), v 3400, 1625, 1510, 1240, 1050, 825 cm$^{-1}$ $^1$H NMR (DMSO-d$_6$, 400 MHz) δ 8.97 (broad s, 1H), 8.77 (broad s, 1H), 7.14 (d, J=8.6 Hz, 2H), 6.91 (d, J=8.8 Hz, 2H), 6.75 (d, J=9.0 Hz, 2H), 6.67 (d, J=9.0 Hz, 2H), 4.48 (m, 1H), 4.15 (m, 1H), 3.87 (dd, J=10.1,5.3Hz, 1H), 3.82 (dd, J=9.9, 5.5 Hz, 1H), 3.65 (dt, J=13.6, 3.7 Hz, 2H), 2.60–3.40 (m, 10H), 1.8–1.9 (m, 2H), 1.32–1.48 (m, 4H), 1.23 (s, 10H), 0.85 (t, J=7.0 Hz, 3H)

Analysis calc'd for C$_{31}$H$_{47}$N$_3$O$_5$.HCl: C 64.40 H 8.37 N 7.27 found: C 62.47 H 8.27 N 6.94.

EXAMPLE 55

N-(8-Fluorooctyl)-4-[4-(2-{[(2S)-2-hydroxy-3-(4-hydroxyphenoxy)propyl]amino}ethyl)anilino]-1-piperidinecarboxamide Step A. Methyl 9-hydroxynonanoate A solution of 9-methoxy-9-oxononanoic acid (azelaic acid monomethyl ester) (40.45 g, 200 mmol) in tetrahydrofuran (200 mL) was treated via syringe with borane-methyl sulfide complex, 10.0 M (20 mL, 200 mmol) and warmed to 40° C. The reaction was stirred for one hour at ambient temperature. The excess borane reagent was destroyed with excess methanol and the solvent evaporated in vacuo to a residue. The residue was dissolved in diethyl ether and extracted sequentially with 2N hydrochloric acid and water. The organic phase was dried over anhydrous sodium sulfate, filtered through a short pad of silica gel, and the solvent evaporated in vacuo to yield the title compound (33.88 g, 180 mmol) as a viscous oil, which was used without further purification.

$^1$H NMR (DMSO-d$_6$, 300 MHz) δ 4.32 (t, J=5.2 Hz, 1H), 3.58 (s, 3H), 3.37 (td, J=6.7, 5.2 Hz, 2H), 2.48 (t, J=7.4 Hz, 2H), 1.58 (p, J=7.1 Hz, 2H), 1.40 (p, J=7.1 Hz, 2H), 1.26 (broad s, 8H)

Step B. Methyl 9-fluorononanoate

A stirred solution of methyl 9-hydroxynonanoate (33.88 g, 180 mmol), in dichloromethane (100 mL) was treated drop-wise under nitrogen at 0° C. with a solution of diethylaminosulfur trifluoride, DAST, (31.77 g, 197 mmol) in dichloromethane (100 mL) over a period of one hour. After the addition was complete, the mixture was stirred for two hours and the reaction temperature allowed to rise to 25° C. The reaction mixture was diluted with dichloromethane and carefully treated with a solution of saturated aqueous sodium bicarbonate. The organic phase was dried over anhydrous sodium sulfate, filtered, and the solvent evaporated in vacuo to a crude oil. The crude oil was re-dissolved in diethyl ether, filtered through a short column of silica gel, and the filtrate evaporated in vacuo to afford 32 g of a yellow oil. The yellow oil was partially purified by flash chromatography on silica gel Merck-60 (eluant: 3:1 hexane-ethyl acetate) to yield 28.25 g (147 mmol) of a clear oil. The clear oil was distilled under vacuum twice to yield the title compound (17.7 g, 93 mmol) as a colorless oil.

$^1$H NMR (DMSO-d$_6$, 300 MHz) δ 4.41 (dt, J$_{H-F}$=47.0 Hz, J 6.0 Hz, 2H), 3.58 (s, 3H), 2.29 (t, J=7.2 Hz, 2H), 1.44–1.72 (m, 4H), 1.20–1.40 (m, 8H)

Step C. 9-Fluorononanoic acid

A solution of methyl 9-fluorononanoate (17.1 g, 90 mmol) in 1,4-dioxane (45 mL) was treated drop-wise with a solution of lithium hydroxide (2.4 g, 100 mmol) in water (15 mL). The reaction mixture was stirred at ambient temperature until no starting material remained by thin layer chromatography. The reaction mixture was acidified to pH 1.0 with 2N hydrochloric acid and extracted with diethyl ether. The combined organic phase was washed with water, dried over anhydrous sodium sulfate, filtered, through a short pad of silica gel, and the filtrate evaporated in vacuo to yield 9-fluorononanoic acid (12.75 g, 72 mmol) as a clear, colorless oil, which solidified on standing in the refrigerator. The product was used without further purification.

$^1$H NMR (DMSO-d$_6$, 300 MHz) δ 4.42 (dt, J$_{H-F}$=47.5 Hz, J=9.3 Hz, 2H), 2.19 (t, J=7.5 Hz, 2H), 1.62 (dp, J$_{H-F}$=25.4 Hz, J=6.9 Hz, 2H), 1.49 (p, J=6.6 Hz, 2H), 1.28 (broad s, 8H)

Step D. tert-Butyl 4-[(1-{[(8-fluorooctyl)amino]carbonyl}-4-piperidinyl)amino]phenethylcarbamate The title compound (0.70 g, 1.42 mmol) was prepared from 9-fluorononanoic acid (0.528 g, 3.0 mmol) and tert-butyl 4-(4-piperidinylamino)phenethylcarbamate (0.958 g, 3.0 mmol) according to Procedure D.

m.p. 78–80° C.

MS ((+)ESI), m/z 985 [2M+H]$^+$, 493 [M+H]$^+$

IR (KBr), v 3600, 3300, 1690, 1620, 1520, 1250, 1175 cm$^{-1}$

1H NMR (DMSO-d$_6$, 400 MHz) δ 6.86 (d, J=8.3 Hz, 2H), 6.78 (t, J=5.5 Hz, 1H), 6.49 (d, J=8.1 Hz, 2H), 6.40 (t, J=5.5 Hz, 1H), 5.25 (d, J=8.3 Hz, 1H), 4.41 (dt, J$_{H-F}$=47.7 Hz, J=6.1 Hz, 2H), 3.84 (broad d, J=13.4 Hz, 2H), 3.32 (m, 1H), 2.95–3.04 (m, 4H), 2.79 (broad t, J=11.4 Hz, 2H), 2.48 (t, 2H), 1.80 (broad d, J=12.7 Hz, 2H), 1.61 (dp, J$_{H-F}$=25.5 Hz, J=6.8 Hz, 2H), 1.35 (s, 9H), 1.24 (s, 10H), 1.18 (m, 2H)

$^{13}$C NMR (DMSO-d$_6$, 100 MHz) δ 157.3 (1C), 155.4 (1C), 146.0 (1 C), 129.0 (2C), 126.1 (1C), 112.5 (2C), 83.7 (d, J$_{C-F}$=161.7 Hz, 1C), 77.4 (1C), 49.0 (1C), 42.4 (2C), 42.0 (1C), 34.7 (1C), 31.6 (2C), 29.8 (1C), 29.7 (1C), 28.7 (1C), 28.6 (1C), 28.3 (3C), 26.3 (1C), 24.6 (1C), 24.6 (1C)

Analysis calc'd for C$_{27}$H$_{45}$FN$_4$O$_3$: C 65.82 H 9.21; N 11.37. found: C 64.07 H 9.10 N 11.01.

Step E. 4-[4-(2-Aminoethyl)anilino]-N-(8-fluorooctyl)-1-piperidinecarboxamide tert-Butyl 4-[(1-{[(8-fluorooctyl)amino]carbonyl}-4-piperidinyl)amino] phenethylcarbamate (0.984 g, 2.0 mmol) was reacted according to Procedure F. The formate salt was partitioned between ethyl acetate and solution of saturated aqueous sodium bicarbonate, the organic layer was washed with water, dried over anhydrous sodium sulfate and taken to dryness in vacuo to furnish the title compound (0.70 g, 1.78 mmol) as an oil.

Step F. 4-[4-(2-{[(2S)-3-(4-{[(tert-Butyl(diphenyl)silyl]oxy}phenoxy)-2-hydroxypropyl]amino}ethyl)anilino]-N-(8-fluorooctyl)-1-piperidinecarboxamide 4-[4-(2-Aminoethyl)anilino]-N-(8-fluorooctyl)-1-piperidinecarboxamide (0.70 g, 1.78 mmol) was reacted with tert-butyl-(4-oxiranylmethoxy-phenoxy)-diphenyl-(0.722 g, 1.78 mmol) according to Procedure G (eluant: 50:1 going to 20:1 dichloromethane-methanol) to give the title compound (0.60 g, 0.75 mmol).

m.p. 53–55° C.
MS ((+)ESI), m/z 797 {M+H}$^+$
IR (KBr), v 3350, 1610, 1505, 1230, 700 cm$^{-1}$
$^1$H NMR (DMSO-d$_6$, 400 MHz) δ 7.65 (dd, J=7.9,1.5 Hz, 4H), 7.39–7.46 (m, 6H), 6.87 (d, J=8.3 Hz, 2H), 6.68 (d, J=9.2 Hz, 2H), 6.63 (d, J=9.2 Hz, 2H), 6.48 (d, J=8.6 Hz, 2H), 6.41 (t, 1H), 5.23 (d, J=8.1 Hz, 1H), 4.98 (broad s, 1H), 4.41 (dt, J$_{H-F}$=47.7 Hz, J=6.1 Hz, 2H), 3.71–3.86 (m, 5H), 3.32 (m, 1H), 2.98 (q, J=6.1 Hz, 2H), 2.79 (t, J=13.4 Hz, 2H), 2.66–2.68 (m, 3H), 2.52–2.65 (m, 3H), 1.76 (broad d, J=12.7 Hz, 2H), 1.61 (dp, J$_{H-F}$=25.5 Hz, J=6.8 Hz, 2H), 1.14–1.38 (m, 12H), 1.02 (s, 9H)
$^{13}$C NMR (DMSO-d$_6$, 100 MHz) δ 157.3 (1C), 152.9 (1C), 148.6 (1C), 145.9 (1C), 135.0 (4C), 132.3 (2C),130.1 (2C), 129.0 (2C), 127.9 (4C), 126.6 (1C), 119.7 (2C), 115.1 (2C), 112.5 (2C), 83.7 (d, J$_{C-F}$=161.7 Hz, 1C), 70.9 (1C), 67.7 (1C), 52.0 (1C), 51.3 (1C), 49.0 (1C), 42.4 (2C), 34.5 (1C), 31.6 (2C), 29.9 (1C), 29.7 (1C), 28.7 (1C), 28.6 (1C), 26.3 (3C), 24.6 (1C), 18.9 (1C)

Analysis calc'd for C$_{47}$H$_{65}$FN$_4$O$_4$Si: C 70.82 H 8.22 N 7.03 found: C 70.05 H 8.11 N 6.85.

Step G. N-(8-Fluorooctyl)-4-[4-(2-{[(2S)-2-hydroxy-3-(4-hydroxyphenoxy)propyl]amino}ethyl)anilino]-1-piperidinecarboxamide 4-[4-(2-{[(2S)-3-(4-{[(tert-Butyl(diphenyl)silyl]oxy}phenoxy)-2-hydroxypropyl]amino}ethyl)anilino]-N-(8-fluorooctyl)-1-piperidinecarboxamide (0.55 g, 0.69 mmol) was reacted according to Procedure H (eluant: 5:1 chloroform-methanol). The residue was dissolved in ethyl acetate and washed sequentially with a saturated aqueous sodium bicarbonate solution and water. The organic phase was dried over anhydrous sodium sulfate, filtered, and the filtrate evaporated in vacuo to afford a second oil (0.39 g). The second oil was re-dissolved in ethyl acetate, filtered, and the filtrate evaporated in vacuo to afford a third oil. The third oil was treated with a solution of anhydrous hydrogen chloride in methanol, followed by diethyl ether. The supernatant was decanted, and the precipitate stirred with diethyl ether under nitrogen overnight. The mixture was filtered in a glove bag under positive nitrogen flow to yield, after drying in vacuo at room temperature for two hours, the title compound (0.253 g, 0.39 mmol) as a slightly hygroscopic solid m.p. 148–150° C.
MS ((+)APCI), m/z 559 [M+H]$^+$
IR (KBr), v 3300, 1610, 1540, 1510, 1225, 1030, 825 cm$^{-1}$
$^1$H NMR (DMSO-d$_6$, 400 MHz) δ 9.16 (broad s, 1H), 8.89 (broad s, 1H), 7.36 (broad s, 4H), 6.76 (d, J=9.0 Hz, 2H), 6.68 (d, J=9.0 Hz, 2H), 6.52 (broad s, 1H), 4.41 (dt, J$_{H-F}$=47.5 Hz, J=6.1 Hz, 2H), 4.15–4.20 (m, 1H), 3.98 (broad d, J=13.4 Hz, 2h), 3.87 (dd, J=9.9, 5.1 Hz, 1H), 3.83 (dd, J=9.9, 5.5 Hz, 1H), 3.51 (broad t, J=11.0 Hz, 1H), 3.16–3.19 (m, 3H), 2.95–3.06 (m, 5H), 2.64 (t, J=12.3 Hz, 2H), 1.83 (broad d, J=10.3 Hz, 2H), 1.61 (dp, J$_{H-F}$=25.3 Hz, J=6.4 Hz, 2H), 1.47 (m, 2H), 1.24–1.40 (m, 10H) 13C NMR (DMSO-d$_6$, 100 MHz) δ 157.1 (1C), 151.5 (1C), 151.0 (1C), 129.8 (6C), 115.7 (2C), 115.5 (2C), 83.7 (d, J$_{C-F}$=161.7 Hz, 1C), 70.4 (1C), 65.0 (1C), 49.6 (2C), 47.9 (1C), 41.9 (1C), 30.8 (1C), 29.9 (1C) 29.8 (1C), 29.7 (1C), 28.7 (1C), 28.6 (2C), 26.3 (1C), 24.7 (1C), 24.6 (1C)

Ionic Halogen calc'd for 2Cl$^-$: 10.34%, found:10.72%;
Karl Fischer calc'd for 1 H$_2$O: 3.12%, found:3.01%;

Analysis calc'd for C$_{31}$H$_{47}$FN$_4$O$_4$.2HCl+H$_2$O: C 57.73 H 7.91 N 8.62 found: C 58.02 H 7.84 N 8.50.

EXAMPLE 56

4-(4-{2-[(2S)2-Hydroxy-3-(4-hydroxy-phenoxy)-propylamino]-ethyl}-phenoxy)-piperidine-1-carboxylic Acid 4-fluoro-benzylamide Step A. N-(4-Fluorobenzyl)-4-hydroxy-1-piperidinecarboxamide The title compound (5.00 g, 19.8 mmol) was prepared from 4-hydroxypiperidine (2.00 g, 19.8 mmol) and 4-fluorobenzyl isocyanate (2.99 g, 19.8 mmol) according to Procedure C.

$^1$H NMR (DMSO-d$_6$, 300 MHz) δ 7.27 (dd, J=8.5, 5.8 Hz, 2H), 7.12 (t, J=9.0 Hz, 2H), 7.05 (t, J=5.8 Hz, 1H), 4.67 (d, J=4.4 Hz, 1H), 4.20 (d, J=5.8 Hz,.2H), 3.72 (dt, J=13.5, 4.4 Hz, 2H), 3.60 (tq, J=8.7, 4.4 Hz,1H), 2.90 (ddd, J=12.8, 9.8, 3.0 Hz, 2H), 1.68 (dq, J=13.5, 3.8 Hz, 2H), 1.26 (dddd, J=13.5, 9.8, 9.8, 3.8 Hz, 2H)

Step B. tert-Butyl 4-[(1-{[(4-fluorobenzyl)amino]carbonyl}-4-piperidinyl)oxy]phenethylcarbamate A stirred solution of N-(4-fluorobenzyl)-4-hydroxy-1-piperidinecarboxamide (2.95 g, 11.7 mmol), and solid triphenylphosphine (3.28 g, 12.5 mmol) in anhydrous tetrahydrofuran (50 mL), was treated drop-wise at 0° C. under nitrogen with a solution of diisopropyl 1,2-diazenedicarboxylate (2.66 g, 12.5 mmol) in anhydrous tetrahydrofuran (10 mL). A solution of tert-butyl 4-hydroxyphenethylcarbamate (2.85 g, 12 mmol) in anhydrous tetrahydrofuran (25 mL) was added drop-wise over a period of three hours while maintaining the reaction temperature at 0° C. during the addition. The stirred reaction mixture was allowed to warm to room temperature overnight. Hexane and diethyl ether were added to the reaction mixture and the precipitate filtered. The precipitate was triturated with diethyl ether and re-filtered. The combined filtrates were evaporated in vacuo, and the resulting residue crystallized from a mixture of acetone-diethyl ether-hexane (1:1:1) to yield, after filtration and washing with cold diethyl ether, the title compound (1.25 g, 2.6 mmol).

m.p. 126–128° C.
MS ((+)APCI), m/z 472 [M+H]$^+$
IR (KBr), v 3400, 1690, 1610, 1525, 1510, 1230, 1180 cm$^{-1}$
$^1$H NMR (DMSO-d$_6$, 400 MHz) δ 7.26 (dd, J=8.8, 5.7 Hz, 2H), 7.11 (t, J=8.8 Hz, 2H), 7.06 (d, J=8.6 Hz, 2H), 7.06 (1H), 6.86 (d, J=8.6 Hz, 2H), 6.83 (t, J=5.7 Hz, 1H), 4.47 (tt, J=7.9, 3.9 Hz, 1H), 4.20 (d, J=5.7 Hz, 2H), 3.68 (dt, J=14.3, 4.2 Hz, 1H), 3.12 (ddd, J=12.7, 9.2, 3.1 Hz, 2H), 3.06 (t, J=5.9 Hz, 2H), 2.59 (t, J=7.9 Hz, 2H), 1.84–1.89 (m, 2H), 1.46 ( dddd, J=12.7, 8.8, 8.8, 3.7 Hz, 2H)
$^{13}$C NMR (DMSO-d$_6$, 100 MHz) δ 161.0 (d, J$_{C-F}$=241.1 Hz, 1C), 157.2 (1C), 155.4 (1C), 155.3 (1C), 137 (1C), 131 (1C), 130 (2C), 128.8 (d, J$_{C-F}$=8.4 Hz, 2C), 116 (2H), 114.7 (d, J$_{C-F}$=21.4 Hz, 2C), 77 (1C), 72 (1C), 42.8 (2C), 41.7 (2C), 40.8 (2C), 34.6 (2C), 30.5 (2C), 28.2 (9C)

Analysis calc'd for C$_{26}$H$_{34}$FN$_3$O$_4$: C 66.22 H 7.27 N 8.91 found: C 66.12 H 7.18 N 8.72

Step C. 4-[4-(2-Aminoethyl)phenoxy]-N-(4-fluorobenzyl)-1-piperidinecarboxamide tert-Butyl 4-[(1-(4-fluorobenzyl)amino]carbonyl}-4-piperidinyl)oxy]phenethylcarbamate (1.25 g, 2.6 mmol) was reacted according to Procedure F. The formate salt was partitioned between ethyl acetate and solution of saturated aqueous sodium bicarbonate, the organic layer was washed with water, dried over anhydrous sodium sulfate and taken to dryness in vacuo. The residue was purified by flash chromatography on silica gel Merck-60 (eluant: 5:1 ethyl acetate-methanol) to furnish the title compound after trituration with hexane (0.740 g, 2.0 mmol).

m.p. 130–134° C.

$^1$H NMR (DMSO-d$_6$, 300 MHz) δ 7.28 (dd, J=8.8, 5.5 Hz, 2H), 7.13 (dd, J=8.8, 6.1 Hz, 2H), 7.10 (d, J=8.5 Hz, 2H), 7.10 (1H), 6.88 (d, J=8.5 Hz, 2H), 4.49 (tt, J=7.7, 3.4 Hz, 1H), 4.21 (d, J=5.8 Hz, 2H), 3.72 (dt, J-14.4, 4.4 Hz, 2H), 3.50 (broad s, 2H), 3.14 (ddd, J=12.8, 8.9, 2.8 Hz, 2H), 2.52–2.80 (m, 4H), 1.80–1.94 (m, 2H), 1.48 (dddd, J=12.5, 8.8, 8.8, 3.7 Hz, 2H)

Step D. 4-[4-(2-{[(2S)-3-(4-{[tert-Butyl(diphenyl)silyl]oxy}phenoxy)-2-hydroxypropyl]amino}ethyl)phenoxy]-N-(4-fluorobenzyl)-1-piperidinecarboxamide 4-[4-(2-Aminoethyl)phenoxy]-N-(4-fluorobenzyl)-1-piperidinecarboxamide (0.56 g, 1.5 mmol), was reacted with tert-butyl-(4-oxiranylmethoxy-phenoxy)-diphenyl-silane (0.606 g, 1.5 mmol) according to Procedure G (eluant: 50:1 going to 20:1 dichloromethane-methanol) to give the title compound (0.47 g, 0.61 mmol).

Step E. N-(4-Fluorobenzyl)-4-[4-(2-{[(2S)-2-hydroxy-3-(4-hydroxyphenoxy)propyl]amino}ethyl)phenoxy]-1-piperidinecarboxamide 4-[4-(2-{[(2S)-3-(4-{[tert-butyl(diphenyl)silyl]oxy}phenoxy)-2-hydroxypropyl]amino}ethyl)phenoxy]-N-(4-fluorobenzyl)-1-piperidinecarboxamide (0.335 g, 0.43 mmol) was reacted according to Procedure H (eluant: 8:1 chloroform-methanol) to give the title compound (0.09 g, 0.145 mmol). The free base was treated with a solution of anhydrous hydrogen chloride in methanol, followed by diethyl ether and hexane. The precipitate was filtered and, after drying in vacuo overnight, yielded the title compound (0.17 g, 0.3 mmol)

m.p. 160–162° C.

MS ((+)ESI), m/z 538 [M+H]$^+$

IR (KBr), v 3250, 1600, 1510, 1230, 820 cm$^{-1}$ $^1$H NMR (DMSO-d$_6$, 400 MHz) δ 9.06 (broad s, 1H), 8.82 (broad s, 1H), 7.27 (dd, J=8.6, 5.9 Hz, 2H), 7.14 (d, J=8.6 Hz, 2H), 7.11 (t, J=8.8 Hz, 2H), 6.92 (d, J=8.6 Hz, 2H), 6.76 (d, J=9.0 Hz, 2H), 6.67 (d, J=9.0 Hz, 2H), 4.50 (tt, J=7.7, 3.5 Hz, 1H), 4.17 (m, 1H), 4.00–4.70 (broad, 1H), 3.87 (dd, J=10.1, 5.3 Hz, 1H), 3.82 (dd, J=9.9, 5.5 Hz, 1H), 3.69 (dt, J=14.1, 5.7 Hz, 2H), 3.10–3.19 (m, 4H), 2.88–3.02 (m, 3H), 1.85–1.88 (m, 2H), 1.46 (dddd, J=12.3, 8.8, 8.8, 3.5 Hz, 2H)

Analysis calc'd for C$_{30}$H$_{36}$FN$_3$O$_5$.HCl: C 62.77, H 6.50, N 7.32. found: C 60.79, H 6.29, N 6.93.

EXAMPLE 57

4-(4-{2-[2-Hydroxy-3-(4-hydroxy-phenoxy)-propylamino]-ethyl}-phenylamino)-piperidine-1-carboxylic Acid [4-(3,4-dimethoxy-phenyl)-butyl]-amide Step A. tert-Butyl 4-{[1-({[4-(3,4-dimethoxyphenyl)butyl]amino}carbonyl)-4-piperidinyl]amino}phenethylcarbamate The title compound (0.79 g, 1.80 mmol) was prepared from 5-(3,4-dimethoxyphenyl)pentanoic acid (prepared according to ref: J. Chem. Soc., 1950, 163, and Ind. J. Chem., 1990, 215,) (0.443 g, 1.86 mmol) and {2-[4-(piperidin-4-ylamino)-phenyl]-ethyl}-carbamic acid tert-butyl ester (0.97 g, 1.75 mmol) according to Procedure D.

Step B. 4-[4-(2-Aminoethyl)anilino]-N-[4-(3,4-dimethoxyphenyl)butyl]-1-piperidinecarboxamide tert-Butyl 4-{[1-({[4-(3,4-dimethoxyphenyl)butyl]amino}carbonyl)-4-piperidinyl]amino}phenethylcarbamate (0.97 g, 1.75 mmol) was reacted according to Procedure F. The formate salt was partitioned between chloroform and 1N sodium hydroxide, the organic layer was washed with brine, dried over anhydrous magnesium sulfate and taken to dryness in vacuo to provide the title compound (0.79 g, 1.42 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-[4-(3,4-dimethoxyphenyl)butyl]-1-piperidinecarboxamide 4-[4-(2-Aminoethyl)anilino]-N-[4-(3,4-dimethoxyphenyl)butyl]-1-piperidinecarboxamide (0.79 g, 1.42 mmol) was reacted with tert-butyl-(4-oxiranylmethoxy-phenoxy)-diphenyl-silane (0.36 g, 0.89 mmol) according to Procedure G (eluant: 20:1 chloroform-methanol) to give the title compound (0.40 g, 0.47 mmol).

Step D. 4-(4-{2-[2-Hydroxy-3-(4-hydroxy-phenoxy)-propylamino]-ethyl}-phenylamino)-piperidine-1-carboxylic acid [4-(3,4-dimethoxy-phenyl)-butyl]-amide 4-[4-(2-{[(2S)-3-(4-{[tert-Butyl(diphenyl)silyl]oxy}phenoxy)-2-hydroxypropyl]amino}ethyl)anilino]-N-[4-(3,4-dimethoxyphenyl)butyl]-1-piperidinecarboxamide (0.40 g, 0.47 mmol) was reacted according to Procedure H (eluant: 10:1 chloroform-methanol containing 2% triethylamine) to give the title compound (0.26 g, 0.42 mmol).

m.p 60–62° C.

MS ((-)ESI, m/z): 619 [M-H]$^-$

Anal. calcd. for C$_{35}$H$_{48}$N$_4$O$_6$ 1.2 H$_2$O+0.33C[CH$_3$(CH2)$_3$]$_4$NF: C 63.56 H 8.30 N 7.97 found: C 63.20 H 8.14 N 8.74

EXAMPLE 58

(4-{[4-(4-{2-[(2S)-2-Hydroxy-3-(4-hydroxy-phenoxy)-propylamino]-ethyl}-phenylamino)-piperidine-1-carbonyl]-amino}-phenoxy)-acetic Acid Step A. Methyl 2-(4-nitrophenoxy)acetate To a stirred solution of 4-nitrophenol (22.68 g, 163.0 mmol) in anhydrous N,N-dimethylformamide (150 mL) was added potassium carbonate (29.3 g, 21.2 mmol) followed by methyl bromoacetate (27.4 g, 179 mmol) over 1 hour. The reaction was stirred for 48 hours and water added. The resulting precipitate was removed by suction and washed well with water and dried. The damp solid was suspended in hexane stirred at ambient temperature for 0.5 hours and filtered. The solid was dried and crystallized from methanol to give the title compound (27.8 g, 131.6 mmol).

$^1$H NMR (DMSO-d$_6$, 400 MHz): d 3.70 (s, 3H), 5.0 (s, 2H), 7.16 (d, 2H), 8.19 (d, 2H)

Step B. Methyl 2-(4-aminophenoxy)acetate

Methyl 2-(4-nitrophenoxy)acetate (3.08 g, 14.59 mmol) was dissolved in ethanol (30 mL) and 10% palladium on carbon (0.75 g) added. The solution was shaken in a Parr apparatus at 50 psi hydrogen atmosphere for 1.5 hours and filtered through a Celite pad. The solvent was removed in vacuoto yield the title compound as an oil (2.61 g,14.4 mmol).

MS (EI, m/z): 181 [M]$^+$

Step C. Methyl 2-[4-({[4-(4-{2-[(tert-butoxycarbonyl)amino]ethyl}anilino)-1-piperidinyl]carbonyl}amino)phenoxy]acetate The title compound (0.52 g, 1.0 mmol) was prepared from methyl 2-(4-aminophenoxy)acetate (0.5 g, 2.79 mmol) and {2-[4-(piperidin-4-ylamino)-phenyl]-ethyl}-carbamic acid tert-butyl ester (0.89 g, 2.79 mmol) according to Procedure C.

MS ((+)ESI, m/z): 527 [M+H]$^+$, 544 [M+NH$_4$]$^+$

Step D. Methyl 2-{4-[({4-[4-(2-aminoethyl)anilino]-1-piperidinyl}carbonyl)-amino]phenoxy}acetate formate Methyl 2-[4-({[4-(4-{2-[(tert-butoxycarbonyl)amino]ethyl}anilino)-1-piperidinyl]carbonyl}amino)phenoxy]

acetate (0.52 g, 1.0 mmol) was reacted according to Procedure F to provide the title compound (0.48 g, 1.0 mmol) which was used without further purification.

Step E. Methyl 2-{4-[({4-[4-(2-{[(2S)-2-hydroxy-3-(4-{[isopropyl-(diphenyl)silyl]-oxy}phenoxy)propyl]amino}ethyl)anilino]-1-piperidinyl}carbonyl)amino]phenoxy}acetate Methyl 2-{4-[({4-[4-(2-aminoethyl)anilino]-1-piperidinyl}carbonyl)amino] phenoxy}acetate formate (0.48 g, 1.0 mmol) was reacted with tert-butyl-(4-oxiranylmethoxy-phenoxy)-diphenyl-silane (0.25 g, 0.62 mmol) according to Procedure G (eluant: 20:1 chloroform-methanol) to give the title compound (0.16 g, 0.192 mmol).

Step F. Methyl 2-{4-[({4-[4-(2-{[(2S)-2-hydroxy-3-(4-hydroxyphenoxy)-propyl]amino}ethyl)anilino]-1-piperidinyl}carbonyl)amino]phenoxy}acetate Methyl 2-{4-[({4-[4-(2-{[(2S)-2-hydroxy-3-(4-{[isopropyl(diphenyl)silyl]oxy}phenoxy)propyl]amino}ethyl)anilino]piperidinyl}carbonyl)amino]phenoxy}acetate (0.16 g, 0.192 mmol) was reacted according to Procedure H (eluant: 10:1 going to 5:1 chloroform-methanol containing 2% triethylamine) to give the title compound (0.64 g, 0.108 mmol)

Step G. (4-{[4-(4-{2-[(2S)-2-Hydroxy-3-(4-hydroxyphenoxy)-propylamino]-ethyl}-phenylamino)-piperidine-1-carbonyl]-amino}-phenoxy)-acetic acid Methyl 2-{4-[({4-[4-(2-{[(2S)-2-hydroxy-3-(4-hydroxyphenoxy)propyl]amino}ethyl)anilino]-1 piperidinyl}carbonyl)amino] phenoxy}acetate (0.064 g, 0.108 mmol) was dissolved in 1N LiOH (0.108 mL) and the reaction stirred at ambient temperature for 4 days. The volatiles were removed and the residue lyophilized to yield the title compound as the lithium salt (0.05 g, 0.085 mmol).

m.p 175° C. (preceded by change in form 160° C.)

Anal. calcd. for $C_{31}H_{38}N_4O_7$+1.0 Li+2.75 $H_2O$+0.40 $CHCl_3$: C 55.31 H 6.34 N 8.22 found: C 55.31 H 5.91 N 7.96

MS ((+) ESI m/z): 579 [M+H]$^+$

EXAMPLE 59

4-(4-{2-[(2R)-2-Hydroxy-2-(4-hydroxy-3-methanesulfonylamino-phenyl)-ethylamino]-ethyl}-phenylamino)-piperidine-1-carboxylic Acidoctylamide Step A. 4-{4-[2-({(2R)-2-{4-(Benzyloxy)-3-[(methylsulfonyl)amino]phenyl}-2-[(triethylsilyl)oxy]ethyl}amino)ethyl]anilino}-N-octyl-1-piperidinecarboxamide N-(2-(Benzyloxy)-5-{(1R)-2-iodo-1-[(triethylsilyl)oxy]ethyl}phenyl)methanesulfonamide (E. J. Corey and J. O. Link, J. Org. Chem., 1991, 56, 422 and WO 9737646) (1.0 g, 1.93 mmol) was refluxed in anhydrous tetrahydrofuran (30 mL) with 4-[4-(2-aminoethyl)anilino]-N-octyl-1-piperidinecarboxamide (1.48 g, 3.98 mmol) and N,N-diisopropylethylamine (0.69 mL). The reaction was stirred at reflux for 7 days. The solvent was removed in vacuo and the residue was purified by flash chromatography on silica gel Merck-60 (eluant: 20:1 chloroform-methanol containing 2% triethylamine) to furnish the title compound (0.92 g, 1.14 mmol).

MS ((+)ESI, m/z): 809 [M+H]$^+$

Step B. 4-(4-{2-[(2R)-2-(4-Benzyloxy-3-methanesulfonylamino-phenyl)- 2-hydroxy-ethylamino]-ethyl}-phenylamino)-piperidine-1-carboxylicacid octylamide 4-{4-[2-({(2R)-2-{4-(Benzyloxy)-3-[(methylsulfonyl)amino]phenyl}-2-[(triethylsilyl)oxy]ethyl}amino)ethyl]anilino}-N-octyl-1-piperidinecarboxamide was dissolved in anhydrous tetrahydrofuran and tert-butylammonium fluoride (1 M in tetrahydrofuran) added. The reaction was stirred at ambient temperature for 4 days. The solvent was removed in vacuo and the residue purified by flash chromatography on silica gel Merck-60 (eluant: 20:1 going to 10:1 chloroform-methanol containing 2% triethylamine) to furnish the title compound (0.36 g, 0.519 mmol).

m.p 58–60° C.

MS ((+)ESI, m/z): 694 [M+H]$^+$

Anal. calcd. for $C_{38}H_{55}N_5O_5S$+1.0 $H_2O$: C 64.11 H 8.07 N 9.84 found: C 64.27 H 8.08 N 9.48

Step C. 4-(4-{2-[(2R)-2-Hydroxy-2-(4-hydroxy-3-methanesulfonylamino-phenyl)- ethylamino]-ethyl}-phenylamino)-piperidine-1-carboxylic acidoctylamide 4-(4-{2-[(2R)-2-(4-Benzyloxy-3-methanesulfonylamino-phenyl)- 2-hydroxy-ethylamino]-ethyl}-phenylamino)-piperidine-1-carboxylicacid octylamide (0.152 g, 0.219 mmol) was dissolved in ethanol (40 mL) and 10% palladium on carbon (0.05 g) added. The solution was shaken in a Parr apparatus at 50 psi hydrogen atmosphere for 2 hours, filtered through a Celite pad and the solvent removed in vacuo. The residue was purified by flash chromatography on silica gel Merck-60 (eluant: 5:1 chloroform-methanol) to furnish the title compound (0.082 g, 0.136 mmol)

m.p 160–162° C.

MS ((+)ESI, m/z): 604 [M+H]$^+$

Anal. calcd. for $C_{31}H_{49}N_5O_5S$+1.00 hydrochloric acid: C 58.15 H 7.87 N 10.94 found: C 58.39 H 8.15 N 10.65

EXAMPLE 60

4-(4-{2-[(2S)-2-Hydroxy-3-(2-oxo-2,3-dihydro-1H-benzoimidazol-4-yloxy)- propylamino]-ethyl}-phenylamino)-piperidine-1-carboxylic Acidoctylamide 4-[4-(2-Aminoethyl)anilino]-N-octyl-1-piperidinecarboxamide formate (0.25 g, 0.59 mmol) was reacted with [(2S)oxiranylmethoxy]-1,3-dihydro-2H-benzimidazol-2-one (0.123 g, 0.59 mmol) according to Procedure G (eluant: 10:1 going to 5:1 chloroform-methanol) to give the title compound (0.079 g, 0.136 mmol).

m.p 113–115° C.

MS ((+)ESI, m/z): 581 [M+H]$^+$

Anal. calcd. for $C_{32}H_{48}N_6O_4$+1.25 $H_2O$: C 63.71 H 8.44 N 13.93 found: C 63.63 H 8.12 N 13.7

EXAMPLE 61 and EXAMPLE 62

1-[4-(4-{2-[(2S)-2-Hydroxy-3-(4-hydroxy-phenoxy)-propylamino]-ethyl}-phenylamino)-piperidine-1-carbonyl]-piperidine-4-carboxylic Acid Ethyl Ester Step A. Ethyl 1-{[4-(4-{2-[(tert-butoxycarbonyl)amino]ethyl}anilino)-1-piperidinyl]carbonyl}-4-piperidinecarboxylate The title compound (0.35 g, 0.696 mmol) was prepared from ethyl 4-piperidinecarboxylate (0.314 g, 2.0 mmol) and (2-[4-(piperidin-4-ylamino)-phenyl]-ethyl}-carbamic acid tert-butyl ester (0.64 g, 2.0 mmol) according to Procedure C.

Step B. Ethyl 1-({4-[4-(2-aminoethyl)anilino]-1-piperidinyl}carbonyl)-4-piperidinecarboxylate formate Ethyl 1-{[4-(4-{2-[(tert-butoxycarbonyl)amino]ethyl}anilino)-1-piperidinyl]carbonyl}-4-piperidinecarboxylate (0.35 g, 0.696 mmol) was reacted according to Procedure F to provide the title compound (0.312 g, 0.696 mmol) which was used without further purification.

Step C. Ethyl 1-({4-[4-(2-{[(2S)-3-(4-{[tert-butyl(diphenyl)silyl]oxy}phenoxy)-2-hydroxypropyl]amino}ethyl)anilino]-1-piperidinyl}carbonyl)-4-piperidinecarboxylate Ethyl 1-({4-[4-(2-aminoethyl)anilino]-1-piperidinyl}carbonyl)-4-piperidinecarboxylate formate (0.312 g, 0.696 mmol) was reacted with tert-butyl-(4-oxiranylmethoxy-phenoxy)-diphenyl-silane (0.20 g, 0.495 mmol) according to Procedure G (eluant: 20:1 chloroform-methanol) to give the title compound (0.17 g, 0.21 mmol).

Step D. 1-[4-(4-{2-[(2S)-2-Hydroxy-3-(4-hydroxy-phenoxy)-propylamino]-ethyl}-phenylamino)-piperidine-1-carbonyl]-piperidine-4-carboxylicacid Ethyl Ester Ethyl 1-({4-[4-(2-{[(2S)-3-(4-{[tert-butyl(diphenyl)silyl]oxy}phenoxy)-2-hydroxy-propyl]amino}ethyl)anilino]-1-piperidinyl}carbonyl)-4-piperidinecarboxylate (0.17 g, 0.21 mmol) was reacted according to Procedure H (eluant: 10:1 going to 5:1 chloroform-methanol containing 2% triethylamine) to give the title compound (0.093 g, 0.164 mmol).

m.p 69–71° C.
MS ((+)ESI, m/z): 569 [M+H]$^+$
Anal. calcd. for $C_{31}H_{44}N_4O_6$+1.50 $H_2O$: C 62.50 H 7.95 N 9.40 found: C 62.41 H 7.62 N 9.06

Step E. 1-[4-(4-{2-[(2S)- 2-Hydroxy-3-(4-hydroxy-phenoxy)-propylamino]-ethyl}-phenylamino)-piperidine-1-carbonyl]-piperidine-4-carboxylic acid 1-[4-(4-2-[(2S)-2-Hydroxy-3-(4-hydroxy-phenoxy)-propylamino]-ethyl}-phenylamino)-piperidine-1-carbonyl]-piperidine-4-carboxylicacid ethyl ester was dissolved in tetrahydofuran (0.5mL) and 1N LiOH (0.109 mL) added. The reaction was stirred at ambient temperature for 7 days followed by 1 hour at 60° C. The volatiles were removed and the residue lyophilized to yield the title compound as the lithium salt (0.048 g, 0.088 mmol).

m.p 135–145° C. (preceded by change in form)
MS ((−)ESI, m/z): 539 [M−H]$^-$
Anal. calcd. for $C_{29}H_{40}N_4O_6$+1.0 Li+5.50 $H_2O$: C 53.95 H 7.81 N 8.68 found: C 53.88 H 6.63 N 8.28

EXAMPLE 63

4-(4-{2-[(2S)-3-(3-Acetylamino-phenoxy)-2-hydroxy-propylamino]-ethyl}-phenylamino)-piperidine-1-carboxylic Acid Octylamide 4-[4-(2-Aminoethyl)anilino]-N-octyl-1-piperidinecarboxamide 0.421 g, 1.0 mmol) was reacted with N-{3-[(2S)oxiranylmethoxy]phenyl}acetamide (0.207 g, 1.0 mmol) according to Procedure G (eluant: 20:1 chloroform-methanol) to give the title compound (0.168 g, 0.289 mmol).

m.p 73–74° C.
MS ((+)ESI, m/z): 582 [M+H]$^+$
Anal. calcd. for $C_{33}H_{51}N_5O_4$+1.0 $H_2O$: C 66.08 H 8.91 N 11.68 found: C 65.86 H 8.63 N 11.56

EXAMPLE 64

4-(4-{2-[(2S)-2-Hydroxy-3-(5-hydroxy-3,4-dihydro-2H-naphthalen-1-ylideneaminooxy)-propylamino]-ethyl}-phenylamino)-piperidine-1-carboxylic Acid Octylamide Step A. 4-[4-(2-{[(2S)-3-({[5-{[tert-Butyl(dimethyl)silyl]oxy}-3,4-dihydro-1(2H)-naphthalenylidene]amino}oxy)-2-hydroxypropyl]amino}ethyl)anilino]-N-octyl-1-piperidinecarboxamide 4-[4-(2-Aminoethyl)anilino]-N-octyl-1-piperidinecarboxamide formate (0.254 g, 0.60 mmol) was reacted with 5-{[tert-butyl(dimethyl)silyl]oxy}-3,4-dihydro-1 (2H)-naphthalenone O-(2S)oxiranylmethyl] oxime (0.21 g, 0.60 mmol) according to Procedure G (eluant: 20:1 chloroform-methanol) to give the title compound (0.10 g, 0.138 mmol).

Step B. 4-(4-{2-[(2S)-2-Hydroxy-3-(5-hydroxy-3,4-dihydro-2H-naphthalen-1-ylideneaminooxy)-propylamino]-ethyl}-phenylamino)-piperidine-1-carboxylic acid octylamide 4-[4-(2-{[(2S)-3-({[5-{[tert-Butyl(dimethyl)silyl]oxy}-3,4-dihydro-1(2H-naphthalenylidene]amino}oxy)-2-hydroxypropyl]amino}ethyl)anilino]-N-octyl-1-piperidinecarboxamide (0.10 g, 0.138 mmol) was reacted according to Procedure H (eluant: 10:1 going to 5:1 chloroform-methanol containing 2% triethylamine) to give the title compound (0.069g,0.11 mmol).

m.p 85–87° C.
MS ((+)ESI, m/z): 608 [M+H]$^+$
Anal. calcd. for $C_{35}H_{53}N_5O_4$+1.0 $H_2O$: C 67.17 H 8.86 N 11.19 found: C 66.91 H 8.68 N 11.08

EXAMPLE 65

4-(4-{2-[(2S)-3-(3-Fluoro-4-hydroxy-phenoxy)-2-hydroxy-propylamino]-ethyl}-phenylamino)-piperidine-1-carboxylic Acid Octylamide Step A. N-({4-[4-(2-{[(2S)-3-(4-{[tert-Butyl(diphenyl)silyl]oxy}-3-fluorophenoxy)-2-hydroxypropyl]amino}ethyl)anilino]-1-piperidinyl}carbonyl)-N-octylurea 4-[4-(2-Aminoethyl)anilino]-N-octyl-1-piperidinecarboxamide formate (0.376 g, 0.87 mmol) was reacted with tert-butyl{2-fluoro-4-[(2S)oxiranylmethoxy]phenoxy} diphenylsilane (0.368 g, 0.87 mmol) according to Procedure G (eluant: 20:1 chloroform-methanol) to give the title compound (0.228 g, 0.271 mmol).

Step B. 4-(4-{2-[(2S)-3-(3-Fluoro-4-hydroxy-phenoxy)-2-hydroxy-propylamino]-ethyl}-phenylamino)-piperidine-1-carboxylic acid octylamide N-({4-[4-(2-{[(2S)-3-(4-{[tert-Butyl(diphenyl)silyl]oxy}-3-fluorophenoxy)-2-hydroxypropyl]amino}ethyl)anilino]-1-piperidinyl}carbonyl)-N'-octylurea (0.228 g, 0.271 mmol) was reacted according to Procedure H (eluant: 10:1 going to 5:1 chloroform-methanol containing 2% triethylamine) to give the title compound (0.126 g, 0.223 mmol).

m.p 60–62° C.
MS ((+)ESI, m/z): 559 [M+H]$^+$
Anal. calcd. for $C_{31}H_{47}FN_4O_4$+0.5 $H_2O$: C 65.58 H 8.52 N 9.87 found: C 65.32 H 8.98 N 9.54

EXAMPLE 66

4-(4-{2-[(2S)-2-Hydroxy-3-(4-hydroxy-3-methanesulfonylamino-phenoxy)-propylamino]-ethyl}-phenylamino)-piperidine-1-carboxylic Acidoctylamide Step A. 4-(4-{2-[((2S)-3-{4-(benzyloxy)-3-[(methylsulfonyl)amino]phenoxy}-2-hydroxypropyl)amino]ethyl}anilino)-N-octyl-1-piperidinecarboxamide 4-[4-(2-Aminoethyl)anilino]-N-octyl-1-piperidinecarboxamide formate (0.516 g, 1.2 mmol) was reacted with N-{2-(benzyloxy)-5-[(2S)oxiranylmethoxy]phenyl} methanesulfonamide (prepared according to patent WO9604233) (0.38 g, 1.09 mmol) according to Procedure G (eluant: 20:1 chloroform-methanol) to give the title compound (0.15 g, 0.207 mmol).

MS ((+)ESI, m/z): 724 [M+H]$^+$

Step B. 4-(4-{2-[(2S)-2-Hydroxy-3-(4-hydroxy-3-methanesulfonviamino-phenoxy)-propylamino]-ethyl}-phenylamino)-piperidine-1-carboxylic acidoctylamide 4-(4-{2-[((2S)-3-{4-(Benzyloxy)-3-[(methylsulfonyl)amino]phenoxy}-2-hydroxypropyl)amino]ethyl}anilino)-N-octyl-1-piperidinecarboxamide (0.15 g, 0.207 mmol) was dissolved in ethanol (70 mL) and 10% palladium on carbon (0.043 g) added. The solution was shaken in a Parr apparatus at 50 psi hydrogen atmosphere for 16 hours, filtered through a Celite pad and the solvent removed in vacuo. The residue was purified by flash chromatography on silica gel Merck-60 (eluant: 10:1 going to 5:1 chloroform-methanol containing 2% triethylamine) to give the title compound (0.052 g, 0.08 mmol).

m.p 115–117° C.

MS ((+)APCI, m/z): 634 [M+H]$^+$

Anal. calcd. for $C_{32}H_{51}N_5O_6S·HCl$: C 57.34 H 7.82 N 10.45 found: C 57.41 H 7.91 N 10.04

EXAMPLE 67

4-(4-{2-[(2S)-2-Hydroxy-3-(4-hydroxy-phenoxy)-propylamino]-ethyl}-phenylamino)-piperidine-1-carboxylic Acid 4-(3-hexyl-ureido)-benzylamide Step A. 2-(4-{[(Hexylamino)carbonyl]amino}phenyl)acetic acid To a solution of 2-(4-aminophenyl)acetic acid (10.0 g, 66 mmol) in 1N sodium hydroxide (72.7 mL) and acetone was added hexyl isocyanate (8.4 g, 66 mmol) and the reaction stirred at ambient temperature overnight. Ice/hydrochloric acid (100 mL) was added and the solid removed to yield the crude title compound (14.0 g). A portion of the crude title compound (2.0 g) was partitioned between 1N sodium hydroxide and ethyl acetate. The aqueous phase was washed twice with ethyl acetate and added to a cooled 2N hydrochloric acid solution. The solid was removed, washed with water and hexane to furnish the title compound (1.4 g, 5.03 mmol).

MS ((+)APCI, m/z): 279 [M+H]$^+$

Step B. tert-Butyl 4-[(1-{[(4-{[(hexylamino)carbonyl]amino}benzyl)amino]carbonyl}-4-piperidinyl)amino]phenethylcarbamate The title compound (0.32 g, 0.54 mmol) was prepared from 2-(4-{[(hexylamino)carbonyl]amino}phenyl)acetic acid (0.80 g, 2.87 mmol) and {2-[4-(piperidin-4-ylamino)-phenyl]-ethyl}-carbamic acid tert-butyl ester (0.92 g, 2.88 mmol) according to Procedure D.

MS ((+)ESI, m/z): 595 [M+H]$^+$

Step C. 4-[4-(2-Aminoethyl)anilino]-N-(4-{[(hexylamino)carbonyl]amino}benzyl)-1-piperidinecarboxamide formate tert-Butyl 4-[(1-{[(4-{[(hexylamino)carbonyl]amino}benzyl)amino]carbonyl}-4-piperidinyl)amino]phenethylcarbamate (0.32 g, 0.54 mmol) was reacted according to Procedure F to provide the title compound (0.29 g, 0.54 mmol) which was used without further purification.

Step D. 4-[4-(2-{[(2S)-3-(4-{[tert-butyl(diphenyl)silyl]oxy}phenoxy)-2-hydroxypropyl]amino}ethyl)anilino]-N-(4-{[(hexylamino)carbonyl]amino}benzyl)-1-piperidinecarboxamide 4-[4-(2-Aminoethyl)anilino]-N-(4-{[(hexylamino)carbonyl]amino}benzyl)-1-piperidinecarboxamide formate (0.29 g, 0.54 mmol) was reacted with tert-butyl-(4-oxiranylmethoxy-phenoxy)-diphenyl-silane (0.220 g, 0.54 mmol) according to Procedure G (eluant: 20:1 going to 10:1 chloroform-methanol) to give the title compound (0.143 g, 0.159 mmol).

Step E. 4-(4-{2-[(2S)-2-Hydroxy-3-(4-hydroxy-phenoxy)-propylamino]-ethyl}-phenylamino)-piperidine-1-carboxylic acid 4-(3-hexyl-ureido)- benzylamide 4-[4-(2-{[(2S)-3-(4-{[tert-Butyl(diphenyl)silyl]oxy}phenoxy)-2-hydroxypropyl]amino}ethyl)aniiino]-N-(4-{[(hexylamino)carbonyl]amino}benzyl)-1-piperidinecarboxamide (0.143 g, 0.159 mmol) was reacted according to Procedure H (eluant: 10:1 going to 5:1 chloroform-methanol containing 2% triethylamine) to give the title compound (0.077 g, 0.12 mmol).

m.p 141–143° C.

MS ((−)ESI, m/z): 659 [M−H]$^-$

Anal. calcd. for $C_{37}H_{52}N_6O_5+1.5 H_2O$: C 64.61 H 8.06 N 12.22 found: C 64.77 H 7.79 N 11.42

EXAMPLE 68

4-(4-{2-[(2S)-2-Hydroxy-3-(4-hydroxy-phenoxy)-propylamino]-ethyl}-phenylamino)-piperidine-1-carboxylic Acid (3-cyclohexyl-propyl)-amide Step A. tert-Butyl 4-[(1-{[(3-cyclohexylpropyl)amino]carbonyl}-4-piperidinyl)amino]phenethylcarbamate The title compound (0.481 g, 0.988 mmol) was prepared from 4-cyclohexylbutanoic acid (0.3 g, 1.76 mmol) and {2-[4-(piperidin-4-ylamino)-phenyl]-ethyl}-carbamic acid tert-butyl ester (0.495 g, 1.55 mmol) according to Procedure D.

MS ((+)ESI, m/z): 487 [M+H]$^+$

Step B. 4-[4-(2-Aminoethyl)anilino]-N-(3-cyclohexylpropyl)-1-piperidinecarboxamide formate tert-Butyl 4-[(1-{[(3-cyclohexylpropyl)amino]carbonyl}-4-piperidinyl)-amino]-phenethylcarbamate (0.39 g, 0.81 mmol) was reacted according to Procedure F to provide the title compound (0.35 g, 0.81 mmol) which was used without further purification.

Step C. 4-[4-(2-{[(2S)-3-(4-{[tert-Butyl(diphenyl)silyl]oxy}phenoxy)-2-hydroxypropyl]amino}ethyl)anilino]-N-(3-cyclohexylpropyl)-1-piperidinecarboxamide tert-Butyl 4-[(1-{[(3-cyclohexylpropyl)amino]carbonyl}-4-piperidinyl)amino]phenethylcarbamate formate (0.35 g, 0.809 mmol) was reacted with tert-butyl-(4-oxiranylmethoxy-phenoxy)-diphenyl-silane (0.327 g, 0.809 mmol) according to Procedure G (eluant: 20:1 going to 10:1 chloroform-methanol) to give the title compound (0.23 g, 0.291 mmol).

Step D. 4-(4-{2-[(2S)-2-Hydroxy-3-(4-hydroxy-phenoxy)-propylamino]-ethyl}-phenylamino)-piperidine-1-carboxylic acid (3-cyclohexyl-propyl)-amide 4-[4-(2-{[(2S)-3-(4-{[tert-Butyl(diphenyl)silyl]oxy}phenoxy)-2-hydroxypropyl]amino}ethyl)anilino]-N-(3-cyclohexylpropyl)-1-piperidinecarboxamide (0.23 g, 0.291 mmol) was reacted according to Procedure H (eluant: 10:1 going to 5:1 chloroform-methanol containing 2% triethylamine) to give the title compound (0.11 g, 0.199 mmol).

m.p 69–71° C.

MS ((+)ESI, m/z): 553 [M+H]$^+$

Anal. calcd. for $C_{32}H_{48}N_4O_4+1.0 H_2O$: C 67.34 H 8.83 N 9.82 found: C 67.62 H 8.92 N 9.6

EXAMPLE 69

4-(4-{2-[(2S)-2-Hydroxy-3-(8-hydroxy-2-oxo-1,2,3,4-tetrahydro-quinolin-5-yloxy)-propylamino]-ethyl}-phenylamino)-piperidine-1-carboxylicacid Octylamide Step A. 4-(4-{2-[((2S)-3-{[8-(benzyloxy)-2-oxo-1,2,3,4-tetrahydro-5-quinolinyl]oxy}-2-hydroxypropyl)amino]ethyl}anilino)-N-octyl-1-piperidinecarboxamide 4-[4-(2-Aminoethyl)anilino]-N-octyl-1-piperidinecarboxamide formate (0.431 g, 1.0 mmol) was reacted with 8-(benzyloxy)-5-[(2S)oxiranylmethoxy]-3,4-dihydro-2(1H-quinolinone (0.325 g, 1.0 mmol) according to Procedure G (eluant: 20:1 chloroform-methanol) to give the title compound (0.19 g, 0.271 mmol).

MS ((+)ESI, m/z): 700 [M+H]$^+$

Step B. 4-(4-{2-[(2S)-2-Hydroxy-3-(8-hydroxy-2-oxo-1,2, 3,4-tetrahydro-quinolin-5-yloxy)-propylamino]-ethyl}-phenylamino)-piperidine-1-carboxylicacid octylamide 4-(4-{2-[((2S)-3-{[8-(Benzyloxy)-2-oxo-1,2,3,4-tetrahydro-5-quinolinyl]oxy}-2-hydroxypropyl)amino]ethyl}anilino)-N-octyl-1-piperidinecarboxamide (0.16 g, 0.228 mmol) was dissolved in ethanol and 10% palladium on carbon (0.07 g) added. The solution was shaken in a Parr apparatus at 50 psi hydrogen atmosphere for 4 hours, filtered through a Celite pad and the solvent removed in vacuo. The residue was purified by flash silica gel chromatography on silica gel Merck-60 to yield the title compound (0.05 g, 0.082 mmol).

m.p 83–85° C.

MS ((+)ESI, m/z): 610 [M+H]$^+$

Anal. calcd. for $C_{34}H_{51}N_5O_5$+1.5 $H_2O$: C 64.13 H 8.55 N 11.00 found: C 64.14 H 8.29 N 10.81

EXAMPLE 70

4-(4-{2-[(2S)-2-Hydroxy-3-(4-hydroxy-phenoxy)-propylamino]-ethyl}-phenylamino)-piperidine-1-carboxylic Acid Cyclopentylmethyl-amide Step A. tert-Butyl 4-[(1-{[(cyclopentylmethyl)amino]carbonyl}-4-piperidinyl)amino]phenethylcarbamate The title compound (1.0 g, 2.25 mmol) was prepared from 2-cyclopentylacetic acid (0.508 g, 3.96 mmol) and {2-[4-(piperidin-4-ylamino)-phenyl]-ethyl}-carbamic acid tert-butyl ester (1.16 g, 3.63 mmol) according to Procedure D.

MS ((+)ESI, m/z): 445 [M+H]$^+$

Step B. 4-[4-(2-Aminoethyl)anilino]-N-(cyclopentylmethyl)-1-piperidinecarboxamide formate tert-Butyl 4-[(1-{[(cyclopentylmethyl)amino]carbonyl}-4-piperidinyl)amino]-phenethylcarbamate (0.56 g, 1.26 mmol) was reacted according to Procedure F to provide the title compound (0.45 g, 1.15 mmol) which was used without further purification.

Step C. 4-[4-(2-{[(2S)-3-(4-{[tert-Butyl(diphenyl)silyl]oxy}phenoxy)-2-hydroxy-propyl]amino}ethyl)anilino]-N-(cyclopentylmethyl)-1-piperidinecarboxamide 4-[4-(2-Aminoethyl)anilino]-N-(cyclopentylmethyl)-1-piperidinecarboxamide formate (0.38 g, 0.818 mmol) was reacted with tert-butyl-(4-oxiranylmethoxy-phenoxy)-diphenyl-silane (0.32 g, 0.792 mmol) according to Procedure G (eluant: 20:1 going to 10:1 chloroform-methanol) to give the title compound (0.24 g, 0.309 mmol).

Step D. 4-(4-{2-[2-Hydroxy-3-(4-hydroxy-phenoxy)-propylamino]-ethyl}-phenylamino)-piperidine-1-carboxylic acid cyclopentylmethyl-amide 4-[4-(2-{[(2S)-3-(4-{[tert-Butyl(diphenyl)silyl]oxy}phenoxy)-2-hydroxypropyl]amino}ethyl)anilino]-N-(cyclopentylmethyl)-1-piperidinecarboxamide (0.24 g, 0.32 mmol) was reacted according to Procedure H (eluant: 10:1 going to 5:1 chloroform-methanol containing 2% triethylamine) to give the title compound (0.095 g, 0.186 mmol).

m.p 76–78° C.

MS ((+)APCI, m/z): 511 [M+H]$^+$

Anal. calcd. for $C_{29}H_{42}N_4O_4$+1.7 $H_2O$+0.1 $C_4H_8O_2$: C 64.19 H 8.47 N 10.18 found: C 64.48 H 8.22 N 9.77

EXAMPLE 71

4-(4-{2-[(2S)-2-Hydroxy-3-(4-hydroU-phenoxy)-propylamino]-ethyl}-phenylamino)-piperidine-1-carboxylic Acid {2-[2-methoxy-4-(3-phenoxy-propoxy)-phenyl]-ethyl}-amide Step A. tert-Butyl 4-{[1-({[2-methoxy-4-(3-phenoxypropoxy)phenethyl]amino}carbonyl)-4-piperidinyl]amino}phenethylcarbamate The title compound (1.33 g, 2.06 mmol) was prepared from 3-[2-methoxy-4-(3-phenoxypropoxy)phenyl]propanoic acid (1.21 g, 3.66 mmol) and {2-[4-(piperidin-4-ylamino)-phenyl]-ethyl}-carbamic acid tert-butyl ester (1.02 g, 3.19 mmol) according to Procedure D.

MS ((+)ESI, m/z): 647 [M+H]$^+$

Step B. 4-[4-(2-Aminoethyl)anilino]-N-[2-methoxy-4-(3-phenoxy-propoxy)phenethyl]-1-piperidinecarboxamide formate tert-Butyl4-{[1-({[2-methoxy-4-(3-phenoxypropoxy)phenethyl]amino}carbonyl)-4-piperidinyl]amino}phenethylcarbamate (1.33 g, 3.19 mmol) was reacted according to Procedure F to provide the title compound (1.22 g, 2.06 mmol) which was used without further purification.

Step C. 4-[4-(2-{[(2S)-3-(4-{[tert-Butyl(diphenyl)silyl]oxy}phenoxy)-2-hydroxypropyl]-amino}ethyl)anilino]-N-[2-methoxy-4-(3-phenoxypropoxy)phenethyl]-1-piperidinecarboxamide 4-[4-(2-Aminoethyl)anilino]-N-[2-methoxy-4-(3-phenoxypropoxy)phenethyl]-1-piperidinecarboxamide formate (0.426 g, 0.718 mmol) was reacted with tert-butyl-(4-oxiranylmethoxy-phenoxy)-diphenyl-silane (0.29 g, 0.718 mmol) according to Procedure G (eluant: 20:1 chloroform-methanol) to give the title compound (0.27 g, 0.284 mmol).

Step D. 4-(4-{2-[(2S)-2-Hydroxy-3-(4-hydroxy-phenoxy)-propylamino]-ethyl}-phenylamino)-piperidine-1-carboxylic acid {2-[2-methoxy-4-(3-phenoxy-propoxy)-phenyl]-ethyl}-amide 4-[4-(2-{[(2S)-3-(4-{[tert-Butyl(diphenyl)silyl]oxyphenoxy)-2-hydroxypropyl]-amino}ethyl)anilino]-N-[2-methoxy-4-(3-phenoxypropoxy)phenethyl]-1-piperidinecarboxamide (0.25 g, 0.26 mmol) was reacted according to Procedure H (eluant: 10:1 chloroform-methanol) to give the title compound (0.11 g, 0.154 mmol).

m.p 67–69° C.

MS ((+)ESI, m/z): 713 [M+H]$^+$

Anal. calcd. for $C_{41}H_{52}N_4O_7$+0.75 $H_2O$: C 67.79 H 7.42 N 7.71 found: C 67.59 H 7.1 N 7.4

EXAMPLE 72

4-(4-{2-[(2S)-2-Hydroxy-3-(2-oxo-2,3-dihydro-1H-benzoimidazol-4-yloxy)-propylamino]-ethoxy}-phenylamino)-piperidine-1-carboxylic Acidoctylamide Step A. 1-(2-Chloroethoxy)-4-nitrobenzene 4-Nitrophenol (18.37 g, 132 mmol) was dissolved in 2-butanone, 2-chloroethyl-p-toluenesulfonate (31.0 g, 132 mmol) and potassium carbonate (20.1 g, 145.4 mmol) were added and the reaction heated at 70° C. for 24 hours. The reaction was cooled, filtered and the residue washed with acetone. The solvent was removed in vacuo and the residue partitioned between chloroform and 1N sodium hydroxide. The organic layer was separated, washed with brine dried over anhydrous magnesium sulfate and filtered. The solvent was removed in vacuo and the title compound obtained as an oil which was used without further purification.

Step B. 1-(2-Azidoethoxy)-4-nitrobenzene 1-(2-Chloroethoxy)-4-nitrobenzene (12.34 g, 61.21 mmol) was dissolved in anhydrous N,N-dimethylformamide (90 mL). Lithium azide (3.3 g, 67.4 mmol) was added and the reaction heated at 90° C. for 12 hours. A further portion of lithium azide (0.3 g) was added and heating continued for a further 6 hours. The solvent was removed in vacuo and the residue partitioned between water and ethyl acetate. The organic layer was washed with brine, dried over anhydrous magnesium sulfate, filtered and the solvent removed in vacuo. The resulting title compound (8.4 g, 40.35 mmol) was obtained as a dark oil.

Step C. 2-(4-Nitrophenoxy)-1-ethanamine 1-(2-Azidoethoxy)-4-nitrobenzene (2.3 g, 11.05 mmol) was dissolved in tetrahydrofuran (30 mL) water (3 mL) was added followed by triphenylphosphine (3.0 g, 11.4 mmol). The reaction was stirred at ambient temperature overnight, the solvent was removed in vacuo and combined with a further reaction of the same type. The combined material was purified by flash chromatography on silica gel Merck-60 (eluant: 20:1 chloroform-methanol). The solvent was removed in vacuo to furnish the title compound as a solid (2.0 g, 10.99 mmol).

MS ((+)ESI, m/z): 183 [M+H]+

Step D. tert-Butyl 2-(4-nitrophenoxy)ethylcarbamate 2-(4-Nitrophenoxy)-1-ethanamine (2.0 g, 10.98 mmol) was dissolved in anhydrous dichloromethane di-tert-butyl dicarbonate (2.4 g, 10.99 mmol) was added and the reaction stirred for 48 hours. The solvent was removed in vacuo and the residue passed through a pad of silica gel eluting with chloroform. The solvent was removed in vacuo to yield the title compound (3.0 g, 10.63 mmol).

Step E. tert-Butyl 2-(4-aminophenoxy)ethylcarbamate tert-Butyl 2-(4-nitrophenoxy)ethylcarbamate (6.87 g, 24.34 mmol) was dissolved in ethanol, 10% palladium on carbon (1.0 g) was added followed by ammonium formate (7.7 g, 122 mmol). The solution was heated to reflux for 0.5 hours. The mixture was cooled to ambient temperature, filtered through a Celite pad and the solvent removed in vacuo. The residue was purified by flash chromatography on silica gel Merck-60 (eluant: 1:1 hexane-ethyl acetate). The solvent was removed in vacuo to furnish the title compound (4.94 g, 19.58 mmol).

Step F. tert-Butyl 2-{4-[(1-benzyl-4-piperidinyl)amino]phenoxy}ethylcarbamate tert-Butyl 2-(4-aminophenoxy)ethylcarbamate (2.34 g, 9.27 mmol) and benzyl piperidone (2.6 g, 13.74 mmol) were dissolved in dichloroethane (40 mL). Anhydrous sodium sulfate (13.2 g) was added followed by acetic acid (2.6 mL). Stirring was continued for 1 hour. Sodium triacetoxyborohydride (3.93 g, 18.54 mmol) was added and stirring continued overnight. The mixture was filtered, diluted with dichloromethane (600 mL), and washed with 40% sodium hydroxide, water and brine. The organic phase was dried over anhydrous magnesium sulfate. The solution was filtered and the solvent evaporated to dryness in vacuo. The residue was purified by flash chromatography on silica gel Merck-60 (eluant: 20:1 chloroform-methanol). The solvent was removed in vacuo and the resulting oil triturated with hexane to furnish the title compound (2.4 g, 5.64 mmol).

MS ((+)ESI, m/z): 426 [M+H]+

Step G. tert-Butyl 2-[4-(4-piperidinylamino)phenoxy]ethylcarbamate tert-Butyl 2-{4-[(1-benzyl-4-piperidinyl)amino]phenoxy}ethylcarbamate (2.3 g, 5.4 mmol) was dissolved in ethanol, 10% palladium on carbon (0.3 g) was added followed by cyclohexene (4 mL). The solution was heated to reflux for 80 minutes. The mixture was cooled to ambient temperature, filtered through a Celite pad, and the solvent removed in vacuo to yield an oil which solidified on standing to yield the title compound (1.84 g, 5.4 mmol).

MS ((+)ESI, m/z): 336 [M+H]+

Step H. tert-Butyl 2-[4-({1-[(octylamino)carbonyl]-4-piperidinyl}amino)phenoxy]ethylcarbamate tert-Butyl 2-[4-(4-piperidinylamino)phenoxy]ethylcarbamate (0.90 g, 2.68 mmol) was reacted with octyl isocyanate (0.416 g, 2.68 mmol) according to Procedure E.

The title compound was obtained (eluant: 1:1 hexane-ethyl acetate) as a solid (1.0 g, mmol 2.04 mmol).

MS ((+)APCI, m/z): 491 [M+H]+

Step I. 4-[4-(2-Aminoethoxy)anilino]-N-octyl-1-piperidinecarboxamide formate tert-Butyl 2-[4-({1-[(octylamino)carbonyl]-4-piperidinyl}amino)phenoxy] ethylcarbamate (1.0 g, 2.04 mmol) was reacted according to Procedure F to provide the title compound (0.89 g, 2.04 mmol) which was used without further purification.

MS ((+)APCI, m/z): 391 [M+H]+

Step J. 4-(4-{2-[(2S)-2-Hydroxy-3-(2-oxo-2,3-dihydro-1H-benzoimidazol-4-yloxy)-propylamino]-ethoxy}-phenylamino)-piperidine-1-carboxylic acidoctylamide 4-[4-(2-Aminoethoxy)anilino]-N-octyl-1-piperidinecarboxamide formate (0.32 g, 0.733 mmol) was reacted with 4-[(2S)oxiranylmethoxy]-1,3-dihydro-2H-benzimidazol-2-one (0.151 g, 0.732 mmol) according to Procedure G (eluant: 20:1 chloroform-methanol) to give the title compound (0.085 g, 0.142 mmol).

MS ((+)ESI, m/z): 597 [M+H]+

Anal. calcd. for $C_{31}H_{48}N_4O_5$+0.5 $H_2O$+0.15 $C_3H_6O$+0.15 $C_2H_6O$: C 65.59 H 8.81 N 9.64 found: C 65.96 H 8.78 N 9.13

EXAMPLE 73

4-(4-{2-[(2S)-2-Hydroxy-3-(4-hydroxy-phenoxy)-propylamino]-ethoxy}-phenylamino)-piperidine-1-carboxylic Acid Octylamide Step A. 4-[4-(2-{[(2S)-3-(4-{[tert-Butyl(diphenyl)silyl]oxy}phenoxy)-2-hydroxypropyl]amino}ethoxy)anilino]-N-octyl-1-piperidinecarboxamide 4-[4-(2-Aminoethoxy)anilino]-N-octyl-1-piperidinecarboxamide formate (0.40 g, 0.916 mmol) was reacted with tert-butyl-(4-oxiranylmethoxy-phenoxy)-diphenyl-silane (0.37 g, 0.916 mmol) according to Procedure G (eluant: 20:1 chloroform-methanol) to give the title compound (0.30 g, 0.377 mmol).

Step B. 4-(4-{2-[(2S)-2-Hydroxy-3-(4-hydroxy-phenoxy)-propylamino]-ethoxy}-phenylamino)-piperidine-1-carboxylic acid octylamide 4-[4-(2-{[(2S)-3-(4-{[tert-Butyl(diphenyl)silyl]oxy}phenoxy)-2-hydroxy-propyl]amino}ethoxy)anilino]-N-octyl-1-piperidinecarboxamide (0.30 g, 0.377 mmol) was reacted according to Procedure H (eluant: 10:1 chloroform-methanol) to give the title compound (0.115 g, 0.206 mmol).

MS ((+)ESI, m/z): 557 [M+H]+

Anal. calcd. for $C_{31}H_{48}N_4O_5$+0.5 $H_2O$+0.15 $C_3H_6O$+0.15 $C_2H_6O$: C 65.59 H 8.81 N 9.64 found: C 65.96 H 8.78 N 9.13

EXAMPLE 74

Dimethyl-carbamic Acid 4-(2-{[4-(4-{2-[(2S)-2-hydroxy-3-(4-hydroxy-phenoxy)-propylamino]-ethyl}-phenylamino)-piperidine-1-carbonyl]-amino}-ethyl)-phenyl Ester Step A. Methyl 3-(4-{[(dimethylamino)carbonyl]oxy}phenyl)propanoate Methyl 3-(4-hydroxyphenyl)propanoate (2.0 g, 11.1 mmol) was dissolved in dichloromethane, 4-nitrophenylchloroformate (1.53 g, 7.59 mmol) was added and the reaction cooled to 0° C. Triethylamine (3.9 mL, 27.99 mmol) was added and the reaction stirred for 30 minutes at 0° C. Dimethylamine (6.7 mL, 2M in tetrahydrofuran, 13.4 mmol) was added and the ice bath removed. The reaction was stirred at room temperature overnight. The reaction was diluted with dichloromethane, washed with 10% aqueous potassium carbonate, brine and dried over anhydrous magnesium sulfate. The solution was filtered and the solvent evaporated to dryness in vacuo to give the title compound (1.72 g, 6.85 mmol).

MS ((+)ESI, m/z): 252 [M+H]$^+$, 269 [M+NH$_4$]$^+$

Step B. 3-(4-{[(Dimethylamino)carbonyl]oxy}phenyl) propanoic acid

Methyl 3-(4-{[(Dimethylamino)carbonyl]oxy}phenyl) propanoate (1.7 g, 6.77 mmol) was dissolved in tetrahydrofuran (3 mL) and 1N LiOH added (7.4 mL). The reaction was stirred at ambient temperature for 48 hours. The reaction was made acidic by the addition of 1N hydrochloric acid, the solvent partially removed in vacuo and chloroform added. The organic phase was washed with brine, dried over anhydrous magnesium sulfate and filtered. The solvent was removed in vacuo and the title compound obtained (1.4 g, 5.9 mmol).

MS ((+)EI, m/z): 237 [M+H]$^+$

Step C. 4-[2-({[4-(4-{2-[(tert-butoxycarbonyl)amino] ethyl}anilino)-1-piperidinyl]carbonyl}amino)ethyl]phenyl dimethylcarbamate The title compound (1.7 g, 3.19 mmol) was prepared from 3-(4-{[(dimethylamino)carbonyl]oxyphenyl)propanoic acid (1.06 g, 4.47 mmol) and (2-[4-(piperidin-4-ylamino)-phenyl]-ethyl]-carbamic acid tert-butyl ester (1.24 g, 3.88 mmol) according to Procedure D.

MS ((+)ESI, m/z): 554 [M+H]$^+$

Step D. 4-[2-[({4-[4-(2-Aminoethyl)anilino]-1-piperidinyl}carbonyl)amino]ethyl}phenyl dimethylcarbamate formate 4-[2-({[4-(4-{2-[(tert-Butoxycarbonyl)amino] ethyl}anilino)-1-piperidinyl]-carbonyl}amino)ethyl]phenyl dimethylcarbamate (1.0 g, 1.8 mmol) was reacted according to Procedure F to provide the title compound (0.9 g, 1.8 mmol) which was used without further purification.

MS ((+)ESI, m/z): 554 [M+H]$^+$

Step E. 4-{2-[({4-[4-(2-{[(2S)-3-(4-{[tert-Butyl(diphenyl) silyl]oxy}phenoxy)-2-hydroxypropyl]amino}ethyl) anilino]-1-piperidinyl}carbonyl)amino]ethyl}phenyl dimethylcarbamate 4-{2-[({4-[4-(2-Aminoethyl)anilino]-1-piperidinyl}carbonyl)amino]ethyl}phenyl dimethylcarbamate formate (0.47 g, 0.94 mmol) was reacted with tert-butyl-(4-oxiranylmethoxy-phenoxy)-diphenyl-silane (0.40 g, 1.0 mmol) according to Procedure G (eluant: 20:1 chloroform-methanol) to give the title compound (0.22 g, 0.256 mmol).

Step F. Dimethyl-carbamic acid 4-(2-{[4-(4-{2-[(2S)-2-hydroxy-3-(4-hydroxy-phenoxy)-propylamino]-ethyl}-phenylamino)-piperidine-1-carbonyl]-amino}-ethyl)-phenyl ester 4-{2-[({4-[4-(2-{[(2S)-3-(4-{[tert-Butyl(diphenyl)silyl] oxy}phenoxy)-2-hydroxypropyl]amino}ethyl)anilino]-1-piperidinyl)carbonyl)amino]ethyl}phenyl dimethylcarbamate (0.22 g, 0.256 mmol) was reacted according to Procedure H (eluant: 10:1 chloroform-methanol) to give the title compound (0.09 g, 0.145 mmol).

m.p 86–88° C.

MS ((+)ESI, m/z): 620 [M+H]$^+$

Anal. calcd. for C$_{34}$H$_{45}$N$_5$O$_6$+0.7 H$_2$O+0.1 C$_3$H$_6$O++0.1 C$_2$H$_6$O: C 64.47 H 7.46 N 10.9 found: C 64.71 H 7.1 N 10.49

EXAMPLE 75

4-(4-{2-[(2S)-2-Hydroxy-3-(3-methanesulfonlamino-phenoxy)-propylamino]-ethyl}-phenylamino)-piperidine-1-carboxylic Acid 4-fluoro-benzylamide 4-[4-(2-Aminoethyl)anilino]-N-(4-fluorobenzyl)-1-piperidinecarboxamide formate (0.591 g, 1.42 mmol) was reacted with tert-butyl methylsulfonyl{3-[(2S) oxiranylmethoxy]phenyl]carbamate (0.488 g, 1.42 mmol) according to Procedure G (eluant: 20:1 going to 10:1 chloroform-methanol) to give tert-butyl 3-{[(2S)-3-({4-[(1-{[(4-fluorobenzyl)amino]carbonyl}-4-piperidinyl)amino] phenethyl}amino)-2-hydroxypropyl]oxy}phenyl (methylsulfonyl)carbamate which was dissolved in formic acid and stirred at ambient temperature overnight. The solvent was removed in vacuo and the residue purified by flash chromatography on silica gel Merck-60 (eluant: 5:1 chloroform-methanol) to furnish the title compound (0.1 g, 0.163 mmol).

m.p 90–92° C.

MS ((+)ESI, m/z): 614 [M+H]$^+$

Anal. calcd. for C$_{31}$H$_{40}$FN$_5$O$_5$S+0.65 H$_2$O: C 59.53 H 6.66 N 11.20 found: C 59.95 H 6.72 N 10.74

EXAMPLE 76

4-(4-{2-[(2R)-2-Hydroxy-2-(4-hydroxY-3-methanesulfonylamino-phenyl)-ethylamino]-ethyl}-phenylamino)-piperidine-1-carboxylic Acid 2,5-difluoro-benzylamide Step A. N-(2,5-Difluorobenzyl)-4-[4-(2,2-dimethoxyethyl) anilino]-1-piperidinecarboxamide The title compound (1.13 g, 2.61 mmol) was prepared from (2,5-difluorophenyl) methanamine (0.544 g, 3.79 mmol) and N-[4-(2,2-dimethoxyethyl)phenyl]-4-piperidinamine (1.0 g, 3.79 mmol) according to Procedure C (eluant: 1:1 ethyl acetate:hexane).

Step B. 4-(4-{2-[2-Hydroxy-2-(4-hydroxn-3-methanesulfonylamino-phenyl)-ethylamino]-ethyl}-phenylamino)-piperidine-1-carboxylic acid 2,5-difluoro-benzylamide N-(2,5-Difluorobenzyl)-4-[4-(2,2-dimethoxyethyl) anilino]-1-piperidinecarboxamide (0.30 g, 0.69 mmol) was added to a pre-prepared mixture of sodium iodide (0.16 g, 1.03 mmol) and trichloro(methyl)silane (0.132 mL, 1.05 mmol) in anhydrous acetonitrile. The reaction was stirred at ambient temperature for 10 minutes. Dichloromethane was added and the reaction washed with 10% sodium thiosulfate solution, water and brine. The organic layer was dried over anhydrous magnesium sulfate, filtered and the solvent partially removed in vacuo. The aldehyde solution was used directly and treated with methanol, acetic acid (0.062 mL, 1.02 mmol), N-{5-[(1R)-2-amino-1-hydroxyethyl]-2-hydroxyphenyl}methanesulfonamide (0.17 g, 0.69 mmol) followed by sodium cyanoborohydride (0.047 g, 0.764 mmol). The reaction was stirred at room temperature for 24 hours. The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.2 g, 0.32 mmol).

m.p 116–118° C.

MS ((−)APCI, m/z): 616 [M−H]$^-$

Anal. calcd. for C$_{30}$H$_{37}$F$_2$N$_5$O$_5$S+1.67 H$_2$O: C 55.63 H 6.28 N 10.81 found: C 55.94 H 5.92 N 10.79

EXAMPLE 77

1-[[4-[[4-[2-[[(2R)-2-Hydroxy-2-[4-hydroxy [(methylsulfonyl)amino]phenyl]ethyl]amino]ethyl] phenyl]amino]-1-piperidinyl]carbonyl]-L-proline, Methyl Ester Step A. Methyl (2S)-1-(1,4-dioxa-8-azaspiro[4.5]dec-8-ylcarbonyl)-2-pyrrol-idinecarboxylate The title compound (4.6 g, 15.42 mmol) was prepared from methyl (2S)-2-pyrrolidinecarboxylate (4.0 g, 24.15 mmol) and 1,4-dioxa-8-azaspiro[4.5]decane (3.46 g, 24.15 mmol) according to Procedure C with an additional purification by high vacuum Kugelrohr distillation (temperature 250° C.).

MS ((+)ESI m/z): 299 [M+H]$^+$

Anal. calcd. for $C_{14}H_{22}N_2O_5$: C 56.36 H 7.43 N 9.39 found: C 56.42 H 7.36 N 9.46

Step B. Methyl (2S)-1-[(4-oxo-1-piperidinyl)carbonyl-2-pyrrolidinecarboxylate

Methyl (2S)-1-(1,4-dioxa-8-azaspiro[4.5]dec-8-ylcarbonyl)-2-pyrrolidinecarboxylate (1.74 g, 5.83 mmol) was dissolved in formic acid and heated at 70° C. for 2.5 hours. The solvent was removed in vacuo and the oily residue dissolved in ethyl acetaete, washed with 1 N sodium hydroxide, brine and dried over anhydrous magnesium sulfate. The solution was filtered and the solvent removed in vacuo. The residue purified by high vacuum Kugelrohr distillation (temperature 245° C.) to furnish the title compound (1.23 g, 4.84 mmol).

Step C. Methyl (2S)-1-({4-[4-(2,2-dimethoxyethyl)anilino]-1-piperidinyl}carbonyl)-2-pyrrolidinecarboxylate Methyl (2S)-1-[(4-oxo-1-piperidinyl)carbonyl]-2-pyrrolidinecarboxylate (1.77 g, 6.97 mmol) and 4-(2,2-dimethoxyethyl)aniline (1.13 g, 6.24 mmol) were dissolved in dichloromethane. Anhydrous sodium sulfate (8.9 g) was added followed by acetic acid (1.9 mL). Stirring was continued for 1 hour. Sodium triacetoxyborohydride (1.46 g, 6.9 mmol) was added and stirring continued overnight. The mixture was filtered, diluted with dichloromethane, and washed with 1 N sodium hydroxide, water and brine. The organic phase was dried over anhydrous magnesium sulfate. The solution was filtered and the solvent evaporated to dryness in vacuo. The residue was purified by flash chromatography on silica gel Merck-60 (eluant: 20:1 chloroform-methanol). The solvent was removed in vacuo to furnish the title compound.

MS ((+)ESI, m/z): 420 [M+H]$^+$

Step D. 1-[[4-[[4-[2-[[(2R)-2-Hydroxy-2-[4-hydroxy-3-[(methylsulfonyl)-amino]phenyl]ethyl]amino]ethyl]phenyl]=amino]-1-piperidinyl]carbonyl]-L-proline, methyl ester Methyl (2S)-1-({4-[4-(2,2-dimethoxyethyl)anilino]-1-piperidinyl}carbonyl)-2-pyrrolidinecarboxylate (1.0 g, 2.38 mmol) was added to a pre-prepared mixture of sodium iodide (0.837 g, 5.58 mmol) and trichloro(methyl)silane (0.525 mL, 4.46 mmol) in anhydrous acetonitrile. The reaction was stirred at ambient temperature for 10 minutes. Dichloromethane was added and the reaction washed with 10% sodium thiosulfate solution, water and brine. The organic layer was dried over anhydrous magnesium sulfate, filtered and the solvent partially removed in vacuo. The aldehyde solution was used directly and treated with methanol, acetic acid (0.146 mL, 2.43 mmol), N-{5-[(1R)-2-amino-1-hydroxyethyl]-2-hydroxyphenyl}methanesulfonamide (0.55 g, 2.23 mmol) followed by sodium cyanoborohydride (0.154 g, 2.24 mmol). The reaction was stirred at ambient temperature for 24 hours. The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.05 g, 0.083 mmol).

m.p 106–108° C.

MS ((+)ESI, m/z): 604 [M+H]$^+$

Anal. calcd. for $C_{29}H_{41}N_5O_7S$+2.0 $H_2O$: C 54.44 H 7.09 N 11.95 found: C 54.79 H 6.7 N 10.7

EXAMPLE 78

1-[[4-[[4-[2-[[(2R)-2-Hydroxy-2-[4-hydroxy-3-[(methylsulfonyl)amino]phenyl]ethyl]amino]ethyl]phenyl]amino]-1-piperidinyl]carbonyl]-3-piperidine Carboxylic Acid, Ethyl Ester Step A. Ethyl 1-(1,4-dioxa-8-azaspiro[4.5]dec-8-ylcarbonyl)-3-piperidinecarboxylate The title compound (8.0 g, 24.51 mmol) was prepared from ethyl 3-piperidinecarboxylate (5.22 g, 33.20 mmol) and 1,4-dioxa-8-azaspiro[4.5]decane (4.76 g, 33.24 mmol) according to Procedure C with an additional purification by high vacuum Kugelrohr distillation (temperature 250° C.).

MS ((+)ESI, m/z): 327 [M+H]$^+$

Step B. Ethyl 1-[(4-oxo-1-piperidinyl)carbonyl]-3-piperidinecarboxylate

Ethyl 1-(1,4-dioxa-8-azaspiro[4.5]dec-8-ylcarbonyl)-3-piperidinecarboxylate (2.11 g, 6.46 mmol) was dissolved in formic acid and heated at 70° C. for 2.5 hours. The solvent was removed in vacuo and the oily residue dissolved in ethyl acetaete, washed with 1 N sodium hydroxide, brine and dried over anhydrous magnesium sulfate. The solution was filtered and the solvent removed in vacuo. The residue was purified by high vacuum Kugelrohr distillation (temperature 245° C.) to furnish the title compound (1.77 g, 6.27 mmol).

Step C. Ethyl 1-({4-[4-(2,2-dimethoxyethyl)anilino]-1-piperidinyl}carbonyl)-3-piperidinecarboxylate Ethyl 1-[(4-oxo-1-piperidinyl)carbonyl]-3-piperidinecarboxylate (1.23 g, 4.36 mmol) and 4-(2,2-dimethoxyethyl)aniline (0.875 g, 4.83 mmol) were dissolved in dichloromethane. Anhydrous sodium sulfate (6.87 g) was added followed by acetic acid (1.45 mL). Stirring was continued for 1 hour. Sodium triacetoxyborohydride (1.28 g, 6.04 mmol) was added and stirring continued overnight. The mixture was filtered, diluted with dichloromethane, and washed with 1 N sodium hydroxide, water and brine. The organic phase was dried over anhydrous magnesium sulfate. The solution was filtered and the solvent evaporated to dryness in vacuo. The residue was purified by flash chromatography on silica gel Merck-60 (eluant: 20:1 chloroform-methanol). The solvent was removed in vacuo to furnish the title compound (1.0 g, 2.23 mmol)

MS ((+)ESI, m/z): 448 [M+H]$^+$, 470 [M+Na]$^+$

Step D. 1-[[4-[[4-[2-[[(2R)-2-Hydroxy-2-[4-hydroxy-3-[(methylsulfonyl)amino]phenyl]ethyl]amino]ethyl]phenyl]=amino]-1-piperidinyl]carbonyl]-3-rpiperidinecarboxylic acid, ethyl ester Ethyl 1-({4-[4-(2,2-dimethoxyethyl)anilino]-1-piperidinyl}carbonyl)-3-piperidinecarboxylate (1.0 g, 2.23 mmol) was added to a pre-prepared mixture of sodium iodide (0.893 g, 5.96 mmol) and trichloro(methyl)silane (0.561 mL, 4.77 mmol) in anhydrous acetonitrile. The reaction was stirred at ambient temperature for 10 minutes. Dichloromethane was added and the reaction washed with 10% sodium thiosulfate solution, water and brine. The organic layer was dried over anhydrous magnesium sulfate, filtered and the solvent partially removed in vacuo. The aldehyde solution was used directly and treated with methanol, acetic acid (0.156 mL, 2.6 mmol), N-{5-[(1R)-2-amino-1-hydroxyethyl]-2-hydroxyphenyl}methanesulfonamide (0.587 g, 2.38 mmol) followed by sodium cyanoborohydride (0.164 g, 2.38 mmol). The reaction was stirred at ambient temperature for 24 hours. The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.07 g, 0.11 mmol).

m.p 106–108° C.

MS ((+)ESI, m/z): 632 [M+H]$^+$
Anal. calcd. for $C_{31}H_{45}N_5O_7S \cdot HCl + 0.25\, H_2O$: C 55.35 H 6.97 N 10.41 found: C 55.36 H7.05N 10.93

EXAMPLE 79

4-(4-{2-[(2S)-2-Hydroxy-3-(4-hydroxy-phenoxy)-propylamino]-ethyl}-phenylamino)-piperidine-1-carboxylic acid 3-methoxy-benzylamide Step A. tert-Butyl 4-[(1-{[(3-methoxybenzyl)amino]carbonyl}-4-piperidinyl)-amino]phenethylcarbamate The title compound (1.0 g, 2.1 mmol) was prepared from 3-methoxybenzyl amine (0.322 g, 2.4 mmol), and {2-[4-(piperidin-4-ylamino)-phenyl]-ethyl}-carbamic acid tert-butyl ester (0.500 g, 1.6 mmol) according to Procedure C.

$^1$H NMR (DMSO-$d_6$, 300 MHz): δ 1.40 (s, 9H), 2.60 (m, 2H), 3 (m, 2H), 3.3 (m, 2H), 3.6 (m, 1H), 3.9 (m, 2H), 4.4 (m, 2H), 6.5 (d, 2H), 6.8 (m, 3H), 7.00 (d, 2H).

Step B. 4-[4-(2-Aminoethyl)anilino]-N-(3-methoxybenzyl)-1-piperidinecarboxamide tert-Butyl 4-[(1-{[(3-methoxybenzyl)amino]carbonyl}-4-piperidinyl)amino]phenethylcarbamate (1.0 g, 2.1 mmol) was dissolved in dichloromethane (10 mL). Trifluoroacetic acid (4 mL, 52.0 mmol) was added. The reaction was stirred for 0.5 hours. The solvent was removed in vacuo. The residue was dissolved in dichloromethane, washed with dilute aqueous sodium bicarbonate and water. The organic layer was dried over anhydrous sodium sulfate. The dichloromethane was removed in vacuo to give the title compound (0.73 g, 2.0 mmol).

Step C. 4-[4-(2-{[(2S)-3-(4-{[tert-Butyl(diphenyl)silyl]oxy}phenoxy)-2-hydroxypropyl]amino}ethyl)anilino]-N-(3-methoxybenzyl)-1-piperidinecarboxamide 4-[4-(2-Aminoethyl)anilino]-N-(3-methoxybenzyl)-1-piperidinecarboxamide (0.73 g, 2.0 mmol) was reacted with tert-butyl-(4-oxiranylmethoxy-phenoxy)-diphenyl-silane according to Procedure G to give the title compound (0.53g, 0.67 mmol).

$^1$H NMR (DMSO-$d_6$, 300 MHz): δ 1.00 (s, 9H), 2.00 (m, 2H), 3.00 (t, 2H), 3.90 (m, 2H), 6.50 (d, 2H), 6.60 (m, 4H), 6.90 (d, 2), 7.40 (m, 6H), 7.65 (m, 4H).

Step D. 4-(4-{2-[(2S)-2-Hydroxy-3-(4-hydroxy-phenoxy)-propylamino]-ethyl}-phenylamino)-piperidine-1-carboxylic acid 3-methoxy-benzylamide 4-(4-{2-[2-Hydroxy-3-((4-tert-butyl-diphenyl-silanyloxy)phenoxy)-propylamino]-ethyl}-phenylamino)-piperidine-1-carboxylic acid 3-methoxy-benzylamide (0.53 g, 0.67 mmol) was reacted according Procedure H to give the title compound (0.210 g, 0.38 mmol).

MS ((+)ESI, m/z): 549 [M+H]$^+$ $^1$H NMR (DMSO-$d_6$, 400 MHz): d 1.25–1.39 (m, 2H), 1.82–1.85 (m, 2H), 2.51–2.64 (m, 3H), 2.67–2.71 (m, 3H), 2.83–2.89 (m, 2H), 3.30 (m, 1 H, obscured by water), 3.72 (s, 3H), 3.73–3.84 (m, 3H), 3.88–3.92 (m, 2H), 4.19–4.20 (d, 2H), 4.91–4.95 (broad s, 1H), 5.24–5.26 (d, 1H), 6.49–6.51 (d, 2H), 6.62–6.66 (m, 2H), 6.70–6.91 (m, 5H), 7.01–7.04 (m, 2H), 7.18–7.22 (m, 1H), 8.62 (broad s, 1H).

Anal. Calcd. for $C_{31}H_{40}N_4O_5 + 1.5 H_2O$: C 64.62 H 7.47 N 9.73. found: C 64.52 H 7.12 N 9.51

EXAMPLE 80

4-(4-{2-[(2S)-2-Hydroxy-3-(4-hydroxy-phenoxy)-propylamino]-ethyl}-phenylamino)-piperidine-1-carboxylic acid 2,4-difluoro-benzylamide Step A. tert-Butyl 4-[(1-{[(2,4-difluorobenzyl)amino]carbonyl}-4-piperidinyl)amino]phenethylcarbamate The title compound (0.52 g, 1.1 mmol) was prepared from 2,4-difluorobenzylamine (0.561 g, 3.9 mmol), and {2-[4-(piperidin-4-ylamino)-phenyl]-ethyl}-carbamic acid tert-butyl according to Procedure C.

$^1$H NMR (DMSO-d6, 300 MHz): δ 1.40 (s, 9H), 2 (m, 2H), 3.00 (t, 3H), 3.90 (m, 2H), 6.6 (m, 2H), 6.80 (m, 3H), 7.00 (d, 2H), 7.20–7.40 (m, 2H).

Step B. 4-[4-(2-aminoethyl)anilino]-N-(2,4-difluorobenzyl)-1-piperidinecarboxamide formate tert-Butyl 4-[(1-{[(2,4-difluorobenzyl)amino]carbonyl}-4-piperidinyl)amino]phenethylcarbamate (0.52 g, 1.1 mmol) was reacted according to Procedure F to obtain the title compound.

Step C. 4-[4-(2-{[(2S)-3-(4-{[tert-Butyl(diphenyl)silyl]oxy}phenoxy)-2-hydroxypropyl]amino}ethyl)anilino]-N-(2,4-difluorobenzyl)-1-piperidinecarboxamide 4-[4-(2-aminoethyl)anilino]-N-(2,4-difluorobenzyl)-1-piperidinecarboxamide formate (0.477 g, 1.1 mmol) was reacted with tert-butyl-(4-oxiranylmethoxy-phenoxy)-diphenyl-silane according to Procedure G to give the title compound (0.25 g, 0.032 mmol).

Step D. 4-(4-{2-[2-Hydroxy-3-(4-hydroxy-phenoxy)-propylamino]-ethyl}-phenylamino)-piperidine-1-carboxylic acid 2,4-difluoro-benzylamide 4-[4-(2-([(2S)-3-(4-{[tert-Butyl(diphenyl)silyl]oxy}phenoxy)-2-hydroxypropyl]-amino}ethyl)anilino]-N-(2,4-difluorobenzyl)-1-piperidinecarboxamide (0.25 g, 0.032 mmol) was reacted according to Procedure H to give the title compound (0.068 g, 0.012 mmol).

MS ((+)ESI, m/z): 555 [M+H]$^+$

Anal. Calcd. for $C_{30}H_{36}N_4O_4F_2 + 0.5\, H_2O$: C 63.87 H 6.56 N 9.93. found: C 63.60 H 6.95 N 9.28

EXAMPLE 81

4-(4-{2-[(2S)-2-Hydroxy-3-(4-hydroxy-phenoxy)-propylamino]-ethyl}-phenylamino)-piperidine-1-carboxylic Acid [2-(4-fluoro-phenylcarbamoyl)-ethyl]-amide Step A. N-(4-Fluorophenyl)succinamic acid 4-Fluoroaniline (11.10 g, 100 mmol) was reacted according to Procedure K. The title compound was used in the next step without further purification.

$^1$H NMR (DMSO-d6, 300 MHz): δ 2.50 (m, 4H), 7.20 (m, 2H), 7.60 (m, 2H), 10.00 (s, 1H), 12.00 (s, 1H).

Step B. [2-(4-{1-[2-(4-Fluoro-phenylcarbamoyl)-ethylcarbamoyl]-piperidin-4-ylamino}-phenyl)-ethyl]-carbamic acid tert-butyl ester N-(p-Fluorophenyl)succinamic acid (1.32 g, 6.0 mmol) was reacted with {2-[4-(Piperidin-4-ylamino)-phenyl]-ethyl}-carbamic acid tert-butyl ester according to Procedure D to give the title compound (0.310 g, 0.6 mmol).

MS ((+)APCI, m/z): 528 [M+H]$^+$

NMR (DMSO-$d_6$, 400 MHz): δ 1.15–1.18 (m, 2H), 1.35 (s, 9H), 1.79–1.82 (m, 2H), 2.48–2.51 (m, 4H), 2.78–2.85 (m, 2H), 2.99–3.04 (m, 2H), 3.26–3.32 (m, 3H, overlaps water and is seen on $D_2O$ exchange), 3.82–3.85 (d, 2H), 5.19–5.21 (d, 1H), 6.48–6.50 (d, 2H), 6.56–6.59 (t, 1H), 6.74–6.77 (t, 1H), 6.85–6.87 (d, 2H), 7.08–7.12 (m, 2H), 7.57–7.61 (m, 2H), 9.95 (broad s, 1H).

Anal. Calcd. for $C_{28}H_{38}N_5O_4F + H_2O$: C 61.58 H 7.33 N 12.82 found: C 61.85 H 7.36 N 2.62

Step C. 4-[4-(2-Aminoethyl)anilino]-N-[3-(4-fluoroanilino)-3-oxopropyl]-1-piperidinecarboxamide formate

[2-(4-{1-[2-(4-Fluoro-phenylcarbamoyl]-ethylcarbamoyl-piperidin-4-ylamino}-phenyl)-ethyl]-carbamic acid tert-butyl ester (0.31 g, 0.6 mmol) was reacted according to Procedure F to provide the title compound (0.28 g, 0.6 mmol).

Step D. 4-[4-(2-{[(2S)-3-(4-{[tert-Butyl(diphenyl)silyl]oxy}phenoxy)-2-hydroxypropyl]amino}ethyl)anilino]-N-[3-(4-fluoroanilino)-3-oxopropyl]-1-piperidinecarboxamide 4-[4-(2-Aminoethyl)anilino]-N-[3-(4-fluoroanilino)-3-oxopropyl]-1-piperidinecarboxamide formate (0.28 g, 0.6 mmol) was reacted with tert-butyl-(4-oxiranylmethoxyphenoxy)-diphenyl-silane according to Procedure G to give the title compound (0.11 g, 0.13 mmol).

$^1$H NMR (DMSO-d6, 300 MHz): δ 1.80 (m, 2H), 2.80 (t, 2H), 3.80 (m, 2H), 6.50 (d, 2H), 6.70 (m,5H), 6.90 (d, 2H), 7.20 (t, 2H), 7.50 (m, 6H), 7.60 (m, 6H).

Step E. 4-(4-{2-[(2S)-2-Hydroxy-3-(4-hydroxy-phenoxy)-propylamino]-ethyl}-phenylamino)-piperidine-1-carboxylic acid [2-(4-fluoro-phenylcarbamoyl)-ethyl]-amide 4-(4-{2-[(2S)-2-Hydroxy-3-(4-4-tert-Butyl-diphenyl-silanyloxy)-phenoxy)-propylamino]-ethyl}-phenylamino)-piperidine-1-carboxylic acid (2-diethylcarbamoylethyl)amide(0.110 g, 0.13 mmol) was reacted according to Procedure H to provide the title compound (0.04 g, 0.065 mmol).

MS ((+)ESI m/z): 594 [M+H]$^+$ $^1$H NMR (DMSO-d$_6$, 400 MHz): d 1.13–1.22 (m, 2H), 1.79–1.83 (d, 2H), 2.43–2.79 (m, 8H), 2.79–2.84 (t, 2H), 3.24–3.29 (m, 3H, overlaps with water and is seen on D$_2$O exchange), 3.73–3.86 (m, 5H), 4.98 (broad s, 1H), 5.19–5.21 (d, 1H), 6.48–6.50 (d, 2H), 6.56–6.59 (t, 1H), 6.63–6.66 (d, 2H), 6.71–6.73 (d, 2H), 6.87–6.90 (d, 2H), 7.08–7.13 (t, 2H), 7.57–7.62 (m, 2H), 8.86 (broad s, 1H), 9.96 (s, 1H).

Anal. Calcd. for C$_{32}$H$_{40}$N$_5$O$_5$F+1.0 H$_2$O: C 62.78 H 6.87 N 11.44. found: C 63.01 H 6.80 N 11.20

EXAMPLE 82

4-(4-{2-[(2S)-2-Hydroxy-3-(4-hydroxy-phenoxy)-propylamino]-ethyl}-phenylamino)-piperidine-1-carboxylic Acid {2-[(4-chloro-phenyl)-methyl-carbamoyl]-ethyl}-amide Step A. N-(4-Chlorophenyl)-N-methylsuccinamic acid N-methyl-4-chloroaniline (3.5 g, 2.5 mmol) was reacted according to Procedure K to give the title compound.

MS (EI, m/z): 241 [M]$^+$ $^1$H NMR (DMSO-d6, 300 MHz): δ 2.40 (m, 2H), 3.00 (m, 2H), 7.40 (d, 2H), 7.60 (d, 2H), 12.00 (s, 1H).

Anal. calcd. for C$_{11}$H$_{12}$NO$_3$Cl: C 54.52 H 4.86 N 5.69 found: C 54.80 H 4.92 N 5.78

Step B. {2-[4-(1-{2-[(4-Chloro-phenyl)-methyl-carbamoyl]-ethylcarbamoyl}-piperidin-4-ylamino)-phenyl]-ethyl}-carbamic acid tert-butyl ester N-(4-Chlorophenyl)-N-methylsuccinamic acid (0.758 g, 3.0 mmol) was reacted with {2-[4-(piperidin-4-ylamino)-phenyl]-ethyl}-carbamic acid tert-butyl ester according to Procedure D to provide the title compound (0.912g, 1.6 mmol).

MS ((+)ESI, m/z): 558[M+H]$^+$ $^1$H NMR (DMSO-d$_6$, 400 MHz): d 1.11–1.14 (m, 2H), 1.35 (s, 9H), 1.76–1.79 (d, 2H), 2.15–2.17 (broad s, 1H), 2.73–2.79 (t, 2H), 2.98–3.02 (q, 2H), 3.12–3.29(m, 4H), 3.74–3.78 (d, 2H), 5.22–5.24 (d, 1H), 6.39–6.40 (broad s, 1H), 6.47–6.49 (d, 2H), 6.76–6.79 (t, 1H), 6.83–6.85 (d, 2H), 7.32–7.34 (d, 2H), 7.47–7.49 (d, 2H).

Anal. Calcd. for C$_{29}$H$_{40}$N$_5$O$_4$Cl+0.33 CHCl$_3$: C 58.24 H 6.75 N 11.71 found: C 58.63 H 6.25 N 11.13

Step C. 4-[4-(2-aminoethyl)anilino]-N-[3-[4-chloro(methyl)anilino]-3-oxopropyl-1-piperidinecarboxamide formate {2-[4-(1-{2-[(4-Chloro-phenyl)-methyl-carbamoyl]-ethylcarbamoyl}piperidin-4-ylamino)-phenyl]-ethyl}-carbamic acid tert-butyl ester (0.864 g, 1.55 mmol) was reacted according to Procedure F to provide the title compound (0.78 g, 1.55 mmol).

$^1$H NMR (DMSO-d6, 300 MHz): δ 1.80 (m, 2H), 2.80 (m, 2H), 3.80 (m, 2H), 6.60 (d, 2H), 6.80 (d, 2H), 7.40 (d, 2H), 7.60 (d, 2H), 8.40 (s, 1H).

Step D. 4-[4-(2-{[(2S)-3-(4-{[tert-Butyl(diphenyl)silyl]oxy}phenoxy)-2-hydroxypropyl]amino}ethyl)anilino]-N-{3-[4-chloro(methyl)anilino]-3-oxopropyl}-1-piperidinecarboxamide 4-[4-(2-Aminoethyl)anilino]-N-{3-[4-chloro(methyl)anilino]-3-oxopropyl}-1-piperidinecarboxamide formate (0.78 g, 1.55 mmol) was reacted with tert-butyl-(4-oxiranylmethoxy-phenoxy)-diphenyl-silane according to Procedure G to provide the title compound (0.27 g, 0.3 mmol)

$^1$H NMR (DMSO-d6, 300 MHz): δ 1.80 (m, 2H), 2.80 (m, 2H), 3.80 (m, 2H), 6.40 (broad s, 1H), 6.50 (d, 2H), 6.70 (m, 4H), 6.90 (d, 2H), 7.20–7.60 (m, 10H), 7.80 (d, 4H).

Step E. 4-(4-{2-[(2S)-2-Hydroxy-3-(4-hydroxy-phenoxy)-propylamino]-ethyl}-phenylamino)-piperidine-1-carboxylic acid {2-[(4-chloro-phenyl)-methyl-carbamoyl]-ethyl}-amide 4-[4-{2-{[(2S)-3-(4-{[tert-Butyl(diphenyl)silyl]oxy}phenoxy)-2-hydroxypropyl]amino}ethyl)anilino]-N-[3-[4-chloro(methyl)anilino]-3-oxopropyl}-1-piperidinecarboxamide (0.27 g, 0.3 mmol) was reacted according to Procedure H to provide the title compound (0.151 g, 0.2 mmol).

MS ((+)ESI, m/z): 624 [M+H]$^+$ $^1$H NMR (DMSO-d$_6$, 400 MHz): d 1.10–1.19(m, 2H), 1.77–2.12 (d, 2H), 2.17–2.19 (broad s, 2H), 2.54–2.79 (m, 8H), 3.08–3.22 (m, 5H), 3.72–3.87 (m, 5H), 4.99–5.04 (broad s, 1H), 5.21–5.23 (d, 1H), 6.39 (broad s, 1H), 6.47–6.49 (d, 2H), 6.62–6.66 (m, 2H), 6.70–6.74 (m, 2H), 6.87–6.89 (d, 2H), 7.33–7.35 (d, 2H), 7.48–7.50 (d, 2H), 8.87(broad s, 1H).

Anal. Calcd. for C$_{33}$H$_{42}$N$_2$O$_5$Cl+1.0 H$_2$O: C 61.66 H 6.85 N 10.90 found: C 61.80 H 6.81 N 10.61

EXAMPLE 83

4-(4-{2-[2-Hydroxy-3-(4-hydroxy-phenoxy)-propylamino]-ethyl}- phenylamino)-piperidine-1-carboxylic Acid 2-fluoro-4-hydroxy-benzylamide Step A. 4-(tert-Butyl-diphenyl-silanyloxy)-2-fluoro-benzonitrile 2-Fluoro-4-hydroxybenzonitrile (19.85 g, 145 mmol) was dissolved in dichloromethane (400 mL). Imidazole (10.86 g, 160 mmol) was added followed by tert-butylchlorodiphenylsilane (39.60 mL, 152 mmol). The reaction was stirred at ambient temperature overnight. The reaction was washed with water, dried over anhydrous sodium sulfate, filtered and the solvent removed in vacuo to furnish the title compound (49.28g, 131.2 mmol).

MS (EI, m/z): 375 [M]$^+$ $^1$H NMR (DMSO-d$_6$, 400 MHz): d 1.04 (s, 9H), 6.58–6.61(m, 1H), 6.87–6.90 (m, 1H), 7.42–7.55 (m, 6H), 7.60–7.71 (m, 5H).

Anal. Calcd. for C$_{23}$H$_{22}$ NOFSi: C 73.57 H 5.91 N 3.73 found: C 73.08 H 6.00 N 3.36

Step B. 4-(tert-Butyl-diphenyl-silanyloxy)-2-fluoro-benzylamine

To a solution of 4-(tert-butyl-diphenyl-silanyloxy)-2-fluoro-benzonitrile (2.07 g, 5.52 mmol) in diethyl ether (17 mL) was added lithium aluminum hydride (6.6 mL, 1M in tetrahydrofuran) slowly. The reaction was heated at reflux for two hours the heat was removed and the reaction allowed to stir overnight at ambient temperature. The reaction was quenched with 1.17 mL of water, then 1.17 mL of sodium hydroxide solution (15%), and 1.17 mL of water. The white solid was filtered and washed with dichloromethane, the organic solvent was dried over anhydrous sodium sulfate. The solvent was removed in vacuo to give the title compound (1.66 g, 4.38 mmol) as an oil, which was used directly in the next step.

$^1$H (DMSO-d6, 300 MHz): δ 1.00 (s, 9H), 6.60 (d, 1H), 7.00 (d, 1H), 7.50 (m, 6H), 7.70 (m, 5H).

Step C. [2-(4-{1-[4-(tert-Butyl-diphenyl-silanyloxy)-2-fluoro-benzylcarbamoyl]-piperidin-4-ylamino}-phenyl)-ethyl]-carbamic acid tert-butyl ester 4-(tert-Butyl-diphenyl-silanyloxy)-2-fluoro-benzylamine (1.44 g, 3.8 mmol), and {2-[4-(piperidin-4-ylamino)-phenyl]-ethyl}-carbamic acid tert-butyl ester (1.21 g, 3.8 mmol) were reacted according to procedure C to give the title compound (0.90 g, 1.3 mmol).

MS ((+)ESI, m/z): 725 [M+H]$^+$

Anal. Calcd. for $C_{42}H_{53}N_4O_4FSi+3.75H_2O+0.3 CH_3CO_2C_2H_5$: C 63.30 H 7.68 N 6.84 found: C 63.10 H 6.79 N 6.79

Step E. N-(4-{[tert-Butyl(diphenyl)silyl]oxy}-2-fluorobenzyl)-4-[4-(2-{[(2S)-3-(4-{[tert-butyl(diphenyl)silyl]oxy}phenoxy)-2-hydroxypropyl]amino}ethyl)anilino]-1-piperidinecarboxamide 4-[4-(2-Aminoethyl)anilino-N-(4-{[tert-butyl(diphenyl)silyl]oxy}-2-fluorobenzyl)-1-piperidinecarboxamide formate (0.855 g, 1.3 mmol) was reacted with tert-butyl-(4-oxiranylmethoxy-phenoxy)-diphenyl-silane according to Procedure G to give the title compound (0.24 g, 0.2 mmol).

Step F. 4-(4-{2-[2-Hydroxy-3-(4-hydroxy-phenoxy)-propylamino]-ethyl}-phenylamino)-piperidine-1-carboxylic acid 2-fluoro-4-hydroxy-benzylamide N-(4-{[tert-Butyl(diphenyl)silyl]oxy}-2-fluorobenzyl)-4-[4-(2-{[(2S)-3-(4-{[tert-butyl(diphenyl)silyl]oxy}phenoxy)-2-hydroxypropyl]amino}ethyl)anilino]-1-piperidinecarboxamide (0.240 g, 0.2 mmol) was reacted according to Procedure H to yield the title compound (0.045 g, 0.08 mmol).

MS ((+)APCI, m/z): 553 [M+H]$^+$

Anal. Calcd. for $C_{30}H_{37}N_4O_5F+1.0H_2O$: C 63.09 H 6.83 N 9.81 found: C 62.92 H 6.94 N 9.40

EXAMPLE 84

Dimethyl-carbamic Acid 3-fluoro-4-({[4-(4-{2-[(2S)-2-hydroxy-3-(4-hydroxy-phenoxy)-propylamino]-ethyl}-phenlamino)-piperidine-1-carbonyl]-amino}-methyl)-phenyl Ester Step A. [4-(tert-Butyl-diphenyl-silanyloxy)-2-fluoro-benzyl]-carbamic acid tert-butyl ester 4-(tert-Butyl-diphenyl-silanyloxy)-2-fluoro-benzylamine (1.66 g, 4.38 mmol) was dissolved in anhydrous tetrahydrofuran (9 mL). Di-tert-butyl dicarbonate (1.05 g, 4.82 mmol) was added. The reaction was stirred at ambient temperature overnight. Diethyl ether was added and the solution washed with phosphoric acid (7 mL of an aqueous 20% solution), saturated sodium chloride (7 mL), saturated sodium bicarbonate (7 mL) and brine (7 mL). The organic layer was dried over anhydrous sodium sulfate, filtered and the solvent removed in vacuo to give the title compound (2.1 g, 4.38 mmol)

MS ((+)ESI, m/z): 497 [M+NH$_4$]$^+$

Anal. Calcd. for $C_{28}H_{34}NO_3FSi$: C 70.11 H 7.14 N 2.92 found: C 70.02 H 7.22 N 2.85

Step B. (2-Fluoro-4-hydroxy-benzyl)-carbamic acid tert-butyl ester

[4-(tert-Butyl-diphenyl-silanyloxy)-2-fluoro-benzyl]-carbamic acid tert-butyl ester was dissolved in anhydrous tetrahydrofuran (5 mL). Tetrabutylammonium fluoride (4.5 mL of a 1M solution) was added. The solvent was removed under vacuo and the residue purified by flash chromatography on silica gel Merck-60 (eluant: 5:1 chloroform-methanol) to furnish the title compound (0.46 g, 1.95 mmol).

MS ((+)ESI, m/z): 242 [M+H]$^+$, 483 [2M+H]$^+$ $^1$H NMR (DMSO-d$_6$, 400 MHz): d 1.37 (s, 9H), 4.01–4.03 (m, 2H), 6.47–6.50 (m, 1H), 6.53–6.56 (m, 1H), 7.05–7.09 (t, 1H), 7.22 (t, 1H), 9.72 (s, 1H).

Step C. tert-Butyl 4-({[1-(dimethylamino)vinyl]oxy}methyl)-2-fluorobenzylcarbamate (2-Fluoro-4-hydroxy-benzyl)-carbamic acid tert-butyl ester (0.70 g, 3.0 mmol) was dissolved in dichloromethane (15 mL), 4-nitrophenylchloroformate (0.585g, 3.0 mmol) was added and the reaction cooled to 0° C. Triethylamine (1.01 mL, 7.5 mmol) was added and the reaction stirred for 30 minutes at 0° C. The ice bath was removed and the reaction stirred at room temperature for a further 30 minutes. The reaction was cooled again to 0° C., and dimethylamine (1.52 mL, 3.15 mmol) added. The ice bath was removed and the reaction stirred at ambient temperature overnight. The reaction was washed with 10% aqueous potassium carbonate, 1N sodium hydroxide, brine and dried over anhydrous sodium sulfate. The solution was filtered and the solvent evaporated to dryness in vacuo to give the title compound (0.64 g, 2.0 mmol).

$^1$H NMR (DMSO-d6, 300 MHz): δ 1.40 (s, 9H), 3.10 (s, 6H), 4.10 (d, 2H), 7.00 (m, 2H), 7.25 (t, 1H), 7.50 (m, 1H).

Step D. 1-{[4-(aminomethyl)-3-fluorobenzyl]oxy}-N,N-dimethyl-1-ethylenamine formate tert-Butyl 4-({[1-(dimethylamino)vinyl]oxy}methyl)-2-fluorobenzylcarbamate (0.64 g, 2.0 mmol) was reacted according to Procedure F to give the title compound (0.365 g, 1.7 mmol).

Step E. (2-{4-[1-(4-Dimethylcarbamoyloxy-2-fluoro-benzylcarbamoyl)-piperidin-4-ylamino]-phenyl}-ethyl)-carbamic acid tert-butyl ester 1-{[4-(Aminomethyl)-3-fluorobenzyl]oxy}-N,N-dimethyl-1-ethylenamine formate (0.365 g, 1.7 mmol) and {2-[4-(pieridin-4-ylamino)-phenyl]-ethyl}-carbamic acid tert-butyl ester were reacted according to Procedure C to give the title compound (0.31 g, 0.6 mmol).

MS ((+)APCI, m/z): 558 [M+H]$^+$ $^1$H NMR (DMSO-d$_6$, 400 MHz): d 1.19–1.28 (m, 2H), 1.36 (s, 9H), 1.81–1.85 (d, 2H), 2.89 (s, 5H), 3.01 (s, 5H), 3.34–4.07 (d, 2H), 4.22–4.24 (m, 3H), 5.25–5.27 (d, 1H), 6.49–6.51 (d, 1H), 6.76 (t, 1H), 6.85–6.87 (d, 2H), 6.91–7.05 (m, 3H), 7.26–7.30 (t, 1H).

Anal. Calcd. for $C_{29}H_{40}N_5O_5F+1.0 H_2O$: C 60.45 H 7.30 N 12.15 found: C 60.56 H 6.67 N 12.31

Step F. 4-{[({4-[4-(2-Aminoethyl)anilino]-1-piperidinyl}carbonyl)amino]methyl}-3-fluorophenyl dimethylcarbamate formate (2-{4-[1-(4-Dimethylcarbamoyoxy-2-fluoro-benzylcarbamoyl)-piperidin-4-ylamino]-phenyl)-ethyl)-carbamic acid tert-butyl ester (0.310 g, 0.6 mmol) was reacted according to Procedure F to give the title compound (0.225 g, 0.6 mmol).

$^1$H NMR (DMSO-d6, 300 MHz): δ1.90 (d, 2H), 3.90 (d, 2H), 4.20 (m, 2H), 6.50 (d, 2H), 6.90 (d, 2H), 7.00 (m, 3H), 7.30 (t, 1H).

Step G. 4-{[({4-[4-(2-{[(2S)-3-(4-{[tert-Butyl(diphenyl)silyl]oxy}phenoxy)-2-hydroxypropyl]amino}ethyl)anilino]-1-piperidinyl}carbonyl)amino]methyl}-3-fluorophenyl dimethylcarbamate 4-{[({4-[4-(2-Aminoethyl)anilino]-1-piperidinyl}carbonyl)amino]methyl}-3-fluorophenyl dimethylcarbamate formate (0.225 g, 0.6 mmol) was reacted with tert-butyl-(4-oxiranylmethoxy-phenoxy)-diphenyl-silane according to Procedure give the title compound (0.125 g, 0.1 mmol).

$^1$H NMR (DMSO-d6, 300 MHz): δ 1.90 (d, 2H), 2.80 (d, 2H), 4.00 (d, 2H), 4.30 (d, 2H), 6.50 (d, 2H), m6.80 (m, 4H), 6.90–7.20 (m, 6H), 7.30 (t, 1H), 7.50 (m, 6H), 7.60 (d, 4H).

Step H. Dimethyl-carbamic acid 3-fluoro-4-({[4-(4-{2-[(2S)-2-hydroxy-3-(4-hydroxy-phenoxy)-propylamino]-ethyl}-phenylamino)-piperidine-1-carbonyl]-amino}-methyl)-phenyl ester 4-{[({4-[4-(2-([[(2S)-3-(4-{[tert-Butyl(diphenyl)silyl]oxy}phenoxy)-2-hydroxypropyl]amino}ethyl)anilino]-1-piperidinyl}carbonyl)amino]methyl}-3-fluorophenyl dimethylcarbamate (0.125 g, 0.1 mmol) was reacted according to Procedure H to yield the title compound (0.036 g, 0.06 mmol)

MS ((-)ESI, m/z): 622 [M-H]$^-$ $^1$H NMR (DMSO-d$_6$, 400 MHz): d 1.15–1.25 (m, 2H), 1.60 (m, 1H), 1.81–1.85 (m, 2H), 3.30–3.32 (m, 1 H, seen on D$_2$O exchange), 4.23–4.24 (d, 2H), 5.26–5.28 (d, 1H), 6.49–6.66 (d, 2H), 6.67–6.71 (m, 2H), 6.72–6.74(m, 2H), 6.88–7.05 (m, 5H), 7.26–7.30 (t, 1H), 8.87(broad s, 1H).

Anal. Calcd. for C$_{33}$H$_{42}$N$_5$O$_6$F+1.0 H$_2$O: C 61.70 H 6.86 N 10.91 found: C 61.45 H 6.78 N 10.48

EXAMPLE 85

4-(4-{2-[(2S)-2-Hydroxy-3-(3-hydroxy-phenoxy)-propylamino]-ethyl}-phenylamino)-piperidine-1-carboxylic Acid 4-fluoro-benzylamide Step A. N-(4-fluorobenzyl)-4-[4-(2-{[(2S)-2-hydroxy-3-(3-{[isopropyl(diphenyl)silyl]oxy}phenoxy)propyl]amino}ethyl)anilino]-1-piperidinecarboxamide 4-[4-(2-Amino-ethyl)-phenylamino]-piperidine-1-carboxylic acid 4-fluoro-benzylamide (0.66 g, 1.6 mmol) was reacted tert-butyl{3-[(2S)oxiranylmethoxy] phenoxy} diphenylsilane according to Procedure G to yield the title compound (0.284 g, 0.4 mmol).

$^1$H NMR (DMSO-d6, 300 MHz): δ 1.90 (m, 2H), 2.90 (m, 2H), 3.90 (m, 2H), 4.20 (d, 2H), 6.30 (m, 2H), 6.50 (m, 4H), 6.80–7.20 (m, 8H), 7.30 (m, 2H), 7.50 (m, 6H), 7.70 (m, 4H).

Step B. 4-(4-{2-[(2S)-2-Hydroxy-3-(3-hydroxy-phenoxy)-propylamino]-ethyl}-phenylamino)-piperidine-1-carboxylic acid 4-fluoro-benzylamide N-(4-Fluorobenzyl)-4-[4-(2-{[(2S)-2-hydroxy-3-(3-{[isopropyl(diphenyl)silyl]oxy}phenoxy)propyl]amino}ethyl)anilino]-1-piperidinecarboxamide (0.284 g, 0.4 mmol) was reacted according to Procedure F to yield the title compound (0.122 g, 0.2 mmol).

MS ((+)APCI, m/z): 537 [M+H]$^+$ $^1$H NMR (DMSO-d$_6$, 400 MHz): d 1.15–1.24 (m, 2H), 1.81–1.85(m, 2H), 2.48–2.89 (m, 8H), 3.76–4.08 (m, 5H), 4.19–4.20 (m, 2H), 4.98–5.02 (broad s, 1H), 5.24–5.26 (m, 1H), 6.29–6.34 (m, 3H), 6.49–6.51 (m, 2H), 6.88–6.90(m, 2H), 7.00–7.13 (m, 4H), 7.24–7.29 (m, 4H), 9.32–9.34 (s, 1H).

Anal. Calcd. for C$_{30}$H$_{37}$N$_4$O$_4$F+3.0 H$_2$O: C 60.95 H 7.28 N 9.48 found: C 61.18 H 6.56 N 9.17

EXAMPLE 86

[3-Fluoro-4-[[[[4-[[4-[2-[[(S)-2-hydroxy-3-(4-hydroxyphenoxy)propyl]amino]ethyl]phenyl]amino]-1-piperidinyl]carbonyl]amino]methyl]phenoxy]acetic Acid Step A. [4-(tert-Butoxycarbonylamino-methyl)-3-fluoro-phenoxy]-acetic acid methyl ester (2-Fluoro-4-hydroxy-benzyl)-carbamic acid tert-butyl ester (0.47 g, 1.95 mmol) was dissolved in anhydrous N,N-dimethylformamide (5 mL). Methyl bromoacetate (0.203 mL, 2.15 mmol) and potassium carbonate (0.431 g, 3.12 mmol) were added and the reaction stirred at ambient temperature overnight. The reaction mixture was diluted with ethyl acetate and repeatedly washed with water. The organic phase was dried over anhydrous sodium sulfate, filtered and the solvent removed under vacuo to yield the title compound (0.59 g, 1.85 mmol).

MS ((+)APCI, m/z): 331 [M+NH$_4$]$^+$ $^1$H NMR (DMSO-d$_6$, 400 MHz): d 1.37 (s, 9H), 3.69 (s, 3H), 4.06–4.07 (d, 2H), 4.80 (s, 2H), 6.74–6.78 (m, 1H), 6.80–6.81(m, 1H), 7.17–7.21 (t, 1H), 7.29(t, 1H).

Anal. Calcd. for C$_{15}$H$_{20}$NO$_5$F+0.33 H$_2$O: C 56.37 H 6.47 N 4.38 found: C 56.58 H 6.09 N 4.26

Step B Methyl 2-[4-(aminomethyl)-3-fluorophenoxy]acetate

[4-(tert-Butoxycarbonylamino-methyl)-3-fluoro-phenoxy]-acetic acid methyl ester (0.94 g, 3.0 mmol) was dissolved in formic acid (13 mL) and heated to 60° C. for 1 hour. The solvent was removed under vacuo and the residue repeatedly co-evaporated with chloroform and ethanol. The residue was dissolved in ethyl acetate washed with saturated sodium bicarbonate. The organic phase was dried over anhydrous sodium sulfate, filtered, and evaporated in vacuo to give the title compound (0.56 g, 2.6 mmol).

$^1$H NMR (DMSO-d6, 300 MHz): δ 3.70 (s, 3H), 4.00 (s, 2H), 4.90 (s, 2H), 7.00 (m, 2H), 7.50 (t, 1H), 8.40 (s, 1H).

Step C. [4-({4-[4-(2-tert-Butoxycarbonylamino-ethyl)-phenylamino]-piperidine-1-carbonyl}-amino)-3-fluoro-phenoxy]-acetic acid methylester Methyl 2-[4-(aminomethyl)-3-fluorophenoxy]acetate (0.56g, 3.0 mmol) and {2-[4-(piperidin-4-ylamino)-phenyl]-ethyl}-carbamic acid tert-butyl ester (0.839 g, 3.0 mmol) were reacted according to procedure C to give the title compound (0.66 g, 1.2 mmol).

MS ((+)APCI, m/z): 559 [M+H]$^+$

Anal. Calcd. for C$_{28}$H$_{37}$N$_4$O$_6$: C 61.75 H 6.85 N 10.29 found: C 61.52 H 6.91 N 9.79

Step D. Methyl 2-(4-{[({4-[4-(2-aminoethyl)anilino]-1-piperidinyl}carbonyl)amino]methyl}-3-fluorophenoxy)acetate

[4-({4-[4-(2- tert-Butoxycarbonylamino-ethyl)-phenylamino]-piperidine-1-carbonyl}-amino)-3-fluoro-phenoxy]-acetic acid methylester (0.660 g, 1.2 mmol) reacted according to Procedure F to yield the title compound (0.605 g, 1.2 mmol).

$^1$H NMR (DMSO-d6, 300 MHz): δ 1.90 (m, 2H), 2.90 (m, 2H), 3.90 (m, 2H), 4.20 (d, 2H), 6.50 (m, 2H), 6.80 (m, 2H), 7.00 (m, 3H), 7.20 (t, 1H), 8.40 (broad s, 1H).

Step E. Methyl 2-(4-{[({4-[4-(2-{[(2S)-3-(4-{[tert-butyl(diphenyl)silyl]oxy}phenoxy)-2-hydroxypropyl]amino}ethyl)anilino]-1-piperidinyl}carbonyl)amino]methyl}-3-fluorophenoxy)acetate Methyl 2-(4-{[({4-[4-(2-aminoethyl)anilino]-1-piperidinyl}carbonyl)amino]methyl}-3-fluorophenoxy)acetate (0.605 g, 1.2 mmol) was reacted with tert-butyl-(4-oxiranylmethoxy-phenoxy)-diphenyl-silane (0.477 g, 1.2 mmol) according to Procedure G to furnish the title compound (0.280 g, 0.33 mmol).

$^1$H NMR (DMSO-d6, 300 MHz): δ 1.90 (m, 2H), 2.90 (m, 2H), 3,90 (m, 2H), 6.50 (m, 2H), 6.80–7.10 (m, 10H0, 7.30 (t, 1H), 7.50 (m, 6H), 7.70, (d, 4H).

Step F. Methyl 2-(3-fluoro-4-{[({4-[4-(2-{[(2S)-2-hydroxy-3-(4-hydroxy-phenoxy)propyl]amino}ethyl)anilino]-1-piperidinyl}carbonyl)amino]methyl}phenoxy)acetate Methyl 2-(4-{[({4-[4-(2-{[(2S)-3-(4-{[tert-butyl(diphenyl)silyl]oxy}phenoxy)-2-hydroxypropyl]

amino}ethyl)anilino]-1-piperidinyl}carbonyl)am ino] methyl}-3-fluorophenoxy)acetate (0.280 g, 0.33 mmol) was reacted according to Procedure H to yield the title compound (0.107 g, 0.2 mmol).

$^1$H NMR (DMSO-d6, 300 MHz): δ 1.90 (m, 2H), 2.90 (m, 2H), 3.90 (m, 2H), 6.50 (d, 2H), 6.60–7.00 (m, 10H), 7.20 (t, 1H), 9.00 (broad s, 1H).

Step G. [3-Fluoro-4-[[[[4-[[4-[2-[[(S)-2-hydroxy-3-(4-hydroxyphenoxy)propyl]amino]ethyl]phenyl]amino]-1-piperidinyl]carbonyl]amino]methyl]phenoxy]acetic acid Methyl 2-(3-fluoro-4-{[({4-[4-(2-{[(2S)-2-hydroxy-3-(4-hydroxyphenoxy)propyl]amino}ethyl)anilino]-1-piperidinyl}carbonyl)amino]methyl}phenoxy)acetate (0.107 g, 0.2 mmol) was dissolved in tetrahydrofuran. To this solution was added 1N LiOH (2 mL, 0.2 mmol) and stirred at ambient temperature for four days. The solvent was removed in vacuo and the resulting solid lyophilized to yield the title compound (0.075 g, 0.1 mmol).

MS ((+)ESI, m/z): 611 [M+H]$^+$ $^1$H NMR (DMSO-d$_6$, 400 MHz): d 1.13–1.22 (m, 2H), 1.80–1.83 (d, 2H), 2.56–5 2.67 (m, 2H), 2.80-2.87 (t, 2H), 4.15–4.16(m, 2H), 5.26(d, 1H), 6.46–6.58 (m, 3H), 6.62–6.73(m, 4H), 6.87–6.92(m, 3H), 7.09–7.13 (t, 1H), 9.05(broad s, 1H).

Anal. Calcd. for C$_{32}$H$_{38}$N$_4$O$_7$F+1.0 Li+4.5 H$_2$O: C 55.04 H 6.73 N 8.03 found: C 55.08 H 5.99 N 7.61

EXAMPLE 87

4-(4-{2-[(2S)-2-Hydroxy-3-(3-hydroxy-phenoxy)-propylamino]-ethyl}-phenylamino)-piperidine-1-carboxylic Acid 2-fluoro-4-hydroxy-benzylamide Step A. N-(4-{[tert-Butyl(diphenyl)silyl]oxy}benzyl)-4-[4-(2-{[(2S)-2-hydroxy-3-(3-{[isopropyl(diphenyl)silyl]oxy}phenoxy)propyl]amino}ethyl)anilino]-1-piperidinecarboxamide

[2-(4-{1-[4-(tert-Butyl-dipheny-silanyloxy)-2-fluoro-benzylcarbamoyl]-piperidin-4-ylamino}-phenyl)-ethyl]-amino formate (1.05 g, 1.59 mmol) was reacted with tert-butyl-(3-oxiranylmethoxy-phenoxy)-diphenyl-silane (0.642 g, 1.59 mmol) according to Procedure G to give the title compound (0.290 g, 0.3 mmol).

$^1$H NMR (DMSO-d6, 300 MHz): δ 1.90 (m, 2H), 2.90 (m, 2H), 3.90 n(m, 2H), 6.40 (s, 1H), 7.00 (m, 2H), 7.10 (m, 1H), 7.50 (m, 12H), 7.80 (m, 8H).

Step B. 4-(4-{2-[(2S)-2-Hydroxy-3-(3-hydroxy-1henoxy)-propylamino]-ethyl}-phenylamino)-piperidine-1-carboxylic acid 2-fluoro-4-hydroxy-benzylamide N-(4-{[tert-Butyl(diphenyl)silyl]oxy}benzyl)-4-[4-(2-{[(2S)-2-hydroxy-3-(3-{[isopropyl(diphenyl)silyl]oxy}phenoxy)propyl]amino}ethyl)anilino]-1-piperidinecarboxamide (0.284 g, 0.3 mmol) was reacted according to Procedure H to give the title compound (0.065 g, 0.11 mmol).

MS ((–)ESI, m/z): 551 [M–H]$^-$

Anal. Calcd. for: C$_{30}$H$_{37}$N$_4$O$_5$+1.0 H$_2$O: C 62.11 H 6.90 N 9.66 found: C 62.81 H 7.00 N 9.34

EXAMPLE 88

4-(4-{2-[(2S)-2-Hydroxy-3-(4-hydroxy-phenoxy)-propylamino]-ethyl}-phenylamino)-piperidine-1-carboxylic Acid [2-(3-fluoro-phenyl)-ethyl]-amide Step A. tert-Butyl 4-[(1-{[(3-fluorophenethyl)amino] carbonyl}-4-piperidinyl)amino]phenethylcarbamate The title compound (1.92 g, 4.0 mmol) was prepared from 3-fluorophenethylamine (0.546 g, 4.0 mmol) and {2-[4-(piperidin-4-ylamino)-phenyl]-ethyl}-carbamic acid tert-butyl ester (1.25 g, 3.92 mmol) according to Procedure C to provide the title compound (1.92 g, 4.0 mmol).

$^1$H NMR (DMSO-d6, 300 MHz): δ 1.40 (s, 9H), 1.80 (m, 2H), 2.70 (m, 2H), 3.90 (m, 2H), 6.50 (m, 2H), 7.00 (m, 5H), 7.30 (m, 2H).

Step B. 4-[4-(2-Aminoethyl)anilino]-N-(3-fluorophenethyl)-1-piperidinecarboxamide tert-Butyl 4-[(1-{[(3-fluorophenethyl)amino]carbonyl}-4-piperidinyl)amino]phenethylcarbamate (1.92 g, 4.0 mmol) was dissolved in anhydrous dichloromethane (18 mL) and trifluoroacetic acid (7 mL) added. The reaction was stirred at ambient temperature for 0.5 hours. The solvent was removed in vacuo. The resulting oil was dissolved in dichloromethane, washed with dilute aqueous sodium hydrogen carbonate, water and brine. The organic phase was dried over anhydrous sodium sulfate, filtered and the solvent removed in vacuo to yield the title compound (0.622 g, 1.62 mmol).

$^1$H NMR (DMSO-d6, 300 MHz): δ 2.00 (m, 2H), 2.60 (m, 2H), 3.80 (m, 2H), 6.50 (m, 2H), 7.00 (m, 5H), 7.400 (m, 2H).

Step C. 4-[4-(2-{[(2S)-3-(4-{[tert-Butyl(diphenyl)silyl]oxy}phenoxy)-2-hydroxy-propyl]amino}ethyl)anilino]-N-(3-fluorophenethyl)-1-piperidinecarboxamide 4-[4-(2-Aminoethyl)anilino]-N-(3-fluorophenethyl)-1-piperidinecarboxamide (0.622 g, 1.62 mmol) was reacted with tert-butyl-(4-oxiranylmethoxy-phenoxy)-diphenyl-silane 0.556 g, 1.40 mmol) according to Procedure G to give the title compound (eluant: 20:1 chloroform-methanol) (0.46 g, 0.580 mmol).

$^1$H NMR (DMSO-d6, 300 MHz): δ 2.00 (m, 2H), 2.70 (m, 2H), 3.80 (m, 2H), 6.40–6.80 (m, 6H), 7.00 (m, 5H), 7.20–7.40 (m, 8H), 7.70 (m, 4H).

Step D. N-(3-Fluorophenethyl)-4-[4-(2-{[(2S)-2-hydroxy-3-(4-hydroxy-phenoxy)propyl]amino}ethyl)anilino]-1-piperidinecarboxamide 4-[4-(2-{[(2S)-3-(4-{[tert-Butyl(diphenyl)silyl]oxy}phenoxy)-2-hydroxypropyl]amino}ethyl)anilino]-N-(3-fluorophenethyl)-1-piperidinecarboxamide (0.46 g, 0.580 mmol) was reacted according to Procedure H to give the title compound (eluant: 5:1 chloroform-methanol containing 1% ammonium hydroxide) (0.125 g, 0.220 mmol).

MS ((+)(ESI m/z): 551 [M+H]$^+$ $^1$H NMR (DMSO-d$_6$, 400 MHz): d 1.15–1.18(m, 2H), 1.78–1.83(m, 2H), 2.50–2.58(m, 3H), 2.64–2.73(m, 5H), 2.77–2.84(m, 2H), 3.19–3.25(m, 2H), 3.71–3.85(m, 5H), 4.87–4.89(broad s, 1H), 5.20–5.21 (d, 1H), 6.48–6.57(m, 2H), 6.62–6.64(t, 1H), 6.65–6.66(m, 2H), 6.70–6.74(m, 2H), 6.88–6.97(m, 2H), 7.30–7.34(m, 1H).

EXAMPLE 89

4-(4-{2-[(2S)-2-Hydroxy-3-(4-hydroxy-phenoxy)-propylamino]-ethyl}-phenylamino)-piperidine-1-carboxylic Acid (2-diethylcarbamoyl-ethyl)-amide Step A. N,N-Diethylsuccinamic acid Diethylamine (10.3 mL, 100 mmol) was reacted according to Procedure K to provide the title compound (2.95 g, 17 mmol).

$^1$H NMR (DMSO-d$_6$, 400 MHz): 1.10 (s, 3H), 1.20 (s, 3H), 2.50 (m, 5H), 3.40 (m, 4H), 12.00 (s, 1H).

Step B. (2-{4-[1-(2-Diethylcarbamoyl-ethylcarbamoyl)-piperidin-4-ylamino]-phenyl}-ethyl)-carbamic acid tert-butyl ester N,N-Diethylsuccinamic acid (0.542 g, 3.13 mmol) was reacted with {2-[4- (piperidin-4-ylamino)-phenyl]-ethyl}-carbamic acid tert-butyl ester according to Procedure D to give the title compound (0.90 g, 3.0 mmol).

MS ((+) APCI m/z): 490 (M+H)+

¹H NMR (DMSO-d₆, 400 MHz) d 0.97–1.00(t, 3H), 1.06(t, 3H), 1.09–1.20(m, 2H), 1.35(s, 9H), 1.78(m, 2H), 2.39–2.43(m, 2H), 2.80–2.83(t,2H), 2.99–3.03(m, 2H), 3.32–3.35(m, 7H), 3.80–3.83(m, 2H), 5.24–5.26(d, 1H), 6.48–6.50(m, 3H), 6.76–6.80(t, 1H), 6.84–6.87(m, 2H).

Anal. Calcd. for: $C_{26}H_{43}N_5O_4$+1.0 $H_2O$: C 62.57 H 8.82 N 14.04 found: C 62.31 H 8.86 N 13.94

Step C. 4-[4-(2-Aminoethyl)anilino]-N-[3-(dimethylamino)-3-oxopropyl]-1-pieridinecarboxamide formate (2-{4-[1-(2-Diethylcarbamoyl-ethylcarbamoyl)-piperidin-4-ylamino]-phenyl}-ethyl)-carbamic acid tert-butyl ester (0.90 g, 3.0 mmol) was reacted according to Procedure F to yield the title compound (0.87 g, 2.0 mmol).

Step D. 4-[4-(2-{[(2S)-3-(4-{[tert-Butyl(diphenyl)silyl]oxy}phenoxy)-2-hydroxypropyl]amino}ethyl)anilino]-N-[3-(dimethylamino)-3-oxopropyl]-piperidinecarboxamide 4-[4-(2-Aminoethyl)anilino]-N-[3-(dimethylamino)-3-oxopropyl]-1-piperidinecarboxamide formate (0.872 g, 2.0 mmol) was reacted with tert-butyl-(4-oxiranylmethoxyphenoxy)-diphenyl-silane (0.744 g, 1.84 mmol) according to procedure G (0.37 g, 0.5 mmol).

¹H NMR (DMSO-d6, 300 MHz): δ 1.00 (m, 15H), 1.80 (m, 2H), 2.80 (m, 2H), 3.80 (m, 2H), 6.50 (m, 3H), 6.70 (m, 4H), 7.00 (m, 2H), 7.50 (m, 6H), 7.70 (m, 4H).

Step E. 4-(4-{2-[(2S)-2-Hydroxy-3-(4-hydroxy-phenoxy)-propylamino]-ethyl}-phenylamino)-piperidine-1-carboxylic acid (2-diethylcarbamoyl-ethyl)-amide 4-[4-(2-{[(2S)-3-(4-{[tert-Butyl(diphenyl)silyl]oxy}phenoxy)-2-hydroxy-propyl]amino}ethyl)anilino]-N-[3-(dimethylamino)-3-oxopropyl]-1-piperidinecarboxamide (0.37 g, 0.5 mmol) was reacted according to Procedure H to yield the title compound (0.107 g, 0.2 mmol).

MS ((+)ESI, m/z): 556 [M+H]+

¹H NMR (DMSO-d₆, 400 MHz): d 0.97–1.00(t, 3H), 1.05–1.08(t, 3H), 1.12–1.22(m, 2H), 1.79–1.83(m, 2H), 2.30–2.84(m, 10H, overlaps DMSO), 3.13–3.34(m, 7H), 3.72–3.84(m, 5H), 5.21–5.24(d, 1H), 6.46–6.50(m, 2H), 6.62–6.66(m, 2H), 6.70–6.74(m, 2H), 6.87–6.89(d, 2H), 8.86(broad s, 1H).

Anal. Calcd. for: $C_{30}H_{45}N_5O_5$+1.0 $H_2O$: C 59.04 H 8.36 N 11.48 found: C 58.93 H 7.55 N 10.99

EXAMPLE 90

4-(4-{2-[(2S)-2-Hydroxy-3-(4-hydroxy-phenoxy)-propylamino]-ethyl}-phenylamino)-piperidine-1-carboxylic Acid (3-morpholin-4-yl-3-oxo-propyl)-amide Step A. Morpholinosuccinamic acid Morphoeine (15.0 g, 150 mmol) was reacted according to Procedure K to provide the title compound (1.17 g, 6.3 mmol).

¹H NMR (DMSO-d₆, 400 MHz): d 2,50 (m, 4H), 3.00–4.00 (m, 8H), 12.00 (bs, 1H).

Step B. (2-{4-[1-(4-Morpholincarbamoyl-ethylcarbamoyl)piperidin-4-ylamino]-phenyl}-ethyl)-carbamic acid tert-butyl ester Morpholinosuccinamic acid (0.587 g, 3.0 mmol) was reacted with {2-[4-(piperidin-4-ylamino)-phenyl]-ethyl}-carbamic acid tert-butyl ester according to Procedure D to yield the title compound (1.06 g, 2.0 mmol).

NMR (DMSO-d₆, 400 MHz): d 1.13–1.21(m, 2H), 1.35(s, 9H), 1.80–1.83(m, 2H), 2.42–2.51(m, 4H, obscured by DMSO), 2.78–2.84(m, 2H), 3.00–3.04(m, 2H), 3.17–3.26 (m, 2H), 3.30(m, 1H, obscured by water), 3.40–3.44(m, 4H), 3.51–3.56(m, 4H), 3.80–3.84(d, 2H), 5.23–5.25(d, 1H), 6.50–6.51 (d, 2H), 6.75–6.77(t, 1H), 6.85–6.87(d, 2H).

MS ((+)APCI, m/z): 504 [M+H]+

Anal. Calcd. for: $C_{26}H_{41}N_5O_5$+3.0 $H_2O$: C 55.94 H 8.43 N 12.55 found: C 56.27 H 7.70 N 12.40

Step C. 4-[4-(2-Aminoethyl)anilino]-N-[3-(4-morpholinyl)-3-oxopropyl]-1-piperidinecarboxamide formate (2-{4-[1-(4-Morpholin-4-yl-4-oxo-butyryl)-piperidin-4-ylamino]-phenyl}-ethyl)-carbamic acid tert-butyl ester (1.06 g, 2.0 mmol) was reacted according to Procedure F to yield the title compound (0.9 g, 2.0 mmol).

Step D. 4-[4-(2-{[(2S)-3-(4-{[tert-Butyl(diphenyl)silyl]oxy}phenoxy)-2-hydroxypropyl]amino}ethyl)anilino]-N-[3-(4-morpholinyl)-3-oxopropyl]-1-piperidinecarboxamide 4-[4-(2-aminoethyl)anilino]-N-[3-(4-morpholinyl)-3-oxopropyl]-1-piperidinecarboxamide formate (0.90 g, 2.0 mmol) was reacted with tert-butyl-(4-oxiranylmethoxyphenoxy)-diphenyl-silane according to Procedure G to yield the title compound (0.39 g, 0.5 mmol).

¹H NMR (DMSO-d₆, 400 MHz): d 1.80 (m, 2H), 2.80 (m, 2H), 3.80 (m, 2H), 6.50 (m, 2H), 6.70 (m, 4H), 6.90 (m, 2H), 7.50 (m, 6H), 7.70 (m, 4H).

Step E. 4-(4-{2-[(2S)-2-Hydroxy-3-(4-hydroxy-phenoxy)-propylamino]-ethyl}-phenylamino)-piperidine-1-carboxylic acid (3-morpholin-4-yl-3-oxo-propyl)-amide 4-[4-(2-{[(2S)-3-(4-{[tert-Butyl(diphenyl)silyl]oxy}phenoxy)-2-hydroxypropyl]amino}ethyl)anilino]-N-[3-(4-morpholinyl)-3-oxopropyl]-1-piperidinecarboxamide (0.39 g, 0.5 mmol) was reacted according to Procedure H to yield the title compound (0.103 g, 0.2 mmol).

¹H NMR (DMSO-d6, 400 MHz): d 1.13–1.22(m, 2H), 1.80–1.84(d, 2H), 2.42–2.84(m, 10H, overlaps DMSO), 3.13–3.56(m, 11H, 3.30 visible with D₂0), 3.72–3.84(m, 5H), 4.92–4.95(broad s, 1H), 5.22–5.24(d, 1H), 6.48–6.65 (m, 2H), 6.65–6.74(m, 4H), 6.88–6.89(d, 2H), 8.86(broad s, 1H).

MS ((+)ESI) m/z): 570 [M+H]+

Anal. Calcd. for $C_{30}H_{43}N_5O_6$+1.0 $H_2O$: C 61.26 H 7.66 N 11.91 found: C 61.82 H 7.93 N 11.88

EXAMPLE 91

1H-Indole-2-carboxylic Acid (4-{2-[(2S)-2-hydroxy-3-(4-hydroxy-phenoxy)-propylamino]-ethyl}-phenyl)-amide Step A. tert-Butyl 4-{[1-(1H-indol-2-ylcarbonyl)-4-piperidinyl]amino}phenethylcarbamate 2-[4-(Piperidin-4-ylamino)-phenyl]-ethyl}-carbamic acid tert-butyl ester (1.40 g, 4.38 mmol) was dissolved in anhydrous tetrahydrofuran (20 mL), 1H-indole-2-carboxylic acid (0.706 g, 4.38 mmol) and 1-[3-(dimethylamino)propyl]-3-ethylcarbodiimide hydrochloride (0.742 g, 3.87 mmol) added. The reaction was stirred at ambient temperature for 2 hours. The solvent was removed in vacuo. The residue was dissolved in ethyl acetate, washed with water and brine. The organic layer was dried over anhydrous magnesium sulfate, filtered and the solvent removed in vacuo. The residue was purified by flash chromatography on silica gel Merck-60 (eluant: 20:1 chloroform-methanol) to furnish the title compound (1.16 g, 2.5 mmol).

MS (EI, m/z): 462 [M]+

Step B. {4-[4-(2-Aminoethyl)anilino]-1-piperidinyl}(1H-indol-2-yl)methanone formate tert-Butyl 4-{[1-(1H-indol-2-ylcarbonyl)-4-piperidinyl]amino}phenethylcarbamate (0.50 g, 1.08 mmol) was reacted according to Procedure F to obtain the title compound (0.44 g, 1.08 mmol) which was used without further purification.

MS ((+)ESI, m/z): 363 [M+H]+

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}(1H-indol-2-yl)methanone {4-[4-(2-Aminoethyl)anilino]-1-piperidinyl}(1H-indol-2-yl)methanone formate (0.44 g, 1.08 mmol) was reacted with tert-butyl-(4-oxiranylmethoxy-phenoxy)-diphenyl-silane (0.28 g, 0.69 mmol) according to Procedure G to give the title compound (0.22 g, 0.287 mmol).

Step D. 1H-Indole-2-carboxylic acid (4-{2-[(2S)-2-hydroxy-3-(4-hydroxy-phenoxy)-propylamino]-ethyl}-phenyl)-amide {4-[4-(2-Aminoethyl)anilino]-1-piperidinyl}(1H-indol-2-yl)methanone (0.220 g, 0.287 mmol) was reacted according to Procedure H (eluant: 5:1 chloroform-methanol) to give the title compound (0.125 g, 0.236 mmol).

m.p 95–97° C.

MS ((+)ESI, m/z): 529 [M+H]$^+$

Anal. calcd. for $C_{31}H_{36}N_4O_4$+1.75 $H_2O$+0.15 $C_6H_{15}N$ C 66.59 H 7.31 N 10.10 found: C 66.34 H 7.19 N 9.96

EXAMPLE 92

4-[4-(4-{2-[(2S)-2-Hydroxy-3-(4-hydroxy-phenoxy)-propylamino]-ethyl}-phenylamino)-piperidine-1-carbonyl]-piperidine-1-carboxylic Acidoctylamide Step A. Ethyl 1-[(octylamino)carbonyl]-4-piperidinecarboxylate Ethyl 4-piperidinecarboxylate (13.94 g, 88.79 mmol) was dissolved with stirring in anhydrous tetrahydrofuran (90 mL). To the solution was added an anhydrous tetrahydrofuran (15 mL) solution of octyl isocyanate (13.77 g, 88.79 mmol) at ambient temperature. The reaction was stirred for 2 hours. The solvent was removed in vacuo and the residue stirred overnight in hexane to yield the title compound as a solid (23.2 g, 74.25 mmol).

Step B. 1-[(Octylamino)carbonyl]-4-piperidinecarboxylic acid

Ethyl 1-[(octylamino)carbonyl]-4-piperidinecarboxylate (10.1 g, 32.33 mmol) was heated at reflux in a mixture of methanol (4 mL) and 1N sodium hydroxide solution (42 mL) for 1.5 hours. The solvents were partially removed in vacuo and the residue cooled and treated with 1N hydrochloric acid solution (50 mL). The aqueous phase was extracted with diethyl ether washed with brine, dried over anhydrous magnesium sulfate, filtered and the solvent removed in vacuo. The resulting oil crystallized on standing to give the title compound (8.04 g, 28.27 mmol).

Step C. tert-Butyl 4-{[1-({1-[(octylamino)carbonyl]-4-piperidinyl}carbonyl)-4-piperidinyl]amino}phenethylcarbamate 2-[4-(Piperidin-4-ylamino)-phenyl]-ethyl}-carbamic acid tert-butyl ester (0.635 g, 1.99 mmol) was dissolved in anhydrous tetrahydrofuran (20 mL), 1-[(octylamino)carbonyl]-4-piperidinecarboxylic acid (0.565 g, 1.99 mmol) and 1-[3-(dimethylamino)propyl]-3-ethylcarbodiimide hydrochloride (0.382 g, 0.199 mmol) added. The reaction was stirred at ambient temperature overnight. The solvent was removed in vacuo. The residue was dissolved in ethyl acetate, washed with water and brine. The organic layer was dried over anhydrous magnesium sulfate, filtered and the solvent removed in vacuo. The residue was purified by flash chromatography on silica gel Merck-60 (eluant: 20:1 chloroform-methanol with 1% triethylamine added) to furnish the title compound (0.49 g, 0.838 mmol).

Step D. 4-({4-[4-(2-Aminoethyl)anilino]-1-piperidinyl}carbonyl)-N-octyl-1-piperidinecarboxamide formate tert-Butyl 4-{[1-({1-[(octylamino)carbonyl]-4-piperidinyl}carbonyl)-4-piperidinyl]amino}phenethylcarbamate (0.49 g, 0.838 mmol) was reacted according to Procedure F to obtain the title compound (0.838 mmol) which was used without further purification.

Step E. 4-({4-[4-(2-{[(2S)-3-(4-{[tert-Butyl(diphenyl)silyl]oxy}phenoxy)-2-hydroxypropyl]amino}ethyl)anilino]-1-piperidinyl}carbonyl)-N-octyl-1-piperidinecarboxamide 4-({4-[4-(2-Aminoethyl)anilino]-1-piperidinyl}carbonyl)-N-octyl-1-piperidinecarboxamide formate(0.41 g, 0.771 mmol) was reacted with tert-butyl-(4-oxiranylmethoxy-phenoxy)-diphenyl-silane (0.27 g, 0.668 mmol) according to Procedure G to give the title compound (0.16 g, 0.180 mmol).

Step F. 4-[4-(4-{2-[(2S)-2-Hydroxy-3-(4-hydroxy-phenoxy)-propylamino]-ethyl}-phenylamino)-piperidine-1-carbonyl]-piperidine-1-carboxylic acidoctylamide 4-({4-[4-(2-{[(2S)-3-(4-{[tert-Butyl(diphenyl)silyl]oxy}phenoxy)-2-hydroxypropyl]amino}ethyl)anilino]-1-piperidinyl}carbonyl)-N-octyl-1-piperidinecarboxamide (0.160 g, 0.180 mmol) was reacted according to Procedure H (eluant: 5:1 chloroform-methanol) to give the title compound (0.02 g, 0.03 mmol).

m.p 88–91° C.

MS ((+)ESI, m/z): 652 [M+H]$^+$

Anal. calcd. for $C_{37}H_{57}N_5O_5$.HCl: C 64.56 H 8.49 N 10.17 found: C 64.75 H 8.56 N 9.98

EXAMPLE 93

1-Hexyl-3-{4-[4-(4-{2-[(2S)-2-hydroxy-3-(4-hydroxy-phenoxy)-propylamino]-ethyl}-phenylamino)-piperidine-1-carbonyl]-phenyl}-urea Step A. tert-Butyl 4-{[1-(4-{[(hexylamino)carbonyl]amino}benzoyl)-4-Piperidinyl]amino}phenethylcarbamate 2-[4-(Piperidin-4-ylamino)-phenyl]-ethyl}-carbamic acid tert-butyl ester (1.00 g, 3.13 mmol) was dissolved in anhydrous N,N-dimethylformamide, 4-{[(hexylamino)carbonyl]amino}benzoic acid (0.868 g, 3.28 mmol) and benzotriazol-1-yloxy-tris(dimethylamino)phosphonium hexafluorophophate (1.50 g, 3.45 mmol) added together with anhydrous triethylamine (0.75 mL). The reaction was stirred at ambient temperature for 16 hours. The solvent was removed in vacuo. The residue was dissolved in methylene chloride, washed with 1N sodium hydroxide and brine. The organic layer was dried over anhydrous magnesium sulfate, filtered and the solvent removed in vacuo to yield the title compound (0.957 g, 1.70 mmol).

Step B. N-[4-({4-[4-(2-Aminoethyl)anilino]-1-piperidinyl}carbonyl)phenyl]-N'-hexylurea tert-Butyl 4-{[1-(4-{[(hexylamino)carbonyl]amino}benzoyl)-4-piperidinyl]-amino}phenethylcarbamate (0.478 g, 0.846 mmol) was reacted according to Procedure F to obtain the title compound (0.846 mmol) which was used without further purification.

Step C. N-[4-({4-[4-(2-{[(2S)-3-(4-{[tert-Butyl(diphenyl)silyl]oxy}phenoxy)-2-hydroxypropyl]amino}ethyl)anilino]-1-piperidinyl}carbonyl)phenyl]-N'-hexylurea N-[4-({4-[4-(2-Aminoethyl)anilino]-1-piperidinyl}carbonyl)phenyl]-N'-hexylurea (0.394 g, 0.846 mmol) was reacted with tert-butyl-(4-oxiranylmethoxy-phenoxy)-diphenyl-silane (0.308 g, 0.761 mmol) according to Procedure G to give the title compound (0.232 g, 0.26 mmol).

Step D. 1-Hexyl-3-{4-[4-(4-{2-[(2S)-2-hydroxy-3-(4-hydroxy-phenoxy)-propylamino]-ethyl}-phenylamino)-piperidine-1-carbonyl]-phenyl}-urea N-[4-({4-[4-(2-{[(2S)-3-(4-{[tert-Butyl(diphenyl)silyl]oxy}phenoxy)-2-hydroxypropyl]aminoethyl)anilino]-1-piperidinyl}carbonyl)phenyl]-N'-hexylurea (0.160 g, 0.180 mmol) was reacted according to Procedure H (eluant: 5:1 chloroform-methanol) to give the title compound (0.06 g, 0.09 mmol).

m.p 108–111° C.

MS ((+)ESI, m/z): 632 [M+H]$^+$

Anal. calcd. for $C_{36}H_{49}N_5O_5$·HC+0.50 $H_2O$: C 63.84 H 7.59 N 10.34 found: C 63.83 H 7.53 N 10.55

EXAMPLE 94

[4-(4-{2-[2-Hydroxy-3-(4-hydroxy-phenoxy)-propylamino]-ethyl}-phenylamino)-piperidin-1-yl]-(5-methoxy-1H-indol-2-yl)-methanone Step A. tert-Butyl 4-({1-[(5-methoxy-1H-indol-2-yl)carbonyl]-4-piperidinyl}-amino)phenethylcarbamate 2-[4-(Piperidin-4-ylamino)-phenyl]-ethyl}-carbamic acid tert-butyl ester (0.754 g, 2.36 mmol) was dissolved in anhydrous tetrahydrofuran (20 mL), 5-methoxy-1H-indole-2-carboxylic acid (0.452 g, 2.36 mmol) and 1-[3-(dimethylamino)propyl]-3-ethylcarbodiimide hydrochloride (0.475 g, 2.47 mmol) added. The reaction was stirred at ambient temperature overnight. The solvent was removed in vacuo. The residue was dissolved in chloroform, washed with water and brine. The organic layer was dried over anhydrous magnesium sulfate, filtered and the solvent removed in vacuo. The residue was purified by flash chromatography on silica gel Merck-60 (eluant: 50:1 chloroform-methanol) to furnish the title compound (0.695 g, 1.41 mmol).

Step B. {4-[4-(2-Aminoethyl)anilino]-1-piperidinyl}(5-methoxy-1H-indol-2-yl)methanone formate tert-Butyl 4-({1-[(5-methoxy-1H-indol-2-yl)carbonyl]-4-piperidinyl}amino)phenethylcarbamate (0.695 g, 1.502 mmol) was reacted according to Procedure F to obtain the title compound (1.502 mmol).

MS ((+)ESI, m/z): 393 [M+H]$^+$

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}(5-methoxy-1H-indol-2-yl)methanone 4-[4-(2-Aminoethyl)anilino]-1-piperidinyl}(5-methoxy-1H-indol-2-yl)methanone formate (0.30 g, 0.684 mmol) was reacted with tert-butyl-(4-oxiranylmethoxy-phenoxy)-diphenyl-silane (0.20 g, 0.495 mmol) according to Procedure G to give the title compound (0.128 g, 0.161 mmol).

Step D. [4-(4-{2-[2-Hydroxy-3-(4-hydroxy-phenoxy)-propylamino]-ethyl}-phenylamino)-piperidin-1-yl]-(5-methoxy-1H-indol-2-yl)-methanone {4-[4-(2-{[(2S)-3-(4-{[tert-Butyl(diphenyl)silyl]oxy}phenoxy)-2-hydroxypropyl]amino}ethyl)anilino]-1-piperidinyl}(5-methoxy-1H-indol-2-yl)methanone (0.128 g, 0.161 mmol) was reacted according to Procedure H (eluant: 5:1 chloroform-methanol) to give the title compound (0.026 g, 0.046 mmol).

m.p 101–103° C.

MS ((+)ESI, m/z): 559 [M+H]$^+$

Anal. calcd. for $C_{32}H_{38}N_4O_5$·HCl: C 64.58 H 6.60 N 9.41 found: C 64.46 H 6.86 N 9.06

EXAMPLE 95

[4-(4-{2-[(2S)-2-Hydroxy-3-(4-hydroxy-phenoxy)-propylamino]-ethyl}-phenylamino)-piperidin-1-yl]-(7-nitro-1H-indol-2-yl)-methanone Step A. tert-Butyl 4-({1-[(7-nitro-1H-indol-2-yl)carbonyl]-4-piperidinyl}amino)phenethylcarbamate 2-[4-(Piperidin-4-ylamino)-phenyl]-ethyl}-carbamic acid tert-butyl ester (1.79 g, 5.60 mmol) was dissolved in anhydrous tetrahydrofuran (60 mL), 7-nitro-1H-indole-2-carboxylic acid (1.16 g, 5.63 mmol) and 1-[3-(dimethylamino)propyl]-3-ethylcarbodiimide hydrochloride (1.2 g, 6.26 mmol) added. Anhydrous triethylamine (0.86 mL) was added and the reaction stirred at ambient temperature for 4 days. The solvent was removed in vacuo. The residue was dissolved in chloroform, washed with water and brine. The organic layer was dried over anhydrous magnesium sulfate, filtered and the solvent removed in vacuo. The residue was purified by flash chromatography on silica gel Merck-60 (eluant: 1:1 hexane-ethyl acetate) to furnish an orange solid which crystallized from acetone-hexane to yield the title compound (1.0 g, 1.97 mmol).

MS ((+)ESI, m/z): 508 [M+H]$^+$

Step B. {4-[4-(2-Aminoethyl)anilino]-1-piperidinyl}(7-nitro-1H-indol-2-yl)methanone tert-Butyl 4-({1-[(7-nitro-1H-indol-2-yl)carbonyl]-4-piperidinyl}amino)phenethylcarbamate (0.275 g, 0.542 mmol) was reacted according to Procedure F to obtain the formate salt. The solid was partitioned between chloroform and 1N sodium hydroxide. The organic phase was separated, washed with brine and dried over anhydrous magnesium sulfate. The solution was filtered and the solvent removed in vacuo to yield the title compound (0.18 g, 0.442 mmol).

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}(7-nitro-1H-indol-2-yl)methanone 4-[4-(2-Aminoethyl)anilino]-1-piperidinyl}(7-nitro-1H-indol-2-yl)methanone formate (0.18 g, 0.442 mmol) was reacted with tert-butyl-(4-oxiranylmethoxy-phenoxy)-diphenyl-silane (0.18 g, 0.445 mmol) according to Procedure G to give the title compound (0.117 g, 0.144 mmol).

Step D. [4-(4-{2-[(2S)-2-Hydroxy-3-(4-hydroxy-phenoxy)-propylamino]-ethyl}-phenylamino)-piperidin-1-yl]-(7-nitro-1H-indol-2-yl)-methanone {4-[4-(2-{[(2S)-3-(4-{[tert-Butyl(diphenyl)silyl]oxy}phenoxy)-2-hydroxypropyl]amino}ethyl)anilino]-1-piperidinyl}(7-nitro-1H-indol-2-yl)methanone (0.117 g, 0.144 mmol) was reacted according to Procedure H (eluant: 5:1 chloroform-methanol) to give the title compound (0.058, 0.101 mmol).

m.p 100–102° C.

MS ((+)ESI, m/z): 574 [M+H]$^+$

Anal. calcd. for $C_{31}H_{35}N_5O_6$+1.90 $H_2O$: C 61.25 H 6.43 N 11.52 found: C 61.58 H 6.15 N 11.07

EXAMPLE 96

(5-Bromo-1H-indol-2-yl)-[4-(4-{2-[(2S)-2-hydroxy-3-(4-hydroxy-phenoxy)-propylamino]-ethyl}-phenylamino)-piperidin-1-yl]-methanone Step A. tert-Butyl 4-({1-[(5-bromo-1H-indol-2-yl)carbonyl]-4-piperidinyl}-amino)phenethylcarbamate 2-[4-(Piperidin-4-ylamino)-phenyl]-ethyl}-carbamic acid tert-butyl ester (1.34 g, 4.20 mmol) was dissolved in anhydrous N,N-dimethylformamide, 5-bromo-1H-indole-2-carboxylic acid (1.01 g, 4.20 mmol) and benzotriazol-1-yloxy-tris(dimethylamino) phosphonium hexafluorophophate (2.02 g, 4.57 mmol) added together with anhydrous triethylamine (1.0 mL). The reaction was stirred at ambient temperature for 2 days. The solvent was removed in vacuo. The residue was dissolved in ethyl acetate, washed with 1 N sodium hydroxide and brine. The organic layer was dried over anhydrous magnesium sulfate, filtered and the solvent removed in vacuo to yield the title compound (2.73 g, 5.04 mmol).

MS ((+)APCI, m/z): 541/543 [M+H]$^+$

Step B. {4-[4-(2-Aminoethyl)anilino]-1-piperidinyl}(5-bromo-1H-indol-2-yl)methanone tert-Butyl 4-({1-[(5-bromo-1H-indol-2-yl)carbonyl]-4-piperidinyl}amino)phenethylcarbamate (0.36 g, 0.665 mmol) was reacted according to Procedure F to obtain the formate salt. The solid was partitioned between chloroform and 1N sodium hydroxide. The organic phase was separated, washed with brine and dried over anhydrous magnesium sulfate. The solution was filtered and the solvent removed in vacuo to yield the title compound (0.222 g, 0.503 mmol).

Step C. (5-Bromo-1H-indol-2-yl){4-[4-(2-{[(2S)-3-(4-{[tert-butyl (diphenyl)silyl]oxy}phenoxy)-2-hydroxypropyl]amino}ethyl)anilino]-1-piperidinyl}methanone {4-[4-(2-Aminoethyl)anilino]-1-piperidinyl}(5-bromo-1H-indol-2-yl)methanone (0.160 g, 0.363 mmol) was reacted with tert-butyl-(4-oxiranylmethoxy-phenoxy)-diphenyl-silane (0.15 g, 0.37 mmol) according to Procedure G to give the title compound (0.119 g, 0.141 mmol).

Step D. (5-Bromo-1H-indol-2-yl)-[4-(4-{2-[(2S)-2-hydroxy-3-(4-hydroxy-phenoxy)-propylamino]-ethyl}-phenylamino)-piperidin-1-yl]-methanone (5-Bromo-1H-indol-2-yl){4-[4-(2-{[(2S)-3-(4-{[tert-butyl(diphenyl)silyl]oxy}phenoxy)-2-hydroxypropyl]amino}ethyl)anilino]-1-piperidinyl}methanone (0.119 g, 0.141 mmol) was reacted according to Procedure H (eluant: 5:1 chloroform-methanol) to give the title compound (0.031 g, 0.05 mmol).

m.p 114–116° C.

MS ((+)ESI, m/z): 607 [M+H]$^+$

Anal. calcd. for $C_{31}H_{35}BrN_4O_4 \cdot HCl + 0.8 H_2O$: C 56.55 H 5.76 N 8.51 found: C 56.73 H 5.7 N 8.15

EXAMPLE 97

[4-(4-{2-[(2S)-2-Hydroxy-3-(4-hydroxy-phenoxy)-propylamino]-ethyl}-phenylamino)-piperidin-1-yl]-(3-methoxy-benzo[b]thiophen-2-yl)-methanone Step A. tert-Butyl 4-({1-[(3-methoxy-1-benzothiophen-2-yl)carbonyl]-4-piperidinyl}amino)phenethylcarbamate 2-[4-(Piperidin-4-ylamino)-phenyl]-ethyl}-carbamic acid tert-butyl ester (1.43 g, 4.48 mmol) was dissolved in anhydrous tetrahydrofuran (20 mL), 3-methoxy-1-benzothiophene-2-carboxylic acid (0.933 g, 4.48 mmol) and 1-[3-(dimethylamino)propyl]-3-ethylcarbodiimide hydrochloride (0.90 g, 4.7 mmol) added. Anhydrous triethylamine (0.9 mL) was added and the reaction stirred at ambient temperature for 2.5 days. The solvent was removed in vacuo. The residue was dissolved in chloroform, washed with water and brine. The organic layer was dried over anhydrous magnesium sulfate, filtered and the solvent removed in vacuo. The residue was purified by flash chromatography on silica gel Merck-60 (eluant: 50:1 chloroform-methanol) to furnish the title compound (0.482 g, 0.946 mmol).

Step B. {4-[4-(2-Aminoethyl)anilino]-1-piperidinyl}(3-methoxy-1-benzothiophen-2-yl)methanone tert-Butyl 4-({1-[(3-methoxy-1-benzothiophen-2-yl)carbonyl]-4-piperidinyl}amino)-phenethylcarbamate (0.482 g, 0.946 mmol) was reacted according to Procedure F to obtain the formate salt. The solid was partitioned between chloroform and 1N sodium hydroxide. The organic phase was separated, washed with brine and dried over anhydrous magnesium sulfate. The solution was filtered and the solvent removed in vacuo to yield the title compound (0.365 g, 0.891 mmol).

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}(3-methoxy-1-benzothiophen-2-yl)methanone {4-[4-(2-Aminoethyl)anilino]-1-piperidinyl}(3-methoxy-1-benzothiophen-2-yl)methanone (0.189 g, 0.461 mmol) was reacted with tert-butyl-(4-oxiranylmethoxy-phenoxy)-diphenyl-silane (0.187 g, 0.461 mmol) according to Procedure G to give the title compound (0.119 g, 0.141 mmol).

Step D. [4-(4-{2-[(2S)-2-Hydroxy-3-(4-hdroxy-phenoxy)-propylamino]-ethyl}-phenylamino)-piperidin-1-yl]-(3-methoxy-benzo[b]thiophen-2-yl)-methanone {4-[4-(2-{[(2S)-3-(4-{[tert-Butyl(diphenyl)silyl]oxy}phenoxy)-2-hydroxypropyl]amino}ethyl)anilino]-1-piperidinyl}(3-methoxy-1-benzothiophen-2-yl)methanone (0.148 g, 0.182 mmol) was reacted according to Procedure H (eluant: 5:1 chloroform-methanol) to give the title compound (0.087 g, 0.151 mmol).

m.p 84–86° C.

MS ((+)ESI, m/z): 576 [M+H]$^+$

Anal. calcd. for $C_{32}H_{37}N_3O_5S \cdot HCl + 0.25 H_2O$: C 62.33 H 6.29 N 6.81 found: C 62.33 H 6.49 N 6.53

EXAMPLE 98

N-{3-[(2S)-2-Hydroxy-3-(2-{4-[1-(3-methoxy-benzo[b]thiophene-2-carbonyl)-piperidin-4-ylamino]-phenyl}-ethylamino)-propoxy]-phenyl}-acetamide {4-[4-(2-Aminoethyl)anilino]-1-piperidinyl}(3-methoxy-1-benzothiophen-2-yl)methanone (0.170 g, 0.415 mmol) was reacted with N-{3-[(2S)oxiranylmethoxy]phenyl}acetamide (0.086 g, 0.415 mmol) according to Procedure G to give the title compound (0.06 g, 0.097 mmol).

m.p 96–98° C.

MS ((+)ESI, m/z): 617 [M+H]$^+$

Anal. calcd. for $C_{34}H_{40}N_4O_5S \cdot HCl + 1.0 H_2O + 0.1 CHCl_3$: C 59.95 H 6.36 N 8.20 found: C 59.72 H 6.01 N 7.77

EXAMPLE 99

[4-(4-{2-[(2S)-2-Hydroxy-3-(4-hydroxy-phenoxy)-propylamino]-ethyl}-phenylamino)-piperidin-1-yl]-(1H-indol-3-yl)-methanone Step A. tert-Butyl 4-{[1-(1H-indol-3-ylcarbonyl)-4-piperidinyl]amino}phenethylcarbamate 2-[4-(Piperidin-4-ylamino)-phenyl]-ethyl}-carbamic acid tert-butyl ester (0.503 g, 1.58 mmol) was dissolved in anhydrous N,N-dimethylformamide, 1H-indole-3-carboxylic acid (0.254 g, 1.58 mmol) and benzotriazol-1-yloxy-tris(dimethylamino)phosphonium hexafluorophophate (0.766 g, 1.73 mmol) added together with anhydrous triethylamine (0.384 mL). The reaction was stirred at ambient temperature for 18 hours. The solvent was removed in vacuo. The residue was dissolved in ethyl acetate, washed with 1N sodium hydroxide and brine. The organic layer was dried over anhydrous magnesium sulfate, filtered and the solvent removed in vacuo. The residue was purified by flash chromatography on silica gel Merck-60 (eluant: 20:1 chloroform-methanol) to furnish the title compound (0.45 g, 0.973 mmol).

Step B. {4-[4-(2-Aminoethyl)anilino]-1-pi;peridinyl}(1H-indol-3-yl)methanone tert-Butyl 4-{[1-(1H-indol-3-ylcarbonyl)-4-piperidinyl]amino}phenethylcarbamate (0.450 g, 0.973 mmol) was reacted according to Procedure F to obtain the formate salt. The solid was partitioned between chloroform and 1N sodium hydroxide. The organic phase was separated, washed with brine and dried over anhydrous magnesium sulfate. The solution was filtered and the solvent removed in vacuo to yield the title compound which was used directly in Step C.

Step C. {4-[4-(2-{[(2S)-3-(4-{[tert-Butyl(diphenyl)silyl]oxy}phenoxy)-2-hydroxypropyl]amino}ethyl)anilino]-1-piperidinyl)(1H-indol-3-yl)methanone {4-[4-(2-Aminoethyl)anilino]-1-piperidinyl}(1H-indol-3-yl)methanone (Step C) was reacted with tert-butyl-(4-oxiranylmethoxy-phenoxy)-diphenyl-silane (0.20 g, 0.495 mmol) according to Procedure G to give the title compound (0.03 g, 0.057 mmol).

Step D. [4-(4-{2-[(2S)-2-Hydroxy-3-(4-hydroxy-phenoxy)-propylamino]-ethyl}- phenylamino)-piperidin-1-yl]-(1H-indol-3-yl)-methanone {4-[4-(2-{[(2S)-3-(4-{[tert-Butyl(diphenyl)silyl]oxy}phenoxy)-2-hydroxypropyl]amino}ethyl)anilino]-1-piperidinyl}(1H-indol-3-yl)methanone (0.148 g, 0.182 mmol) was reacted according to Procedure H (eluant: 5:1 chloroform-methanol) to give the title compound (0.087 g, 0.151 mmol).

m.p 90–92° C.

MS ((+)ESI, m/z): 529 [M+H]$^+$

Anal. calcd. for $C_{31}H_{36}N_4O_4$+1.25 $H_2O$: C 67.55 H 7.04 N 10.16 found: C 66.67 N 6.92 N 9.73

EXAMPLE 100

[4-(4-{2-[(2S)-2-Hydroxy-3-(4-hydroxy-phenoxy)-propylamino]-ethyl}-phenylamino)-piperidin-1-yl]-(3-methyl-thiophen-2-yl)-methanone Step A. tert-Butyl 4-({1-[(3-methyl-2-thienyl)carbonyl]-4-piperidinyl}amino)phenethylcarbamate 2-[4-(Piperidin-4-ylamino)-phenyl]-ethyl}-carbamic acid tert-butyl ester (1.08 g, 3.38 mmol) was dissolved in anhydrous N,N-dimethylformamide, 3-methyl-2-thiophenecarboxylic acid (0.481, 3.38 mmol) and benzotriazol-1-yloxy-tris(dimethyl-amino)phosphonium hexafluorophophate (0.766 g, 1.73 mmol) added together with anhydrous triethylamine (0.384 mL). The reaction was stirred at ambient temperature for 18 hours. The solvent was removed in vacuo. The residue was dissolved in ethyl acetate, washed with 1 N sodium hydroxide and brine. The organic layer was dried over anhydrous magnesium sulfate, filtered and the solvent removed in vacuo to furnish the crude title compound (1.417 g, 3.17 mmol).

Step B. {4-[4-(2-aminoethyl)anilino]-1-piperidinyl}(3-methyl-2-thienyl)methanone tert-Butyl 4-({1-[(3-methyl-2-thienyl)carbonyl]-4-piperidinyl}amino)phenethylcarbamate (0.75 g, 0.1.68 mmol) was reacted according to Procedure F to obtain the formate salt. The solid was partitioned between chloroform and 1N sodium hydroxide. The organic phase was separated, washed with brine and dried over anhydrous magnesium sulfate. The solution was filtered and the solvent removed in vacuo to yield the title compound which was used without further purification.

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}(3-methyl-2-thienyl)methanone {4-[4-(2-Aminoethyl)anilino]-1-piperidinyl}(3-methyl-2-thienyl)methanone (0.174, 0.507 mmol) was reacted with tert-butyl-(4-oxiranylmethoxy-phenoxy)-diphenyl-silane (0.206 g, 0.51 mmol) according to Procedure G to give the title compound (0.083 g, 0.111 mmol).

Step D. [4-(4-{2-[(2S)-2-Hydroxy-3-(4-hydron-phenoxy)-propylamino]-ethyl}-phenylamino)-piperidin-1-yl]-(3-methyl-thiophen-2-yl)-methanone {4-[4-(2-{[(2S)-3-(4-{[tert-Butyl(diphenyl)silyl]oxy}phenoxy)-2-hydroxypropyl]amino}ethyl)anilino]-1-piperidinyl}(3-methyl-2-thienyl)methanone (0.083 g, 0.111 mmol) was reacted according to Procedure H (eluant: 5:1 chloroform-methanol) to give the title compound (0.048 g, 0.094 mmol).

m.p 88–90° C.

MS ((+)ESI, m/z): 510 [M+H]$^+$

Anal. calcd. for $C_{28}H_{35}N_3O_4S$.HCl+0.25 $H_2O$: C 61.08 H 6.68 N 7.63 found: C 61.32 H 6.66 N 7.23

EXAMPLE 101

4-[(2S)-2-Hydroxy-3-(2-{4-[1-(3-methyl-thiophene-2-carbonyl)-piperidin-4-ylamino]-phenyl}-ethylamino)-propoxy]-1,3-dihydro-benzoimidazol-2-one {4-[4-(2-Aminoethyl)anilino]-1-piperidinyl}(3-methyl-2-thienyl)methanone (0.174, 0.507 mmol) was reacted with 4-[(2S)oxiranylmethoxy]-1,3-dihydro-2H-benzimidazol-2-one (0.108 g, 524 mmol) according to Procedure G to give the title compound (0.04 g, 0.073 mmol).

m.p 128–130° C.

MS ((+)ESI, m/z): 550 [M+H]$^+$

Anal. calcd. for $C_{29}H_{35}N_5O_4S$.HCl+0.50 $C_4H_{10}O$+0.25 $H_2O$: C 59.32 H 6.66 N 11.16 found: C 59.01 H 6.53 N 10.75

EXAMPLE 102

[4-(4-{2-[(2S)-2-Hydroxy-3-(4-hydroxy-phenoxy)-propylamino]-ethyl}-phenylamino)-piperidin-1-yl]-(1H-indazol-3-yl)-methanone Step A. tert-Butyl 4-{[1-(1H-indazol-3-ylcarbonyl)-4-piperidinyl]amino}phenethylcarbamate 2-[4-(Piperidin-4-ylamino)-phenyl]-ethyl}-carbamic acid tert-butyl ester (1.97 g, 6.17 mmol) was dissolved in anhydrous N,N-dimethylformamide, 1H-indazole-3-carboxylic acid (1.0 g, 6.17 mmol) and benzotriazol-1-yloxy-tris (dimethylamino)phosphonium hexafluorophophate (3.0 g, 6.79 mmol) added together with anhydrous triethylamine (1.5 mL). The reaction was stirred at ambient temperature for 2 days. The solvent was removed in vacuo. (1.417 g, 3.17 mmol). The residue was purified by flash chromatography on silica gel Merck-60 (eluant: 50:1 chloroform-methanol then 1:1 ethyl acetate-hexane) to furnish the title compound (0.90 g, 1.94 mmol).

MS ((+)ESI, m/z): 464 [M+H]$^+$

Step B. {4-[4-(2-Aminoethyl)anilino]-1-piperidinyl}(1H-indazol-3-yl)methanone tert-Butyl 4-([1-(1H-indazol-3-ylcarbonyl)-4-piperidinyl]amino}phenethylcarbamate (0.90 g, 1.94 mmol) was reacted according to Procedure F to obtain the formate salt. The solid was partitioned between chloroform and saturated sodium hydrogencarbonate solution. The organic phase was separated, washed with brine and dried over anhydrous magnesium sulfate. The solution was filtered and the solvent removed in vacuo to yield the title compound which was used without further purification.

Step C. {4-[4-(2-{[(2S)-3-(4-{[tert-Butyl(diphenyl)silyl]oxy}phenoxy)-2-hydroxypropyl]amino}ethyl)anilino]-1-piperidinyl}(1H-indazol-3-yl)methanone {4-[4-(2-Aminoethyl)anilino]-1-piperidinyl}(1H-indazol-3-yl)methanone (0.20 g, 0.55 mmol) was reacted with tert-butyl-(4-oxiranylmethoxy-phenoxy)-diphenyl-silane (0.222 g, 0.55 mmol) according to Procedure G to give the title compound (0.093 g, 0.176 mmol).

Step D. [4-(4-{2-[(2S)-2-Hydroxy-3-(4-hydroxy-phenoxy)-propylamino]-ethyl}-phenylamino)-piperidin-1-yl]-(1H-indazol-3-yl)-methanone {4-[4-(2-{[(2S)-3-(4-{[tert-Butyl(diphenyl)silyl]oxy}phenoxy)-2-hydroxypropyl]amino}ethyl)anilino]-1-piperidinyl}(1H-indazol-3-yl)methanone (0.093 g, 0.176 mmol) was reacted according to Procedure H (eluant: 5:1 chloroform-methanol) to give the title compound (0.059 g, 0.111 mmol).

m.p 111–113° C.
MS ((+)ESI, m/z): 530 [M+H]$^+$
Anal. calcd. for $C_{30}H_{35}N_5O_4 \cdot HCl + 0.25$ CHCl$_3$: C 60.97 H 6.13 N 11.75 found: C 60.92 H 5.94 N 11.41

EXAMPLE 103

1-[4-(4-{2-[(2S)-2-Hydroxy-3-(4-hydroxy-phenoxy)-propylamino]-ethyl}-phenylamino)-piperidin-1-yl]-hexan-1-one Step A. tert-Butyl 4-[(1-hexanoyl-4-piperidinyl)amino]phenethylcarbamate 2-[4-(Piperidin-4-ylamino)-phenyl]-ethyl}-carbamic acid tert-butyl ester (1.036 g, 3.24 mmol) was dissolved in anhydrous dichloromethane. To this solution was added hexanoyl chloride (0.46 g, 3.42 mmol) and anhydrous N,N-diisopropylethylamine (0.721 mL) at 0° C. The reaction was stirred at 0° C. for 30 minutes and then at ambient temperature for 1 hour. Dichloromethane was added and the organic phase washed with waster and brine, dried and filtered. The solution was evaporated to dryness in vacuo and the residue purified by flash chromatography on silica gel Merck-60 (eluant: 1:1 ethyl acetate-hexane) to yield the title compound (1.0 g, 2.39 mmol).

MS ((+)ESI, m/z): 418 [M+H]$^+$

Step B. 1-[4-[4-(2-Aminoethyl)anilino]-1-piperidinyl]-1-hexanone formate tert-Butyl 4-[(1-hexanoyl-4-piperidinyl)amino]phenethylcarbamate (1.0 g, 2.39 mmol) was reacted according to Procedure F to obtain the title compound (2.39 mmol) which was used without further purification.

Step C. 1-{4-[4-(2-{[(2S)-3-(4-{[tert-Butyl(diphenyl)silyl]oxy}phenoxy)-2-hydroxypropyl]amino}ethyl)anilino]-1-piperidinyl}-1-hexanone 1-{4-[4-(2-Aminoethyl)anilino]-1-piperidinyl}-1-hexanone formate (0.234 g, 0.645 mmol) was reacted with tert-butyl-(4-oxiranylmethoxy-phenoxy)-diphenyl-silane (0.26 g, 0.644 mmol) according to Procedure G to give the title compound (0.13 g, 0.180 mmol).

Step D. 1-[4-(4-{2-[(2S)-2-Hydroxy-3-(4-hydroxy-phenoxy)-propylamino]-ethyl}-phenylamino)-piperidin-1-yl]-hexan-1-one 1-{4-[4-(2-{[(2S)-3-(4-{[tert-Butyl(diphenyl)silyl]oxy}phenoxy)-2-hydroxypropyl]-amino}ethyl)anilino]-1-piperidinyl}-1-hexanone (0.13 g, 0.168 mmol) was reacted according to Procedure H (eluant: 5:1 chloroform-methanol containing 1% ammonium hydroxide) to give the title compound (0.058 g, 0.120 mmol).

m.p 57–59° C.
MS ((+)ESI, m/z): 484 [M+H]$^+$
Anal. calcd. for $C_{28}H_{41}N_3O_4 + 1.25$ H$_2$O: C 66.44 H 8.66 N 8.30 found: C 66.58 H 8.33 N 8.11

EXAMPLE 104

[(2S)-1-(4-Fluoro-benzenesulfonyl)-pyrrolidin-2-yl]-[4-(4-{2-[(2S)-2-hydroxy-3-(4-hydroxy-phenoxy)-propylamino]-ethyl}-phenylamino)-piperidin-1-yl]-methanone Step A. tert-Butyl (2S)-1-[(4-fluorophenyl)sulfonyl]-2-pyrrolidinecarboxylate tert-Butyl (2S)-2-pyrrolidinecarboxylate (2.20 g, 12.8 mmol) in anhydrous tetrahydrofuran (20 mL) was treated with anhydrous triethylamine (2.43 mL, 12.8 mmol) followed by 4-fluorobenzenesulfonyl chloride (2.5 g, 12.8 mmol). The reaction was stirred overnight at ambient temperature. The solids were filtered and the solvent removed in vacuo to yield the title compound (3.6 g, 10.93 mmol).

MS ((+)ESI, m/z): 330 [M+H]$^+$, 347 [M+NH$_4$]$^+$

Step B. tert-Butyl (2S)-1-[(4-fluorophenyl)sulfonyl]-2-pyrrolidinecarboxylate (3.6 g, 10.9 mmol) was dissolved in formic acid (70 mL) and stirred at ambient temperature for 6 hours. The solvent was removed in vacuo to yield the title compound (3.0 g, 10.9 mmol).

MS ((−)ESI, m1z): 272 [M−H]$^-$

Step C. tert-Butyl 4-{[1-({(2S)-1-[(4-fluorophenyl)sulfonyl]pyrrolidinyl}carbonyl)-4-piperidinyl]amino}phenethylcarbamate 2-[4-(Piperidin-4-ylamino)-phenyl]-ethyl}-carbamic acid tert-butyl ester (1.31 g, 4.1 mmol) was dissolved in anhydrous N,N-dimethylformamide, (2S)-1-[(4-fluorophenyl)sulfonyl]-2-pyrrolidinecarboxylic acid (1.12 g, 4.1 mmol) and benzotriazol-1-yloxy-tris(dimethylamino)phosphonium hexafluorophophate (1.9 g, 4.3 mmol) added together with anhydrous N,N-diisopropyethylamine (1.24 mL). The reaction was stirred at ambient temperature for 1.5 hours. The solvent was removed in vacuo. The residue was dissolved in chloroform, washed with water, 1N sodium hydroxide, 1N hydrochloric acid and brine. The organic layer was dried over anhydrous magnesium sulfate, filtered and the solvent removed in vacuo to furnish the crude title compound (2.36 g, 4.1 mmol).

MS ((+)APCI, m/z): 575 [M+H]$^+$

Step D. {4-[4-(2-Aminoethyl)anilino]-1-piperidinyl}{(2S)-1-[(4-fluorophenyl)-sulfonyl]pyrrolidinyl}methanone formate tert-Butyl 4-{[1-({(2S)-1-[(4-fluorophenyl)sulfonyl]pyrrolidinyl}carbonyl)-4-piperidinyl]amino}phenethylcarbamate (0.33 g, 0.574 mmol) was reacted according to Procedure F to obtain the title compound (0.30 g, 0.574 mmol) which was used without further purification.

Step E. {4-[4-(2-{[(2S)-3-(4-{[tert-Butyl(diphenyl)silyl]oxy}phenoxy)-2-hydroxypropyl]amino}ethyl)anilino]-1-piperidinyl}{(2S)-1-[(4-fluorophenyl)sulfonyl]pyrrolidinyl}methanone formate {4-[4-(2-Aminoethyl)anilino-1-piperidinyl}{(2S)-1-[(4-fluorophenyl)sulfonyl]-pyrrolidinyl}methanone formate (0.30 g, 0.574 mmol) was reacted with tert-butyl-(4-oxiranylmethoxy-phenoxy)-diphenyl-silane (0.232 g, 0.574 mmol) according to Procedure G to give the title compound (0.11 g, 0.125 mmol).

Step F. [(2S)-1-(4-Fluoro-benzenesulfonyl)-pyrrolidin-2-yl]-[4-(4-{2-[(2S)-2-hydroxy-3-(4-hydroxy-phenoxy)-propylamino]-ethyl}-phenylamino)-piperidin-1-yl]-methanone {4-[4-(2-aminoethyl)anilino]-1-piperidinyl}{(2S)-1-[(4-fluorophenyl)-sulfonyl]pyrrolidinyl}methanone (0.11 g, 0.125 mmol) was reacted according to Procedure H (eluant: 5:1 chloroform-methanol) to give the title compound (0.06 g, 0.094 mmol).

m.p 87–89° C.
MS ((+)APCI, m/z): 641 [M+H]$^+$
Anal. calcd. for $C_{33}H_{41}FN_4O_6S + 0.7$ H$_2$O+0.3 CHCl$_3$: C 58.03 H 6.24 N 8.13 found: C 58.33 H 6.52 N 7.66

EXAMPLE 105

4-[4-(4-{2-[(2R)-2-Hydroxy-2-(4-hydroxy-3-methanesulfonylamino-phenyl)-ethylamino]-ethyl}-phenylamino)-piperidine-1-carbonyl]-benzoic Acid Step A. Methyl 4-({4-[4-(2,2-dimethoxyethyl)anilino]-1-piperidinyl}-carbonyl)benzoate N-[4-(2,2-Dimethoxyethyl)phenyl]-4-piperidinamine (0.445 g, 1.68 mmol) was dissolved in anhydrous tetrahydrofuran, 4-(methoxycarbonyl)benzoic acid (0.303 g, 1.68 mmol) and 1-[3-(dimethylamino)propyl]-3-ethylcarbodiimide hydrochloride (0.339 g, 1.77 mmol) added. Anhydrous N,N-diisopropylethylamine (0.33 mL) was added and the reaction stirred at ambient temperature for 14 hours. The solvent was removed in vacuo. The residue was dissolved in dichloromethane, washed with water and brine. The organic layer was dried over anhydrous magnesium sulfate, filtered and the solvent removed in vacuo. The residue was purified by flash chromatography on silica gel Merck-60 (eluant: 2:1 hexane-ethyl acetate) to furnish the title compound (0.30 g, 0.7 mmol).

MS (EI, m/z): 426 [M]+

Step B. Methyl 4-{[4-(4-{2-[((2R)-2-hydroxy-2-{4-hydroxy-3-[(methylsulfonyl)amino]phenyl}ethyl)amino]ethyl}anilino)-1-piperidinyl]carbonylbenzoate Methyl 4-({4-[4-(2,2-dimethoxyethyl)anilino]-1-piperidinyl}carbonyl)benzoate (0.30 g, 0.703 mmol) was added to a pre-prepared mixture of sodium iodide (0.264 g, 1.76 mmol) and trichloro(methyl)silane (0.166 mL, 1.4 mmol) in anhydrous acetonitrile. The reaction was stirred at ambient temperature for 10 minutes. Dichloromethane was added and the reaction washed with 10% sodium thiosulfate solution, water and brine. The organic layer was dried over anhydrous magnesium sulfate, filtered and the solvent partially removed under vacuo. The aldehyde solution was used directly and treated with methanol (17 mL), acetic acid (0.043 mL, 0.75 mmol), N-{5-[(1R)-2-amino-1-hydroxyethyl]-2-hydroxyphenyl}methanesulfonamide (0.127 g, 0.516 mmol) followed by sodium cyanoborohydride (0.048g, 0.764 mmol). The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.127 g, 0.208 mmol).

Step C. 4-[4-(4-{2-[(2R)-2-Hydroxy-2-(4-hydroxy-3-methanesulfonylamino-phenyl)-ethylamino]-ethyl]-phenylamino)-piperidine-1-carbonyl]-benzoic acid Methyl 4-{[4-(4-{2-[((2R)-2-hydroxy-2-{4-hydroxy-3-[(methylsulfonyl)amino]-phenyl}ethyl)amino]ethyl}anilino)-1-piperidinyl]carbonyl}benzoate (0.127 g, 0.208 mmol) was dissolved in methanol (12 mL) and 1N sodium hydroxide (0.416 mL) added. The reaction was stirred at reflux for 24 hours. A further portion of 1N sodium hydroxide (0.1 mL) was added and the reaction stirred at reflux for a further 24 hours. The solvent was removed in vacuo. The residue was extracted with ethyl acetate and the solvent removed in vacuo. The residue was extracted with methanol, filtered through Celite and the solvent removed in vacuo to furnish the title compound (0.032 g, 0.054 mmol).

m.p >200° C.

MS ((−)APCI, m/z): 595 [M−H]−

Anal. calcd. for $C_{30}H_{36}N_4O_7S \cdot HCl + 1.33 H_2O$: C 60.39 H 6.08 N 9.39 found: C 52.65 H 5.31 N 7.86

EXAMPLE 106

[4-(4-{2-[(2S)-2-Hydroxy-3-(4-hydroxy-phenoxy)-propylamino]-ethyl}-phenylsulfanyl)-piperidin-1-yl]-(3-methyl-thiophen-2-yl)-methanone Step A. (4-Hydroxy-1-piperidinyl)(3-methyl-2-thienyl)methanone To a solution of 3-methyl-2-thiophenecarboxylic acid (1.76 g, 12.39 mmol), 1-[3-(dmethylamino)propyl]-3-ethylcarbodiimide hydrochloride (2.85 g, 14.87 mmol), 1-hydroxybenzotriazole (2.18 g, 16.10 mmol), N-methylmorpholine (1.88 g, 18.58 mmol) and 4-hydroxypiperidine (1.25 g, 12.39 mmol) in N,N-dimethylformamide (50 mL) was stirred at room temperature for 72 hours. The reaction mixture was poured into water (100 mL) and extracted with chloroform. The combined organic extracts were dried over anhydrous sodium sulfate, filtered and evaporated. The residue was purified by flash chromatography on silica gel Merck-60 (eluant: ethyl acetate) to afford the title compound (1.78 g, 7.9 mmol).

MS ((+)ESI, m/z): 226 [M+H]+

1H NMR (DMSO-d6, 300 MHz) d 7.35 (d, J=5.0 Hz, 2H), 6.90 (d, J=5.0 Hz, 2H), 4.74 (d, J=4.4 Hz, 1H), 3.82 (m, 2H), 3.65 (m, 1H), 3.01 (m, 2H), 2.22 (s, 3H), 1.77 (m, 2H) and 1.34 (m, 2H).

Step B. (4-Bromo-1-piperidinyl)(3-methyl-2-thienyl)methanone (4-Hydroxy-1-piperidinyl)(3-methyl-2-thienyl)methanone (1.78 g 7.90 mmol) was reacted according to Procedure L to afford the title compound (2.18 g, 7.56 mmol).

Step C. tert-butyl 4-({1-[(3-methyl-2-thienyl)carbonyl]-4-piperidinyl}sulfanyl) phenethylcarbamate (4-Bromo-1-piperidinyl)(3-methyl-2-thienyl)methanone (1.76 g, 6.09 mmol) and S-(4-{2-[(tert-butoxycarbonyl)amino]ethyl}phenyl) O-ethyl carbonodithioate (2.08 g, 6.09 mmol) were reacted according to Procedure M to afford the title compound (1.08 g, 2.34 mmol).

Step D. (4-{[4-(2-aminoethyl)phenyl]sulfanyl}-1-piperidinyl) (3-methyl-2-thienyl)methanone tert-Butyl 4-({1-[(3-methyl-2-thienyl)carbonyl]-4-piperidinyl}sulfanyl)phenethylcarbamate (0.748 g, 1.62 mmol) was reacted according to Procedure N to afford the title compound (0.57 g, 1.58 mmol).

MS ((+)ESI, m/z): 361 [M+H]+

Step E. (4-{[4-(2-{[(2S)-3-(4-{[tert-butyl(diphenyl)silyl]oxy}phenoxy)-2-hydroxypropyl]amino}ethyl)phenyl]sulfanyl-1-piperidinyl)(3-methyl-2-thienyl)methanone (4-{[4-(2-Aminoethyl)phenyl]sulfanyl}-1-piperidinyl)(3-methyl-2-thienyl)methanone (0.57 g, 1.58 mmol) was reacted with tert-butyl-(4-oxiranylmethoxy-phenoxy)-diphenylsilane (0.58 g, 1.44 mmol) according to Procedure G to give the title compound (eluant: 20:1 chloroform-methanol) (0.656 g, 0.858 mmol).

MS ((+)ESI, m/z): 765 [M+H]+

Step F. (4-([4-(2-{[(2S)-2-hydroxy-3-(4-hydroxyphenoxy)propyl]amino}ethyl)phenyl]sulfanyl}-1-piperidinyl)(3-methyl-2-thienyl)methanone

[4-(4-[2-[2-Hydroxy-3-(4{[tert-butyl(diphenyl)silyl]oxy}phenoxy)-propylamino]-ethyl}-phenylsulfanyl)-piperidin-1-yl]-(3-methyl-thiophen-2-yl)-methanone (0.654 g, 0.856 mmol) was reacted according to Procedure H to give the title compound (eluant: 20:3 chloroform/methanol) (0.140 g, 0.266 mmol).

m.p. 135–144° C.

MS ((+)ESI, m/z): 527 [M+H]+

1H NMR (DMSO-d6, 400 MHz) d 8.88 (s, 1H), 7.54 (d, J=5.0 Hz, 2H), 7.31 (d, J 8.1 Hz, 2H), 7.18 (d, J=8.1 Hz, 2H), 6.90 (d, J=5.0 Hz, 2H), 6.71 (d, J=9.0 Hz, 2H), 6.64 (d, J=9.0 Hz, 2H), 4.97 (br s, 1H), 3.90 (br s, 1H), 3.80 (m, 3H), 3.42 (m, 1H), 3.1 0 (t, J=1 1.0 Hz, 2H), 2.77 (m, 2H), 2.70 (m, 3H), 2.60 (m, 1H), 2.14 (s, 3H), 1.90 (m, 2H) and 1.39 (m, 2H).

Anal: calcd. for $C_{28}H_{34}N_2O_4S_2$: C 63.85 H 6.51 N 5.32: found C 63.81 H 6.65 N 4.77

EXAMPLE 107

[4-(4-{2-[(2S)-2-Hydroxy-3-(4-hydroxy-phenoxy)-propylamino]-ethyl}benenesulfonyl)-piperidin-1-yl]-(2-methyl-thiophen-3-yl)-methanone Step A. tert-Butyl 4-({1-[(3-methyl-2-thienyl)carbonyl]-4-piperidinyl}sulfonyl)phenethylcarbamate tert-Butyl 4-({1-[(3-methyl-2-thienyl)carbonyl]-4-piperidinyl}sulfanyl)phenethylcarbamate (0.330 g, 0.716 mmol) was reacted according to Procedure O to afford the title compound (0.315 g, 0.639 mmol).

Step B. (4-{[4-(2-aminoethyl)phenyl]sulfonyl}-1-piperidinyl)(3-methyl-2-thienyl)methanone (tert-Butyl 4-({1-[(3-methyl-2-thienyl)carbonyl]-4-piperidinyl}sulfonyl) phenethylcarbamate (0.748 g, 1.62 mmol) was reacted according to Procedure N to afford the title compound (0.57 g, 1.58 mmol).

MS ((+)ESI, m/z): 393 [M+H]$^+$

Step C. (4-{[4-(2-{[(2S)-3-(4-{[tert-butyl(diphenyl)silyl]oxy}phenoxy)-2-hydroxypropyl]amino}ethyl)phenyl]sulfonyl]-1-piperidinyl)(3-methyl-2-thienyl)methanone (4-{[4-(2-Aminoethyl)phenyl]sulfonyl}-1-piperidinyl)(3-methyl-2-thienyl) methanone(0.207 g, 0.527 mmol) was reacted with tert-butyl-(4-oxiranylmethoxy-phenoxy)-diphenylsilane (0.182 g, 0.448 mmol) according to Procedure G to give the title compound (eluant: 20:1 chloroform:methanol)(0 195 g, 0.245 mmol).

MS ((+)ESI, m/z): 798 [M+H]$^+$

Step D. [4-(4-{2-[(2S)-2-Hydroxy-3-(4-hydroxy-phenoxy)-propylamino]-ethyl}-benzenesulfonyl)-piperidin-1-yl]-(2-methyl-thiophen-3-yl)-methanone

[4-(4-{2-[2-Hydroxy-3-(4--{[tert-butyl(diphenyl)silyl]oxy}phenoxy)-propylamino]-ethyl}-phenylsulfonyl)-piperidin-1-yl]-(3-methyl-thiophen-2-yl)-methanone (0.195 g, 0.245 mmol) was reacted according to Procedure H to give the title compound (eluant: 20:3 chloroform-methanol) (0.108 g, 0.193 mmol).

MS ((+)ESI, m/z): 559 [M+H]$^+$ $^1$H NMR (DMSO-d$_6$, 400 MHz) d 8.87 (s, 1H), 7.72 (d, J=8.4 Hz, 2H), 7.55 (d, J=4.8 Hz, 2H), 7.51 (d, J=8.4 Hz, 2H), 6.91 (d, J=4.8 Hz, 2H), 6.71 (d, J=9.0 Hz, 2H), 6.64 (d, J=9.0 Hz, 2H), 4.94 (br s,1H), 4.10 (br s,1H), 3.83–3.70 (m, 3H), 3.55 (m, 2H), 3.30 (m,1H), 2.90 (m, 2H), 2.83 (brs, 4H), 2.70 (m, 1H), 2.60 (m, 1H), 2.10 (s, 3H), 1.86 (m, 2H) and 1.39 (m, 2H)

Anal. calcd. for C$_{28}$H$_{34}$N$_2$O$_6$S$_2$: C 60.19 H 6.13 N 5.01 found: C 59.55 H 6.45 N 4.62.

EXAMPLE 108

1-Hexyl-3-{4-[4-(4-{2-[(2S)-2-hydroxy-3-(4-hydroxy-phenoxy)-propylamino]-ethyl}-phenylamino)-piperidine-1-sulfonyl]-phenyl}-urea Step A. N-Hexyl-N'-phenylurea To a stirred solution of phenyl isocyanate (11.23 g, 94.3 mmol) in anhydrous tetrahydrofuran (170 mL) at 0° C. was added hexylamine (9.54 g, 94.3 mmol). The reaction was stirred at 0° C. for 1 hour. The solvent was removed in vacuo and the crude title compound (21.2 g, 96.23 mmol) used without further purification.

Step B. 4-{[(Hexylamino)carbonyl]amino}benzenesulfonyl chloride

N-Hexyl-N'-phenylurea (6.0 g, 27.23 mmol) was added with stirring over 20 minutes to chlorosulfonic acid (17 mL) at 0° C. The reaction was heated at 60° C. for 2 hours. The mixture was cooled and poured cautiously into ice with stirring. The aqueous phase was extracted with ethyl acetate and washed with brine. The organic layer was dried over anhydrous magnesium sulfate, filtered and the solvent removed in vacuo. The residue was purified by flash chromatography on silica gel Merck-60 (eluant: 3:1 ethyl hexane-acetate) to furnish the title compound (6.2 g, 19.45 mmol).

MS ((−)ESI, m/z): 317 [M−H]$^−$

Step C. tert-Butyl 4-({1-[(4-{[(hexylamino)carbonyl]amino}phenyl)sulfonyl]-4-piperidinyl}amino) phenethylcarbamate To a stirred solution of 2-[4-(piperidin-4-ylamino)-phenyl]-ethyl}-carbamic acid tert-butyl ester (0.8 g, 2.5 mmol) in anhydrous dichloromethane at 0° C. was added 4-{[(hexylamino)carbonyl]amino}benzenesulfonyl chloride (0.88 g, 2.76 mmol) and anhydrous N,N-diisopropylethylamine (0.567 mL). The reaction was stirred at 0° C. for 2.5 hours, diluted with dichloromethane and washed with 1N sodium hydroxide, brine and water. The organic layer was dried over anhydrous magnesium sulfate, filtered and the solvent removed in vacuo. The residue was purified by flash chromatography on silica gel Merck-60 (eluant: 1:1 followed by 2:1 ethyl acetate-hexane) to furnish the title compound (0.92 g, 1.53 mmol).

MS ((+)ESI, m/z): 602 [M+H]$^+$

Step D. N-[4-({4-[4-(2-aminoethyl)anilino]-1-piperidinyl}sulfonyl)phenyl]-N'-hexylurea formate tert-Butyl 4-({1-[(4-{[(hexylamino)carbonyl]amino}phenyl)sulfonyl]-4-piperidinyl}amino) phenethylcarbamate (0.92 g, 1.53 mmol) was reacted according to Procedure F to obtain the title compound (0.84 g, 1.53 mmol) which was used without further purification.

MS ((+)ESI, m/z): 502 [M+H]$^+$

Step E. N-[4-({4-[4-(2-{[(2S)-3-(4-{[tert-Butyl(diphenyl)silyl]oxy}phenoxy)-2-hydroxypropyl]amino}ethyl)anilino]-1-pirperidinyl}sulfonyl)phenyl]-N'-hexylurea N-[4-([4-[4-(2-Aminoethyl)anilino]-1-piperidinyl}sulfonyl)phenyl]-N'-hexylurea formate (0.327 g 0.597 mmol) was reacted with tert-butyl-(4-oxiranylmethoxy-phenoxy)-diphenyl-silane (0.242 g, 0.598 mmol) according to Procedure G to give the title compound (0.180 g, 0.199 mmol).

Step F. 1-Hexyl-3-{4-[4-(4-{2-[(2S)-2-hydroxy-3-(4-hydroxy-phenoxy)-propylamino]-ethyl}-phenylamino)-piperidine-1-sulfonyl]-phenyl}-urea N-[4-({4-[4-(2-{[(2S)-3-(4-{[tert-Butyl(diphenyl)silyl]oxy}phenoxy)-2-hydroxypropyl]amino}ethyl)anilino]-1-piperidinyl}sulfonyl)phenyl]-N'-hexylurea (0.18 g, 0.199 mmol) was reacted according to Procedure H (eluant: 5:1 chloroform-methanol) to give the title compound as the hydrochloride salt (0.1 g, 0.142 mmol).

m.p 165–168° C.

MS ((+)ESI, m/z): 668 [M+H]$^+$

Anal. calcd. for C$_{35}$H$_{49}$N$_5$O$_6$S.HCl+2.0 H$_2$O: C 53.77 H 6.96 N 8.96 found: C 53.82 H 7.21 N 8.86

EXAMPLE 109

1-{4-[4-(4-{2-[(2S)-3-(4-Fluoro-bhenoxy)-2-hydroxy-propylamino]-ethyl}-phenylamino)-piperidine-1-sulfonyl]-phenyl}-3-hexyl-urea N-[4-({4-[4-(2-Aminoethyl)anilino]-1-piperidinyl}sulfonyl)phenyl]-N-hexylurea formate (0.20 g 0.365 mmol) was reacted with (2S)-2-[(4-fluorophenoxy) methyl]oxirane (0.061 mL, 0.365 mmol) according to Procedure G to give the title compound (0.078 g, 0.116 mmol).

m.p 86–88° C.

MS ((+)ESI, m/z): 670 [M+H]$^+$

Anal. calcd. for C$_{35}$H$_{48}$FN$_5$O$_5$S+1.0 H$_2$O: C 61.11 H 7.33 N 10.18 found: C 61.36 H 6.89 N 9.92

EXAMPLE 110

N-[4-({4-[4-(2-{[(2S)-3-(2-allylphenoxy)-2-hydroxypropyl]amino}ethyl)anilino]-1-piperidinyl}sulfonyl)phenyl]-N-hexylurea N-[4-({4-[4-(2-Aminoethyl)anilino]-1-piperidinyl}sulfonyl)phenyl]-N'-hexylurea formate (0.172 g 0.314 mmol) was reacted (2S)-2-[(4-fluorophenoxy)methyl] oxirane (0.06 g, 0.315 mmol) according to Procedure G to give the title compound (0.04 g, 0.058 mmol).

MP: 68–70° C.

Anal. calcd. for $C_{38}H_{53}N_5O_5S+1.75\ H_2O$: C 63.09 H 7.87 N 9.68 found: C 63.33 H 7.42 N 9.3

EXAMPLE 111

4-[(2S)-2-Hydroxy-3-(2-{4-[1-(octane-1-sulfonyl)-piperidin-4-ylamino]-ethyl}-phenylamino)-piperidine-1-carboxylic Acid Octylamide Step A. tert-Butyl 4-({1-(octylsulfonyl)-4-piperidinyl]amino}phenethylcarbamate To a stirred solution of 2-[4-(piperidin-4-ylamino)-phenyl]-ethyl}-carbamic acid tert-butyl ester (1.0 g, 3.13 mmol) in anhydrous dichloromethane at 0° C. was added 1-octanesulfonyl chloride (0.732 g, 3.43 mmol) and anhydrous N,N-diisopropylethylamine (0.65 mL). The reaction was stirred at 0° C. for 2.5 hours, diluted with dichloromethane and washed with 1N sodium hydroxide, brine and water. The organic layer was dried over anhydrous magnesium sulfate, filtered and the solvent removed in vacuo. The residue was purified by flash chromatography on silica gel Merck-60 (eluant: 1:1 followed by 2:1 ethyl acetate-hexane) to furnish the title compound (1.3 g, 2.62 mmol).

Step B. N-[4-(2-aminoethyl)phenyl]-11-(octylsulfonyl)-4-piperidinamine tert-Butyl 4-{[1-(octylsulfonyl)-4-piperidinyl]amino}phenethylcarbamate (0.609 g, 1.23 mmol) was reacted according to Procedure F to obtain the title compound (1.23 mmol) which was used without further purification.

Step C. (2S)-1-(4-{[tert-Butyl(diphenyl)silyl]oxy}phenoxy)-3-[(4-{[1-(octylsulfonyl)-4-piperidinyl]amino}phenethyl)amino]-2-propanol N-[4-(2-aminoethyl)phenyl]-1-(octylsulfonyl)-4-piperidinamine (0.547 g, 1.23 mmol) was reacted with tert-butyl-(4-oxiranylmethoxy-phenoxy)-diphenyl-silane (0.375 g, 0.93 mmol) according to Procedure G to give the title compound (0.196 g, 0.245 mmol).

Step D. 4-[(2S)-2-Hydroxy-3-(2-{4-[1-(octane-1-sulfonyl)-piperidin-4-ylamino]-ethyl}-phenylamino)-piperidine-1-carboxylic acid octylamide (2S)-1-(4-{[tert-Butyl(diphenyl)silyl]oxy}phenoxy)-3-[(4-{[1-(octylsulfonyl)-4-piperidinyl]amino}phenethyl)amino]-2-propanol (0.196 g, 0.245 mmol) was reacted according to Procedure H (eluant: 5:1 chloroform-methanol) to give the title compound (0.02 g, 0.035 mmol).

m.p. 64–68° C.

Anal. calcd. for $C_{30}H_{47}N_3O_5S+1.25\ H_2O$: C 61.67 H 8.54 N 7.19 found: C 61.61 H 8.14 N 6.96

EXAMPLE 112

4-[(2S)-2-Hydroxy-3-(2-{4-[1-(toluene-4-sulfonyl)-piperidin-4-ylamino]-phenyl}-ethylamino)-propoxy]-phenol Step A. tert-Butyl 4-({1-[(4-methylphenyl)sulfonyl]-4-piperidinyl}amino)phenethylcarbamate To a stirred solution of 2-[4-(piperidin-4-ylamino)-phenyl]-ethyl}-carbamic acid tert-butyl ester (1.03 g, 3.22 mmol) in anhydrous dichloromethane at 0° C. was added 4-methyl-benzenesulfonic acid annhydride (1.05 g, 3.22 mmol) and anhydrous N,N-diisopropylethylamine (0.475 mL). The reaction was stirred at 0° C. for 2.5 hours, diluted with dichloromethane and washed with 1N sodium hydroxide, brine and water. The organic layer was dried over anhydrous magnesium sulfate, filtered and the solvent removed in vacuo. The residue was purified by flash chromatography on silica gel Merck-60 (eluant: 1:1 followed by 2:1 ethyl acetate-hexane) to furnish the title compound (0.9 g, 1.9 mmol).

Step B. N-[4-(2-Aminoethyl)phenyl]-1-[(4-methylphenyl)sulfonyl]-4-piperidinamine tert-Butyl 4-({1-[(4-methylphenyl)sulfonyl]-4-piperidinyl}amino)phenethylcarbamate (0.307 g, 0.65 mmol) was reacted according to Procedure F to obtain the title compound (0.65 mmol) which was used without further purification.

Step C. (2S)-1-(4-{[tert-Butyl(diphenyl)silyl]oxy}phenoxy)-3-{[4-({1-[(4-methylphenyl)sulfonyl]-4-piperidinyl}amino)phenethyl]amino}-2-propanol N-[4-(2-Aminoethyl)phenyl]-1-[(4-methylphenyl)sulfonyl]-4-piperidinamine (0.275 g, 0.65 mmol) was reacted with tert-butyl-(4-oxiranylmethoxy-phenoxy)-diphenyl-silane (0.251 g, 0.62 mmol) according to Procedure G to give the title compound (0.130 g, 0.167 mmol).

Step D. 4-[(2S)-2-Hydroxy-3-(2-{4-r1-(toluene-4-sulfonyl)-piperidin-4-ylamino]-phenyl}-ethylamino)-propoxy]-phenol (2S)-1-(4-{[tert-Butyl(diphenyl)silyl]oxy}phenoxy)-3-{[4-({1-[(4-methylphenyl)sulfonyl]-4-piperidinyl}amino)phenethyl]amino}-2-propanol (0.130 g, 0.167 mmol) was reacted according to Procedure H (eluant: 5:1 chloroform-methanol) to give the title compound (0.035 g, 0.064 mmol).

m.p 89–92° C.

Anal. calcd. for $C_{29}H_{37}N_3O_5S\cdot HCl+0.33\ H_2O$: C 59.84 H 6.69 N 7.22 found: C 59.76 H 6.68 N 7.08

EXAMPLE 113

4-[(2S)-2-Hydroxy-3-(2-{4-[-(1-methyl-1H-imidazole-4-sulfonyl)-piperidin-4-ylamino]-phenyl}-ethylamino)-propoxy]-phenol Step A. tert-Butyl 4-({1-[(1-methyl-1H-imidazol-4-y1)sulfonyl]-4-piperidin}-amino)phenethylcarbamate To a stirred solution of 2-[4-(piperidin-4-ylamino)-phenyl]-ethyl}-carbamic acid tert-butyl ester (1.3 g, 4.1 mmol) in anhydrous dichloromethane was 1-methyl-1H-imidazole-4-sulfonyl chloride (0.77 g, 4.27 mmol) and anhydrous N,N-diisopropylethylamine (1.1 mL). The reaction was stirred at ambient temperature for 4 days, diluted with dichloromethane and washed with brine and water. The organic layer was dried over anhydrous magnesium sulfate, filtered and the solvent removed in vacuo. The residue was purified by flash chromatography on silica gel Merck-60 (eluant: 20:1 chloroform-methanol) to furnish the title compound (1.47 g, 3.17 mmol).

MS ((+)ESI, m/z): 464 [M+H]⁺

Step B. tert-Butyl 4-({1-[(1-methyl-1H-imidazol-4-yl)sulfonyl]-4-piperidinyl}-amino)phenethylcarbamate tert-Butyl 4-({1-[(1-methyl-1H-imidazol-4-yl)sulfonyl]-4-piperidinyl}amino)phenethylcarbamate (0.40 g, 0.86 mmol) was reacted according to Procedure F to obtain the title compound (0.35 g, 0.86 mmol) which was used without further purification.

Step C. (2S)-1-(4-{[tert-Butyl(diphenyl)silyl]oxy}phenoxy)-3-{[4-({1-[(1-methyl-1H-imidazol-4-yl)sulfonyl]-4-piperidinyl}amino)phenethyl]amino}-2-propanol tert-Butyl 4-({1-[(1-methyl-1H-imidazol-4-yl)sulfonyl]-4-piperidinyl}amino)-phenethylcarbamate (0.353 g 0.86 mmol) was reacted with tert-butyl-(4-oxiranylmethoxyphenoxy)-diphenyl-silane (0.35 g, 0.87 mmol) according to Procedure G to give the title compound (0.15 g, 0.195 mmol).

Step D. 4-[(2S)-2-Hydroxy-3-(2-{4-r1-(1-methyl-1H-imidazole-4-sulfonyl)- piperidin-4-ylamino]-phenyl}-ethylamino)-propoxy]-phenol (2S)-1-(4-{[tert-Butyl(diphenyl)silyl]oxy}phenoxy)-3-{[4-({1-[(1-methyl-1H-imidazol-4-yl)sulfonyl]-4-piperidinyl}amino)phenethyl]amino}-2-propanol (0.14 g, 0.182 mmol) was reacted according to Procedure H (eluant: 5:1 chloroform-methanol containing 1% ammonium hydroxide) to give the title compound (0.09 g, 0.17 mmol). m.p 93–95° C.

MS ((+)ESI, m/z): 530 [M+H]$^+$

Anal. calcd. for $C_{26}H_{35}N_5O_5S+0.7\ H_2O+0.1\ CHCl_3$: C 54.64 H 6.40 N 12.11 found: C 54.4 H 6.2 N 11.71

EXAMPLE 114

N-{4-[4-(4-{2-[(2S)-2-Hydroxy-3-(4-hydroxyphenoxy)-propylamino]-ethyl}-phenylamino)-piperidine-1-sulfonyl]-phenyl}-acetamide Step A. tert-Butyl 4-[(1-{[4-(acetlamino)phenyl]sulfonyl}-4-piperidinyl)-amino]phenethylcarbamate To a stirred solution of 2-[4-(piperidin-4-ylamino)-phenyl]-ethyl}-carbamic acid tert-butyl ester (1.56 g, 4.88 mmol) in anhydrous dichloromethane at 0° C. was added 4-(acetylamino)-benzenesulfonyl chloride (1.25 g, 5.37 mmol) and anhydrous N,N-diisopropylethylamine (1.02 mL). The reaction was stirred at 0° C. for 2.5 hours, diluted with dichloromethane and washed with 1N sodium hydroxide, brine and water. The organic layer was dried over anhydrous magnesium sulfate, filtered and the solvent removed in vacuo. The residue was purified by flash chromatography on silica gel Merck-60 (eluant: 1:1 followed by 2:1 ethyl acetate-hexane) to furnish the title compound (1.24 g, 2.32 mmol).

MS ((+)ESI, m/z): 517 [M+H]$^+$

Step B. N-[4-({4-[4-(2-Aminoethyl)anilino]-1-piperidinyl}sulfonyl)phenyl]acetamide tert-Butyl 4-[(1-{[4-(acetylamino)phenyl]sulfonyl}-4-piperidinyl)amino]phenethyl carbamate (0.557 g, 1.08 mmol) was reacted according to Procedure F to obtain the title compound (1.08 mmol) which was used without further purification.

Step C. N-[4-({4-[4-(2-{[(2S)-3-(4-{[tert-Butyl(diphenyl)silyl]oxy}phenoxy)-2-hydroxypropyl]amino}ethyl)anilino]-1-piperidinyl}sulfonyl)phenyl]acetamide N-[4-({4-[4-(2-Aminoethyl)anilino]-1-piperidinyl}sulfonyl)phenyl]acetamide (0.500 g, 1.08 mmol) was reacted with tert-butyl-(4-oxiranylmethoxy-phenoxy)-diphenyl-silane (0.4 g, 0.973 mmol) according to Procedure G to give the title compound (0.185 g, 0.225 mmol).

Step D. N-{4-[4-(4-{2-[(2S)-2-Hydroxy-3-(4-hydroxyphenoxy)-propylamino]- ethyl}-phenylamino)-piperidine-1-sulfonyl]-phenyl}-acetamide N-[4-({4-[4-(2-{[(2S)-3-(4-{[tert-Butyl(diphenyl)silyl]oxy}phenoxy)-2-hydroxypropyl]amino}ethyl)anilino]-1-piperidinyl}sulfonyl)phenyl] (0.185 g, 0.225 mmol) was reacted according to Procedure H (eluant: 5:1 chloroform-methanol) to give the title compound (0.115 g, 0.19mmol). m.p 98–104° C.

Anal. calcd. for $C_{30}H_{38}N_4O_6S\cdot HCl+0.7\ CHCl_3$: C 52.47 H 5.69 N 7.97 found: C 52.05 H 5.55 N 7.7

EXAMPLE 115

N-(5-{[4-(4-{2-[((2R)-2-hydroxy-2-{4-hydroxy-3-[(methylsulfonyl)amino]phenyl}-ethyl)amino]ethyl}anilino)piperidin-1-yl]sulfonyl}-4-methyl-1,3-thiazol-2-yl)acetamide Step A. N-[5-(1,4-dioxa-8-azaspiro[4.5]dec-8-ylsulfonyl)-4-methyl-1,3-thiazol-2-yl]acetamide To a solution of 1,4-dioxa-8-asaspiro[4.5]decane(1.98 g., 13.83 mmol) and triethylamine (1.40 g, 13.83 mmol) in dichloromethane at 0° C. was added 2-acetamido-4-methyl-5-thiazolesulfonyl chloride (3.52 g., 13.83 mmol) and this mixture was stirred overnight. The reaction mixture was washed with water, dried over anhydrous sodium sulfate, filtered and evaporated to dryness in vacuo. The title compound (2.38 g., 6.58 mmol) was obtained pure by crystallization from a mixture of solvents comprising acetone, acetonitrile and diethyl ether.

Step B. N-{4-methyl-5-[(4-oxo-1-piperidinyl)sulfonyl]-1,3-thiazol-2-yl}acetamide N-[5-(1,4-dioxa-8-azaspiro[4.5]dec-8-ylsulfonyl)-4-methyl-1,3-thiazol-2-yl]acetamide (1.83 g, 5.07 mmol) was dissolved in formic acid and heated at 60° C. for 2.0 hours. The solvent was removed in vacuo and the oily residue treated with water (100 mL). The pH was adjusted to neutral with an aqueous sodium hydrogen carbonate solution. The solid was filtered, washed well with water and the solvent removed in vacuo to yield the title compound (1.44 g, 5.05 mmol).

Step C. N-[5-({4-[4-(2,2-dimethoxyethyl)anilino]-1-piperidinyl}sulfonyl)-4-methyl-1,3-thiazol-2-yl]acetamide N-{4-methyl-5-[(4-oxo-1-piperidinyl)sulfonyl]-1,3-thiazol-2-yl}acetamide (1.44 g, 5.04 mmol) and 4-(2,2-dimethoxyethyl)aniline (0.91 g, 5.04 mmol) were dissolved in dichloroethane. Anhydrous sodium sulfate (7.17 g) was added followed by acetic acid (1.52 mL). Stirring was continued for 1 hour. Sodium triacetoxyborohydride (3.21 g, 15.14 mmol) was added and stirring continued overnight. The mixture was filtered, diluted with dichloromethane, and washed with 1 N sodium hydroxide, water and brine. The organic phase was dried over anhydrous magnesium sulfate. The solution was filtered and the solvent evaporated to dryness in vacuo. The residue was purified by flash chromatography on silica gel Merck-60 (eluant: 20:1 chloroform-methanol). The solvent was removed in vacuo to furnish the title compound.

MS ((+)ESI, m/z): 481 [M+H]$^+$

Step D. N-(5-{[4-(4-{2-[((2R)-2-hydroxy-2-{4-hydroxy-3-[(methylsulfonyl)amino]-phenyl}ethyl)amino]ethyl}anilino)piperidin-1-yl]sulfonyl}-4-methyl-1,3-thiazol-2-yl)acetamide N-[5-({4-[4-(2,2-dimethoxyethyl)anilino]-1-piperidinyl}sulfonyl)-4-methyl-1,3-thiazol-2-yl]acetamide (0.46 g, 0.953 mmol) was added to a pre-prepared mixture of sodium iodide (0.357 g, 2.38 mmol) and trichloro(methyl)silane (0.224 mL, 1.91 mmol) in anhydrous acetonitrile. The reaction was stirred at ambient temperature for 10 minutes. Dichloromethane was added and the reaction washed with 10% sodium thiosulfate solution, water and brine. The organic layer was dried over anhydrous magnesium sulfate, filtered and the solvent partially removed in vacuo. The aldehyde solution was used directly and treated with methanol, acetic acid (0.146 mL, 2.43 mmol), N-{5-[(1R)-2-amino-1-hydroxyethyl]-2-hydroxyphenyl}methanesulfonamide (0.235 g, 0.953 mmol) followed by sodium cyanoborohydride (0.06 g, 0.953 mmol). The reaction was stirred at ambient temperature for 24 hours. The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.045 g, 0.067 mmol).

MS ((+)ESI, m/z): 666 [M+H]$^+$

EXAMPLE 116

N-(2-Hydroxy-5-{(1R)-1-hydroxy-2-[2-(4-{1-[4-(3-octyl-ureido)-benzenesulfonyl]-piperidin-4-ylamino}-phenyl)-ethylamino]-ethyl}- phenyl)-methanesulfonamide Step A. N-Octyl-N'-phenylurea To a stirred solution of phenyl isocyanate (21.0 g, 176 mmol) in anhydrous tetrahydrofuran (200 mL) at 0° C. was added octylamine (22.79 g, 176 mmol). The reaction was stirred at ambient temperature for 2 hour. The solvent was removed in vacuo and the crude title compound triturated with hexane to obtain the title compound (21.2 g, 96.23 mmol) which was used without further purification.

Step B. 4-{[(Octylamino)carbonyl]amino}benzenesulfonyl chloride

N-Octyl-N'-phenylurea (5.0 g, 20.13 mmol) was added with stirring over 5 minutes to chlorosulfonic acid (18 mL) at ambient temperature. The reaction stirred at this temperature for 1 hour. The mixture was cooled and poured cautiously into ice with stirring. The aqueous phase was extracted with ethyl acetate and washed with brine. The organic layer was dried over anhydrous magnesium sulfate, filtered and the solvent removed in vacuo. The residue was triturated with hexane to furnish the title compound (6.0 g, 17.3 mmol).

MS (EI, m/z): 346 [M]$^+$

Step C. N-[4-({4-[4-(2,2-Dimethoxyethyl)anilino]-1-piperidinyl}sulfonyl)phenyl]-N'-octylurea To a stirred solution of N-[4-(2,2-dimethoxyethyl)phenyl]-4-piperidinamine (0.52 g, 1.97 mmol) in anhydrous dichloromethane at 0° C. was added 4-{[(octylamino)carbonyl]-amino}benzenesulfonyl chloride (0.684 g, 1.97 mmol) and anhydrous N,N-diisopropylethylamine (0.422 mL). The reaction was stirred at ambient temperature for 16 hours, diluted with dichloromethane and washed with 1N sodium hydroxide, brine and water. The organic layer was dried over anhydrous magnesium sulfate, filtered and the solvent removed in vacuo. The residue was purified by flash chromatography on silica gel Merck-60 (eluant: 50:1 chloroform-ethanol) to furnish the title compound (0.90 g, 1.57 mmol).

MS ((+)APCI, m/z): 575 [M+H]$^+$

Step D. N-(2-Hydroxy-5-{(1R)-1-hydroxy-2-r2-(4-{1-[4-(3-octyl-ureido)-benzenesulfonyl]-piperidin-4-ylamino}-phenyl)-ethylamino]-ethyl}- phenyl)-methanesulfonamide N-[4-({4-[4-(2,2-Dimethoxyethyl)anilino]-1-piperidinyl}sulfonyl)phenyl]-N-octylurea (0.53 g, 0.92 mmol) was added to a pre-prepared mixture of sodium iodide (0.346 g, 2.31 mmol) and trichloro(methyl)silane (0.217 mL, 1.85 mmol) in anhydrous acetonitrile (27 mL). The reaction was stirred at ambient temperature for 10 minutes. Dichloromethane was added and the reaction washed with 10% sodium thiosulfate solution, water and brine. The organic layer was dried with anhydrous magnesium sulfate, filtered and the solvent partially removed in vacuo. The aldehyde solution was used directly and treated with methanol, acetic acid (0.066 mL, 1.1 mmol), N-{5-[(1R)-2-amino-1-hydroxyethyl]-2-hydroxyphenyl}methanesulfonamide (0.227 g, 0.92 mmol) followed by sodium cyanoborohydride (0.063 g, 0.92 mmol). The reaction was stirred at ambient temperature overnight. The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.097 g, 0.128 mmol).

m.p 134–136° C.

MS ((+)APCI, m/z): 759 [M+H]$^+$

Anal. calcd. for $C_{37}H_{54}N_6O_7S_2HCl+0.5\ H_2O$: C 55.24 H 7.02 N 10.45 found: C 55.29 H 7.15 N 10.39

EXAMPLE 117

4-[(2S)-2-Hydroxy-3-(2-{4-[1l-(4-phenyl-thiazol-2-yl)-piperidin-4-ylamino]-phenyl}-ethylamino)-propoxy]-phenol Step A. N-(1,4-Dioxa-8-azaspiro[4.5]dec-8-ylcarbothioyl)benzamide 1,4-Dioxa-8-azaspiro[4.5]decane (17.55 g, 122.56 mmol) was dissolved in acetone (200 mL). To this stirred solution was added, initially at 000C, benzoyl isothiocyanate (16.5 mL, 122.8 mmol). The reaction was allowed to warm to ambient temperature and stirred overnight. The resulting precipitate was filtered and washed with hexane. The filtrate was evaporated partially in vacuo and the solid removed and washed with warm acetone. The solids were combined to yield the title compound (15.5 g, 50.59 mmol).

MS ((+)ESI, m/z): 307 [M+H]$^+$, 613 [2M+H]$^+$

Step B. 1,4-Dioxa-8-azaspiro[4.5]decane-8-carbothioamide

N-(1,4-Dioxa-8-azaspiro[4.5]dec-8-ylcarbothioyl)benzamide (14.54 g, 47.47 mmol) was heated at reflux for 24 hours in methanol (160 mL) and water (60 mL) containing potassium carbonate (13.1 g). The volume was reduced by half in vacuo and extracted with ethyl acetate after a dilution with saturated potassium carbonate. Several extractions with ethyl acetate were combined dried over anhydrous magnesium sulfate, filtered and the solvent removed in vacuo to furnish the title compound (8.5 g, 42.02 mmol).

MS ((+)ESI, m/z): 203 [M+H]$^+$

Step C. 1-(4-Phenyl-1,3-thiazol-2-yl)-4-piperidinone 1,4-Dioxa-8-azaspiro[4.5]decane-8-carbothioamide (4.6 g, 22.74 mmol) and 2-bromo-1-phenyl-1-ethanone (4.3 g, 21.60 mmol) were dissolved in anhydrous N,N-dimethylformamide (20 mL) and heated at 70° C. for 2 days. The solvent was removed in vacuo and the residue purified by passage through a pad of silica gel eluting with chloroform. The solvent was removed in vacuo and the residue dissolved in tetrahydrofuran (5 mL). 2N hydrochloric acid (25 mL) was added and the reaction heated at 70° C. for 2 hours. The solution was cooled and extracted with ethyl acetate which was washed with saturated sodium hydrogencarbonate solution and brine. The solvent was removed in vacuo to yield the title compound (2.14 g, 8.28 mmol).

MS ((+)ESI, m/z): 259 [M+H]$^+$

Step D. tert-Butyl 4-{[-(4-phenyl-1,3-thiazol-2-yl)-4-piperidinyl]amino}phenethylcarbamate formate tert-Butyl 4-aminophenethylcarbamate (1.92 g, 8.13 mmol) and 1-(4-phenyl-1,3-thiazol-2-yl)-4-piperidinone (2.1 g, 8.13 mmol) were dissolved in dichloroethane. Anhydrous sodium sulfate (11.5 g) was added followed by acetic acid (2.3 mL). Stirring was continued for 45 minutes. Sodium triacetoxyborohydride (2.6 g, 12.27 mmol) was added and stirring continued overnight. The mixture was filtered, diluted with dichloromethane, and washed with 40% sodium hydroxide, water and brine. The organic layer was dried over anhydrous magnesium sulfate. The solution was filtered and the solvent evaporated to dryness in vacuo. The residue was purified by flash chromatography on silica gel Merck-60 (eluant: 3:1 hexane-ethyl acetate) to furnish the title compound (2.24 g, 4.68 mmol).

MS ((+)ESI, m/z): 479 [M+H]$^+$

Step E. (2S)-1-(4-{[tert-Butyl(diphenyl)silyl]oxy}phenoxy)-3-[(4-{[1-(4-phenyl-1,3-thiazol-2-yl)-4-piperidinyl]amino}phenethyl)amino]-2-propanol tert-Butyl 4-{[1-(4-phenyl-1,3-thiazol-2-yl)-4-piperidinyl]amino}phenethylcarbamate formate (0.40 g 1.04 mmol) was reacted with tert-butyl-(4-oxiranylmethoxy-phenoxy)-diphenyl-silane (0.42 g, 1.04 mmol) according to Procedure G to give the title compound (0.25 g, 0.319 mmol).

Step F. 4-[(2S)-2-Hydroxy-3-(2-{4-[1-(4-phenyl-thiazol-2-yl)-piperidin-4-ylamino]-phenyl}-ethylamino)-propoxy]-phenol (2S)-1-(4-{[tert-Butyl(diphenyl)silyl]oxy}phenoxy)-3-[(4-{[1-(4-phenyl-1,3-thiazol-2-yl)-4-piperidinyl]

amino}phenethyl)amino]-2-propanol (0.25 g, 0.319 mmol) was reacted following general Procedure H (eluant: 5:1 chloroform-methanol) to give the title compound as the hydrochloride salt (0.12 g, 0.22 mmol).

m.p 80–82° C.

MS ((+)ESI, m/z): 545 [M+H]$^+$

Anal. calcd. for $C_{31}H_{36}N_4O_3S+1.0\ H_2O$: C 66.17 H 6.81 N 9.96 found: C 66.03 H 6.56 N 9.64

EXAMPLE 118

(R)-N-{2-Hydroxy-5-[1-hydroxy-2-(2-{4-[1-(4-phenyl-thiazol-2-yl)-piperidin-4-ylamino]-phenyl}-ethylamino)-ethyl]-phenyl}-methanesulfonamide Step A. N-[4-(2,2-Dimethoxyethyl)phenyl]-1-(4-phenyl-1,3-thiazol-2-yl)-4-piperidinamine 4-(2,2-Dimethoxyethyl)aniline (0.280 g, 1.55 mmol) and 1-(4-phenyl-1,3-thiazol-2-yl)-4-piperidinone (0.40 g, 1.55 mmol) were dissolved in dichloromethane. Anhydrous sodium sulfate (2.2 g) was added followed by acetic acid (0.46 mL, 7.7 mmol). Stirring was continued for 45 minutes. Sodium triacetoxyborohydride (0.361 g, 1.70 mmol) was added and stirring continued overnight. The mixture was filtered, diluted with dichloromethane, and -washed with 1N sodium hydroxide, water and brine. The organic layer was dried over anhydrous magnesium sulfate. The solution was filtered and the solvent evaporated to dryness in vacuo. The residue was crystallized fro ethyl acetate/hexane to furnish the title compound (0.42 g, 0.99 mmol).

MS ((+)APCI, m/z): 424 [M+H]$^+$

Step B. (R)-N-{2-Hydroxy-5-[1-hydroxy-2-(2-{4-[1-(4-phenyl-thiazol-2-yl)- piperidin-4-ylamino]-phenyl}-ethylamino)-ethyl]-phenyl}-methanesulfonamide N-[4-(2,2-Dimethoxyethyl)phenyl]-1-(4-phenyl-1,3-thiazol-2-yl)-4-piperidinamine (0.415 g, 30 0.98 mmol) was added to a pre-prepared mixture of sodium iodide (0.367 g, 2.45 mmol) and trichloro(methyl)silane (0.229 mL, 1.95 mmol) in anhydrous acetonitrile (70 mL). The reaction was stirred at ambient temperature for 10 minutes. Dichloromethane was added and the reaction washed with 10% sodium thiosulfate solution, water and brine. The organic layer was dried with anhydrous magnesium sulfate, filtered and the solvent partially removed in vacuo. The aldehyde solution was used directly and treated with methanol, acetic acid (0.088 mL, 1.47 mmol), N-{5-[(1R)-2-amino-1-hydroxyethyl]-2-hydroxyphenyl}methanesulfonamide (0.241 g, 0.98 mmol) followed by sodium cyanoborohydride (0.067 g, 0.97 mmol). The reaction was stirred at ambient temperature overnight. The reaction was taken to dryness in vacuo, adsorbed onto silica and purified by flash chromatography on silica gel Merck-60 (eluant: 5:1 chloroform-methanol containing 1% ammonium hydroxide) to yield the title compound (0.092 mmol, 0.151 mmol).

m.p 142–145° C.

MS ((+)APCI, m/z): 608 [M+H]$^+$

Anal. calcd. for $C_{31}H_{37}N_5O_4S_2 \cdot HCl+2.5\ H_2O$: C 54.02 H 6.29 N 10.16 found: C 54.03 H 6.03 N 9.98

EXAMPLE 119

N-(2-Hydroxy-5-{(1R)-1-hydroxy-2-[2-(4-{1-[4-(piperidine-1-sulfonyl)-phenyl]-piperidin-4-ylamino{-phenyl)-ethylamino]-ethyl}-phenyl)-methanesulfonamide Step A. 1-[(4-Fluorophenyl)sulfonyl]piperidine Piperidine (5.64 g, 66.24 mmol) was stirred at 0° C. in anhydrous tetrahydrofuran. 4-fluorobenzenesulfonyl chloride (11.72 g, 60.22 mmol) and anhydrous N,N-diisopropylethylamine (13.64 mL, 78.30 mmol) were added. The reaction was stirred at this temperature for 2 hours. The solvent was removed in vacuo and the residue partitioned between water and ethyl acetate. The organic layer was separated washed with 1 N hydrochloric acid and brine, dried over anhydrous magnesium sulfate and filtered. The solvent was removed in vacuo and the residue crystallized from ethyl acetate/hexane. The title compound was used without further purification.

MS ((+)APCI, m/z): 244 [M+H]$^+$

Step B. 8-[4-(1-Piperidinylsulfonyl)phenyl-1,4-dioxa-8-azaspiro[4.5]decane

1-[(4-Fluorophenyl)sulfonyl]piperidine (5.17 g, 21.28 mmol) and 1,4-dioxa-8-azaspiro[4.5]decane (3.05 g, 21.28 mmol) were dissolved in anhydrous N,N-dimethylformamide (3 mL). Potassium carbonate (3.53 g, 25.54 mmol) was added and the reaction heated at 100° C. for 16 hours. The solvent was removed in vacuo and the residue dissolved in chloroform and washed with water and brine. The organic layer was dried over anhydrous magnesium sulfate, filtered and the solvent removed in vacuo. The residue was twice crystallized from ethanol to provide the title compound (4.1 g, 11.19 mmol).

Step C 1-[4-(1-Piperidinylsulfonyl)phenyl]-4-piperidinone

8-[4-(1-Piperidinylsulfonyl)phenyl]-1,4-dioxa-8-azaspiro [4.5]decane (1.0 g, 2.73 mmol) was dissolved in formic acid and heated at 60° C. for 1 hour. The solvent was removed in vacuo and the residue crystallized from ethanol to give the title compound (0.70 g, 2.17 mmol).

MS ((+)ESI, m/z): 323 [M+H]$^+$

Step D. N-[4-(2,2-Dimethoxyethyl)phenyl]-1-4-(1-piperidinylsulfonyl)phenyl]-4-piperidinamine 4-(2,2-Dimethoxyethyl)aniline (0.387 g, 2.14 mmol) and 1-[4-(1-piperidinylsulfonyl) phenyl]-4-piperidinone (0.69 g, 2.14 mmol) were dissolved in dichloromethane. Anhydrous sodium sulfate (3.0 g) was added followed by acetic acid (0.63 mL, 10.66 mmol). Stirring was continued for 45 minutes. Sodium triacetoxyborohydride (0.50 g, 2.36 mmol) was added and stirring continued overnight. The mixture was filtered, diluted with dichloromethane, and washed with 1N sodium hydroxide, water and brine. The organic layer was dried over anhydrous magnesium sulfate. The solution was filtered and the solvent evaporated to dryness in vacuo. The residue was purified by flash chromatography on silica gel Merck-60 (eluant: 50:1 chloroform-methanol) and crystallized from ethyl acetate/hexane to yield the title compound (0.47 g, 0.964 mmol).

MS ((+)APCI, m/z): 488 [M+H]$^+$

Step E. N-(2-Hydroxy-5-{(1R)-1-hydroxy-2-[2-(4-{1-[4-(piperidine-1-sulfonyl)-phenyl]-piperidin-4-ylamino}-phenyl)-ethylamino]-ethyl}-phenyl)-methanesulfonamide N-[4-(2,2-Dimethoxyethyl)phenyl]-1-[4-(1-piperidinylsulfonyl)phenyl]-4-piperidinamine (0.395 g, 0.81 mmol) was added to a pre-prepared mixture of sodium iodide (0.303 g, 2.02 mmol) and trichloro(methyl)silane (0.191 mL, 1.62 mmol) in anhydrous acetonitrile. The reaction was stirred at ambient temperature for 3 minutes. Dichloromethane was added and the reaction washed with 10% sodium thiosulfate solution, water and brine. The organic layer was dried with anhydrous magnesium sulfate, filtered and the solvent partially removed in vacuo. The aldehyde solution was used directly and treated with methanol, acetic acid (0.06 mL, 1.01 mmol), N-{5-[(1R)-2-amino-1-hydroxyethyl]-2-hydroxyphenyl}methanesulfonamide (0.20 g, 0.812 mmol) followed by sodium cyanoborohydride (0.056 g, 0.81 mmol). The reaction was stirred at ambient temperature for 4 hours. The reaction was taken to dryness in vacuo, adsorbed onto silica and purified by flash chromatography on silica gel Merck-60 (eluant: 10:1 chloroform-containing 1% ammonium hydroxide) to yield the title compound (0.130 mmol, 0.19 mmol).

m.p 118–120° C.

MS ((+)APCI, m/z): 672 [M+H]$^+$

Anal. calcd. for $C_{33}H_{45}N_5O_6S_2$+2.0 $H_2O$: C 55.99 H 6.98 N 9.89 found: C 55.73 H 6.81 N 9.59

EXAMPLE 120

4-[4-(4-{2-[(2R)-2-Hydroxy-2-(4-hydroxy-3-methanesulfonylamino-phenyl)-ethylamino]-ethyl}-phenylamino)-piperidin-1-yl]-benzoic Acid Ethyl Ester Step A. Ethyl 4-(1,4-dioxa-8-azaspiro[4.5]dec-8-yl)benzoate Ethyl 4-fluorobenzoate (7.80 g, 46.38 mmol) and 1,4-dioxa-8-azaspiro[4.5]decane (7.30 g, 46.43 mmol) were dissolved in anhydrous N,N-dimethylformamide. Potassium carbonate (7.7 g, 55.71 mmol) was added and the reaction heated at 100° C. overnight followed by a further 24 hours at 120° C. The solvent was removed in vacuo and water added. The resulting solid was removed and washed with water and hexane. The dried residue was crystallized from methanol to yield the title compound (4.0 g, 13.73 mmol).

MS (EI, m/z): 291 [M]$^+$

Step B. Ethyl 4-(4-oxo-1-piperidinyl)benzoate

Ethyl 4-(1,4-dioxa-8-azaspiro[4.5]dec-8-yl)benzoate (1.56 g, 5.4 mmol) was dissolved in formic acid (15 mL) and heated at 67° C. for 1 hour. The solvent was removed in vacuo and the residue dissolved in chloroform, washed with water, saturated sodium hydrogen carbonate solution, brine, dried over anhydrous magnesium sulfate and filtered. The solvent was removed in vacuo to generate the title comound (1.15 g, 4.65 mmol) which was used without further purification.

MS ((+)APCI, m/z): 248 [M+H]$^+$

Step C. Ethyl 4-{4-[4-(dimethoxymethyl)anilino]-1-piperidinyl}benzoate 4-(2,2-Dimethoxyethyl)aniline (0.842 g, 4.65 mmol) and ethyl 4-(4-oxo-1-piperidinyl)benzoate (1.15 g, 4.65 mmol) were dissolved in dichloromethane. Anhydrous sodium sulfate (6.6 g) was added followed by acetic acid (1.1 mL, 18.32 mmol). Stirring was continued for 45 minutes. Sodium triacetoxyborohydride (1.1 g, 5.19 mmol) was added and stirring continued overnight. The mixture was filtered, diluted with dichloromethane, and washed with 1N sodium hydroxide, water and brine. The organic layer was dried over anhydrous magnesium sulfate. The solution was filtered and the solvent evaporated to dryness in vacuo. The residue was purified by flash chromatography on silica gel Merck-60 (eluant: 50:1 chloroform-methanol) and crystallized from ethyl acetate/hexane to yield the title compound (0.63 g, 1.53 mmol).

MS ((+)APCI, m/z): 413 [M+H]$^+$

Step D. 4-[4-(4-{2-[(2R)-2-Hydroxy-2-(4-hydroxy-3-methanesulfonylamino-phenyl)-ethylamino]-ethyl}-phenylamino)-piperidin-1-yl]-benzoic acid ethyl ester Ethyl 4-{4-[4-(dimethoxymethyl)anilino]-1-piperidinyl}benzoate (0.63 g, 01.53 mmol) was added to a pre-prepared mixture of sodium iodide (0.572 g, 3.82 mmol) and trichloro(methyl)silane (0.36 mL, 3.07 mmol) in anhydrous acetonitrile. The reaction was stirred at ambient temperature for 3 minutes. Dichloromethane was added and the reaction washed with 10% sodium thiosulfate solution, water and brine. The organic layer was dried with anhydrous magnesium sulfate, filtered and the solvent partially removed in vacuo. The aldehyde solution was used directly and treated with methanol, tetrahydrofuran, acetic acid (0.091 mL, 1.53 mmol), N-{5-[(1R)-2-amino-1-hydroxyethyl]-2-hydroxyphenyl}methanesulfonamide (0.377 g, 0.1.53 mmol) followed by sodium cyanoborohydride (0.105 g, 1.53 mmol). The reaction was stirred at ambient temperature overnight. The reaction was taken to dryness in vacuo, adsorbed onto silica and purified by flash chromatography on silica gel Merck-60 (eluant: 5:1 chloroform-methanol containing 1% ammonium hydroxide). The hydrochoride salt of the title compound was generated from anhydrous etheral hydrochloric acid in ethyl acetate (0.14 g, 0.221 mmol).

m.p Discolors at 155° C. Foams >210° C.

MS ((+)ESI, m/z): 597 [M+H]$^+$

Anal. calcd. for $C_{31}H_{40}N_4O_6S$+2.0 HCl+2.00 $H_2O$+0.6 $C_4H_8O_2$: C 52.89 H 6.75 N 7.39 found: C 52.70 H 6.46 N 7.23

EXAMPLE 121

4-(4-{2-[(2S)-2-Hydroxy-3-(4-hydroxy-phenoxy)-propylamino]-ethyl}-phenylamino)-piperidine-1-carboxylic acid 4-fluoro-benzyl Ester Step A. 4-Fluorobenzyl 4-(4-{2-[(tert-butoxycarbonyl)amino]ethyl}anilino)-1-piperidinecarboxylate 4-Fluorophenyl)methanol (0.50 g, 3.96 mmol) was dissolved in dichloromethane (20 mL) 4-nitrophenylchloroformate (0.8 g, 3.97 mmol) was added and the reaction cooled to 0° C. Triethylamine (1.38 mL, 9.9 mmol) was added and the reaction stirred for 30 minutes at 0° C. tert-Butyl 4-(4-piperidinylamino)phenethylcarbamate (1.16 g, 4.17 mmol) was added and the ice bath removed. The reaction was stirred at room temperature overnight. The reaction was diluted with dichloromethane, washed with 10% aqueous potassium carbonate, brine and dried with anhydrous magnesium sulfate. The solution was filtered and the solvent evaporated to dryness in vacuo to give the title compound (1.363 g, 2.89 mmol).

MS ((+)ESI, m/z): 472 [M+H]$^+$

Step B. 4-Fluorobenzyl 4-[4-(2-aminoethyl)anilino]-1-piperidinecarboxylate formate 4-Fluorobenzyl 4-(4-{2-[(tert-butoxycarbonyl)amino]ethyl}anilino)-1-piperidinecarboxylate (1.36 g, 2.88 mmol) was reacted according to Procedure F to obtain the title compound which was used without further purification.

Step C. 4-Fluorobenzyl 4-[4-(2-{[(2S)-3-(4-{[tert-butyl(diphenyl)silyl]oxy}phenoxy)-2-hydroxypropyl]amino}ethyl)anilino]-1-piperidinecarboxylate 4-Fluorobenzyl 4-[4-(2-aminoethyl)anilino]-1-piperidinecarboxylate formate (0.33 g, 0.792 ) was reacted with tert-butyl-(4-oxiranylmethoxy-phenoxy)-diphenyl-silane (0.32 g, 0.792 mmol) according to the method described in Procedure G to give the title compound (0.18 g, 0.232 mmol).

Step D. 4-(4-{2-[(2S)-2-Hydroxy-3-(4-hydroa-phenoxy)-propylamino]-ethyl}-phenylamino)-piperidine-1-carboxylic acid 4-fluoro-benzyl ester 4-Fluorobenzyl 4-[4-(2-{[(2S)-3-(4-{[tert-butyl(diphenyl)silyl]oxy}phenoxy)-2-hydroxypropyl]amino}ethyl)anilino]-1-piperidinecarboxylate (0.18 g, 0.232 mmol) was reacted according to Procedure H (eluant: 10:1 chloroform-methanol) to give the title compound (0.125 g, 0.197 mmol).

m.p 60–62° C.

MS ((+)ESI, m/z): 538 [M+H]$^+$

Anal. calcd. for $C_{30}H_{36}FN_3O_5$+0.5 $H_2O$: C 65.81 H 6.83 N 7.67 found: C 65.44 H 6.74 N 7.04

EXAMPLE 122

4-(4-{2-[(2S)-2-Hydroxy-3-(4-hydroxy-phenoxy)-propylamino]-ethyl}-phenylamino)-piperidine-1-carboxylic Acid 2,5-difluoro-benzyl Ester Step A. 4-[4-(2-tert-Butoxycarbonylamino-ethyl)-phenylamino]-piperidine-1-carboxylic acid 2,5-difluoro-benzyl ester 2,5-Difluorobenzyl alcohol (0.430 g, 3.0 mmol) was dissolved in dichloromethane (15 mL), 4-nitrophenylchloroformate (0.600 g, 3.0 mmol) was added and the reaction cooled to 0° C. Triethylamine (1.03 mL, 7.5 mmol) was added and the reaction stirred for 30 minutes at 0° C. The ice bath was removed and the reaction stirred at room temperature for a further 30 minutes. The reaction was cooled again to 0° C. and 4-[4-(2-tert-Butoxycarbonylamino-ethyl)-phenylamino]-piperidine (1.0 g, 3.15 mmol) was added. The ice bath was removed and the reaction stirred at ambient temperature overnight. The reaction was washed with 10% aqueous potassium carbonate, 1N sodium hydroxide, brine and dried over anhydrous sodium sulfate. The solution was filtered and the solvent evaporated to dryness in vacuo to give the title compound (0.690 g, 1.4 mmol).

MS ((+)ESI m/z): 490 [M+H]$^+$
$^1$H NMR (DMSO-d$_6$, 400 MHz): d 1.18–1.23(m, 2H), 1.35(s, 9H), 1.85–1.89(d, 2H), 3.40(m, 1H), 3.88–3.91(d, 2H), 5.10(s, 2H), 5.28–5.30(d, 1H), 6.49–6.51(d, 2H), 6.78–6.80(t, 1H), 6.86–6.88(d, 2H), 7.23–7.29(m, 3H).
Anal. Calcd. for C$_{26}$H$_{33}$N$_3$O$_4$F$_2$: C 63.79 H 6.79 N 8.58 Found C 63.27 H 6.56 N 8.19

Step B. 2,5-Difluorobenzyl 4-[4-(2-aminoethyl)anilino]-1-pireridinecarboxylate formate 4-[4-(2-tert-Butoxycarbonylamino-ethyl)-phenylamino]-piperidine-1-carboxylic acid 2,5-difluoro-benzyl ester (0.690 g, 1.4 mmol) was reacted according to Procedure F to yield the title compound (0.609 g, 1.4 mmol).
$^1$H NMR (DMSO-d$_6$, 400 MHz): d 1.80 (m, 2H), 2.80 (m, 2H),;3.80 (m, 2H), 6.50 (d, 2H), 7.00 (d, 2.00), 7.20–7.40 (m, 3H), 8.40 (s, 1H).

Step C. 2,5-Difluorobenzyl 4-[4-(2-{[(2S)-3-(4-{[tert-butyl (diphenyl)silyl]oxy}phenoxy)-2-hydroxypropyl]amino}ethyl)anilino]-1-piperidinecarboxylate 2,5-Difluorobenzyl 4-[4-(2-aminoethyl)anilino]-1-piperidinecarboxylate formate (0.609 g, 1.4 mmol) was reacted with tert-butyl-(4-oxiranylmethoxy-phenoxy)-diphenyl-silane according to Procedure G to yield the title compound (0.260 g, 0.3 mmol).
$^1$H NMR (DMSO-d$_6$, 400 MHz): d 1.80 (m, 2H), 2.80m (m, 2H), 3.80 (m, 2H), 6.50 (d, 2H), 6.70 (m, 4H), 6.90 (d,2H), 7.30 (m,3H), 7.50 (m,6H), 7.80 (m, 4H).

Step D. 4-(4-[2-[(2S)-2-Hydroxy-3-(4-hydroxy-phenoxy)-propylamino]-ethyl}-phenylamino)-piperidine-1-carboxylic acid 2,5-difluoro-benzyl ester 2,5-Difluorobenzyl 4-[4-(2-{[(2S)-3-(4-([tert-butyl (diphenyl)silyl]oxy}phenoxy)-2-hydroxypropyl]amino}ethyl)anilino]-1-piperidinecarboxylate (0.260 g, 0.3 mmol) was reacted according to Procedure H to give the title compound (0.038 g, 0.066 mmol).

MS ((-)ESI, m/z): 554 [M–H]$^-$
$^1$H NMR (DMSO-d$_6$, 400 MHz): d 1.18–1.27(m, 2H), 1.85–1.89(m, 2H), m 5.09(s, 2H), 5.26–5.28(d, 1H), 6.48–6.51(d, 2H), 6.63–6.66(m, 2H), 6.70–6.74(m, 2H), 6.88–6.90(d, 2H), 7.21–7.31 (m, 3H), 8.86(broad s, 1H).
Anal. calcd. for C$_{30}$H$_{35}$N3O$_5$F$_2$+1.0 H$_2$O: C 62.76 H 6.45 N 7.32 Found C 62.88 H 6.78 N 7.01

What is claimed is:

1. A compound of formula I having the structure

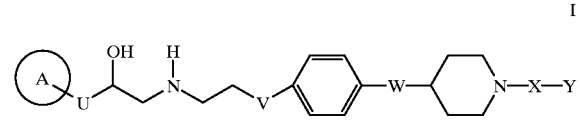

wherein,

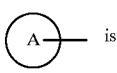 is (a) a 5–6 membered heterocyclic ring having 1–4 heteroatoms selected from O, N, and S, substituted with (R$^1$)$_m$;
(b) a phenyl ring substituted with (R$^1$)$_m$;
(c) a naphthyl ring substituted with (R$^1$)$_m$; or
(d) a phenyl fused heterocycle selected from the group consisting of

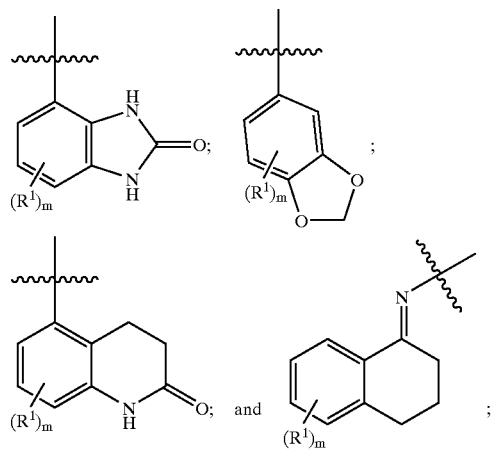

U is —OCH$_2$— or a bond;
V is O or a bond;
W is O, S(O)$_a$, NR$^2$, or NCOR$^2$;
X is SO$_2$, CO, —(CH$_2$)$_b$—, a bond, or Ar;
Y is —NR$^3$R$^4$, Het, Ar, alkyl of 1–8 carbon atoms, or —O(CH$_2$)$_d$R$^5$;
R$^1$ is alkyl of 1–8, carbon atoms, alkenyl of 2–7 carbon atoms, —OR$^6$, halogen, cyano, trifluoromethyl, —CO$_2$R$^6$, —CONR$^6$R$^7$, —NHCOR$^6$, or NHSO$_2$R$^8$;
R$^2$ is hydrogen, alkyl of 1–8 carbon atoms, or arylalkyl having 1–8 carbon atoms in the alkyl moiety;
R$^3$ and R$^4$ are each, independently, hydrogen, alkyl of 1–8 carbon atoms, cycloalkyl of 3–8 carbon atoms, arylalkyl having 1–8 carbon atoms in the alkyl group, —(CH$_2$)$_g$R$^9$, —(CH$_2$)$_h$COR$^9$, —(CH$_2$)$_j$CR$^{10}$R$^{11}$(CH$_2$)$_j$R$^9$, or —(CH$_2$)$_k$CONR$^{12}$R$^{13}$; or R$^3$ and R$^4$ may be taken together together with the nitrogen to which they are attached to form a 3–7 membered saturated heterocycle, which may optionally contain 1–2 additional heteroatoms selected from O and S, and said heterocycle may optionally be substituted with R$^{14}$;
R$^5$ is hydrogen; alkyl of 1–8 carbon atoms optionally substituted by 1–3 substituents selected from hydroxy, halogen, and aryl; cycloalkyl of 1–8 carbon atoms; Ar or Het;
R$^6$, R$^7$, and R$^8$ are each, independently, hydrogen, or alkyl of 1–8 carbon atoms, or aryl of 6–10 carbon atoms;

R⁹ is hydrogen; alkyl optionally substituted with 1–3 substitutents selected from hydroxy, halogen, and aryl; cycloalkyl of 3–8 carbon atoms; Ar, or Het;

R¹⁰ and R¹¹ are each, independently, hydrogen, alkyl, or aryl optionally substituted with alkyl of 1–8 carbon atoms or halogen; or R¹⁰ and R¹¹ are taken together to form a spiro fused cycloalkyl ring of 3–8 carbon atoms;

R¹² and R¹³ are each, independently, hydrogen, alkyl of 1–8 carbon atoms, aryl optionally substituted with alkyl of 1–8 carbon atoms or halogen; or R¹² and R¹³ are taken together with the nitrogen to which they are attached to form a 3–7 membered saturated heterocycle, which may optionally contain 1–2 additional heteroatoms selected from O and S, and said heterocycle may optionally be substituted with R¹⁴;

R¹⁴ is CO₂R¹⁵ or aryl optionally substituted with a 1–3 substituents selected from —OR¹⁵ and cycioalkyloxy of 3–8 carbon atoms;

R¹⁵ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with R¹⁶;

Het is (a) a 5–6 membered heterocyclic ring having 1–4 heteroatoms selected from O, S, and N which may be optionally mono- or di-substituted with R¹⁶; or (b) a heterocyclic ring system optionally mono- or di-substituted by R¹⁶ containing a 5–6 membered heterocyclic ring fused to one or two carbocyclic or heterocyclic rings such that the heterocyclic ring system contains 1–4 heteroatoms selected from O, S, and N;

R¹⁶ is aryl, halogen, alkyl of 1–8 carbon atoms, —OR¹⁷, cycloalkyl of 3–8 carbon atoms, trifluoromethyl, cyano, —CO₂R¹⁷,—CONR¹⁷R¹⁸, —SO₂NR¹⁷R¹⁸, —NR¹⁹CONR¹⁷R¹⁸, —NR¹⁷R¹⁸, —NR¹⁷COR¹⁸, —NO₂, —O(CH₂)ₚCO₂R¹⁷, —OCONR¹⁷R¹⁸, —O(CH₂)qOR¹⁷, or a 5–6 membered heterocyclic ring containing 1–4 heteroatoms selected from O, S, and N;

R¹⁷, R¹⁸, and R¹⁹ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when R¹⁷ and R¹⁸ are contained on a common nitrogen, R¹⁷ and R¹⁸ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
j=0–6;
k=0–6;
m=0–2;
p=1–6;
q=1–6;

or a pharmaceutically acceptable salt thereof.

2. The compound according to claim 1, wherein

is
(a) a 5–6 membered heterocyclic ring having 1–4 heteroatoms selected from O, N, and S, substituted with (R¹)ₘ;
(b) a phenyl ring substituted with (R¹)ₘ;
(c) a phenyl fused heterocycle selected from the group consisting of

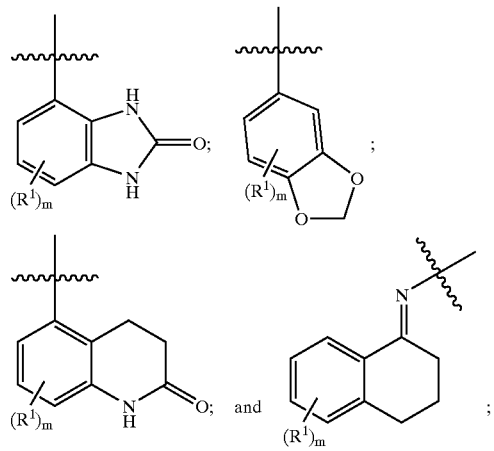

U is —OCH₂— or a bond;
V is O or a bond;
W is O, S(O)ₐ; or NR²;
X is SO₂, CO, —(CH₂)ᵦ—, a bond, or Ar;
Y is —NR³R⁴, Het, Ar, alkyl of 1–8 carbon atoms, or —O(CH₂)dR⁵;
R¹ is alkyl of 1–8 carbon atoms, alkenyl of 2–7 carbon atoms, aryl of 6–10 carbon atoms, —OR⁶, cycloalkyl of 3–8 carbon atoms, halogen, cyano, trifluoromethyl, —CO₂R⁶, —CONR⁶R⁷, —NHCOR⁶, NHSO₂R⁶, —NR⁶CONR⁷R⁸, —NR⁶R⁷, alkenyl of 2–7 carbon atoms, S(O)ₐR⁶, NO₂, —O(CH₂)ₑCO₂R⁶, —OCONR⁶R⁷, —O(CH₂)fOR⁶, or a 5–6 membered heterocyclic ring containing 1 to 4 heteroatoms selected from O, S, and N;
R² is hydrogen, alkyl of 1–8 carbon atoms, or arylalkyl having 1–8 carbon atoms in the alkyl moiety;
R³ and R⁴ are each, independently, hydrogen, alkyl of 1–8 carbon atoms, cycloalkyl of 3–8 carbon atoms, arylalkyl having 1–8 carbon atoms in the alkyl group, —(CH₂)gR⁹, —(CH₂)hCOR⁹, —(CH₂)jCR¹⁰R¹¹(CH₂)jR⁹, or —(CH₂)kCONR¹²R¹³; or R³ and R⁴ may be taken together together with the nitrogen to which they are attached to form a 3–7 membered saturated heterocycle, which may optionally contain 1–2 additional heteroatoms selected from O and S, and said heterocycle may optionally be substituted with R¹⁴;
R⁵ is hydrogen; alkyl of 1–8 carbon atoms optionally substituted by 1–3 substituents selected from hydroxy, halogen, and aryl; cycloalkyl of 1–8 carbon atoms; Ar or Het;
R⁶, R⁷, and R⁸ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;

R⁹ is hydrogen; alkyl optionally substituted with 1–3 substitutents selected from hydroxy, halogen, and aryl; cycloalkyl of 3–8 carbon atoms; Ar, or Het;

$R^{10}$ and $R^{11}$ are each, independently, hydrogen, alkyl, or aryl optionally substituted with alkyl of 1–8 carbon atoms or halogen; or $R^{10}$ and $R^{11}$ are taken together to form a spiro fused cycloalkyl ring of 3–8 carbon atoms;

$R^{12}$ and $R^{13}$ are each, independently, hydrogen, alkyl of 1–8 carbon atoms, aryl optionally substituted with alkyl of 1–8 carbon atoms or halogen; or $R^{12}$ and $R^{13}$ are taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^{14}$ is $CO_2R^{15}$ or aryl optionally substituted with a 1–3 substituents selected from $—OR^{15}$ and cycloalkyloxy of 3–8 carbon atoms;

$R^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with $R^{16}$;

Het is (a) a 5–6 membered heterocyclic ring having 1–4 heteroatoms selected from O, S, and N which may be optionally mono- or di-substituted with $R^{16}$; or (b) a heterocyclic ring system optionally mono- or di-substituted by $R^{16}$ containing a 5–6 membered heterocyclic ring fused to one or two carbocyclic or heterocyclic rings such that the heterocyclic ring system contains 1–4 heteroatoms selected from O, S, and N;

$R^{16}$ is aryl, halogen, alkyl of 1–8 carbon atoms, $—OR^{17}$, cycloalkyl of 3–8 carbon atoms, trifluoromethyl, cyano, $—CO_2R^{17}$, $—CONR^{17}R^{18}$, $—SO_2NR^{17}R^{18}$, $—NR^{17}OR^{18}$, $—NR^{19}CONR^{17}R^{18}$, $—NR^{17}R^{18}$, $—NR^{17}COR^{18}$, $—S(O)_nR^{17}$, $—NO_2$, $—O(CH_2)_pCO_2R^{17}$, $—OCONR^{17}R^{18}$, $—O(CH_2)_qOR^{17}$, or a 5–6 membered heterocyclic ring containing 1–4 heteroatoms selected from O, S, and N;

$R^{17}$, $R^{18}$, and $R^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when $R^{17}$ and $R^{18}$ are contained on a common nitrogen, $R^{17}$ and $R^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
e=1–6;
f=1–6;
g=0–6;
h=0–6;
j=0–6;
k=0–6;
m=0–2;
n=0–2;
p=1–6;
q=1–6;

or a pharmaceutically acceptable salt thereof.

3. A compound of claim 1, which is a) 4-(4-{2-[(2S)-2-Hydroxy-3-(4-hydroxy-phenoxy)-propylamino]-ethyl}-phenylamino)-piperidine-1-carboxylic acid 4-fluoro-benzylamide;

b) 4-(4-{2-[(2S)-2-Hydroxy-3-(4-hydroxy-phenoxy)-propylamino]-ethyl}-phenylamino)-piperidine-1-carboxylic acid cyclohexylamide;

c) 4-(4-{2-[(2S)-3-(4-Fluoro-phenoxy)-2-hydroxy-propylamino]-ethyl}-phenylamino)-piperidine-1-carboxylic acid octylamide;

d) 4-(4-{2-[(2S)-3-(2-Allyl-phenoxy)-2-hydroxy-propylamino]-ethyl}-phenylamino)-piperidine-1-carboxylic acid octylamide;

e) 4-(4-{2-[(2S)-3-(6-Amino-pyridin-3-yloxy)-2-hydroxy-propylamino]-ethyl}-phenylamino)-piperidine-1-carboxylic acid octylamide;

f) 4-(4-{2-[(2S)-2-Hydroxy-3-(4-hydroxy-phenoxy)-propylamino]-ethyl}-phenylamino)-piperidine-1-carboxylic acid [2-(3-methoxy-phenyl)-ethyl]-amide;

g) 4-(4-{2-[2-(3-Carbamoyl-4-hydroxy-phenyl)-2-hydroxy-ethylamino]-ethyl}-phenylamino)-piperidine-1-carboxylic acid octylamide;

h) 4-[Acetyl-(4-{2-[(2S)-2-hydroxy-3-(4-hydroxy-phenoxy)-propylamino]-ethyl}-phenyl)-amino]-piperidine-1-carboxylic acid octylamide;

i) 4-(4-{2-[(2S)-2-Hydroxy-3-(4-hydroxy-phenoxy)-propylamino]-ethyl}-phenylamino)-piperidine-1-carboxylic acid methylamide;

j) 4-(4-{2-[(2S)-2-Hydroxy-3-(4-hydroxy-phenoxy)-propylamino]-ethyl}-phenylamino)-piperidine-1-carboxylic acid ethylamide;

k) 4-(4-{2-[(2S)-2-Hydroxy-3-(4-hydroxy-phenoxy)-propylamino]-ethyl}-phenylamino)-piperidine-1-carboxylic acid isopropyl-amide;

l) 4-(4-{2-[(2S)-2-Hydroxy-3-(4-hydroxy-phenoxy)-propylamino]-ethyl}-phenylamino)-piperidine-1-carboxylic acid (3-cyclopentyl-propyl)-amide;

m) 4-(4-{2-[(2S)-2-Hydroxy-3-(4-hydroxy-phenoxy)-propylamino]-ethyl}-phenylamino)-piperidine-1-carboxylic acid (2,2,2-trifluoro-ethyl)-amide;

n) 4-(4-{2-[(2S)-2-Hydroxy-3-(4-hydroxy-phenoxy)-propylamino]-ethyl}-phenylamino)-piperidine-1-carboxylic acid diethylamide;

o) 4-(4-{2-[(2S)-2-Hydroxy-3-(4-hydroxy-phenoxy)-propylamino]-ethyl}-phenylamino)-piperidine-1-carboxylic acid [2-(4-fluoro-phenyl)-ethyl]-amide;

p) 4-(4-{2-[(2S)-3-(2-Chloro-4-hydroxy-phenoxy)-2-hydroxy-propylamino]-ethyl}-phenylamino)-piperidine-1-carboxylic acid octylamide;

q) [4-(3-Cyclopentyloxy-4-methoxy-phenyl)-piperidin-1-yl]-[4-(4-{2-[(2S)-2-hydroxy-3-(4-hydroxy-phenoxy)-propylamino]-ethyl}-phenylamino)-piperidin-1-yl]-methanone;

r) 4-(4-{2-[(2S)-2-Hydroxy-3-(4-hydroxy-phenoxy)-propylamino]-ethyl}-phenylamino)-piperidine-1-carboxylic acid amide;

s) 4-[4-(2-{(2S)-3-[4-(3-Ethyl-ureido)-phenoxy]-2-hydroxy-propylamino}-ethyl)-phenylamino]-piperidine-1-carboxylic acid [2-(4-fluoro-phenyl)-ethyl]-amide;

t) 4-(4-{2-[(2S)-2-Hydroxy-3-(4-hydroxy-phenoxy)-propylamino]-ethyl}-phenylamino)-piperidine-1-carboxylic acid 2,4-dichloro-benzylamide;

u) 4-(4-{2-[(2S)-2-Hydroxy-3-(4-hydroxy-phenoxy)-propylamino]-ethyl}-phenylamino)-piperidine-1-carboxylic acid 3,4-dichloro-benzylamide;

v) 4-(4-{2-[(2S)-2-Hydroxy-3-(4-methanesulfonylamino-phenoxy)-propylamino]-ethyl}-phenylamino)-piperidine-1-carboxylic acid octylamide;

w) 4-(4-{2-[(2S)-2-Hydroxy-3-(4-hydroxy-phenoxy)-propylamino]-ethyl}-phenylamino)-piperidine-1-carboxylic acid (3-thiophen-2-yl-propyl)-amide;

x) 4-(4-{2-[(2S)-2-Hydroxy-3-(4-hydroxy-phenoxy)-propylamino]-ethyl}-phenylamino)-piperidine-1-carboxylic acid 3,5-difluoro-benzylamide;

y) 4-(4-{2-[(2S)-2-Hydroxy-3-(4-hydroxy-phenoxy)-propylamino]-ethyl}-phenylamino)-piperidine-1-carboxylic acid 2,3-dimethoxy-benzylamide;

z) 4-(4-{2-[(2S)-2-Hydroxy-3-(4-hydroxy-phenoxy)-propylamino]-ethyl}-phenylamino)-piperidine-1-carboxylic acid 2-fluoro-benzylamide;

aa) 4-(4-{2-[(2S)-2-Hydroxy-3-(4-hydroxy-phenoxy)-propylamino]-ethyl}-phenylamino)-piperidine-1-carboxylic acid 3-fluoro-benzylamide;

bb) 4-(4-{2-[(2S)-2-Hydroxy-3-(4-hydroxy-phenoxy)-propylamino]-ethyl}-phenylamino)-piperidine-1-carboxylic acid (3-oxo-3-p-tolyl-propyl)-amide;

cc) 4-(4-{2-[(2S)-2-Hydroxy-3-(4-hydroxy-phenoxy)-propylamino]-ethyl}-phenylamino)-piperidine-1-carboxylic acid (3-p-tolyl-propyl)-amide;

dd) 4-(4-{2-[(2S)-2-Hydroxy-3-(4-hydroxy-phenoxy)-propylamino]-ethyl}-phenylamino)-piperidine-1-carboxylic acid [2-(4-ethyl-phenyl)-ethyl]-amide;

ee) 4-(4-{2-[(2S)-2-Hydroxy-3-(4-hydroxy-phenoxy)-propylamino]-ethyl}-phenylamino)-piperidine-1-carboxylic acid (2,2-diphenyl-ethyl)-amide;

ff) 4-(4-{2-[(2S)-2-Hydroxy-3-(4-hydroxy-phenoxy)-propylamino]-ethyl}-phenylamino)-piperidine-1-carboxylic acid 2,6-difluoro-benzylamide;

gg) 4-(4-{2-[(2S)-2-Hydroxy-3-(4-hydroxy-phenoxy)-propylamino]-ethyl}-phenylamino)-piperidine-1-carboxylic acid 2-trifluoromethyl-benzylamide;

hh) 4-(4-{2-[(2S)-2-Hydroxy-3-(4-hydroxy-phenoxy)-propylamino]-ethyl}-phenylamino)-piperidine-1-carboxylic acid 4-pyrazol-1-yl-2-trifluoromethyl-benzylamide;

ii) 4-(4-{2-[(2S)-2-Hydroxy-3-(4-hydroxy-phenoxy)-propylamino]-ethyl}-phenylamino)-piperidine-1-carboxylic acid (3-methyl-butyl)-amide;

jj) 4-(4-{2-[(2R)-2-(3-Chloro-phenyl)-2-hydroxy-ethylamino]-ethyl}-phenylamino)-piperidine-1-carboxylic acid octylamide;

kk) 4-(4-{2-[(2S)-2-Hydroxy-3-(4-hydroxy-phenoxy)-propylamino]-ethyl}-phenylamino)-piperidine-1-carboxylic acid 2,5-difluoro-benzylamide;

ll) 5-[(S)-3-[[2-[4-[[1-[[[(2,5-Difluorophenyl)methyl]amino]carbonyl]-4-piperidinyl]amino]phenyl]ethyl]amino]-2-hydroxypropoxy]-2-hydroxybenzoic acid;

mm) 4-(4-{2-[(2S)-2-Hydroxy-3-(4-hydroxy-phenoxy)-propylamino]-ethoxy}-phenylamino)-piperidine-1-carboxylic acid 4-fluoro-benzylamide;

nn) 4-(4-{2-[(2S)-2-Hydroxy-3-(4-hydroxy-phenoxy)-propylamino]-ethyl}-phenylsulfanyl)-piperidine-1-carboxylic acid phenylamide;

oo) 4-(4-{2-[(2S)-2-Hydroxy-3-(4-hydroxy-phenoxy)-propylamino]-ethyl}-phenylsulfanyl)-piperidine-1-carboxylic acid hexylamide;

pp) 4-(4-{2-[(2S)-2-Hydroxy-3-(4-hydroxy-phenoxy)-propylamino]-ethyl}-phenylsulfanyl)-piperidine-1-carboxylic acid 4-fluoro-benzylamide;

qq) 4-(4-{2-[(2S)-2-Hydroxy-3-(4-hydroxy-phenoxy)-propylamino]-ethyl}-phenylsulfanyl)-piperidine-1-carboxylic acid (1-phenyl-cyclopentylmethyl)-amide;

rr) 4-(4-{2-[(2S)-2-Hydroxy-3-(4-hydroxy-phenoxy)-propylamino]-ethyl}-benzenesulfonyl)-piperidine-1-carboxylic acid hexylamide;

ss) 4-(4-{2-[(2S)-2-Hydroxy-3-(4-hydroxy-phenoxy)-propylamino]-ethyl}-benzenesulfonyl)-piperidine-1-carboxylic acid 4-fluoro-benzylamide;

tt) 4-(4-{2-[(2S)-2-Hydroxy-3-(4-hydroxy-phenoxy)-propylamino]-ethyl}-benzenesulfonyl)-piperidine-1-carboxylic acid (1-phenyl-cyclopentylmethyl)-amide;

uu) 4-(4-{2-[(2S)-2-Hydroxy-3-(4-hydroxy-phenoxy)-propylamino]-ethyl}-benzenesulfonyl)-piperidine-1-carboxylic acid octylamide;

vv) 4-(4-{2-[(2S)-2-Hydroxy-3-(4-hydroxy-3-methyl-phenoxy)-propylamino]-ethyl}-benzenesulfonyl)-piperidine-1-carboxylic acid octylamide;

ww) 4-(4-{2-[(2S)-3-(Benzo[1,3]dioxol-5-yloxy)-2-hydroxy-propylamino]-ethyl}-benzenesulfonyl)-piperidine-1-carboxylic acid octylamide;

xx) 4-(4-{2-[(2S)-2-Hydroxy-3-(4-hydroxy-3-methanesulfonylamino-phenoxy)-propylamino]-ethyl}-phenylamino)-piperidine-1-carboxylic acid 2,5-difluoro-benzylamide;

yy) 1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic acid ethyl ester;

zz) 1-[4-(4-{2-[(2R)-2-Hydroxy-2-(4-hydroxy-3-methanesulfonylamino-phenyl)-ethylamino]-ethyl}-phenylamino)-piperidine-1-carbonyl]-piperidine-4-carboxylic acid;

aaa) 4-(4-{2-[(2S)-2-Hydroxy-3-(4-hydroxy-phenoxy)-propylamino]-ethyl}-phenylamino)-piperidine-1-carboxylic acid octylamide;

bbb) 4-(4-{2-[(2S)-2-Hydroxy-3-(4-hydroxy-phenoxy)-propylamino]-ethyl}-phenoxy)-piperidine-1-carboxylic acid octylamide;

ccc) 4-(4-{2-[(2S)-2-Hydroxy-3-(4-hydroxy-phenoxy)-propylamino]-ethyl}-phenylamino)-piperidine-1-carboxylic acid (8-fluoro-octyl)-amide;

ddd) 4-(4-{2-[(2S)2-Hydroxy-3-(4-hydroxy-phenoxy)-propylamino]-ethyl}-phenoxy)-piperidine-1-carboxylic acid 4-fluoro-benzylamide;

eee) 4-(4-{2-[2-Hydroxy-3-(4-hydroxy-phenoxy)-propylamino]-ethyl}-phenylamino)-piperidine-1-carboxylic acid [4-(3,4-dimethoxy-phenyl)-butyl]-amide;

fff) (4-{[4-(4-{2-[(2S)-2-Hydroxy-3-(4-hydroxy-phenoxy)-propylamino]-ethyl}-phenylamino)-piperidine-1-carbonyl]-amino}-phenoxy)-acetic acid;

ggg) 4-(4-{2-[(2R)-2-Hydroxy-2-(4-hydroxy-3-methanesulfonylamino-phenyl)-ethylamino]-ethyl}-phenylamino)-piperidine-1-carboxylic acid octylamide;

hhh) 4-(4-{2-[(2S)-2-Hydroxy-3-(2-oxo-2,3-dihydro-1H-benzoimidazol-4-yloxy)-propylamino]-ethyl}-phenylamino)-piperidine-1-carboxylic acid octylamide;

iii) 1-[4-(4-{2-[(2S)-2-Hydroxy-3-(4-hydroxy-phenoxy)-propylamino]-ethyl}-phenylamino)-piperidine-1-carbonyl]-piperidine-4-carboxylic acid ethyl ester;

jjj) 1-[4-(4-{2-[(2S)-2-Hydroxy-3-(4-hydroxy-phenoxy)-propylamino]-ethyl}-phenylamino)-piperidine-1-carbonyl]-piperidine-4-carboxylic acid;

kkk) 4-(4-{2-[(2S)-3-(3-Acetylamino-phenoxy)-2-hydroxy-propylamino]-ethyl}-phenylamino)-piperidine-1-carboxylic acid octylamide;

lll) 4-(4-{2-[(2S)-2-Hydroxy-3-(5-hydroxy-3,4-dihydro-2H-naphthalen-1-ylideneaminooxy)-propylamino]-ethyl}-phenylamino)-piperidine-1-carboxylic acid octylamide;

mmm) 4-(4-{2-[(2S)-3-(3-Fluoro-4-hydroxy-phenoxy)-2-hydroxy-propylamino]-ethyl]-phenylamino)-piperidine-1-carboxylic acid octylamide;

nnn) 4-(4-{2-[(2S)-2-Hydroxy-3-(4-hydroxy-3-methanesulfonylamino-phenoxy)-propylamino]-ethyl}-phenylamino)-piperidine-1-carboxylic acid octylamide;

ooo) 4-(4-{2-[(2S)-2-Hydroxy-3-(4-hydroxy-phenoxy)-propylamino]-ethyl}-phenylamino)-piperidine-1-carboxylic acid 4-(3-hexyl-ureido)-benzylamide;

ppp) 4-(4-{2-[(2S)-2-Hydroxy-3-(4-hydroxy-phenoxy)-propylamino]-ethyl}-phenylamino)-piperidine-1-carboxylic acid (3-cyclohexyl-propyl)-amide;

qqq) 4-(4-{2-[(2S)-2-Hydroxy-3-(8-hydroxy-2-oxo-1,2,3,4-tetrahydro-quinolin-5-yloxy)-propylamino]-ethyl}-phenylamino)-piperidine-1-carboxylicacid octylamide;

rrr) 4-(4-{2-[(2S)-2-Hydroxy-3-(4-hydroxy-phenoxy)-propylamino]-ethyl}-phenylamino)-piperidine-1-carboxyaic acid cyclopentylmethyl-amide;

sss) 4-(4-{2-[(2S)-2-Hydroxy-3-(4-hydroxy-phenoxy)-propylamino]-ethyl4-phenylamino)-piperidine-1-carboxylic acid {2-[2-methoxy-4-(3-phenoxy-propoxy)-phenyl]-ethyl}-amide;

ttt) 4-(4-{2-[(2S)-2-Hydroxy-3-(2-oxo-2,3-dihydro-1H-benzoimidazol-4-yloxy)-propylamino]-ethoxy}-phenylamino)-piperidine-1-carboxylic acid octylamide;

uuu) 4-(4-{2-[(2S)-2-Hydroxy-3-(4-hydroxy-phenoxy)-propylamino]-ethoxy}-phenylamino)-piperidine-1-carboxylic acid octylamide;

vvv) Dimethyl-carbamic acid 4-(2-{[4-(4-{2-[(2S)-2-hydroxy-3-(4-hydroxy-phenoxy)-propylamino]-ethyl}-phenylamino)-piperidine-1-carbonyl]-amino}-ethyl)-phenyl ester;

www) 4-(4-{2-[(2S)-2-Hydroxy-3-(3-methanesulfonylamino-phenoxy)-propylamino]-ethyl}-phenylamino)-piperidine-1-carboxylic acid 4-fluoro-benzylamide;

xxx) 4-(4-{2-[(2R)-2-Hydroxy-2-(4-hydroxy-3-methanesulfonylamino-phenyl)-ethylamino]-ethyl}-phenylamino)-piperidine-1-carboxylic acid 2,5-difluoro-benzylamide;

yyy) 1-[[4-[[4-[2-[[(2R)-2-Hydroxy-2-[4-hydroxy-3-[(methylsulfonyl)amino]phenyl]ethyl]amino]ethyl]phenyl]amino]-1-piperidinyl]carbonyl]-L-proline, methyl ester;

zzz) 1-[[4-[[4-[2-[[(2R)-2-Hydroxy-2-[4-hydroxy-3-[(methylsulfonyl)amino]phenyl]ethyl]amino]ethyl]phenyl]amino]-1-piperidinyl]carbonyl]-3-piperidine carboxylic acid, ethyl ester;

aaaa) 4-(4-{2-[(2S)-2-hydroxy-3-(4-hydroxy-phenoxy)-propylamino]ethyl}-phenylamino)-piperidine-1-carboxylic acid 3-methoxy-benzylamide;

bbbb) 4-(4-{2-[(2S)-2-Hydroxy-3-(4-hydroxy-phenoxy)-propylamino]-ethyl}-phenylamino)-piperidine-1-carboxylic acid 2,4-difluoro-benzylamide;

cccc) 4-(4-{2-[(2S)-2-Hydroxy-3-(4-hydroxy-phenoxy)-propylamino]-ethyl}-phenylamino)-piperidine-1-carboxylic acid [2-(4-fluoro-phenylcarbamoyl)-ethyl]-amide;

dddd) 4-(4-{2-[(2S)-2-Hydroxy-3-(4-hydroxy-phenoxy)-propylamino]-ethyl}-phenylamino)-piperidine-1-carboxylic acid {2-[(4-chloro-phenyl)-methyl-carbamoyl]-ethyl}-amide;

eeee) 4-(4-{2-[2-Hydroxy-3-(4-hydroxy-phenoxy)-propylamino]-ethyl}-phenylamino)-piperidine-1-carboxylic acid 2-fluoro-4-hydroxy-benzylamide;

ffff) Dimethyl-carbamic acid 3-fluoro-4-({[4-(4-{2-[(2S)-2-hydroxy-3-(4-hydroxy-phenoxy)-propylamino]-ethyl}-phenylamino)-piperidine-1-carbonyl]-amino}-methyl)-phenyl ester;

gggg) 4-(4-{2-[(2S)-2-Hydroxy-3-(3-hydroxy-phenoxy)-propylamino]-ethyl}-phenylamino)-piperidine-1-carboxylic acid 4-fluoro-benzylamide;

hhhh) [3-Fluoro-4-[[[[4-[[4-[2-[[(S)-2-hydroxy-3-(4-hydroxyphenoxy)propyl]amino]ethyl]phenyl]amino]-1-piperidinyl]carbonyl]amino]methyl]phenoxy]acetic acid;

iiii) 4-(4-{2-[(2S)-2-Hydroxy-3-(3-hydroxy-phenoxy)-propylamino]-ethyl}-phenylamino)-piperidine-1-carboxylic acid 2-fluoro-4-hydroxy-benzylamide;

jjjj) 4-(4-{2-[(2S)-2-Hydroxy-3-(4-hydroxy-phenoxy)-propylamino]-ethyl}-phenylamino)-piperidine-1-carboxylic acid [2-(3-fluoro-phenyl)-ethyl]-amide;

kkkk) 4-(4-{2-[(2S)-2-Hydroxy-3-(4-hydroxy-phenoxy)-propylamino]-ethyl}-phenylamino)-piperidine-1-carboxylic acid (2-diethylcarbamoyl-ethyl)-amide;

llll) 4-(4-{2-[(2S)-2-Hydroxy-3-(4-hydroxy-phenoxy)-propylamino]-ethyl}-phenylamino)-piperidine-1-carboxylic acid (3-morpholin-4-yl-3-oxo-propyl)-amide;

mmmm) [4-(4-{2-[(2S)-2-Hydroxy-3-(4-hydroxy-phenoxy)-propylamino]-ethyl}-phenylamino)-piperidin-1-yl]-(1H-indol-2-yl)-methanone;

nnnn) 4-[4-(4-{2-[(2S)-2-Hydroxy-3-(4-hydroxy-pheroxy)-propylamino]-ethyl}-phenylamino)-piperidine-1-carbonyl]-piperidine-1-carboxylic acid octylamide;

oooo) 1-Hexyl-3-(4-[4-(4-{2-[(2S)-2-hydroxy-3-(4-hydroxy-phenoxy)-propylamino]-ethyl}-phenylamino)-piperidine-1-carbonyl]-phenyl}-urea;

pppp) [4-(4-{2-[2-Hydroxy-3-(4-hydroxy-phenoxy)-propylamino]-ethyl}-phenylamino)-piperidin-1-yl]-(5-methoxy-1H-indol-2-yl)-methanone;

qqqq) [4-(4-{2-[(2S)-2-Hydroxy-3-(4-hydroxy-phenoxy)-propylamino]-ethyl}-phenylamino)-piperidin-1-yl]-(7-nitro-1H-indol-2-yl)-methanone;

rrrr) (5-Bromo-1H-indol-2-yl)-[4-(4-{2-[(2S)-2-hydroxy-3-(4-hydroxy-phenoxy)-propylamino]-ethyl}-phenylamino)-piperidin-1-yl]-methanone;

ssss) [4-(4-{2-[(2S)-2-Hydroxy-3-(4-hydroxy-phenoxy)-propylamino]-ethyl}-phenylamino)-piperidin-1-yl]-(3-methoxy-benzo[b]thiophen-2-yl)-methanone;

tttt) N-{3-[(2S)-2-Hydroxy-3-(2-{4-[1-(3-methoxy-benzo[b]thiophene-2-carbonyl)-piperidin-4-ylamino]-phenyl}-ethylamino)-propoxy]-phenyl}-acetamide;

uuuu) [4-(4-{2-[(2S)-2-Hydroxy-3-(4-hydroxy-phenoxy)-propylamino]-ethyl}-phenylamino)-piperidin-1-yl]-(1H-indol-3-yl)-methanone;

vvvv) [4-(4-{2-[(2S)-2-Hydroxy-3-(4-hydroxy-phenoxy)-propylamino]-ethyl}-phenylamino)-piperidin-1-yl]-(3-methyl-thiophen-2-yl)-methanone;

wwww) 4-[(2S)-2-Hydroxy-3-(2-{4-[i-(3-methyl-thiophene-2-carbonyl)-piperidin-4-ylamino]-phenyl}-ethylamino)-propoxy]-1,3-dihydro-benzoimidazol-2-one;

xxxx) [4-(4-{2-[(2S)-2-Hydroxy-3-(4-hydroxy-phenoxy)-propylamino]-ethyl}-phenylamino)-piperidin-1-yl]-(1H-indazol-3-yl)-methanone;

yyyy) 1-[4-(4-{2-[(2S)-2-Hydroxy-3-(4-hydroxy-phenoxy)-propylamino]-ethyl}-phenylamino)-piperidin-1-yl]-hexan-1-one;

zzzz) [(2S)-1-(4-Fuoro-benzenesulfonyl)-pyrrolidin-2-yl]-[4-(4-{2-[(2S)-2-hydroxy-3-(4-hydroxy-phenoxy)-propylamino]-ethyl}-phenylamino)-piperidin-1-yl]-methanone;

aaaaa) 4-[4-(4-{2-[(2R)-2-Hydroxy-2-(4-hydroxy-3-methanesulfonylamino-phenyl)-ethylamino]-ethyl}-phenylamino)-piperidine-1-carbonyl]-benzoic acid;

bbbbb) [4-(4-{2-[(2S)-2-Hydroxy-3-(4-hydroxy-phenoxy)-propylamino]-ethyl}-phenylsulfanyl)-piperidin-1-yl]-(3-methyl-thiophen-2-yl)-methanone;

ccccc) [4-(4-{2-[(2S)-2-Hydroxy-3-(4-hydroxy-phenoxy)-propylamino]-ethyl}-benzenesulfonyl)-piperidin-1-yl]-(2-methyl-thiophen-3-yl)-methanone;

ddddd) 1-Hexyl-3-{4-[4-(4-{2-[(2S)-2-hydroxy-3-(4-hydroxy-phenoxy)-propylamino]-ethyl}-phenylamino)-piperidine-1-sulfonyl]-phenyl}-urea;

eeeee) 1-{4-[4-(4-{2-[(2S)-3-(4-Fluoro-phenoxy)-2-hydroxy-propylamino]-ethyl}-phenylamino)-piperidine-1-sulfonyl]-phenyl}-3-hexyl-urea;

fffff) 1-{4-[4-(4-{2-[3-(2-allyl-phenoxy)-2-hydroxy-propylamino]ethyl}-phenylamino)-piperidine-1-sulfonyl]-phenyl}-3-hexyl-urea;

ggggg) 4-[(2S)-2-Hydroxy-3-(2-{4-[1-(octane-1-sulfonyl)-piperidin-4-ylamino]-phenyl}-ethylamino)-propoxy]-phenol;

hhhhh) 4-[(2S)-2-Hydroxy-3-(2-{4-[1-(toluene-4-sulfonyl)-piperidin-4-ylamino]-phenyl}-ethylamino)-propoxy]-phenol;

iiiii) 4-[(2S)-2-Hydroxy-3-(2-{4-[1-(1-methyl-1H-imidazole-4-sulfonyl)-piperidin-4-ylamino]-phenyl}-ethylamino)-propoxy]-phenol;

jjjjj) N-(4-[4-(4-{2-[(2S)-2-Hydroxy-3-(4-hydroxy-phenoxy)-propylamino]-ethyl}-phenylamino)-piperidine-1-sulfonyl]-phenyl}-acetamide;

kkkkk) N-(5-{[4-(4-{2-[((2R)-2-hydroxy-2-{4-hydroxy-3-[(methylsulfonyl)amino]phenyl}ethyl)amino]ethyl}anilino)piperidin-1-yl]sulfonyl}-4-methyl-1,3-thiazol-2-yl)acetamide;

lllll) N-(2-Hydroxy-5-{(1R)-1-hydroxy-2-[2-(4-{1-[4-(3-octyl-ureido)-benzenesulfonyl]-piperidin-4-ylamino}-phenyl)-ethylamino]-ethyl}-phenyl)-methanesulfonamide;

mmmmm) 4-[(2S)-2-Hydroxy-3-(2-{4-[1-(4-phenyl-thiazol-2-yl)-piperidin-4-ylamino]-phenyl}-ethylamino)-propoxy]-phenol;

nnnnn) (R)-N-{2-Hydroxy-5-[1-hydroxy-2-(2-{4-[1-(4-phenyl-thiazol-2-yl)-piperidin-4-ylamino]-phenyl}-ethylamino)-ethyl]-phenyl}-methanesulfonamide;

ooooo) N-(2-Hydroxy-5-{(1R)-1-hydroxy-2-[2-(4-{1-[4-(piperidine-1-sulfonyl)-phenyl]-piperidin-4-ylamino}-phenyl)-ethylamino]-ethyl}-phenyl)-methanesulfonamide;

ppppp) 4-[4-(4-{2-[(2R)-2-Hydroxy-2-(4-hydroxy-3-methanesulfonylamino-phenyl)-ethylamino]-ethyl}-phenylamino)-piperidin-1-yl]-benzoic acid ethyl ester;

qqqqq) 4-(4-{2-[(2S)-2-Hydroxy-3-(4-hydroxy-phenoxy)-propylamino]-ethyl}-phenylamino)-piperidine-1-carboxylic acid 4-fluoro-benzyl ester;

rrrrr) 4-(4-{2-[(2S)-2-Hydroxy-3-(4-hydroxy-phenoxy)-propylamino]-ethyl}-phenylamino)-piperidine-1-carboxylic acid 2,5-difluoro-benzyl ester sssss) or a pharmaceutically acceptable salt thereof.

4. A method of treating hyperglycemia or metabolic disorders mediated by insulin resistance in a mammal in need thereof which comprises providing to said mammal, an effective amount of a compound of formula I having the structure

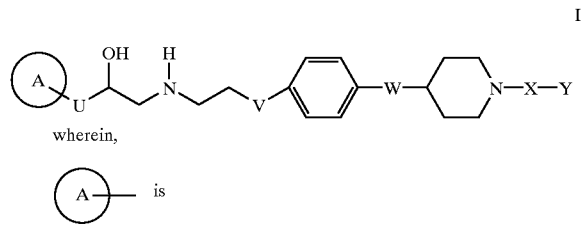

wherein,

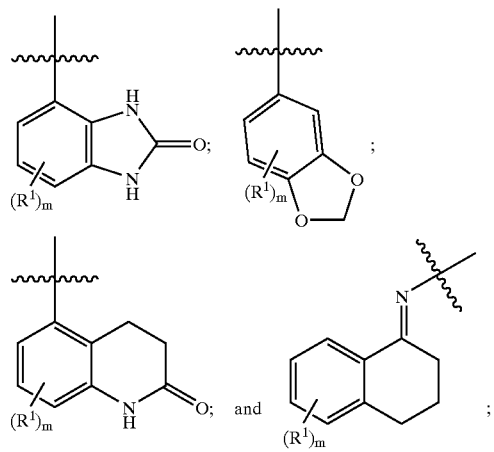

(a) a 5–6 membered heterocyclic ring having 1–4 heteroatoms selected from O, N, and S, substituted with $(R^1)_m$;
(b) a phenyl ring substituted with $(R^1)_m$;
(c) a naphthyl ring substituted with $(R^1)_m$; or
(d) a phenyl fused heterocycle selected from the group consisting of U is —OCH$_2$— or a bond;
V is O or a bond;
W is O, S(O)$_a$; NR$^2$, or NCOR$^2$;
X is SO$_2$, CO, —(CH$_2$)$_b$—, a bond, or Ar;
Y is —NR$^3$R$^4$, Het, Ar, alkyl of 1–8 carbon atoms, or —O(CH$_2$)$_d$R$^5$;
R$^1$ is alkyl of 1–8 carbon atoms, alkenyl of 2–7 carbon atoms, —OR$^6$, halogen, cyano, trifluoromethyl, —CO$_2$R$^6$, —CONR$^6$R$^7$, —NHCOR$^6$, or NHSO$_2$R$^8$;
R$^2$ is hydrogen, alkyl of 1–8 carbon atoms, or arylalkyl having 1–8 carbon atoms in the alkyl moiety;
R$^3$ and R$^4$ are each, independently, hydrogen, alkyl of 1–8 carbon atoms, cycloalkyl of 3–8 carbon atoms, arylalkyl having 1–8 carbon atoms in the alkyl group, —(CH$_2$)$_g$R$^9$, —(CH$_2$)$_h$COR$^9$, —(CH$_2$)$_j$CR$^{10}$R$^{11}$(CH$_2$)$_j$R$^9$, or —(CH$_2$)$_k$CONR$^{12}$R$^{13}$; or R$^3$ and R$^4$ may be taken together together with the nitrogen to which they are attached to form a 3–7 membered saturated heterocycle, which may optionally contain 1–2 additional heteroatoms selected from O and S, and said heterocycle may optionally be substituted with $R^{14}$;

$R^5$ is hydrogen; alkyl of 1–8 carbon atoms optionally substituted by 1–3 substituents selected from hydroxy, halogen, and aryl; cycloalkyl of 1–8 carbon atoms; Ar or Het;

$R^6$, $R^7$, and $R^8$ are each, independently, hydrogen, or alkyl of 1–8 carbon atoms, or aryl of 6–10 carbon atoms;

$R^9$ is hydrogen; alkyl optionally substituted with 1–3 substitutents selected from hydroxy, halogen, and aryl; cycloalkyl of 3–8 carbon atoms; Ar, or Het;

$R^{10}$ and $R^{11}$ are each, independently, hydrogen, alkyl, or aryl optionally substituted with alkyl of 1–8 carbon atoms or halogen; or $R^{10}$ and $R^{11}$ are taken together to form a spiro fused cycloalkyl ring of 3–8 carbon atoms;

$R^{12}$ and $R^{13}$ are each, independently, hydrogen, alkyl of 1–8 carbon atoms, aryl optionally substituted with alkyl of 1–8 carbon atoms or halogen; or $R^{12}$ and $R^{13}$ are taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^{14}$ is $CO_2R^{15}$ or aryl optionally substituted with a 1–3 substituents selected from —$OR^{15}$ and cycloalkyloxy of 3–8 carbon atoms;

$R^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with $R^{16}$;

Het is (a) a 5–6 membered heterocyclic ring having 1–4 heteroatoms selected from O, S, and N which may be optionally mono- or di-substituted with $R^{16}$; or (b) a heterocyclic ring system optionally mono- or di-substituted by $R^{16}$ containing a 5–6 membered heterocyclic ring fused to one or two carbocyclic or heterocyclic rings such that the heterocyclic ring system contains 1–4 heteroatoms selected from O, S, and N;

$R^{16}$ is aryl, halogen, alkyl of 1–8 carbon atoms, —$OR^{17}$, cycloalkyl of 3–8 carbon atoms, trifluoromethyl, cyano, —$CO_2R^{17}$, —$CONR^{17}R^{18}$, —$SO_2NR^{17}R^{18}$, —$NR^{19}CONR^{17}R^{18}$, —$NR^{17}R^{18}$, —$NR^{17}COR^{18}$, —$NO_2$, —$O(CH_2)_pCO_2R^{17}$, —$OCONR^{17}R^{18}$, —$O(CH_2)_qOR^{17}$, or a 5–6 membered heterocyclic ring containing 1–4 heteroatoms selected from O, S, and N;

$R^{17}$, $R^{18}$, and $R^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when $R^{17}$ and $R^{18}$ are contained on a common nitrogen, $R^{17}$ and $R^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
j=0–6;
k=0–6;
m=0–2;
p=1–6;
q=1–6;

or a pharmaceutically acceptable salt thereof.

5. A method of modulating glucose levels in a mammal in need thereof which comprises providing to said mammal, an effective amount of a compound of formula I having the structure

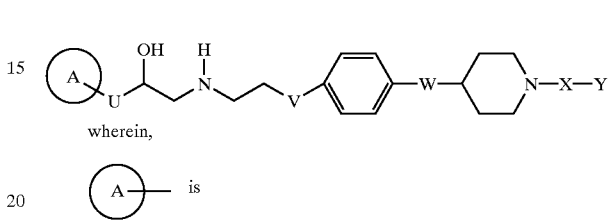

wherein, (A)— is (a) a 5–6 membered heterocyclic ring having 1–4 heteroatoms selected from O, N, and S, substituted with $(R^1)_m$;
(b) a phenyl ring substituted with $(R^1)_m$;
(c) a naphthyl ring substituted with $(R^1)_m$; or
(d) a phenyl fused heterocycle selected from the group consisting of

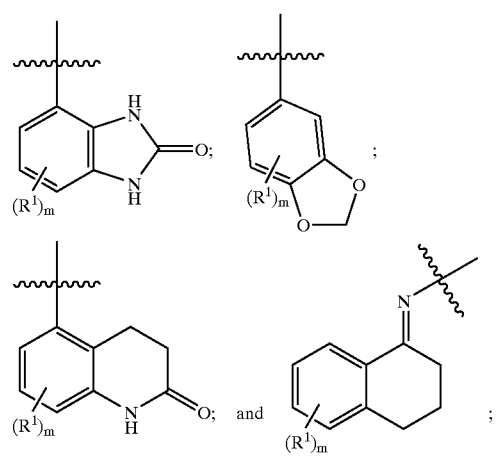

U is —$OCH_2$— or a bond;
V is O or a bond;
W is O, $S(O)_a$; $NR_2$, or $NCOR^2$;
X is $SO_2$, CO, —$(CH_2)_b$—, a bond, or Ar;
Y is —$NR^3R^4$, Het, Ar, alkyl of 1–8 carbon atoms, or —$O(CH_2)_dR^5$;
$R^1$ is alkyl of 1–8 carbon atoms, alkenyl of 2–7 carbon atoms, —$OR^6$, halogen, cyano, trifluoromethyl, —$CO_2R^6$, —$CONR^6R^7$, —$NHCOR^6$, or $NHSO_2R^8$;
$R^2$ is hydrogen, alkyl of 1–8 carbon atoms, or arylalkyl having 1–8 carbon atoms in the alkyl moiety;
$R^3$ and $R^4$ are each, independently, hydrogen, alkyl of 1–8 carbon atoms, cycloalkyl of 3–8 carbon atoms, arylalkyl having 1–8 carbon atoms in the alkyl group, $(CH2)_gR^9$, —$(CH_2)_hCOR^9$, —$(CH_2)_jCR^{10}R^{11}(CH_2)_jR^9$, or —$(CH_2)_kCONR^{12}R^{13}$; or $R^3$ and $R^4$ may be taken together together with the nitrogen to which they are attached to form a 3–7 membered saturated heterocycle, which may optionally contain 1–2 additional heteroatoms selected from O and S, and said heterocycle may optionally be substituted with $R^{14}$;

$R^5$ is hydrogen; alkyl of 1–8 carbon atoms optionally substituted by 1–3 substituents selected from hydroxy, halogen, and aryl; cycloalkyl of 1–8 carbon atoms; Ar or Het;

$R^6$, $R^7$, and $R^8$ are each, independently, hydrogen, or alkyl of 1–8 carbon atoms, or aryl of 6–10 carbon atoms;

$R^9$ is hydrogen; alkyl optionally substituted with 1–3 substitutents selected from hydroxy, halogen, and aryl; cycloalkyl of 3–8 carbon atoms; Ar, or Het;

$R^{10}$ and $R^{11}$ are each, independently, hydrogen, alkyl, or aryl optionally substituted with alkyl of 1–8 carbon atoms or halogen; or $R^{10}$ and $R^{11}$ are taken together to form a spiro fused cycloalkyl ring of 3–8 carbon atoms;

$R^{12}$ and $R^{13}$ are each, independently, hydrogen, alkyl of 1–8 carbon atoms, aryl optionally substituted with alkyl of 1–8 carbon atoms or halogen; or $R^{12}$ and $R^{13}$ are taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^{14}$ is $CO_2R^{15}$ or aryl optionally substituted with a 1–3 substituents selected from —$OR^{15}$ and cycloalkyloxy of 3–8 carbon atoms;

$R^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with $R^{16}$;

Het is (a) a 5–6 membered heterocyclic ring having 1–4 heteroatoms selected from O, S, and N which may be optionally mono- or di-substituted with $R^{16}$; or (b) a heterocyclic ring system optionally mono- or di-substituted by $R^{16}$ containing a 5–6 membered heterocyclic ring fused to one or two carbocyclic or heterocyclic rings such that the heterocyclic ring system contains 1–4 heteroatoms selected from O, S, and N;

$R^{16}$ is aryl, halogen, alkyl of 1–8 carbon atoms, —$OR^{17}$, cycloalkyl of 3–8 carbon atoms, trifluoromethyl, cyano, —$CO_2R^{17}$,—$CONR^{17}R^{18}$, —$SO_2NR^{17}R^{18}$, —$NR^{19}CONR^{17}R^{18}$, —$NR^{17}R^{18}$, —$NR^{17}COR^{18}$, —$NO_2$, —$O(CH_2)_pCO_2R^{17}$, —$OCONR^{17}R^{18}$, —$O(CH_2)_qOR^{17}$, or a 5–6 membered heterocyclic ring containing 1–4 heteroatoms selected from O, S, and N;

$R^{17}$, $R^{18}$, and $R^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when $R^{17}$ and $R^{18}$ are contained on a common nitrogen, $R^{17}$ and $R^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
j=0–6;
k=0–6;
m=0–2;
p=1–6;
q=1–6;

or a pharmaceutically acceptable salt thereof.

6. A method of treating or inhibiting urinary incontinence in a mammal in need thereof which comprises providing to said mammal an effective amount of a compound of formula I having the structure

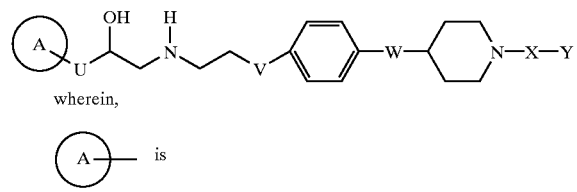

wherein,

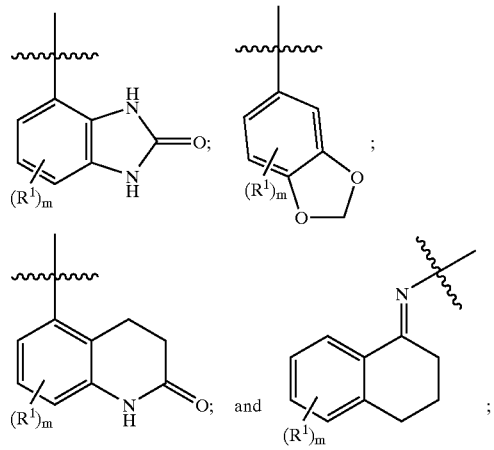

(a) a 5–6 membered heterocyclic ring having 1–4 heteroatoms selected from O, N, and S, substituted with $(R^1)_m$;
(b) a phenyl ring substituted with $(R^1)_m$;
(c) a naphthyl ring substituted with $(R^1)_m$; or
(d) a phenyl fused heterocycle selected from the group consisting of U is —$OCH_2$— or a bond;
V is O or a bond;
W is O, $S(O)_a$; $NR^2$, or $NCOR^2$;
X is $SO_2$, CO, —$(CH_2)_b$—, a bond, or Ar;
Y is —$NR^3R^4$, Het, Ar, alkyl of 1–8 carbon atoms, or —$O(CH_2)_dR^5$ $R^1$ is alkyl of 1–8 carbon atoms, alkenyl of 2–7 carbon atoms, —$OR^6$, halogen, cyano, trifluoromethyl, —$CO_2R^6$, —$CONR^6R^7$, —$NHCOR^6$, or $NHSO_2R^8$;

$R^2$ is hydrogen, alkyl of 1–8 carbon atoms, or arylalkyl having 1–8 carbon atoms in the alkyl moiety;

$R^3$ and $R^4$ are each, independently, hydrogen, alkyl of 1–8 carbon atoms, cycloalkyl of 3–8 carbon atoms, arylalkyl having 1–8 carbon atoms in the alkyl group, —$(CH_2)_gR^9$, —$(CH_2)_hCOR^9$, —$(CH_2)_jCR^{10}R^{11}(CH_2)_jR^9$, or —$(CH_2)_kCONR^{12}R^{13}$; or $R^3$ and $R^4$ may be taken together with the nitrogen to which they are attached to form a 3–7 membered saturated heterocycle, which may optionally contain 1–2 additional heteroatoms selected from O and S, and said heterocycle may optionally be substituted with $R^{14}$;

R⁵ is hydrogen; alkyl of 1–8 carbon atoms optionally substituted by 1–3 substituents selected from hydroxy, halogen, and aryl; cycloalkyl of 1–8 carbon atoms; Ar or Het;

R⁶, R⁷, and R⁸ are each, independently, hydrogen, or alkyl of 1–8 carbon atoms, or aryl of 6–10 carbon atoms;

R⁹ is hydrogen; alkyl optionally substituted with 1–3 substitutents selected from hydroxy, halogen, and aryl; cycloalkyl of 3–8 carbon atoms; Ar, or Het;

R¹⁰ and R¹¹ are each, independently, hydrogen, alkyl, or aryl optionally substituted with alkyl of 1–8 carbon atoms or halogen; or R¹⁰ and R¹¹ are taken together to form a spiro fused cycloalkyl ring of 3–8 carbon atoms;

R¹² and R¹³ are each, independently, hydrogen, alkyl of 1–8 carbon atoms, aryl optionally substituted with alkyl of 1–8 carbon atoms or halogen; or R¹² and R¹³ are taken together with the nitrogen to which they are attached to form a 3–7 membered saturated heterocycle, which may optionally contain 1–2 additional heteroatoms selected from O and S, and said heterocycle may optionally be substituted with R¹⁴;

R¹⁴ is CO₂R¹⁵ or aryl optionally substituted with a 1–3 substituents selected from —OR¹⁵ and cycloalkyloxy of 3–8 carbon atoms;

R¹⁵ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with R¹⁶;

Het is (a) a 5–6 membered heterocyclic ring having 1–4 heteroatoms selected from O, S, and N which may be optionally mono- or di-substituted with R¹⁶; or (b) a heterocyclic ring system optionally mono- or di-substituted by R¹⁶ containing a 5–6 membered heterocyclic ring fused to one or two carbocyclic or heterocyclic rings such that the heterocyclic ring system contains 1–4 heteroatoms selected from O, S, and N;

R¹⁶ is aryl, halogen, alkyl of 1–8 carbon atoms, —OR¹⁷, cycloalkyl of 3–8 carbon atoms, trifluoromethyl, cyano, —CO₂R¹⁷, —CONR¹⁷R¹⁸, —SO₂NR¹⁷R¹⁸, —NR¹⁹CONR¹⁷R¹⁸, —NR¹⁷R¹⁸, —NR¹⁷COR¹⁸, —NO₂, —O(CH₂)$_p$CO₂R¹⁷, —OCONR¹⁷R¹⁸, —O(CH₂)$_q$OR¹⁷, or a 5–6 membered heterocyclic ring containing 1–4 heteroatoms selected from O, S, and N;

R¹⁷, R¹⁸, and R¹⁹ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when R¹⁷ and R¹⁸ are contained on a common nitrogen, R¹⁷ and R¹⁸ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
j=0–6;
k=0–6;
m=0–2;
p=1–6;
q=1–6;

or a pharmaceutically acceptable salt thereof.

7. A method of treating or inhibiting atherosclerosis, gastrointestinal disorders, neurogenetic inflammation, glaucoma, or ocular hypertension in a mammal in need thereof, which comprises providing to said mammal an effective amount of a compound of formula I having the structure

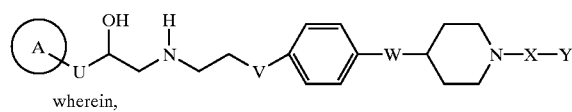

wherein,

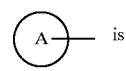 is (a) a 5–6 membered heterocyclic ring having 1–4 heteroatoms selected from O, N, and S, substituted with (R¹)$_m$;
(b) a phenyl ring substituted with (R¹)$_m$;
(c) a naphthyl ring substituted with (R¹)$_m$; or
(d) a phenyl fused heterocycle selected from the group consisting of

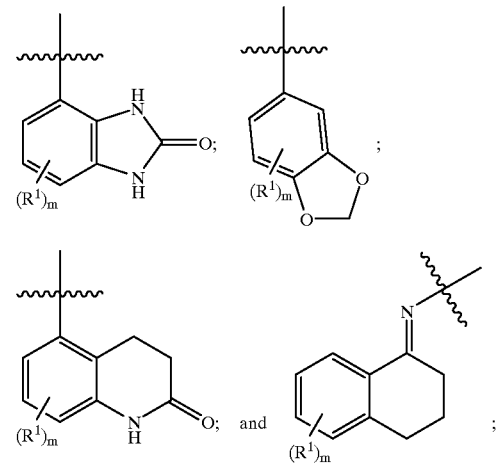

U is —OCH₂— or a bond;
V is O or a bond;
W is O, S(O)$_a$; NR², or NCOR²;
X is SO₂, CO, —(CH₂)$_b$—, a bond, or Ar;
Y is —NR³R⁴, Het, Ar, alkyl of 1–8 carbon atoms, or —O(CH₂)$_d$R⁵;
R¹ is alkyl of 1–8 carbon atoms, alkenyl of 2–7 carbon atoms, —OR⁶, halogen, cyano, trifluoromethyl, —CO₂R⁶, —CONR⁶R⁷, —NHCOR⁶, or NHSO₂R⁸;
R² is hydrogen, alkyl of 1–8 carbon atoms, or arylalkyl having 1–8 carbon atoms in the alkyl moiety;
R³ and R⁴ are each, independently, hydrogen, alkyl of 1–8 carbon atoms, cycloalkyl of 3–8 carbon atoms, arylalkyl having 1–8 carbon atoms in the alkyl group, —(CH₂)$_g$R⁹, —(CH₂)$_h$COR⁹, —(CH₂)$_j$CR¹⁰OR¹¹ (CH₂)$_j$R⁹, or —(CH₂)$_k$CONR¹²R¹³; or R³ and R⁴ may be taken together together with the nitrogen to which they are attached to form a 3–7 membered saturated heterocycle, which may optionally contain 1–2 additional heteroatoms selected from O and S, and said heterocycle may optionally be substituted with R¹⁴;

157

R⁵ is hydrogen; alkyl of 1–8 carbon atoms optionally substituted by 1–3 substituents selected from hydroxy, halogen, and aryl; cycloalkyl of 1–8 carbon atoms; Ar or Het;

$R^6, R^7$, and $R^8$ are each, independently, hydrogen, or alkyl of 1–8 carbon atoms, or aryl of 6–10 carbon atoms;

$R^9$ is hydrogen; alkyl optionally substituted with 1–3 substitutents selected from hydroxy, halogen, and aryl; cycloalkyl of 3–8 carbon atoms; Ar, or Het;

$R^{10}$ and $R^{11}$ are each, independently, hydrogen, alkyl, or aryl optionally substituted with alkyl of 1–8 carbon atoms or halogen; or $R^{10}$ and $R^{11}$ are taken together to form a spiro fused cycloalkyl ring of 3–8 carbon atoms;

$R^{12}$ and $R^{13}$ are each, independently, hydrogen, alkyl of 1–8 carbon atoms, aryl optionally substituted with alkyl of 1–8 carbon atoms or halogen; or $R^{12}$ and $R^{13}$ are taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^{14}$ is $CO_2R^{15}$ or aryl optionally substituted with a 1–3 substituents selected from —$OR^{15}$ and cycloalkyloxy of 3–8 carbon atoms;

$R^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with $R^{16}$;

Het is (a) a 5–6 membered heterocyclic ring having 1–4 heteroatoms selected from O, S, and N which may be optionally mono- or di-substituted with $R^{16}$; or (b) a heterocyclic ring system optionally mono- or di-substituted by $R^{16}$ containing a 5–6 membered heterocyclic ring fused to one or two carbocyclic or heterocyclic rings such that the heterocyclic ring system contains 1–4 heteroatoms selected from O, S, and N; $R^{16}$ is aryl, halogen, alkyl of 1–8 carbon atoms, —$OR^{17}$, cycloalkyl of 3–8 carbon atoms, trifluoromethyl, cyano, —$CO_2R^{17}$, —$CONR^{17}R^{18}$, —$SO_2NR^{17}R^{18}$, —$NR^{19}CONR^{17}R^{18}$, —$NR^{17}R^{18}$, —$NR^{17}COR^{18}$, —$NO_2$, —$O(CH_2)_pCO_2R^{17}$, —$OCONR^{17}R^{18}$, —$O(CH_2)_qOR^{17}$, or a 5–6 membered heterocyclic ring containing 1–4 heteroatoms selected from O, S, and N;

$R^{17}$, $R^{18}$, and $R^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when $R^{17}$ and $R^{18}$ are contained on a common nitrogen, $R^{17}$ and $R^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
j=0–6;
k=0–6;
m=0–2;
p=1–6;
q=1–6;

158 or a pharmaceutically acceptable salt thereof.

8. A pharmaceutical composition which comprises a compound of formula I having the structure

I

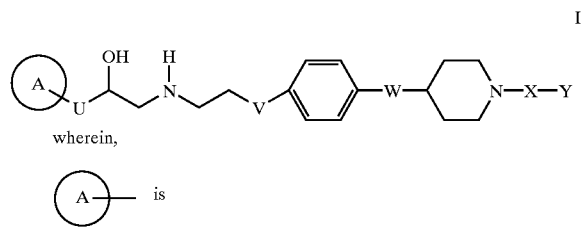

wherein, (A)— is (a) a 5–6 membered heterocyclic ring having 1–4 heteroatoms selected from O, N, and S, substituted with $(R^1)_m$;
(b) a phenyl ring substituted with $(R^1)_m$;
(c) a naphthyl ring substituted with $(R^1)_m$; or
(d) a phenyl fused heterocycle selected from the group consisting of

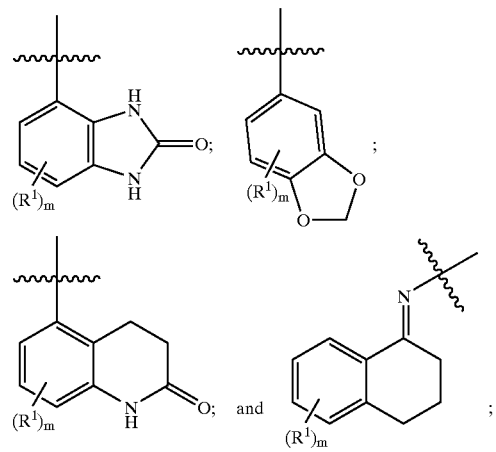

U is —$OCH_2$— or a bond;
V is O or a bond;
W is O, $S(O)_a$; $NR^2$, or $NCOR^2$;
X is $SO_2$, CO, —$(CH_2)_b$—, a bond, or Ar;
Y is —$NR^3R^4$, Het, Ar, alkyl of 1–8 carbon atoms, or —$O(CH_2)_dR^5$;

$R^1$ is alkyl of 1–8 carbon atoms, alkenyl of 2–7 carbon atoms, —$OR^6$, halogen, cyano, trifluoromethyl, —$CO_2R^6$, —$CONR^6R^7$, —$NHCOR^6$, or $NHSO_2R^8$;

$R^2$ is hydrogen, alkyl of 1–8 carbon atoms, or arylalkyl having 1–8 carbon atoms in the alkyl moiety;

$R^3$ and $R^4$ are each, independently, hydrogen, alkyl of 1–8 carbon atoms, cycloalkyl of 3–8 carbon atoms, arylalkyl having 1–8 carbon atoms in the alkyl group, —$(CH_2)_gR^9$, —$(CH_2)_hCOR^9$, —$(CH_2)_jCR^{10}R^{11}(CH_2)_jR^9$, or —$(CH_2)_kCONR^{12}R^{13}$; or $R^3$ and $R^4$ may be taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^5$ is hydrogen; alkyl of 1–8 carbon atoms optionally substituted by 1–3 substituents selected from hydroxy, halogen, and aryl; cycloalkyl of 1–8 carbon atoms; Ar or Het;

$R^6$, $R^7$, and $R^8$ are each, independently, hydrogen, or alkyl of 1–8 carbon atoms, or aryl of 6–10 carbon atoms;

$R^9$ is hydrogen; alkyl optionally substituted with 1–3 substitutents selected from hydroxy, halogen, and aryl; cycloalkyl of 3–8 carbon atoms; Ar, or Het;

$R^{10}$ and $R^{11}$ are each, independently, hydrogen, alkyl, or aryl optionally substituted with alkyl of 1–8 carbon atoms or halogen; or $R^{10}$ and $R^{11}$ are taken together to form a spiro fused cycloalkyl ring of 3–8 carbon atoms;

$R^{12}$ and $R^{13}$ are each, independently, hydrogen, alkyl of 1–8 carbon atoms, aryl optionally substituted with alkyl of 1–8 carbon atoms or halogen; or $R^{12}$ and $R^{13}$ are taken together with the nitrogen to which they are attached to form a 3–7 membered saturated heterocycle, which may optionally contain 1–2 additional heteroatoms selected from O and S, and said heterocycle may optionally be substituted with $R^{14}$;

$R^{14}$ is $CO_2R^{15}$ or aryl optionally substituted with a 1–3 substituents selected from —$OR^{15}$ and cycloalkyloxy of 3–8 carbon atoms;

$R^{15}$ is alkyl of 1–8 carbon atoms or arylalkyl having 1–8 carbon atoms in the alkyl moiety;

Ar is an aromatic ring system containing 1–2 carbocyclic aromatic rings having 6–10 carbon atoms optionally mono-, di-, or tri-substituted with $R^{16}$;

Het is (a) a 5–6 membered heterocyclic ring having 1–4 heteroatoms selected from O, S, and N which may be optionally mono- or di-substituted with $R^{16}$; or (b) a heterocyclic ring system optionally mono- or di-substituted by $R^{16}$ containing a 5–6 membered heterocyclic ring fused to one or two carbocyclic or heterocyclic rings such that the heterocyclic ring system contains 1–4 heteroatoms selected from O, S, and N;

$R^{16}$ is aryl, halogen, alkyl of 1–8 carbon atoms, —$OR^{17}$, cycloalkyl of 3–8 carbon atoms, trifluoromethyl, cyano, —$CO_2R^{17}$, —$CONR^{17}R^{18}$, —$SO_2NR^{17}R^{18}$, —$NR^{19}CONR^{17}R^{18}$, —$NR^{17}R^{18}$, —$NR^{17}COR^{18}$, —$NO_2$, —$O(CH_2)_pCO_2R^{17}$, —$OCONR^{17}R^{18}$, —$O(CH_2)_qOR^{17}$, or a 5–6 membered heterocyclic ring containing 1–4 heteroatoms selected from O, S, and N;

$R^{17}$, $R^{18}$, and $R^{19}$ are each, independently, hydrogen, alkyl of 1–8 carbon atoms, arylalkyl having 1–8 carbon atoms in the alkyl moiety, or aryl optionally mono-, di-, or tri-substituted with halogen, cyano, nitro, hydroxy, alkyl of 1–8 carbon atoms, or alkoxy of 1–8 carbon atoms; or when $R^{17}$ and $R^{18}$ are contained on a common nitrogen, $R^{17}$ and $R^{18}$ may be taken together with the nitrogen to which they are attached to form a 3–7 membered saturated heterocycle, which may optionally contain 1–2 additional heteroatoms selected from O and S;

a=0–2;
b=1–6;
d=0–3;
g=0–6;
h=0–6;
i=0–6;
k=0–6;
m=0–2;
p=1–6;
q=1–6;

\* \* \* \* \*